US007205417B2

(12) United States Patent
Fukami et al.

(10) Patent No.: US 7,205,417 B2
(45) Date of Patent: Apr. 17, 2007

(54) SPIRO COMPOUNDS

(75) Inventors: Takehiro Fukami, Tsukuba (JP); Katsumasa Nonoshita, Tsukuba (JP); Takeshi Sagara, Tsukuba (JP); Hiroyuki Kishino, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/485,955

(22) PCT Filed: Aug. 2, 2002

(86) PCT No.: PCT/JP02/07922

§ 371 (c)(1), (2), (4) Date: Apr. 12, 2004

(87) PCT Pub. No.: WO03/014083

PCT Pub. Date: Feb. 20, 2003

(65) Prior Publication Data

US 2004/0259890 A1 Dec. 23, 2004

(30) Foreign Application Priority Data

Aug. 7, 2001 (JP) ............................ 2001-239567

(51) Int. Cl.

| | |
|---|---|
| ***C07D 307/94*** | (2006.01) |
| ***C07D 407/12*** | (2006.01) |
| ***A61K 31/4525*** | (2006.01) |

(52) U.S. Cl. ...................... 549/331; 546/196; 514/320; 514/462

(58) Field of Classification Search .................. 546/18, 546/196; 514/320, 462; 548/331

See application file for complete search history.

(56) References Cited

U.S. PATENT DOCUMENTS

| | | | | |
|---|---|---|---|---|
| 5,869,489 A | 2/1999 | Shah et al. | ................. | 514/253 |
| 6,191,160 B1 | 2/2001 | Gao et al. | ................... | 514/409 |
| 6,326,375 B1 | 12/2001 | Fukami et al. | .............. | 514/278 |
| 6,803,372 B2 * | 10/2004 | Fukami et al. | .............. | 514/275 |
| 6,939,966 B2 * | 9/2005 | Burns et al. | ................ | 544/331 |

FOREIGN PATENT DOCUMENTS

| | | |
|---|---|---|
| EP | 1 323 709 | 7/2003 |
| GB | 2 311 523 | 10/1997 |
| WO | 99/22735 | 5/1999 |
| WO | 00/27845 | 5/2000 |
| WO | 01/14328 | 3/2001 |
| WO | 01/14376 | 3/2001 |
| WO | 02/48152 | 6/2002 |

OTHER PUBLICATIONS

H. Qi et al., "L-Tryptophan Urea, Amides as $NK_1/NK_2$ Dual Antagonists", Bioorganic & Medicinal Chemistry Letters, vol. 8, 1998, No. 16, pp. 2259-2262.

A. Poulsen et al., "A pharmacophore model for NK2 antagonist comprising compounds from several structurally diverse classes", Journal of Computer-Aided Molecular Design, vol. 16, No. 4, pp. 273-286, 2002.

* cited by examiner

*Primary Examiner*—Rita Desai
(74) *Attorney, Agent, or Firm*—Wenderoth, Lind & Ponack, L.L.P.

(57) ABSTRACT

Compounds of the formula (I):

(I)

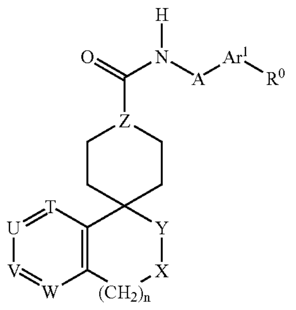

(wherein

A is an optionally substituted straight-chain hydrocarbon having 1 to 6 carbon atoms, which is optionally intervened by oxygen or nitrogen atom;

$Ar^1$ is aryl or heteroaryl, any of which is optionally substituted;

n is 0 or 1;

$R^0$ is hydrogen, or lower alkylene attached to an arbitrary, bondable position of A;

T, U, V and W are independently nitrogen atom or optionally substituted methine, and at least two of T, U, V and W are said methine group;

X is $—N(SO_2R^1)—$, $—N(COR^2)—$ or $—CO—$;

Y is $—C(R^3)(R^4)—$, $—O—$ or $—N(R^5)—$;

Z is methine or nitrogen atom) exhibit NPY antagonistic activities and are useful as agents for the treatment of various diseases related to NPY, for example, cardiovascular disorders such as hypertension, nephropathy, heart disease, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, etc., metabolic diseases such as obesity, diabetes, hormone abnormality, hypercholesterolemia, hyperlipidemia, etc., sexual and reproductive dysfunctions, and gastro-intestinal motility disorder.

9 Claims, No Drawings

SPIRO COMPOUNDS

This application is a U.S. national stage of International Application No. PCT/JP02/07922 filed Aug. 2, 2002.

TECHNICAL FIELD

The present invention is useful in medical fields. In more detail, spiro compounds of the present invention have an effect as neuropeptide Y receptor antagonists and are useful as agents for the treatment of various kinds of cardiovascular disorders, central nervous system disorders, metabolic diseases, and the like.

BACKGROUND ART

Neuropeptide Y (hereinafter referred to as NPY), a peptide consisting of 36 amino acids, was first isolated from porcine brain by Tatemoto et al in 1982 (NATURE, vol. 296, p 659(1982)). NPY is widely distributed in central nervous system and peripheral nervous system, and plays various roles as one of the most abundant peptides in the nervous system. That is, npy acts as an orexigenic substance in the central nervous system and markedly promotes fat accumulation via the mediation of secretion of various hormones or the action of the nervous system. It is known that continuous intracerebroventricular administration of NPY induces obesity and insulin resistance due to these actions (INTERNATIONAL JOURNAL OF OBESITY, vol. 19, p. 517(1995); Endocrinology, vol. 133, p. 1753(1993)). It is also known that NPY has central actions such as depression, anxiety, schizophrenia, pain, dementia, circadian rhythm control and the like (DRUGS, vol. 52, p. 371(1996); THE JOURNAL OF NEUROSCIENCE, vol. 18, p. 3014(1998)). Furthermore, in the periphery, NPY coexists with norepinephrine in sympathetic-nerve terminals and is related to the tonicity of the sympathetic nervous system. It is known that peripheral administration of NPY causes vasoconstriction and enhances the activities of other vasoconstrictive substances such as norepinephrine (BRITISH JOURNAL OF PHARMACOLOGY, vol. 95, p. 419(1988)). It is also reported that NPY could participate in the development of cardiac hypertrophy as a result of the sympathetic stimulation (PROCEEDINGS OF THE NATIONAL ACADEMY OF SCIENCES OF THE UNITED STATES OF AMERICA, vol. 97, p. 1595(2000)).

On the other hand, it is reported that NPY is also involved in the secretory function of sexual hormones and growth hormone, sexual behavior and reproductive function, gastrointestinal motility, bronchoconstriction, inflammation and alcohol preference (LIFE SCIENCE, vol. 55, p. 551(1994); THE JOURNAL OF ALLERGY AND CLINICAL IMMUNOLOGY, vol. 101, p. S345(1998); NATURE, vol. 396, p. 366(1998)).

NPY has a variety of pharmacological effects resulting from NPY binding to some NPY receptors to which peptide YY and pancreatic polypeptide, which are the analogs of NPY, also bind. It is known that these pharmacological effects of NPY are mediated by the action of at least five receptors with or without synergistic interactions (TRENDS IN NEUROSCIENCES, vol. 20, p. 294(1997)).

It is reported that the central effects mediated by NPY Y1 receptor include remarkable orexigenic effect (ENDOCRINOLOGY, vol. 137, p. 3177(1996); ENDOCRINOLOGY, vol. 141, p. 1011(2000)). Further, NPY Y1 receptor is reported to be involved in anxiety and pain (NATURE, vol. 259, p. 528(1993); BRAIN RESEARCH, vol. 859, p. 361

(2000). In addition, the pressor effect mediated by the strong vasoconstrictor action in the periphery is also reported (FEBS LETTERS, vol. 362, p. 192(1995); NATURE MEDICINE, vol. 4, p. 722(1998)).

It is known that the effects mediated by NPY Y2 receptor include an inhibitory effect on the release of various neurotransmitters in the sympathetic nerve endings (BRITISH JOURNAL OF PHARMACOLOGY, vol. 102, p. 41(1991); SYNAPSE, vol. 2, p. 299(1988)). In periphery, NPY Y2 causes constriction of blood vessel or vas deferens directly or via the control of release of various neurotransmitters (THE JOURNAL OF PHARMACOLOGY AND EXPERIMENTAL THERAPEUTICS, vol. 261, p. 863(1992); BRITISH JOURNAL OF PHARMACOLOGY, vol. 100, p. 190 (1990)). Inhibition of lipolysis in adipose tissues is also known (ENDOCRINOLOGY, vol. 131, p. 1970(1992)). Further, inhibition of ion secretion in the gastro-intestinal tract is reported (BRITISH JOURNAL OF PHARMACOLOGY, vol. 101, p. 247(1990)). On the other hand, the effects on the central nervous system functions such as memory, anxiety and the like are also known (BRAIN RESEARCH, vol. 503, p. 73(1989); PEPTIDES, vol. 19, p. 359(1998)).

It is reported that NPY Y3 receptor exists mainly in brainstem and heart, and is related to the regulation of blood pressure and heart rate (THE JOURNAL OF PHARMACOLOGY AND EXPERIMENTAL THERAPEUTICS, vol. 258, p. 633(1991); PEPTIDES, vol. 11, p. 545(1990)). It is also known that NPY Y3 is involved in the control of catecholamine secretion in adrenal gland (THE JOURNAL OF PHARMACOLOGY AND EXPERIMENTAL THERAPEUTICS, vol. 244, p. 468(1988); LIFE SCIENCE, vol. 50, p. PL7(1992)).

NPY Y4 receptor has high affinity for pancreatic polypeptide in particular. As for the pharmacological effects of NPY Y4, inhibition of pancreatic exocrine secretion and gastrointestinal motility is reported (GASTROENTEROLOGY, vol. 85, p. 1411(1983)). Further, it is reported that NPY enhances the secretion of sexual hormones in the central nervous system (ENDOCRINOLOGY, vol. 140, p. 5171 (1999)).

As for the effects mediated by NPY Y5 receptor, fat accumulation effects including orexigenic effect are prominent (NATURE, vol. 382, p. 168(1996); AMERICAN JOURNAL OF PHYSIOLOGY, vol. 277, p. R1428(1999)). It is also reported that the NPY Y5 receptor mediates some CNS effects, such as seizure and epilepsy, or pain and morphine withdrawal symptoms, and the control of circadian rhythm (NATURE MEDICINE, vol. 3, p. 761(1997); PROCEEDINGS OF THE NATIONAL ACADEMY OF SCIENCES OF THE UNITED STATES OF AMERICA, vol. 96, p. 13518(1999); THE JOURNAL OF PHARMACOLOGY AND EXPERIMENTAL THERAPEUTICS, vol. 284, p. 633(1998); THE JOURNAL OF NEUROSCIENCE, vol. 21, p. 5367(2001). In addition, diuretic effect and hypoglicemic effect in the periphery are reported (BRITISH JOURNAL OF PHARMACOLOGY, vol. 120, p. 1335(1998); ENDOCRINOLOGY, vol. 139, p. 3018(1998)). NPY is also reported to enhance cardiac hypertrophy as a result of the sympathetic accentuation (PROCEEDINGS OF THE NATIONAL ACADEMY OF SCIENCES OF THE UNITED STATES OF AMERICA, vol. 97, p. 1595 (2000)).

The effects of NPY are expressed when NPY binds to the NPY receptors in the central or peripheral nervous system. Therefore, the action of NPY can be prevented by blocking its binding to NPY receptors. For this reason, it is expected that substances antagonize NPY binding to NPY receptors may be useful for the prophylaxis or treatment of various diseases related to NPY, for example, cardiovascular disorders such as hypertension, nephropathy, heart disease, vasospasm, etc., central nervous system disorders such as bulimia, depression, anxiety, seizure, epilepsy, dementia, pain, alcoholism, drug withdrawal, circadian rhythm disorders, schizophrenia, etc., metabolic diseases such as obesity, diabetes, hormone abnormality, etc., sexual and reproductive dysfunctions, gastro-intestinal motility disorders, respiratory disorders, inflammatory diseases or glaucoma, and the like. (TRENDS IN PHARMACOLOGICAL SCIENCES, vol. 15, p. 153(1994); LIFE SCIENCE, vol. 55, p. 551 (1994); DRUGS, vol. 52, p. 371(1996); THE JOURNAL OF ALLERGY AND CLINICAL IMMUNOLOGY, vol. 101, p. S345(1998); NATURE, vol. 396, p. 366(1998); THE JOURNAL OF PHARMACOLOGY AND EXPERIMENTAL THERAPEUTICS, vol. 284, p. 633(1998); TRENDS IN PHARMACOLOGICAL SCIENCES, vol. 20, p. 104(1999); PROCEEDINGS OF THE NATIONAL ACADEMY OF SCIENCES OF THE UNITED STATES OF AMERICA, vol. 97, p. 1595(2000); THE JOURNAL OF NEUROSCIENCE, vol. 21, p. 5367(2001); PHARMACOLOGY & THERAPEUTICS, vol. 65, p. 397(1995).

It was recently found that, as a result of the study by the present inventors, certain NPY receptor antagonists are useful for the prophylaxis or treatment of hypercholesterolemia, hyperlipidemia and arteriosclerosis (International application publication WO99/27965).

DISCLOSURE OF THE INVENTION

The object of the present invention is to provide novel medicines which have NPY antagonistic actions.

The present inventors have discovered that compounds of the formula (I):

(I)

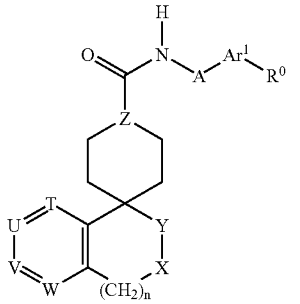

(wherein

A is a straight-chain hydrocarbon having 1 to 6 carbon atoms, which is optionally substituted by a substituent selected from the group consisting of oxo, amino, lower alkylamino, di-lower alkylamino, hydroxy, lower alkoxy, lower alkoxycarbonyl, lower alkylene, aryl, heteroaryl and —$R^a$, and is optionally intervened by oxygen or nitrogen atom;

$Ar^1$ is aryl or heteroaryl, any of which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl, lower alkoxycarbonyl and -Q-$Ar^2$;

$Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

n is 0 or 1;

Q is a single bond or carbonyl;

$R^a$ is lower alkyl which is optionally substituted by a substituent selected from the group consisting of amino, lower alkylamino, di-lower alkylamino and hydroxy, and cyclo-lower alkyl, aryl and heteroaryl, the last three groups being optionally substituted by fluorine;

$R^0$ is hydrogen, or lower alkylene attached to an arbitrary, bondable position of A;

$R^1$, $R^2$ and $R^5$ are independently hydrogen, lower alkyl, aralkyl or aryl;

$R^3$ and $R^4$ are independently hydrogen, hydroxy, lower alkyl, aralkyl or aryl;

T, U, V and W are independently methine or nitrogen atom, said methine being optionally substituted by a substituent-selected from the group consisting of halogen, lower alkyl, hydroxy and lower alkoxy, and at least two of T, U, V and W are said methine group;

X is —$N(SO_2R^1)$—, —$N(COR^2)$— or —CO—;

Y is —$C(R^3)(R^4)$—, —O— or —$N(R^5)$—;

Z is methine or nitrogen atom)

exhibit NPY antagonistic activities and are useful as agents for treatment of various kinds of diseases related to NPY, thereby completed the present invention.

The compounds of the present invention (I) are useful as agents for the treatment of various diseases related to NPY, that is, cardiovascular disorders such as hypertension, nephropathy, heart disease, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, etc., metabolic diseases such as obesity, diabetes, hormone abnormality, hypercholesterolemia, hyperlipidemia, etc., sexual and reproductive dysfunctions, gastro-intestinal disorders such as gastro-intestinal motility disorder, respiratory disorders, inflammatory diseases or glaucoma, and the like.

The compounds of the present invention (I) are particularly useful as agents for the treatment of bulimia, obesity, diabetes and the like.

The present invention relates to the compounds of the formula (I), or the salts or esters thereof, and the production methods and the use thereof.

The means of terms used in the present specification are defined, and more detailed description of this invention is described below.

"Halogen" refers to fluorine, chlorine, bromine and iodine.

"Lower alkyl" refers to a straight- or branched-chain alkyl group having 1 to 6 carbon atoms, and its examples are methyl, ethyl, propyl, isopropyl, butyl, isobutyl, sec-butyl, tert-butyl, pentyl, isopentyl, hexyl, isohexyl and the like.

"Halo-lower alkyl" refers to said lower alkyl substituted with identically or differently one, two or more, preferably one to three said halogen at the arbitrary, substitutable position(s), and its examples are fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl and the like.

"Hydroxy-lower alkyl" refers to said lower alkyl substituted with one, two or more, preferably one or two hydroxy at the arbitrary, substitutable position(s), and its examples are hydroxymethyl, 2-hydroxyethyl, 1-hydroxy-1-methylethyl, 1,2-dihydroxyethyl, 3-hydroxypropyl and the like.

"Cyclo-lower alkyl" refers to a cycloalkyl group having 3 to 6 carbon atoms, and its examples are cyclopropyl, cyclobutyl, cyclopentyl, cyclohexyl and the like.

"Lower alkenyl" refers to a straight- or branched-chain alkenyl group having 2 to 6 carbon atoms, and its examples are vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl and the like.

"Lower alkoxy" refers to a straight- or branched-chain alkoxy group having 1 to 6 carbon atoms, and its examples are methoxy, ethoxy, propoxy, isopropoxy, butoxy, sec-butoxy, isobutoxy, tert-butoxy, pentyloxy, isopentyloxy, hexyloxy, isohexyloxy, and the like.

"Halo-lower alkoxy" refers to said lower alkoxy substituted with identically or differently one, two or more, preferably one to three said halogen at the arbitrary, substitutable position(s), audits examples are fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy and the like.

"Lower alkylthio" refers to a straight-or branched-chain alkylthio group having 1 to 6 carbon atoms, and its examples are methylthio, ethylthio, propylthio, isopropylthio, butylthio, sec-butylthio, isobutylthio, tert-butylthio, pentylthio, isopentylthio, hexylthio, isohexylthio and the like.

"Lower alkanoyl" refers to an alkanoyl group containing said lower alkyl, that is, an alkanoyl group having 2 to 7 carbon atoms, and its examples are acetyl, propionyl, butyryl, isobutyryl, valeryl, isovaleryl, pivaloyl and the like.

"Lower alkoxycarbonyl" refers to an alkoxycarbonyl group containing said lower alkoxy, that is, an alkoxycarbonyl group having 2 to 7 carbon atoms, and its examples are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl and the like.

"Aryl" refers to phenyl, naphthyl and the like.

"Heteroaryl" refers to 5- or 6-membered monocyclic heteroaromatic group which contains one, two or more, preferably one to three hetero atom(s) identically or differently selected from the group consisting of oxygen, nitrogen and sulfur; or condensed cyclic heteroaromatic group, where said monocyclic heteroaromatic group is condensed with said aryl group or condensed each other with the same or different said monocyclic heteroaromatic group, and its examples are pyrrolyl, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthalazinyl, naphthylidinyl, quinoxalinyl, quinazolinyl, cinnolinyl, pteridinyl, pyrido[3,2-b]pyridyl and the like.

"A straight-chain hydrocarbon having 1 to 6 carbon atoms, which is optionally intervened by oxygen or nitrogen atom" refers to a saturated or unsaturated straight-chain hydrocarbon having 1 to 6 carbon atoms, which may or may not be intervened by one, two or more, preferably one oxygen or nitrogen atom(s), at the arbitrary position(s) capable of being intervened, and examples thereof are methylene, ethylene, trimethylene, tetramethylene, pentamethylene, 1-azatrimethylene, 1-azatetramethylene, 2-azatetramethylene, 2-oxatetramethylene, 2-oxapentamethylene, 3-oxapentamethylene and the like.

"Lower alkylamino" refers to an amino group mono-substituted with said lower alkyl, and its examples are methylamino, ethylamino, propylamino, isopropylamino, butylamino, sec-butylamino, tert-butylamino and the like.

"Di-lower alkylamino" refers to an amino group di-substituted with identical or different said lower alkyl, and its examples are dimethylamino, diethylamino, ethylmethylamino, dipropylamino, methylpropylamino, diisopropylamino and the like.

"Lower alkylene" refers to a straight- or branched-chain alkylene group having 1 to 6 carbon atoms, and its examples are methylene, ethylene, trimethylene, tetramethylene, pentamethylene, hexamethylene and the like.

"Aralkyl" refers to said lower alkyl substituted with one, two or more, preferably one or two aryl at the arbitrary, substitutable position(s), and its examples are benzyl, 2-phenylethyl, 3-phenylethyl, 1-phenylethyl and the like.

The salts of the compounds of the formula (I) refer to the pharmaceutically acceptable, common salts, and examples thereof are base addition salt to said carboxyl group when the compound has a carboxyl group, or acid addition salt to an amino or said basic heterocyclyl when the compound has a basic heterocyclyl group, and the like.

Said base addition salts include salts with alkali metals (e.g. sodium, potassium); salts with alkaline earth metals (e.g. calcium, magnesium); ammonium salts; salts with organic amines (e.g. trimethylamine, triethylamine, dicyclohexylamine, ethanolamine, diethanolamine, triethanolamine, procaine, N,N'-dibenzylethylenediamine) and the like.

Said acid addition salts include salts with inorganic acids (e.g. hydrochloric acid, sulfuric acid, nitric acid, phosphoric acid, perchloric acid), salts with organic acids (e.g. maleic acid, fumaric acid, tartaric acid, citric acid, ascorbic acid, trifluoroacetic acid), salts with sulfonic acids (e.g. methanesulfonic acid, isethionic acid, benzenesulfonic acid, p-toluenesulfonic acid) and the like.

The esters of the compounds of the formula (I) refer to, for example, the pharmaceutically acceptable, common esters of said carboxyl group when the compound has a carboxyl group, and examples thereof are esters with lower alkyl (e.g. methyl, ethyl, propyl, isopropyl, butyl, sec-butyl, tert-butyl, pentyl, isopentyl, neopentyl, cyclopropyl, cyclobutyl, cyclopentyl), esters with aralkyl (e.g. benzyl, phenethyl), esters with lower alkenyl (e.g. allyl, 2-butenyl), esters with lower-alkoxy-lower-alkyl (e.g. methoxymethyl, 2-methoxyethyl, 2-ethoxyethyl), esters with lower-alkanoyloxy-lower-alkyl (e.g. acetoxymethyl, pivaloyloxymethyl, 1-pivaloyloxyethyl), esters with lower-alkoxycarbonyl-lower-alkyl (e.g. methoxycarbonylmethyl, isopropoxycarbonylmethyl), esters with carboxy-lower alkyl (e.g. carboxymethyl), esters with lower-alkoxycarbonyloxy-lower-alkyl (e.g. 1-(ethoxycarbonyloxy)ethyl, 1-(cyclohexyloxycarbonyloxy)ethyl), esters with carbamoyloxy-lower alkyl (e.g. carbamoyloxymethyl), esters with phthalidyl, esters with (5-substituted-2-oxo-1,3-dioxol-4-yl)methyl (e.g. (5-methyl-2-oxo-1,3-dioxol-4-yl)methyl) and the like.

"An agent for treatment" refers to a medicament which is employed for the treatment and/or prophylaxis of various diseases.

In order to disclose the aforesaid compounds of the formula (I) of the present invention more specifically, the various symbols used in the formula (I) are explained in more detail by presenting preferred embodiments.

A refers to a straight-chain hydrocarbon having 1 to 6 carbon atoms, which is optionally substituted by a substituent selected from the group consisting of oxo, amino, lower alkylamino, di-lower alkylamino, hydroxy, lower alkoxy, lower alkoxycarbonyl, lower alkylene, aryl, heteroaryl and —$R^a$, and is optionally intervened by oxygen or nitrogen atom.

"A straight-chain hydrocarbon having 1 to 6 carbon atoms, which is optionally substituted by a substituent selected from the group consisting of oxo, amino, lower alkylamino, di-lower alkylamino, hydroxy, lower alkoxy, lower alkoxycarbonyl, lower alkylene, aryl, heteroaryl and —$R^a$, and is optionally intervened by oxygen or nitrogen atom" refers to unsubstituted said straight-chain hydrocarbon having 1 to 6 carbon atoms, which is optionally intervened by oxygen or nitrogen atom; or said straight-chain hydrocarbon having 1 to 6 carbon atoms, which has substituent(s) at the arbitrary, substitutable position(s), and is optionally intervened by oxygen or nitrogen atom, wherein said substituent may be one, two or more member(s), preferably one member identically or differently selected from the group consisting of oxo, amino, lower alkylamino, di-lower alkylamino, hydroxy, lower alkoxy, lower alkoxycarbonyl, lower alkylene, aryl, heteroaryl and —$R^a$.

The preferable examples of lower alkylamino as said substituent include methylamino, ethylamino, propylamino and the like.

The preferable examples of di-lower alkylamino as said substituent include dimethylamino, diethylamino and the like.

The preferable examples of lower alkoxy as said substituent include methoxy, ethoxy, propoxy and the like.

The preferable examples of lower alkoxycarbonyl as said substituent include methoxycarbonyl, ethoxycarbonyl and the like.

The preferable examples of lower alkylene as said substituent include methylene, ethylene, trimethylene and the like.

The preferable examples of aryl as said substituent include phenyl, naphthyl and the like.

The preferable examples of heteroaryl as said substituent include pyridyl, quinolyl, indolyl and the like.

A group represented by the formula: —$R^a$ as said substituent refers to lower alkyl which is optionally substituted by a substituent selected from the group consisting of amino, lower alkylamino, di-lower alkylamino and hydroxy, and cyclo-lower alkyl, aryl and heteroaryl, the last three groups being optionally substituted by fluorine.

"Lower alkyl which is optionally substituted by a substituent selected from the group consisting of amino, lower alkylamino, di-lower alkylamino and hydroxy, and cyclo-lower alkyl, aryl and heteroaryl, the last three groups being optionally substituted by fluorine" refers to unsubstituted said lower alkyl, or said lower alkyl having substituent(s) at the arbitrary, substitutable position(s), wherein said substituent may be one, two or more, preferably one member(s) identically or differently selected from the group consisting of amino, lower alkylamino, di-lower alkylamino and hydroxy, and cyclo-lower alkyl, aryl and heteroaryl, the last three groups being optionally substituted by fluorine.

The preferable examples of lower alkylamino as said substituent include methylamino, ethylamino, propylamino and the like.

The preferable examples of di-lower alkylamino as said substituent include dimethylamino, diethylamino and the like.

The preferable examples of cyclo-lower alkyl being optionally substituted by fluorine as said substituent include cyclopentyl, cyclohexyl and the like.

The preferable examples of aryl being optionally substituted by fluorine as said substituent include phenyl, 4-fluorophenyl, naphthyl and the like.

The preferable examples of heteroaryl being optionally substituted by fluorine as said substituent include pyridyl, quinolyl, indolyl and the like.

The preferable examples of lower alkyl of "lower alkyl which is optionally substituted" as $R^a$ include methyl, ethyl, propyl and the like.

The preferable examples of $R^a$ include hydroxymethyl, cyclohexylmethyl, benzyl, 4-fluorobenzyl, 3-pyridylmethyl, 4-pyridylmethyl, 3-indolylmethyl and the like.

The preferable examples of substituent of A include oxo, hydroxy, lower alkoxycarbonyl, lower alkylene, aryl, —$R^a$ and the like.

To be more specific, A includes, for example, a group of the formula (A-1) and (A-2):

(A-1)

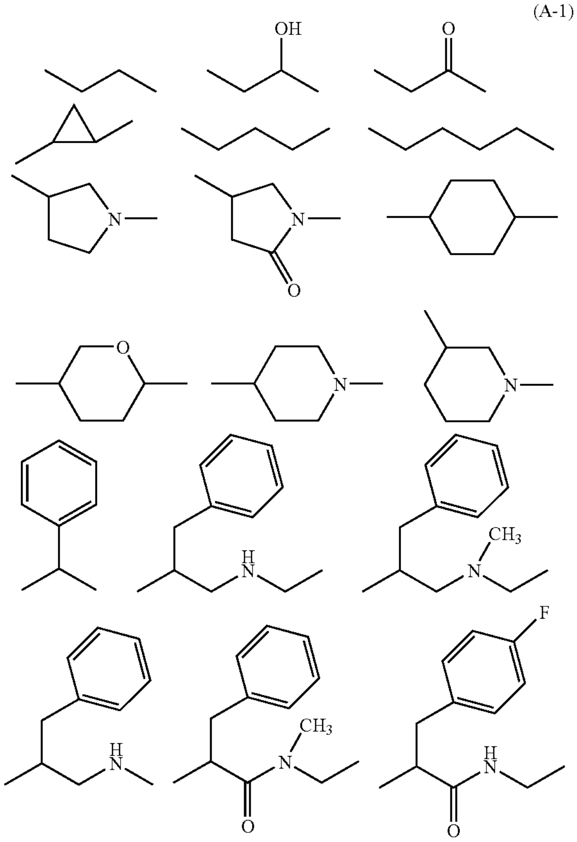

(A-2)

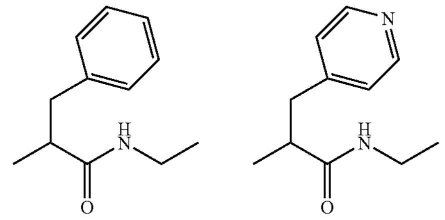

-continued

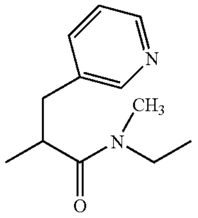
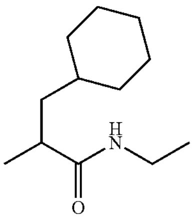
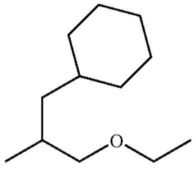
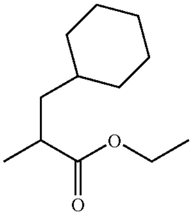
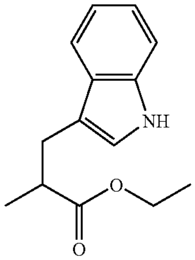
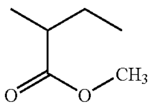
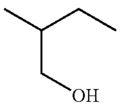
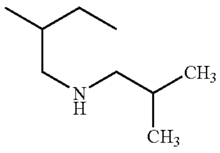

and the like.

$Ar^1$ is aryl or heteroaryl, any of which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl, lower alkoxycarbonyl and -Q-$Ar^2$.

"Aryl or heteroaryl, any of which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl, lower alkoxycarbonyl and -Q-$Ar^2$" refers to unsubstituted said aryl or said heteroaryl, or said aryl or said heteroaryl, the last two groups having substituent(s) at the arbitrary, substitutable position(s) wherein said substituent may be one, two or more, preferably one or two member(s) identically or differently selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl, lower alkoxycarbonyl and -Q-$Ar^2$.

The preferable examples of halogen as said substituent include fluorine, chlorine and the like.

The preferable examples of lower alkyl as said substituent include methyl, ethyl, propyl, isopropyl and the like.

The preferable examples of halo-lower alkyl as said substituent include difluoromethyl, trifluoromethyl and the like.

The preferable examples of hydroxy-lower alkyl as said substituent include hydroxymethyl, 2-hydroxyethyl, 1-hydroxy-methylethyl and the like.

The preferable examples of cyclo-lower alkyl as said substituent include cyclopropyl, cyclobutyl and the like.

The preferable examples of lower alkenyl as said substituent include vinyl, 1-propenyl, 2-methyl-1-propenyl and the like.

The preferable examples of lower alkoxy as said substituent include methoxy, ethoxy and the like The preferable examples of halo-lower alkoxy as said substituent include fluoromethoxy, difluoromethoxy, trifluoromethoxy and the like.

The preferable examples of lower alkylamino as said substituent include methylamino, ethylamino, propylamino and the like.

The preferable examples of di-lower alkylamino as said substituent include dimethylamino, diethylamino and the like.

The preferable examples of lower alkylthio as said substituent include methylthio, ethylthio and the like.

The preferable examples of lower alkanoyl as said substituent include acethyl, propionyl and the like.

The preferable examples of lower alkoxycarbonyl as said substituent include methoxycarbonyl, ethoxycarbonyl and the like.

In a group represented by the formula: -Q-$Ar^2$ as said substituent, $Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl; Q is a single bond or carbonyl.

"Aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl" refers to unsubstituted said aryl or said heteroaryl, or said aryl or said heteroaryl, the last two groups having substituent(s) at the arbitrary, substitutable position(s) wherein said substituent may be one, two or more, preferably one or two member(s) identically or differently selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl.

The preferable examples of halogen as said substituent include fluorine, chlorine and the like.

The preferable examples of lower alkyl as said substituent include methyl, ethyl, propyl, isopropyl and the like.

The preferable examples of halo-lower alkyl as said substituent include difluoromethyl, trifluoromethyl and the like.

The preferable examples of hydroxy-lower alkyl as said substituent include hydroxymethyl, 2-hydroxyethyl, 1-hydroxy-1-methylethyl and the like.

The preferable examples of lower alkoxy as said substituent include methoxy, ethoxy and the like.

The preferable examples of halo-lower alkoxy as said substituent include fluoromethoxy, difluoromethoxy, trifluoromethoxy and the like.

The preferable examples of lower alkylamino as said substituent include methylamino, ethylamino and the like.

The preferable examples of di-lower alkylamino as said substituent include dimethylamino, diethylamino and the like.

The preferable examples of lower alkanoyl as said substituent include acetyl, propionyl and the like.

The preferable examples of aryl as said substituent include phenyl and the like.

The preferable examples of the substituent of $Ar^2$ include halogen, cyano, lower alkyl, halo-lower alkyl, hydroxy-lower alkyl, hydroxy, halo-lower alkoxy and the like.

The preferable examples of aryl as $Ar^2$ include phenyl and the like, and preferred examples of heteroaryl as $Ar^2$ include imidazolyl, pyridyl, benzofuranyl, quinolyl and the like.

Thus, the preferable examples of a group represented by the formula: -Q-$Ar^2$ include phenyl, 2-fluorophenyl, 3-fluorophenyl, 4-fluorophenyl, 2,3-difluorophenyl, 2,4-difluorophenyl, 3,5-difluorophenyl, 2-chlorophenyl, 3-chlorophenyl, 4-chlorophenyl, 2-cyanophenyl, 3-cyanophenyl, 4-cyanophenyl, 2-methylphenyl, 3-methylphenyl, 4-methylphenyl, 2-fluoro-5-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 3-fluoro-5-methoxyphenyl, 3-fluoromethoxyphenyl, 3-difluoromethoxyphenyl, 3-(2-hydroxyethyl)phenyl, 3-hydroxymethylphenyl, 3-(1-hydroxy-1-methylethyl)phenyl, 3-hydroxyphenyl, 4-hydroxyphenyl, 2-imidazolyl, 1-ethyl-2-imidazolyl, 1,2,4-thiadiazol-5-yl, 1,3,4-thiadiazol-2-yl, 2-pyridyl, 3-pyridyl, 4-pyridyl, 2-ethyl-4-pyridyl, 4-pyrimidinyl, 5-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 8-quinolyl, benzoyl, 2-pyridylcarbonyl and the like, among which the more preferable examples are phenyl, 2-fluorophenyl, 3-fluorophenyl, 3,5-difluorophenyl, 3-chlorophenyl, 4-chlorophenyl, 3-cyanophenyl, 3-trifluoromethylphenyl, 3-difluoromethoxyphenyl, 3-(2-hydroxyethyl)phenyl, 3-hydroxyphenyl, 4-hydroxyphenyl, 1-ethyl-2-imidazolyl, 2-pyridyl, 7-benzo[b]furanyl, 2-quinolyl, 3-quinolyl, benzoyl, 2-pyridylcarbonyl and the like.

The preferable examples of the substituent of $Ar^1$ include halogen, lower alkyl, halo-lower alkyl, lower alkenyl, lower alkoxy, di-lower alkylamino, lower alkanoyl, -Q-$Ar^2$ and the like, more preferably, halogen, halo-lower alkyl, lower alkoxy, di-lower alkylamino and the like.

The preferable examples of aryl as $Ar^1$ preferably include phenyl and the like, and the preferable examples of heteroaryl as $Ar^1$ preferably include imidazolyl, pyrazolyl, thiazolyl, oxazolyl, isoxazolyl, 1,2,4-thiadiazolyl, pyridyl, pyrazinyl, pyrimidinyl, 1,2,4-triazinyl, benzoxazolyl, benzothiazolyl, quinolyl, pyrido[3,2-b]pyridyl and the like, more preferably, pyridyl and the like.

$R^0$ refers to hydrogen, or lower alkylene attached to an arbitrary, bondable position of A.

The preferable examples of lower alkylene as $R^0$ include methylene, ethylene, trimethylene, tetramethylene and the like.

Thus, a group represented by the formula: -A-$Ar^1$—$R^0$ includes, for example, 1-phenyl-3-pyrrolidinyl, 1-(2-fluorophenyl)-3-pyrrolidinyl, 1-(3-fluorophenyl)-3-pyrrolidinyl, 1-(4-fluorophenyl)-3-pyrrolidinyl, 1-(2-pyridyl)-3-pyrrolidinyl, 1-(3-pyridyl)-3-pyrrolidinyl, 1-(4-pyridyl)-3-pyrrolidinyl, 1-(3,5-difluorophenyl)-3-pyrrolidinyl, 1-(3-trifluoromethylphenyl)-3-pyrrolidinyl, 1-(2-pyrimidinyl)-3-pyrrolidinyl, 5-oxo-1-phenyl-3-pyrrolidinyl, 1-phenyl-4-piperidyl, 1-(2-fluorophenyl)-4-piperidyl, 1-(3-fluorophenyl)-4-piperidyl, 1-(4-fluorophenyl)-4-piperidyl, 1-(3,5-difluorophenyl)-4-piperidyl, 1-(2-pyridyl)-4-piperidyl, 1-(3-pyridyl)-4-piperidyl, 1-(4-pyridyl)-4-piperidyl, 3-hydroxymethyl-1-phenyl-4-piperidyl, 3-methoxycarbonyl-1-phenyl-4-piperidyl, 3-ethoxycarbonyl-1-phenyl-4-piperidyl, 3-isopropoxycarbonyl-1-phenyl-4-piperidyl, 1-phenyl-3-piperidyl, 1-(2-fluorophenyl)-3-piperidyl, 1-(3-fluorophenyl)-3-piperidyl, 1-(4-fluorophenyl)-3-piperidyl, 1-(3,5-difluorophenyl)-3-piperidyl, 1-(2-pyridyl)-3-piperidyl, 1-(3-pyridyl)-3-piperidyl, 1-(4-pyridyl)-3-piperidyl, 3-phenylcyclopentyl, 3-phenylcyclohexyl, 4-phenylcyclohexyl, 4-(2-fluorophenyl)cyclohexyl, 4-(3-fluorophenyl)cyclohexyl, 4-(4-fluorophenyl)cyclohexyl, 4-(2-pyridyl)cyclohexyl, 4-(3-pyridyl)cyclohexyl, 4-(4-pyridyl)cyclohexyl, 4-(4-fluoro-3-pyridyl)cyclohexyl, 4-(3-quinolyl)cyclohexyl, 4-(3-fluorophenyl)-4-hydroxycyclohexyl, 6-phenyl-3-tetrahydropyranyl, 6-(3-fluorophenyl)-3-tetrahydropyranyl, 2-phenylcyclopropyl, 2-(2-pyridyl)cyclopropyl, 2-(3-pyridyl)cyclopropyl, 2-(4-pyridyl)cyclopropyl, 2-indanyl, 2-tetrahydronaphthyl, 6-methoxy-2-tetrahydronaphthyl, benzyl, phenethyl, 3-phenylpropyl, 4-phenylbutyl, 4-bromophenethyl, 3-methoxyphenethyl, 2-propyloxyphenethyl, 4-dimethylaminophenethyl, 3,5-difluorophenethyl, 3,4-dimethoxyphenethyl, 4-(dimethylamino)-2-methoxyphenethyl, 2-(3-quinolyl)ethyl, 2-hydroxy-2-(3-quinolyl)ethyl, 2-hydroxy-2-phenylethyl, benzoylmethyl, 2-hydroxy-2-(4-dimethylaminophenyl)ethyl, 2-hydroxy-2-(3,5-difluorophenyl)ethyl, 1-(hydroxymethyl)-2-phenylethyl, 1-(methoxycarbonyl)-2-phenylethyl, 1-(aminomethyl)-2-phenylethyl, 1-(isobutylaminomethyl)-2-phenylethyl, 1-benzyl-2-(benzylamino)ethyl, 1-benzyl-2-anilinoethyl, 1-benzyl-2-(2-pyridylmethylamino)ethyl, 1-benzyl-2-(3-pyridylmethylamino)ethyl, 1-benzyl-2-(N-benzyl-N-methylamino)ethyl, 1-benzyl-2-(benzyloxy)ethyl, 1-(cyclohexylmethyl)-2-(benzyloxy)ethyl, 1-benzyloxycarbonyl-2-cyclohexylethyl, 1-(benzyloxycarbonyl)-2-(3-indolyl)ethyl, 1-(benzylcarbamoyl)-2-phenylethyl, 1-(benzylcarbamoyl)-2-cyclohexylethyl, 1-(benzylcarbamoyl)-2-(4-pyridyl)ethyl, 1-(4-pyridylmethylcarbamoyl)-2-(4-fluorophenyl)ethyl, 1-(N-methylbenzylcarbamoyl)-2-phenylethyl, 1-(N-methylbenzylcarbamoyl)-2-(3-pyridyl)ethyl and the like, among which the more preferable examples are 1-phenyl-3-pyrrolidinyl, 1-(2-fluorophenyl)-3-pyrrolidinyl, 1-(3-fluorophenyl)-3-pyrrolidinyl, 1-(4-fluorophenyl)-3-pyrrolidinyl, 1-phenyl-4-piperidyl, 1-(2-fluorophenyl)-4-piperidyl, 1-(3-fluorophenyl)-4-piperidyl, 1-(3,5-difluorophenyl)-4-piperidyl, 4-phenylcyclohexyl, 4-(2-fluorophenyl)cyclohexyl, 4-(3-fluorophenyl)cyclohexyl, 4-dimethylaminophenethyl, 1-benzyl-2-(benzylamino)ethyl, 1-benzyl-2-(2-pyridylmethylamino)ethyl, 1-benzyl-2-(3-pyridylmethylamino)ethyl, 1-benzyl-2-(benzyloxy)ethyl, 1-(benzylcarbamoyl)-2-phenylethyl, 1-(benzylcarbamoyl)-2-(4-pyridyl)ethyl and the like.

n is 0 or 1, preferably 0.

T, U, V and W are independently methine or nitrogen atom, said methane being optionally substituted by a substituent selected from the group consisting of halogen, lower alkyl, hydroxy and lower alkoxy, and at least two of T, U, V and W are said methine group;

"Methine being optionally substituted by a substituent selected from the group consisting of halogen, lower alkyl, hydroxy and lower alkoxy" refers to unsubstituted methine or methine having a substituent selected from the group consisting of halogen, lower alkyl, hydroxy and lower alkoxy.

The preferable examples of halogen as said substituent include fluorine, chlorine and the like.

The preferable examples of lower alkyl as said substituent include methyl, ethyl and the like.

The preferable examples of lower alkoxy as said substituent include methoxy, ethoxy and the like.

The preferable examples of the said substituent include halogen atom and the like.

The preferred embodiments of T, U, V and W include the case where T, U, V and W are independently methine optionally having said substituent, preferably halogen; or the case where one of T, U, V and W is nitrogen atom; and the like.

X is $—N(SO_2R^1)—$, $—N(COR^2)—$ or —CO—;

Y is $—C(R^3)(R^4)—$, —O— or $—N(R^5)—$;

$R^1$, $R^2$ and $R^5$ are independently hydrogen, lower alkyl, aralkyl or aryl;

$R^3$ and $R^4$ are independently hydrogen, hydroxy, lower alkyl, aralkyl or aryl.

The preferable examples of lower alkyl as $R^1$, $R^2$, $R^3$, $R^4$ or $R^5$ include each independently methyl, ethyl, propyl and the like.

The preferable examples of aralkyl as $R^1$, $R^2$, $R^3$, $R^4$ or $R^5$ include each independently benzyl and the like.

The preferable examples of aryl as $R^1$, $R^2$, $R^3$, $R^4$ or $R^5$ include each independently phenyl and the like.

The preferable examples of $R^1$ and $R^2$ include lower alkyl and the like.

The preferred embodiments of $R^3$ and $R^4$ are the case where both $R^3$ and $R^4$ are hydrogen, and the like.

The preferable examples of $R^5$ include hydrogen, lower alkyl and the like, more preferably hydrogen and the like.

The preferred embodiment of X, Y and n includes, for example, the case where X is $—N(SO_2R^1)—$ or $—N(COR^2)—$, preferably $—N(SO_2R^1)—$, n is 0, and Y is $—C(R^3)(R^4)—$; or the case where X is —CO—, and Y is —O— or $—N(R^5)—$, more preferably —O—, and among which the case where X is —CO— and Y is —O— or —NH—; and the case where X is —CO— and Y is —O— are more preferable.

Z is methine or nitrogen atom, preferably methine.

In more detail, the preferable examples of a group of the formula (VII):

(VII)

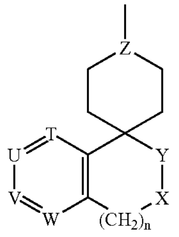

include a group represented by the following formulas (VIII):

(VIII)

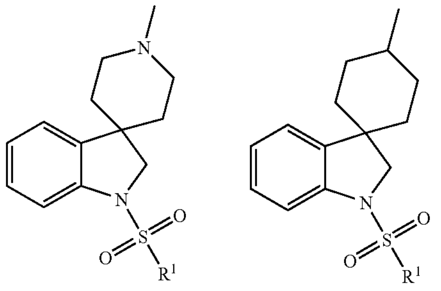

-continued

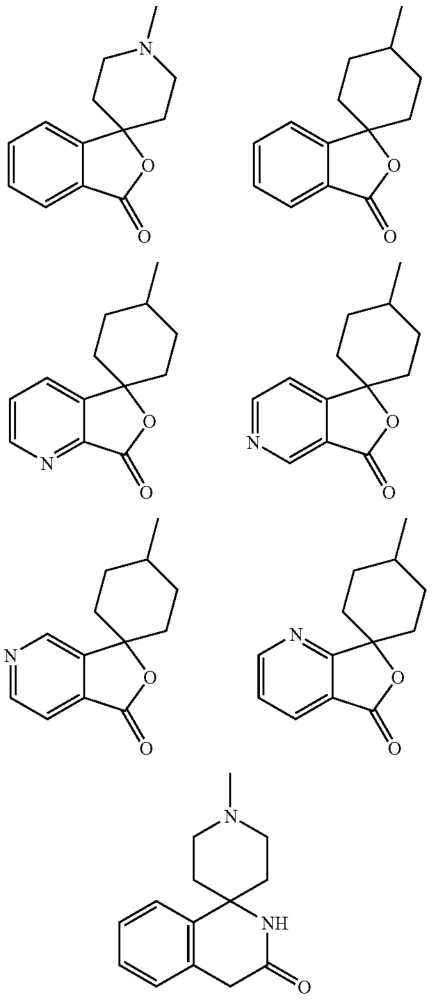

(wherein $R^1$ has the same meaning as defined above) and the like.

Preferred compounds of the formula (I) are, for example, compounds of the formula (I-a):

(I-a)

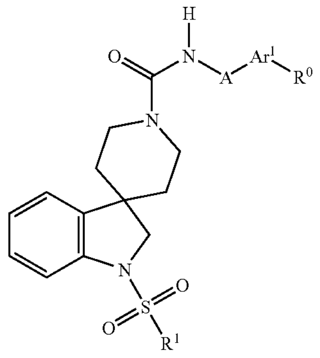

wherein A, $Ar^1$, $R^0$ and $R^1$ have the same meaning as defined above, compounds of the formula (I-b):

(I-b)

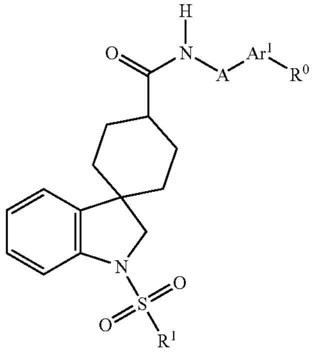

wherein A, $Ar^1$, $R^0$ and $R^1$ have the same meaning as defined above, compounds of the formula (I-c):

(I-c)

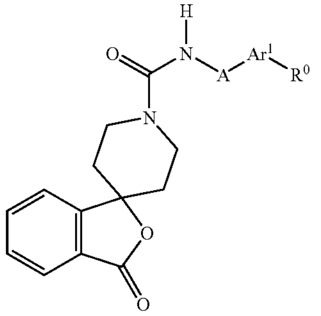

wherein A, $Ar^1$ and $R^0$ have the same meaning as defined above, compounds of the formula (I-d):

(I-d)

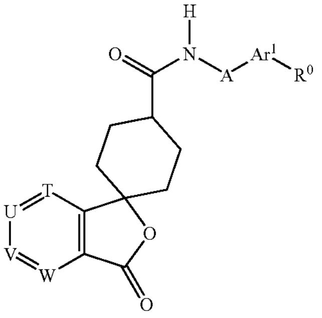

wherein A, $Ar^1$, $R^0$, T, U, V and W have the same meaning as defined above, and compounds of the formula (I-e):

(I-e)

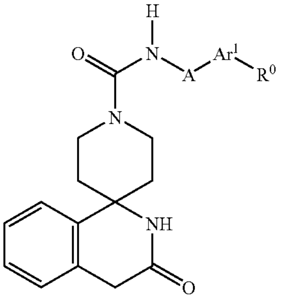

wherein A, $Ar^1$ and $R^0$ have the same meaning as defined above.

Preferred compounds of the formula (I-d) are, for example, compounds wherein all of T, U, V and W are unsubstituted methine, or compounds wherein one of T, U, V and W is nitrogen atom.

Preferred compounds of the formula (I), (I-a), (I-b), (I-c), (I-d) or (I-e) are, for example, compounds wherein aryl as $Ar^1$ is phenyl, or compounds wherein $Ar^1$ is heteroaryl which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl, lower alkoxycarbonyl and -Q-$Ar^2$.

The compounds of the present invention may include stereoisomers such as optical isomers, diastereoisomers and geometrical isomers, or tautomers depending upon the mode of substituents. The compounds of the present invention include all the stereoisomers, tautomers and their mixtures.

For example, compounds of the formula (I-b) include stereoisomers such as trans-form compound of the formula (I-1b):

(I-1b)

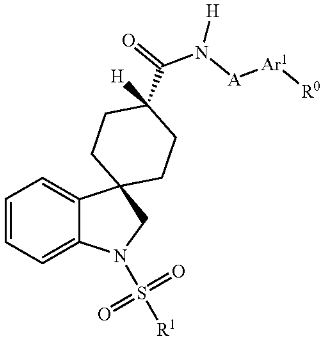

and cis-form compound of the formula (I-2b):

(I-2b)

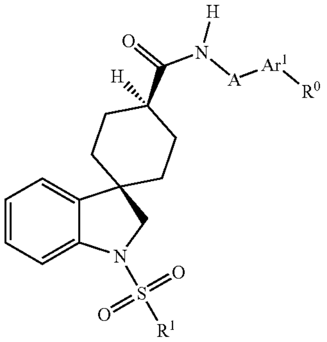

among which trans-form compound is preferred.

Also, compounds of the formula (I-d) include stereoisomers such as trans-form compound of the formula (I-1d):

(I-1d)

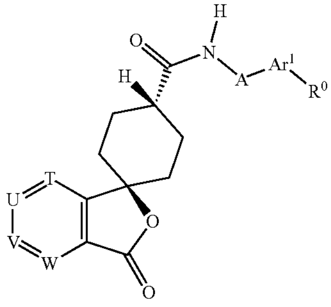

and cis-form compound of the formula (I-2d):

(I-2d)

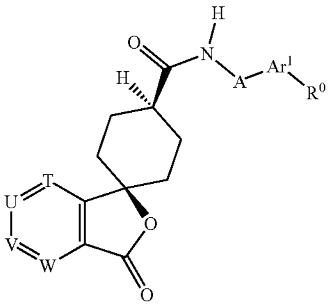

among which trans-form compound is preferred.

Also included within the scope of the invention are polymorphs, hydrates and solvates of the compounds of the present invention.

The present invention also includes prodrugs of the compounds of the present invention within its scope. In general, such prodrugs are functional derivatives of the compounds of the present invention which can be readily converted in vivo into the required compound. Thus, in the treatment methods for various diseases according to the present invention, the term "administering" shall encompass not only administration of the compound specified in this disclosure but also administration of a compound which is converted in vivo into the specified compound when it is administered to a patient. Conventional procedures for selection and preparation of suitable prodrug derivatives are described, for example, in "Design of Prodrugs," ed. H. Bundgaard, Elsevier (1985), which are referred and entirely incorporated in this specification. The metabolites of these compounds include active compounds which are produced upon introduction of compounds of the present invention into the biological milieu, and they are encompassed in the scope of the present invention.

The specific compounds of the formula (I) are, for example, following compounds.

In the tables, Me refers to methyl group, and Et refers to ethyl group.

TABLE 1

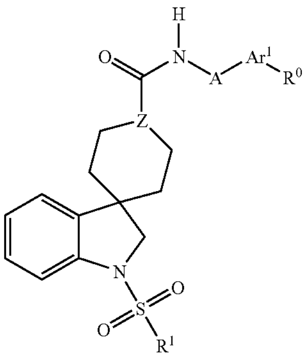

| No. | $R^1$ | Z | A—$Ar^1$—$R^0$ |
|---|---|---|---|
| 1 | Me | CH | 1-phenyl-3-pyrrolidinyl |
| 2 | Me | CH | 1-(2-fluorophenyl)-3-pyrrolidinyl |
| 3 | Me | CH | 1-(3-fluorophenyl)-3-pyrrolidinyl |
| 4 | Me | CH | 1-(4-fluorophenyl)-3-pyrrolidinyl |
| 5 | Me | CH | 1-(2-chlorophenyl)-3-pyrrolidinyl |

TABLE 1-continued

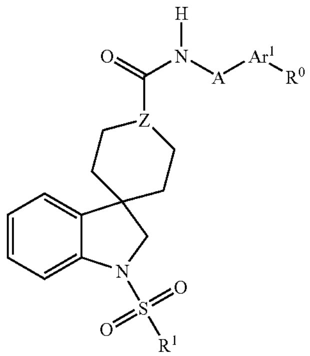

| No. | $R^1$ | Z | A—$Ar^1$—$R^0$ |
|---|---|---|---|
| 6 | Me | CH | 1-(3-chlorophenyl)-3-pyrrolidinyl |
| 7 | Me | CH | 1-(4-chlorophenyl)-3-pyrrolidinyl |
| 8 | Me | CH | 1-(2-methylphenyl)-3-pyrrolidinyl |
| 9 | Me | CH | 1-(3-methylphenyl)-3-pyrrolidinyl |
| 10 | Me | CH | 1-(4-methylphenyl)-3-pyrrolidinyl |
| 11 | Me | CH | 1-(2-methoxyphenyl)-3-pyrrolidinyl |
| 12 | Me | CH | 1-(3-methoxyphenyl)-3-pyrrolidinyl |
| 13 | Me | CH | 1-(4-methoxyphenyl)-3-pyrrolidinyl |
| 14 | Me | CH | 1-(2-trifluoromethylphenyl)-3-pyrrolidinyl |
| 15 | Me | CH | 1-(3-trifluoromethylphenyl)-3-pyrrolidinyl |
| 16 | Me | CH | 1-(4-trifluoromethylphenyl)-3-pyrrolidinyl |
| 17 | Me | CH | 1-(3,5-difluorophenyl)-3-pyrrolidinyl |
| 18 | Me | CH | 1-(2-difluoromethoxyphenyl)-3-pyrrolidinyl |
| 19 | Me | CH | 1-(3-difluoromethoxyphenyl)-3-pyrrolidinyl |
| 20 | Me | CH | 1-(4-difluoromethoxyphenyl)-3-pyrrolidinyl |
| 21 | Me | CH | 1-(2-pyridyl)-3-pyrrolidinyl |
| 22 | Me | CH | 1-(3-pyridyl)-3-pyrrolidinyl |
| 23 | Me | CH | 1-(4-pyridyl)-3-pyrrolidinyl |
| 24 | Me | CH | 1-(2-pyrimidinyl)-3-pyrrolidinyl |
| 25 | Me | CH | 5-oxo-1-phenyl-3-pyrrolidinyl |
| 26 | Me | CH | 1-phenyl-3-piperidyl |
| 27 | Me | CH | 1-(2-fluorophenyl)-3-piperidyl |
| 28 | Me | CH | 1-(3-fluorophenyl)-3-piperidyl |
| 29 | Me | CH | 1-(4-fluorophenyl)-3-piperidyl |
| 30 | Me | CH | 1-(2-chlorophenyl)-3-piperidyl |
| 31 | Me | CH | 1-(3-chlorophenyl)-3-piperidyl |
| 32 | Me | CH | 1-(4-chlorophenyl)-3-piperidyl |
| 33 | Me | CH | 1-(2-methylphenyl)-3-piperidyl |
| 34 | Me | CH | 1-(3-methylphenyl)-3-piperidyl |
| 35 | Me | CH | 1-(4-methylphenyl)-3-piperidyl |
| 36 | Me | CH | 1-(2-methoxyphenyl)-3-piperidyl |
| 37 | Me | CH | 1-(3-methoxyphenyl)-3-piperidyl |
| 38 | Me | CH | 1-(4-methoxyphenyl)-3-piperidyl |
| 39 | Me | CH | 1-(2-trifluoromethylphenyl)-3-piperidyl |
| 40 | Me | CH | 1-(3-trifluoromethylphenyl)-3-piperidyl |
| 41 | Me | CH | 1-(4-trifluoromethylphenyl)-3-piperidyl |
| 42 | Me | CH | 1-(3,5-difluorophenyl)-3-piperidyl |
| 43 | Me | CH | 1-(2-difluoromethoxyphenyl)-3-piperidyl |
| 44 | Me | CH | 1-(3-difluoromethoxyphenyl)-3-piperidyl |
| 45 | Me | CH | 1-(4-difluoromethoxyphenyl)-3-piperidyl |
| 46 | Me | CH | 1-(2-pyridyl)-3-piperidyl |
| 47 | Me | CH | 1-(3-pyridyl)-3-piperidyl |
| 48 | Me | CH | 1-(4-pyridyl)-3-piperidyl |
| 49 | Me | CH | 1-phenyl-4-piperidyl |
| 50 | Me | CH | 1-(2-fluorophenyl)-4-piperidyl |
| 51 | Me | CH | 1-(3-fluorophenyl)-4-piperidyl |
| 52 | Me | CH | 1-(4-fluorophenyl)-4-piperidyl |
| 53 | Me | CH | 1-(2-chlorophenyl)-4-piperidyl |
| 54 | Me | CH | 1-(3-chlorophenyl)-4-piperidyl |
| 55 | Me | CH | 1-(4-chlorophenyl)-4-piperidyl |
| 56 | Me | CH | 1-(2-methylphenyl)-4-piperidyl |
| 57 | Me | CH | 1-(3-methylphenyl)-4-piperidyl |
| 58 | Me | CH | 1-(4-methylphenyl)-4-piperidyl |
| 59 | Me | CH | 1-(2-methoxyphenyl)-4-piperidyl |
| 60 | Me | CH | 1-(3-methoxyphenyl)-4-piperidyl |
| 61 | Me | CH | 1-(4-methoxyphenyl)-4-piperidyl |
| 62 | Me | CH | 1-(2-trifluoromethylphenyl)-4-piperidyl |
| 63 | Me | CH | 1-(3-trifluoromethylphenyl)-4-piperidyl |
| 64 | Me | CH | 1-(4-trifluoromethylphenyl)-4-piperidyl |

TABLE 1-continued

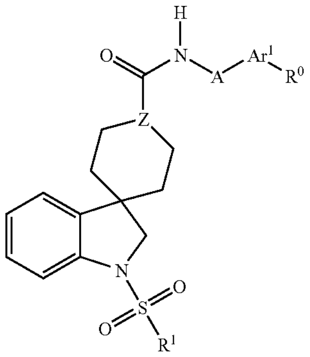

| No. | R$^1$ | Z | A—Ar$^1$—R$^0$ |
|---|---|---|---|
| 65 | Me | CH | 1-(3,5-difluorophenyl)-4-piperidyl |
| 66 | Me | CH | 1-(2-difluoromethoxyphenyl)-4-piperidyl |
| 67 | Me | CH | 1-(3-difluoromethoxyphenyl)-4-piperidyl |
| 68 | Me | CH | 1-(4-difluoromethoxyphenyl)-4-piperidyl |
| 69 | Me | CH | 1-(2-pyridyl)-4-piperidyl |
| 70 | Me | CH | 1-(3-pyridyl)-4-piperidyl |
| 71 | Me | CH | 1-(4-pyridyl)-4-piperidyl |
| 72 | Me | CH | 3-hydroxymethyl-1-phenyl-4-piperidyl |
| 73 | Me | CH | 3-methoxycarbonyl-1-phenyl-4-piperidyl |
| 74 | Me | CH | 3-ethoxycarbonyl-1-phenyl-4-piperidyl |
| 75 | Me | CH | 3-isopropoxycarbonyl-1-phenyl-4-piperidyl |
| 76 | Me | CH | 4-phenylcyclohexyl |
| 77 | Me | CH | 4-(2-fluorophenyl)cyclohexyl |
| 78 | Me | CH | 4-(3-fluorophenyl)cyclohexyl |
| 79 | Me | CH | 4-(4-fluorophenyl)cyclohexyl |
| 80 | Me | CH | 4-(2-chlorophenyl)cyclohexyl |
| 81 | Me | CH | 4-(3-chlorophenyl)cyclohexyl |
| 82 | Me | CH | 4-(4-chlorophenyl)cyclohexyl |
| 83 | Me | CH | 4-(2-methylphenyl)cyclohexyl |
| 84 | Me | CH | 4-(3-methylphenyl)cyclohexyl |
| 85 | Me | CH | 4-(4-methylphenyl)cyclohexyl |
| 86 | Me | CH | 4-(2-methoxyphenyl)cyclohexyl |
| 87 | Me | CH | 4-(3-methoxyphenyl)cyclohexyl |
| 88 | Me | CH | 4-(4-methoxyphenyl)cyclohexyl |
| 89 | Me | CH | 4-(2-trifluoromethylphenyl)cyclohexyl |
| 90 | Me | CH | 4-(3-trifluoromethylphenyl)cyclohexyl |
| 91 | Me | CH | 4-(4-trifluoromethylphenyl)cyclohexyl |
| 92 | Me | CH | 4-(3,5-difluorophenyl)cyclohexyl |
| 93 | Me | CH | 4-(3-acetylphenyl)cyclohexyl |
| 94 | Me | CH | 4-(3-cyanophenyl)cyclohexyl |
| 95 | Me | CH | 4-(2-difluoromethoxyphenyl)cyclohexyl |
| 96 | Me | CH | 4-(3-difluoromethoxyphenyl)cyclohexyl |
| 97 | Me | CH | 4-(4-difluoromethoxyphenyl)cyclohexyl |
| 98 | Me | CH | 4-(2-pyridyl)cyclohexyl |
| 99 | Me | CH | 4-(3-pyridyl)cyclohexyl |
| 100 | Me | CH | 4-(4-pyridyl)cyclohexyl |
| 101 | Me | CH | 4-(4-fluoro-3-pyridyl)cyclohexyl |
| 102 | Me | CH | 4-(3-quinolyl)cyclohexyl |
| 103 | Me | CH | 4-(3-fluorophenyl)-4-hydroxycyclohexyl |
| 104 | Me | CH | 3-phenylcyclohexyl |
| 105 | Me | CH | 3-phenylcyclopentyl |
| 106 | Me | CH | 6-phenyl-3-tetrahydropyranyl |
| 107 | Me | CH | 6-(3-fluorophenyl)-3-tetrahydropyranyl |
| 108 | Me | CH | 2-phenylcyclopropyl |
| 109 | Me | CH | 2-(2-pyridyl)cyclopropyl |
| 110 | Me | CH | 2-(3-pyridyl)cyclopropyl |
| 111 | Me | CH | 2-(4-pyridyl)cyclopropyl |
| 112 | Me | CH | 2-(3-fluorophenyl)cyclopropyl |
| 113 | Me | CH | 2-indanyl |
| 114 | Me | CH | 2-tetrahydronaphthyl |
| 115 | Me | CH | 6-methoxy-2-tetrahydronaphthyl |
| 116 | Me | CH | benzyl |
| 117 | Me | CH | phenethyl |
| 118 | Me | CH | 3-phenylpropyl |
| 119 | Me | CH | 4-phenylbutyl |
| 120 | Me | CH | 2-methoxyphenethyl |
| 121 | Me | CH | 3-methoxyphenethyl |
| 122 | Me | CH | 4-methoxyphenethyl |
| 123 | Me | CH | 4-fluorophenethyl |

TABLE 1-continued

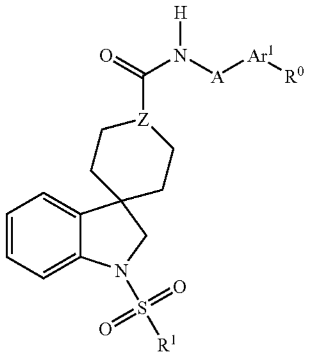

| No. | R$^1$ | Z | A—Ar$^1$—R$^0$ |
|---|---|---|---|
| 124 | Me | CH | 4-bromophenethyl |
| 125 | Me | CH | 4-chlorophenethyl |
| 126 | Me | CH | 3-trifluoromethylphenethyl |
| 127 | Me | CH | 3,4-dimethoxyphenethyl |
| 128 | Me | CH | 3-propoxyphenethyl |
| 129 | Me | CH | 3,5-difluorophenethyl |
| 130 | Me | CH | 4-dimethylaminophenethyl |
| 131 | Me | CH | 3-difluoromethoxyphenethyl |
| 132 | Me | CH | 2-methylphenethyl |
| 133 | Me | CH | 4-acetylphenethyl |
| 134 | Me | CH | 4-dimethylamino-2-methoxyphenethyl |
| 135 | Me | CH | cyclohexylethyl |
| 136 | Me | CH | 2-(2-pyridyl)ethyl |
| 137 | Me | CH | 2-(3-pyridyl)ethyl |
| 138 | Me | CH | 2-(4-pyridyl)ethyl |
| 139 | Me | CH | 2-(2-quinolyl)ethyl |
| 140 | Me | CH | 2-(3-quinolyl)ethyl |
| 141 | Me | CH | 2-(4-quinolyl)ethyl |
| 142 | Me | CH | 2-(6-quinolyl)ethyl |
| 143 | Me | CH | 2-(2-indolyl)ethyl |
| 144 | Me | CH | 2-(3-indolyl)ethyl |
| 145 | Me | CH | 2-(7-aza-3-indolyl)ethyl |
| 146 | Me | CH | 2-(benzimidazolyl)ethyl |
| 147 | Me | CH | 2-(benzoxazolyl)ethyl |
| 148 | Me | CH | 2-(benzothiazolyl)ethyl |
| 149 | Me | CH | 2-(1-naphthyl)ethyl |
| 150 | Me | CH | 2-(2-naphthyl)ethyl |
| 151 | Me | CH | 1-(hydroxymethyl)-2-phenylethyl |
| 152 | Me | CH | 1-(methoxycarbonyl)-2-phenylethyl |
| 153 | Me | CH | 1-(ethoxycarbonyl)-2-phenylethyl |
| 154 | Me | CH | 1-carboxy-2-phenylethyl |
| 155 | Me | CH | 1-(benzyloxycarbonyl)-2-phenylethyl |
| 156 | Me | CH | 1-(phenoxymethyl)-2-phenylethyl |
| 157 | Me | CH | 1-(benzyloxymethyl)-2-phenylethyl |
| 158 | Me | CH | 1-(benzylcarbamoyl)-2-phenylethyl |
| 159 | Me | CH | 1-(N-methylbenzylcarbamoyl)-2-phenylethyl |
| 160 | Me | CH | 1-(phenylcarbamoyl)-2-phenylethyl |
| 161 | Me | CH | 1-(M-methylphenylcarbamoyl)-2-phenylethyl |
| 162 | Me | CH | 1-(N-benzylaminomethyl)-2-phenylethyl |
| 163 | Me | CH | 1-(N-benzyl-N-methylaminomethyl)-2-phenylethyl |
| 164 | Me | CH | 1-(anilinomethyl)-2-phenylethyl |
| 165 | Me | CH | 1-(N-methylanilinomethyl)-2-phenylethyl |
| 166 | Me | CH | 1-(N-methylaminomethyl)-2-phenylethyl |
| 167 | Me | CH | 1-(N-ethylaminomethyl)-2-phenylethyl |
| 168 | Me | CH | 1-(N-isobutylaminomethyl)-2-phenylethyl |
| 169 | Me | CH | 1-(N-cyclopropylmethylaminomethyl)-2-phenylethyl |
| 170 | Me | CH | 1-(aminomethyl)-2-phenylethyl |
| 171 | Me | CH | 1-benzyl-2-(2-pyridylmethylamino)ethyl |
| 172 | Me | CH | 1-benzyl-2-(3-pyridylmethylamino)ethyl |
| 173 | Me | CH | 1-benzyl-2-(4-pyridylmethylamino)ethyl |
| 174 | Me | CH | 2-phenyl-1-(2-pyridylmethylcarbamoyl)ethyl |
| 175 | Me | CH | 2-phenyl-1-(3-pyridylmethylcarbamoyl)ethyl |
| 176 | Me | CH | 2-phenyl-1-(4-pyridylmethylcarbamoyl)ethyl |
| 177 | Me | CH | 2-hydroxy-2-phenylethyl |
| 178 | Me | CH | benzoylmethyl |
| 179 | Me | CH | 1-(benzyloxycarbonyl)-2-(3-indolyl)ethyl |
| 180 | Me | CH | 1-(benzyloxycarbonyl)-2-cyclohexylethyl |
| 181 | Me | CH | 1-(phenoxymethyl)-2-(3-indolyl)ethyl |

TABLE 1-continued

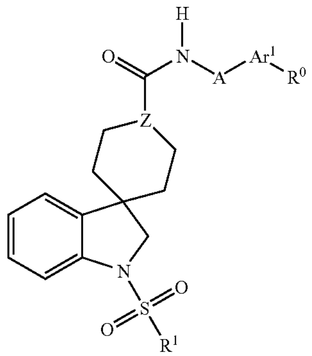

| No. | $R^1$ | Z | A—$Ar^1$—$R^0$ |
|---|---|---|---|
| 182 | Me | CH | 2-(2-methoxyphenoxy)ethyl |
| 183 | Me | CH | 1-(benzylcarbamoyl)-2-cyclohexylethyl |
| 184 | Me | CH | 1-(N-methylbenzylcarbamoyl)-2-cyclohexylethyl |
| 185 | Me | CH | 1-(phenylcarbamoyl)-2-cyclohexylethyl |
| 186 | Me | CH | 1-(N-methylphenylcarbamoyl)-2-cyclohexylethyl |
| 187 | Me | CH | 1-(benzyloxycarbonyl)-2-(3-pyridyl)ethyl |
| 188 | Me | CH | 1-(benzylaminomethyl)-2-(3-pyridyl)ethyl |
| 189 | Me | CH | 1-(benzylcarbamoyl)-2-(4-pyridyl)ethyl |
| 190 | Me | CH | 1-(4-pyridylmethylcarbamoyl)-2-(4-fluoro-phenyl) ethyl |
| 191 | Me | CH | 1-(benzylcarbamoyl)-2-(7-aza-3-indolyl)ethyl |
| 192 | Me | CH | 1-(benzyloxymethyl)-2-(2-indolyl)ethyl |
| 193 | Me | CH | 1-(N-benzyl-N-methylaminomethyl)-2-(3-pyridyl)ethyl |
| 194 | Me | CH | 1-(N-methylbenzylcarbamoyl)-2-(3-pyridyl)ethyl |
| 195 | Me | CH | 2-hydroxy-2-(4-dimethylaminophenyl)ethyl |
| 196 | Me | CH | 2-hydroxy-2-(2-quinolyl)ethyl |
| 197 | Me | CH | 2-hydroxy-2-(3-quinolyl)ethyl |
| 198 | Me | CH | 2-hydroxy-2-(4-quinolyl)ethyl |
| 199 | Me | CH | 2-hydroxy-2-(3,5-difluorophenyl)ethyl |
| 200 | Me | CH | 1-carboxy-2-cyclohexylethyl |
| 201 | Me | CH | 2-hydroxy-2-(6-quinolyl)ethyl |
| 202 | Me | CH | 2-(benzylamino)-2-phenylethyl |
| 203 | Me | CH | 2-amino-2-(2-naphthyl)propyl |
| 204 | Me | CH | 2-(phenylamino)ethyl |
| 205 | Me | CH | diphenylmethyl |
| 206 | Me | CH | 2,2-diphenylethyl |
| 207 | Me | CH | 2-phenyl-2-(2-pyridyl)ethyl |
| 208 | Me | CH | 2-phenyl-2-(3-pyridyl)ethyl |
| 209 | Me | CH | 2-phenyl-2-(4-pyridyl)ethyl |
| 210 | Me | CH | 2-phenoxy-2-phenylethyl |
| 211 | Me | CH | 2-(benzyloxy)-2-phenylethyl |
| 212 | Et | CH | 1-phenyl-3-pyrrolidinyl |
| 213 | Et | CH | 1-(2-fluorophenyl)-3-pyrrolidinyl |
| 214 | Et | CH | 1-(3-fluorophenyl)-3-pyrrolidinyl |
| 215 | Et | CH | 1-(4-fluorophenyl)-3-pyrrolidinyl |
| 216 | Et | CH | 1-(2-chlorophenyl)-3-pyrrolidinyl |
| 217 | Et | CH | 1-(3-chlorophenyl)-3-pyrrolidinyl |
| 218 | Et | CH | 1-(4-chlorophenyl)-3-pyrrolidinyl |
| 219 | Et | CH | 1-(2-methylphenyl)-3-pyrrolidinyl |
| 220 | Et | CH | 1-(3-methylphenyl)-3-pyrrolidinyl |
| 221 | Et | CH | 1-(4-methylphenyl)-3-pyrrolidinyl |
| 222 | Et | CH | 1-(2-methoxyphenyl)-3-pyrrolidinyl |
| 223 | Et | CH | 1-(3-methoxyphenyl)-3-pyrrolidinyl |
| 224 | Et | CH | 1-(4-methoxyphenyl)-3-pyrrolidinyl |
| 225 | Et | CH | 1-(2-trifluoromethylphenyl)-3-pyrrolidinyl |
| 226 | Et | CH | 1-(3-trifluoromethylphenyl)-3-pyrrolidinyl |
| 227 | Et | CH | 1-(4-trifluoromethylphenyl)-3-pyrrolidinyl |
| 228 | Et | CH | 1-(3,5-difluorophenyl)-3-pyrrolidinyl |
| 229 | Et | CH | 1-(2-difluoromethoxyphenyl)-3-pyrrolidinyl |
| 230 | Et | CH | 1-(3-difluoromethoxyphenyl)-3-pyrrolidinyl |
| 231 | Et | CH | 1-(4-difluoromethoxyphenyl)-3-pyrrolidinyl |
| 232 | Et | CH | 1-(2-pyridyl)-3-pyrrolidinyl |
| 233 | Et | CH | 1-(3-pyridyl)-3-pyrrolidinyl |
| 234 | Et | CH | 1-(4-pyridyl)-3-pyrrolidinyl |
| 235 | Et | CH | 1-(2-pyrimidinyl)-3-pyrrolidinyl |
| 236 | Et | CH | 5-oxo-1-phenyl-3-pyrrolidinyl |
| 237 | Et | CH | 1-phenyl-3-piperidyl |
| 238 | Et | CH | 1-(2-fluorophenyl)-3-piperidyl |

TABLE 1-continued

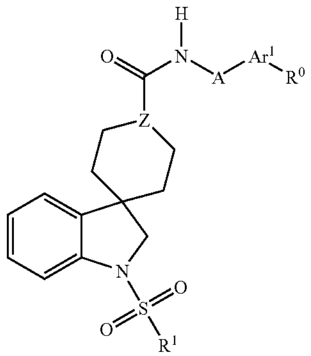

| No. | $R^1$ | Z | A—$Ar^1$—$R^0$ |
|---|---|---|---|
| 239 | Et | CH | 1-(3-fluorophenyl)-3-piperidyl |
| 240 | Et | CH | 1-(4-fluorophenyl)-3-piperidyl |
| 241 | Et | CH | 1-(2-chlorophenyl)-3-piperidyl |
| 242 | Et | CH | 1-(3-chlorophenyl)-3-piperidyl |
| 243 | Et | CH | 1-(4-chlorophenyl)-3-piperidyl |
| 244 | Et | CH | 1-(2-methylphenyl)-3-piperidyl |
| 245 | Et | CH | 1-(3-methylphenyl)-3-piperidyl |
| 246 | Et | CH | 1-(4-methylphenyl)-3-piperidyl |
| 247 | Et | CH | 1-(2-methoxyphenyl)-3-piperidyl |
| 248 | Et | CH | 1-(3-methoxyphenyl)-3-piperidyl |
| 249 | Et | CH | 1-(4-methoxyphenyl)-3-piperidyl |
| 250 | Et | CH | 1-(2-trifluoromethylphenyl)-3-piperidyl |
| 251 | Et | CH | 1-(3-trifluoromethylphenyl)-3-piperidyl |
| 252 | Et | CH | 1-(4-trifluoromethylphenyl)-3-piperidyl |
| 253 | Et | CH | 1-(3,5-difluorophenyl)-3-piperidyl |
| 254 | Et | CH | 1-(2-difluoromethoxyphenyl)-3-piperidyl |
| 255 | Et | CH | 1-(3-difluoromethoxyphenyl)-3-piperidyl |
| 256 | Et | CH | 1-(4-difluoromethoxyphenyl)-3-piperidyl |
| 257 | Et | CH | 1-(2-pyridyl)-3-piperidyl |
| 258 | Et | CH | 1-(3-pyridyl)-3-piperidyl |
| 259 | Et | CH | 1-(4-pyridyl)-3-piperidyl |
| 260 | Et | CH | 1-phenyl-4-piperidyl |
| 261 | Et | CH | 1-(2-fluorophenyl)-4-piperidyl |
| 262 | Et | CH | 1-(3-fluorophenyl)-4-piperidyl |
| 263 | Et | CH | 1-(4-fluorophenyl)-4-piperidyl |
| 264 | Et | CH | 1-(2-chloropheny)-4-piperidyl |
| 265 | Et | CH | 1-(3-chloropheny)-4-piperidyl |
| 266 | Et | CH | 1-(4-chloropheny)-4-piperidyl |
| 267 | Et | CH | 1-(2-methylpheny)-4-piperidyl |
| 268 | Et | CH | 1-(3-methylpheny)-4-piperidyl |
| 269 | Et | CH | 1-(4-methylpheny)-4-piperidyl |
| 270 | Et | CH | 1-(2-methoxypheny)-4-piperidyl |
| 271 | Et | CH | 1-(3-methoxypheny)-4-piperidyl |
| 272 | Et | CH | 1-(4-methoxypheny)-4-piperidyl |
| 273 | Et | CH | 1-(2-trifluoromethylpheny)-4-piperidyl |
| 274 | Et | CH | 1-(3-trifluoromethylpheny)-4-piperidyl |
| 275 | Et | CH | 1-(4-trifluoromethylpheny)-4-piperidyl |
| 276 | Et | CH | 1-(3,5-difluorophenyl)-4-piperidyl |
| 277 | Et | CH | 1-(2-difluoromethoxyphenyl)-4-piperidyl |
| 278 | Et | CH | 1-(3-difluoromethoxyphenyl)-4-piperidyl |
| 279 | Et | CH | 1-(4-difluoromethoxyphenyl)-4-piperidyl |
| 280 | Et | CH | 1-(2-pyridyl)-4-piperidyl |
| 281 | Et | CH | 1-(3-pyridyl)-4-piperidyl |
| 282 | Et | CH | 1-(4-pyridyl)-4-piperidyl |
| 283 | Et | CH | 3-hydroxymethyl-1-phenyl-4-piperidyl |
| 284 | Et | CH | 3-methoxycarbonyl-1-phenyl-4-piperidyl |
| 285 | Et | CH | 3-ethoxycarbonyl-1-phenyl-4-piperidyl |
| 286 | Et | CH | 3-isopropoxycarbonyl-1-phenyl-4-piperidyl |
| 287 | Et | CH | 4-phenylcyclohexyl |
| 288 | Et | CH | 4-(2-fluorophenyl)cyclohexyl |
| 289 | Et | CH | 4-(3-fluorophenyl)cyclohexyl |
| 290 | Et | CH | 4-(4-fluorophenyl)cyclohexyl |
| 291 | Et | CH | 4-(2-chlorophenyl)cyclohexyl |
| 292 | Et | CH | 4-(3-chlorophenyl)cyclohexyl |
| 293 | Et | CH | 4-(4-chlorophenyl)cyclohexyl |
| 294 | Et | CH | 4-(2-methylphenyl)cyclohexyl |
| 295 | Et | CH | 4-(3-methylphenyl)cyclohexyl |
| 296 | Et | CH | 4-(4-methylphenyl)cyclohexyl |
| 297 | Et | CH | 4-(2-methoxyphenyl)cyclohexyl |

TABLE 1-continued

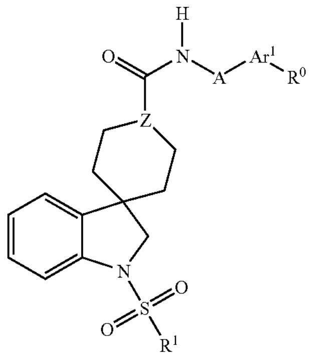

| No. | $R^1$ | Z | A—$Ar^1$—$R^0$ |
|---|---|---|---|
| 298 | Et | CH | 4-(3-methoxyphenyl)cyclohexyl |
| 299 | Et | CH | 4-(4-methoxyphenyl)cyclohexyl |
| 300 | Et | CH | 4-(2-trifluoromethylphenyl)cyclohexyl |
| 301 | Et | CH | 4-(3-trifluoromethylphenyl)cyclohexyl |
| 302 | Et | CH | 4-(4-trifluoromethylphenyl)cyclohexyl |
| 303 | Et | CH | 4-(3,5-difluorophenyl)cyclohexyl |
| 304 | Et | CH | 4-(3-acetylphenyl)cyclohexyl |
| 305 | Et | CH | 4-(3-cyanophenyl)cyclohexyl |
| 306 | Et | CH | 4-(2-difluoromethoxyphenyl)cyclohexyl |
| 307 | Et | CH | 4-(3-difluoromethoxyphenyl)cyclohexyl |
| 308 | Et | CH | 4-(4-difluoromethoxyphenyl)cyclohexyl |
| 309 | Et | CH | 4-(2-pyridyl)cyclohexyl |
| 310 | Et | CH | 4-(3-pyridyl)cyclohexyl |
| 311 | Et | CH | 4-(4-pyridyl)cyclohexyl |
| 312 | Et | CH | 4-(4-fluoro-3-pyridyl)cyclohexyl |
| 313 | Et | CH | 4-(3-quinolyl)cyclohexyl |
| 314 | Et | CH | 4-(3-fluorophenyl)-4-hydroxycyclohexyl |
| 315 | Et | CH | 3-phenylcyclohexyl |
| 316 | Et | CH | 3-phenylcyclopentyl |
| 317 | Et | CH | 6-phenyl-3-tetrahydropyranyl |
| 318 | Et | CH | 6-(3-fluorophenyl)-3-tetrahydropyranyl |
| 319 | Et | CH | 2-phenylcyclopropyl |
| 320 | Et | CH | 2-(2-pyridyl)cyclopropyl |
| 321 | Et | CH | 2-(3-pyridyl)cyclopropyl |
| 322 | Et | CH | 2-(4-pyridyl)cyclopropyl |
| 323 | Et | CH | 2-(3-fluorophenyl)cyclopropyl |
| 324 | Et | CH | 2-indanyl |
| 325 | Et | CH | 2-tetrahydronaphthyl |
| 326 | Et | CH | 6-methoxy-2-tetrahydronaphthyl |
| 327 | Et | CH | benzyl |
| 328 | Et | CH | phenethyl |
| 329 | Et | CH | 3-phenylpropyl |
| 330 | Et | CH | 4-phenylbutyl |
| 331 | Et | CH | 2-methoxyphenethyl |
| 332 | Et | CH | 3-methoxyphenethyl |
| 333 | Et | CH | 4-methoxyphenethyl |
| 334 | Et | CH | 4-fluorophenethyl |
| 335 | Et | CH | 4-bromophenethyl |
| 336 | Et | CH | 4-chlorophenethyl |
| 337 | Et | CH | 3-trifluoromethylphenethyl |
| 338 | Et | CH | 3,4-dimethoxyphenethyl |
| 339 | Et | CH | 3-propoxyphenethyl |
| 340 | Et | CH | 3,5-difluorophenethyl |
| 341 | Et | CH | 4-dimethylaminophenethyl |
| 342 | Et | CH | 3-difluoromethoxyphenethyl |
| 343 | Et | CH | 2-methylphenethyl |
| 344 | Et | CH | 4-acetylphenethyl |
| 345 | Et | CH | 4-dimethylamino-2-methoxyphenethyl |
| 346 | Et | CH | cyclohexylethyl |
| 347 | Et | CH | 2-(2-pyridyl)ethyl |
| 348 | Et | CH | 2-(3-pyridyl)ethyl |
| 349 | Et | CH | 2-(4-pyridyl)ethyl |
| 350 | Et | CH | 2-(2-quinolyl)ethyl |
| 351 | Et | CH | 2-(3-quinolyl)ethyl |
| 352 | Et | CH | 2-(4-quinolyl)ethyl |
| 353 | Et | CH | 2-(6-quinolyl)ethyl |
| 354 | Et | CH | 2-(2-indolyl)ethyl |
| 355 | Et | CH | 2-(3-indolyl)ethyl |
| 356 | Et | CH | 2-(7-aza-3-indolyl)ethyl |

TABLE 1-continued

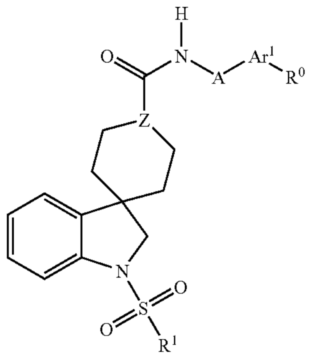

| No. | $R^1$ | Z | A—$Ar^1$—$R^0$ |
|---|---|---|---|
| 357 | Et | CH | 2-(benzimidazolyl)ethyl |
| 358 | Et | CH | 2-(benzoxazolyl)ethyl |
| 359 | Et | CH | 2-(benzothiazolyl)ethyl |
| 360 | Et | CH | 2-(1-naphthyl)ethyl |
| 361 | Et | CH | 2-(2-naphthyl)ethyl |
| 362 | Et | CH | 1-(hydroxymethyl)-2-phenylethyl |
| 363 | Et | CH | 1-(methoxycarbonyl)-2-phenylethyl |
| 364 | Et | CH | 1-(ethoxycarbonyl)-2-phenylethyl |
| 365 | Et | CH | 1-carboxy-2-phenylethyl |
| 366 | Et | CH | 1-(benzyloxycarbonyl)-2-phenylethyl |
| 367 | Et | CH | 1-(phenoxymethyl)-2-phenylethyl |
| 368 | Et | CH | 1-(benzyloxymethyl)-2-phenylethyl |
| 369 | Et | CH | 1-(benzylcarbamoyl)-2-phenylethyl |
| 370 | Et | CH | 1-(N-methylbenzylcarbamoyl)-2-phenylethyl |
| 371 | Et | CH | 1-(phenylcarbamoyl)-2-phenylethyl |
| 372 | Et | CH | 1-(N-methylphenylcarbamoyl)-2-phenylethyl |
| 373 | Et | CH | 1-(N-benzylaminomethyl)-2-phenylethyl |
| 374 | Et | CH | 1-(N-benzyl-N-methylaminomethyl)-2-phenylethyl |
| 375 | Et | CH | 1-(anilinomethyl)-2-phenylethyl |
| 376 | Et | CH | 1-(N-methylanilinomethyl)-2-phenylethyl |
| 377 | Et | CH | 1-(N-methylaminomethyl)-2-phenylethyl |
| 378 | Et | CH | 1-(N-ethylaxninomethyl)-2-phenylethyl |
| 379 | Et | CH | 1-(N-isobutylaminomethyl)-2-phenylethyl |
| 380 | Et | CH | 1-(N-cyclopropylmethylaminomethyl)-2-phenyl-ethyl |
| 381 | Et | CH | 1-(aminomethyl)-2-phenylethyl |
| 382 | Et | CH | 1-benzyl-2-(2-pyridylmethylamino)ethyl |
| 383 | Et | CH | 1-benzyl-2-(3-pyridylmethylamino)ethyl |
| 384 | Et | CH | 1-benzyl-2-(4-pyridylmethylamino)ethyl |
| 385 | Et | CH | 2-phenyl-1-(2-pyridylmethylcarbamoyl)ethyl |
| 386 | Et | CH | 2-phenyl-1-(3-pyridylmethylcarbamoyl)ethyl |
| 387 | Et | CH | 2-phenyl-1-(4-pyridylmethylcarbamoyl)ethyl |
| 388 | Et | CH | 2-hydroxy-2-phenylethyl |
| 389 | Et | CH | benzoylmethyl |
| 390 | Et | CH | 1-(benzyloxycarbonyl)-2-(3-indolyl)ethyl |
| 391 | Et | CH | 1-(benzyloxycarbonyl)-2-cyclohexylethyl |
| 392 | Et | CH | 1-(phenoxymethyl)-2-(3-indolyl)ethyl |
| 393 | Et | CH | 2-(2-methoxyphenoxyy)ethyl |
| 394 | Et | CH | 1-(benzylcarbamoyl)-2-cyclohexylethyl |
| 395 | Et | CH | 1-(N-methylbenzylcarbamoyl)-2-cyclohexylethyl |
| 396 | Et | CH | 1-(phenylcarbamoyl)-2-cyclohexylethyl |
| 397 | Et | CH | 1-(N-methylphenylcarbamoyl)-2-cyclohexylethyl |
| 398 | Et | CH | 1-(benzyloxycarbonyl)-2-(3-pyridyl)ethyl |
| 399 | Et | CH | 1-(benzylaminomethyl)-2-(3-pyridyl)ethyl |
| 400 | Et | CH | 1-(benzylcarbamoyl)-2-(4-pyridyl)ethyl |
| 401 | Et | CH | 1-(4-pyridylmethylcarbamoyl)-2-(4-fluoro-phenyl)ethyl |
| 402 | Et | CH | 1-(benzylcarbamoyl)-2-(7-aza-3-indolyl)ethyl |
| 403 | Et | CH | 1-(benzyloxymethyl)-2-(2-indolyl)ethyl |
| 404 | Et | CH | 1-(N-benzyl-N-methylaminomethyl)-2-(3-pyridyl)ethyl |
| 405 | Et | CH | 1-(N-methylbenzylcarbamoyl)-2-(3-pyridyl)ethyl |
| 406 | Et | CH | 2-hydroxy-2-(4-dimethylaminophenyl)ethyl |
| 407 | Et | CH | 2-hydroxy-2-(2-quinolyl)ethyl |
| 408 | Et | CH | 2-hydroxy-2-(3-quinolyl)ethyl |
| 409 | Et | CH | 2-hydroxy-2-(4-quinolyl)ethyl |
| 410 | Et | CH | 2-hydroxy-2-(3,5-difluorophenyl)ethyl |
| 411 | Et | CH | 1-carboxy-2-cyclohexylethyl |
| 412 | Et | CH | 2-hydroxy-2-(6-quinolyl)ethyl |

TABLE 1-continued

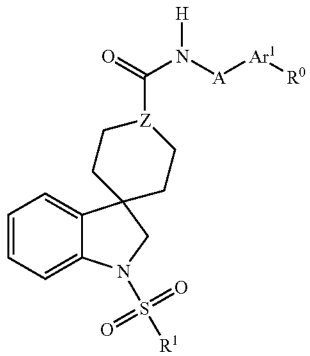

| No. | $R^1$ | Z | A—$Ar^1$—$R^0$ |
|---|---|---|---|
| 413 | Et | CH | 2-(benzylamino)-2-phenylethyl |
| 414 | Et | CH | 2-amino-2-(2-naphthyl)propyl |
| 415 | Et | CH | 2-(phenylamino)ethyl |
| 416 | Et | CH | diphenylmethyl |
| 417 | Et | CH | 2,2-diphenylethyl |
| 418 | Et | CH | 2-phenyl-2-(2-pyridyl)ethyl |
| 419 | Et | CH | 2-phenyl-2-(3-pyridyl)ethyl |
| 420 | Et | CH | 2-phenyl-2-(4-pyridyl)ethyl |
| 421 | Et | CH | 2-phenoxy-2-phenylethyl |
| 422 | Et | CH | 2-(benzyloxy)-2-phenylethyl |
| 423 | Me | N | 1-phenyl-3-pyrrolidinyl |
| 424 | Me | N | 1-(2-fluorophenyl)-3-pyrrolidinyl |
| 425 | Me | N | 1-(3-fluorophenyl)-3-pyrrolidinyl |
| 426 | Me | N | 1-(4-fluorophenyl)-3-pyrrolidinyl |
| 427 | Me | N | 1-(2-chlorophenyl)-3-pyrrolidinyl |
| 428 | Me | N | 1-(3-chlorophenyl)-3-pyrrolidinyl |
| 429 | Me | N | 1-(4-chlorophenyl)-3-pyrrolidinyl |
| 430 | Me | N | 1-(2-methylphenyl)-3-pyrrolidinyl |
| 431 | Me | N | 1-(3-methylphenyl)-3-pyrrolidinyl |
| 432 | Me | N | 1-(4-methylphenyl)-3-pyrrolidinyl |
| 433 | Me | N | 1-(2-methoxyphenyl)-3-pyrrolidinyl |
| 434 | Me | N | 1-(3-methoxyphenyl)-3-pyrrolidinyl |
| 435 | Me | N | 1-(4-methoxyphenyl)-3-pyrrolidinyl |
| 436 | Me | N | 1-(2-trifluoromethylphenyl)-3-pyrrolidinyl |
| 437 | Me | N | 1-(3-trifluoromethylphenyl)-3-pyrrolidinyl |
| 438 | Me | N | 1-(4-trifluoromethylphenyl)-3-pyrrolidinyl |
| 439 | Me | N | 1-(3,5-difluorophenyl)-3-pyrrolidinyl |
| 440 | Me | N | 1-(2-difluoromethoxyphenyl)-3-pyrrolidinyl |
| 441 | Me | N | 1-(3-difluoromethoxyphenyl)-3-pyrrolidinyl |
| 442 | Me | N | 1-(4-difluoromethoxyphenyl)-3-pyrrolidinyl |
| 443 | Me | N | 1-(2-pyridyl)-3-pyrrolidinyl |
| 444 | Me | N | 1-(3-pyridyl)-3-pyrrolidinyl |
| 445 | Me | N | 1-(4-pyridyl)-3-pyrrolidinyl |
| 446 | Me | N | 1-(2-pyrimidinyl)-3-pyrrolidinyl |
| 447 | Me | N | 5-oxo-1-phenyl-3-pyrrolidinyl |
| 448 | Me | N | 1-phenyl-3-piperidyl |
| 449 | Me | N | 1-(2-fluorophenyl)-3-piperidyl |
| 450 | Me | N | 1-(3-fluorophenyl)-3-piperidyl |
| 451 | Me | N | 1-(4-fluorophenyl)-3-piperidyl |
| 452 | Me | N | 1-(2-chlorophenyl)-3-piperidyl |
| 453 | Me | N | 1-(3-chlorophenyl)-3-piperidyl |
| 454 | Me | N | 1-(4-chlorophenyl)-3-piperidyl |
| 455 | Me | N | 1-(2-methylphenyl)-3-piperidyl |
| 456 | Me | N | 1-(3-methylphenyl)-3-piperidyl |
| 457 | Me | N | 1-(4-methylphenyl)-3-piperidyl |
| 458 | Me | N | 1-(2-methoxyphenyl)-3-piperidyl |
| 459 | Me | N | 1-(3-methoxyphenyl)-3-piperidyl |
| 460 | Me | N | 1-(4-methoxyphenyl)-3-piperidyl |
| 461 | Me | N | 1-(2-trifluoromethylphenyl)-3-piperidyl |
| 462 | Me | N | 1-(3-trifluoromethylphenyl)-3-piperidyl |
| 463 | Me | N | 1-(4-trifluoromethylphenyl)-3-piperidyl |
| 464 | Me | N | 1-(3,5-difluorophenyl)-3-piperidyl |
| 465 | Me | N | 1-(2-difluoromethoxyphenyl)-3-piperidyl |
| 466 | Me | N | 1-(3-difluoromethoxyphenyl)-3-piperidyl |
| 467 | Me | N | 1-(4-difluoromethoxyphenyl)-3-piperidyl |
| 468 | Me | N | 1-(2-pyridyl)-3-piperidyl |
| 469 | Me | N | 1-(3-pyridyl)-3-piperidyl |
| 470 | Me | N | 1-(4-pyridyl)-3-piperidyl |
| 471 | Me | N | 1-phenyl-4-piperidyl |

TABLE 1-continued

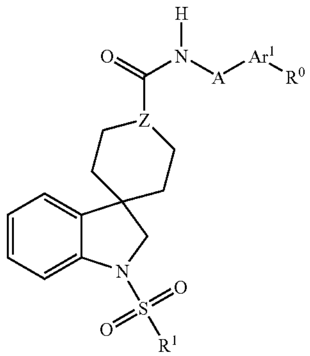

| No. | $R^1$ | Z | A—$Ar^1$—$R^0$ |
|---|---|---|---|
| 472 | Me | N | 1-(2-fluorophenyl)-4-piperidyl |
| 473 | Me | N | 1-(3-fluorophenyl)-4-piperidyl |
| 474 | Me | N | 1-(4-fluorophenyl)-4-piperidyl |
| 475 | Me | N | 1-(2-chlorophenyl)-4-piperidyl |
| 476 | Me | N | 1-(3-chlorophenyl)-4-piperidyl |
| 477 | Me | N | 1-(4-chlorophenyl)-4-piperidyl |
| 478 | Me | N | 1-(2-methylphenyl)-4-piperidyl |
| 479 | Me | N | 1-(3-methylphenyl)-4-piperidyl |
| 480 | Me | N | 1-(4-methylphenyl)-4-piperidyl |
| 481 | Me | N | 1-(2-methoxyphenyl)-4-piperidyl |
| 482 | Me | N | 1-(3-methoxyphenyl)-4-piperidyl |
| 483 | Me | N | 1-(4-methoxyphenyl)-4-piperidyl |
| 484 | Me | N | 1-(2-trifluoromethylphenyl)-4-piperidyl |
| 485 | Me | N | 1-(3-trifluoromethylphenyl)-4-piperidyl |
| 486 | Me | N | 1-(4-trifluoromethylphenyl)-4-piperidyl |
| 487 | Me | N | 1-(3,5-difluorophenyl)-4-piperidyl |
| 488 | Me | N | 1-(2-difluoromethoxyphenyl)-4-piperidyl |
| 489 | Me | N | 1-(3-difluoromethoxyphenyl)-4-piperidyl |
| 490 | Me | N | 1-(4-difluoromethoxyphenyl)-4-piperidyl |
| 491 | Me | N | 1-(2-pyridyl)-4-piperidyl |
| 492 | Me | N | 1-(3-pyridyl)-4-piperidyl |
| 493 | Me | N | 1-(4-pyridyl)-4-piperidyl |
| 494 | Me | N | 3-hydroxymethyl-1-phenyl-4-piperidyl |
| 495 | Me | N | 3-methoxycarbonyl-1-phenyl-4-piperidyl |
| 496 | Me | N | 3-ethoxycarbonyl-1-phenyl-4-piperidyl |
| 497 | Me | N | 3-isopropoxycarbonyl-1-phenyl-4-piperidyl |
| 498 | Me | N | 4-phenylcyclohexyl |
| 499 | Me | N | 4-(2-fluorophenyl)cyclohexyl |
| 500 | Me | N | 4-(3-fluorophenyl)cyclohexyl |
| 501 | Me | N | 4-(4-fluorophenyl)cyclohexyl |
| 502 | Me | N | 4-(2-chlorophenyl)cyclohexyl |
| 503 | Me | N | 4-(3-chlorophenyl)cyclohexyl |
| 504 | Me | N | 4-(4-chlorophenyl)cyclohexyl |
| 505 | Me | N | 4-(2-methylphenyl)cyclohexyl |
| 506 | Me | N | 4-(3-methylphenyl)cyclohexyl |
| 507 | Me | N | 4-(4-methylphenyl)cyclohexyl |
| 508 | Me | N | 4-(2-methoxyphenyl)cyclohexyl |
| 509 | Me | N | 4-(3-methoxyphenyl)cyclohexyl |
| 510 | Me | N | 4-(4-methoxyphenyl)cyclohexyl |
| 511 | Me | N | 4-(2-trifluoromethylphenyl)cyclohexyl |
| 512 | Me | N | 4-(3-trifluoromethylphenyl)cyclohexyl |
| 513 | Me | N | 4-(4-trifluoromethylphenyl)cyclohexyl |
| 514 | Me | N | 4-(3,5-difluorophenyl)cyclohexyl |
| 515 | Me | N | 4-(3-acetylphenyl)cyclohexyl |
| 516 | Me | N | 4-(3-cyanophenyl)cyclohexyl |
| 517 | Me | N | 4-(2-difluoromethoxyphenyl)cyclohexyl |
| 518 | Me | N | 4-(3-difluoromethoxyphenyl)cyclohexyl |
| 519 | Me | N | 4-(4-difluoromethoxyphenyl)cyclohexyl |
| 520 | Me | N | 4-(2-pyridyl)cyclohexyl |
| 521 | Me | N | 4-(3-pyridyl)cyclohexyl |
| 522 | Me | N | 4-(4-pyridyl)cyclohexyl |
| 523 | Me | N | 4-(4-fluoro-3-pyridyl)cyclohexyl |
| 524 | Me | N | 4-(3-quinolyl)cyclohexyl |
| 525 | Me | N | 4-(3-fluorophenyl)-4-hydroxycyclohexyl |
| 526 | Me | N | 3-phenylcyclohexyl |
| 527 | Me | N | 3-phenylcyclopentyl |
| 528 | Me | N | 6-phenyl-3-tetrahydropyranyl |
| 529 | Me | N | 6-(3-fluorophenyl)-3-tetrahydropyranyl |
| 530 | Me | N | 2-phenylcyclopropyl |

TABLE 1-continued

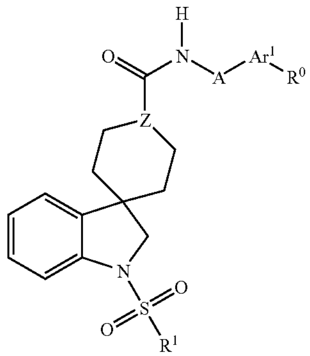

| No. | $R^1$ | Z | A—$Ar^1$—$R^0$ |
|---|---|---|---|
| 531 | Me | N | 2-(2-pyridyl)cyclopropyl |
| 532 | Me | N | 2-(3-pyridyl)cyclopropyl |
| 533 | Me | N | 2-(4-pyridyl)cyclopropyl |
| 534 | Me | N | 2-(3-fluorophenyl)cyclopropyl |
| 535 | Me | N | 2-indanyl |
| 536 | Me | N | 2-tetrahydronaphthyl |
| 537 | Me | N | 6-methoxy-2-tetrahydronaphthyl |
| 538 | Me | N | benzyl |
| 539 | Me | N | phenethyl |
| 540 | Me | N | 3-phenylpropyl |
| 541 | Me | N | 4-phenylbutyl |
| 542 | Me | N | 2-methoxyphenethyl |
| 543 | Me | N | 3-methoxyphenethyl |
| 544 | Me | N | 4-methoxyphenethyl |
| 545 | Me | N | 4-fluorophenethyl |
| 546 | Me | N | 4-bromophenethyl |
| 547 | Me | N | 4-chlorophenethyl |
| 548 | Me | N | 3-trifluoromethylphenethyl |
| 549 | Me | N | 3,4-dimethoxyphenethyl |
| 550 | Me | N | 3-propoxyphenethyl |
| 551 | Me | N | 3,5-difluorophenethyl |
| 552 | Me | N | 4-dimethylaminophenethyl |
| 553 | Me | N | 3-difluoromethoxyphenethyl |
| 554 | Me | N | 2-methylphenethyl |
| 555 | Me | N | 4-acetylphenethyl |
| 556 | Me | N | 4-dimethylamino-2-methoxyphenethyl |
| 557 | Me | N | cyclohexylethyl |
| 558 | Me | N | 2-(2-pyridyl)ethyl |
| 559 | Me | N | 2-(3-pyridyl)ethyl |
| 560 | Me | N | 2-(4-pyridyl)ethyl |
| 561 | Me | N | 2-(2-quinolyl)ethyl |
| 562 | Me | N | 2-(3-quinolyl)ethyl |
| 563 | Me | N | 2-(4-quinolyl)ethyl |
| 564 | Me | N | 2-(6-quinolyl)ethyl |
| 565 | Me | N | 2-(2-indolyl)ethyl |
| 566 | Me | N | 2-(3-indolyl)ethyl |
| 567 | Me | N | 2-(7-aza-3-indolyl)ethyl |
| 568 | Me | N | 2-(benzimidazolyl)ethyl |
| 569 | Me | N | 2-(benzoxazolyl)ethyl |
| 570 | Me | N | 2-(benzothiazolyl)ethyl |
| 571 | Me | N | 2-(1-naphthyl)ethyl |
| 572 | Me | N | 2-(2-naphthyl)ethyl |
| 573 | Me | N | 1-(hydroxymethyl)-2-phenylethyl |
| 574 | Me | N | 1-(methoxycarbonyl)-2-phenylethyl |
| 575 | Me | N | 1-(ethoxycarbonyl)-2-phenylethyl |
| 576 | Me | N | 1-carboxy-2-phenylethyl |
| 577 | Me | N | 1-(benzyloxycarbonyl)-2-phenylethyl |
| 578 | Me | N | 1-(phenoxymethyl)-2-phenylethyl |
| 579 | Me | N | 1-(benzyloxymethyl)-2-phenylethyl |
| 580 | Me | N | 1-(benzylcarbamoyl)-2-phenylethyl |
| 581 | Me | N | 1-(N-methylbenzylcarbamoyl)-2-phenylethyl |
| 582 | Me | N | 1-(phenylcarbamoyl)-2-phenylethyl |
| 583 | Me | N | 1-(N-methylphenylcarbamoyl)-2-phenylethyl |
| 584 | Me | N | 1-(N-benzylaminomethyl)-2-phenylethyl |
| 585 | Me | N | 1-(N-benzyl-N-methylaminomethyl)-2-phenylethyl |
| 586 | Me | N | 1-(anilinomethyl)-2-phenylethyl |
| 587 | Me | N | 1-(N-methylanilinomethyl)-2-phenylethyl |
| 588 | Me | N | 1-(N-methylaminomethyl)-2-phenylethyl |
| 589 | Me | N | 1-(N-ethylaminomethyl)-2-phenylethyl |

TABLE 1-continued

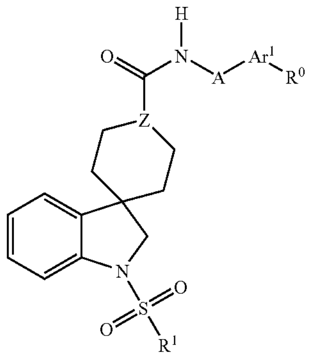

| No. | $R^1$ | Z | A—$Ar^1$—$R^0$ |
|---|---|---|---|
| 590 | Me | N | 1-(N-isobutylaminomethyl)-2-phenylethyl |
| 591 | Me | N | 1-(N-cyclopropylmethylaminomethyl)-2-phenyl-ethyl |
| 592 | Me | N | 1-(aminomethyl)-2-phenylethyl |
| 593 | Me | N | 1-benzyl-2-(2-pyridylmethylamino)ethyl |
| 594 | Me | N | 1-benzyl-2-(3-pyridylmethylamino)ethyl |
| 595 | Me | N | 1-benzyl-2-(4-pyridylmethylamino)ethyl |
| 596 | Me | N | 2-phenyl-1-(2-pyridylmethylcarbamoyl)ethyl |
| 597 | Me | N | 2-phenyl-1-(3-pyridylmethylcarbamoyl)ethyl |
| 598 | Me | N | 2-phenyl-1-(4-pyridylmethylcarbamoyl)ethyl |
| 599 | Me | N | 2-hydroxy-2-phenylethyl |
| 600 | Me | N | benzoylmethyl |
| 601 | Me | N | 1-(benzyloxycarbonyl)-2-(3-indolyl)ethyl |
| 602 | Me | N | 1-(benzyloxycarbonyl)-2-cyclohexylethyl |
| 603 | Me | N | 1-(phenoxymethyl)-2-(3-indolyl)ethyl |
| 604 | Me | N | 2-(2-methoxyphenoxy)ethyl |
| 605 | Me | N | 1-(benzylcarbamoyl)-2-cyclohexylethyl |
| 606 | Me | N | 1-(N-methylbenzylcarbamoyl)-2-cyclohexylethyl |
| 607 | Me | N | 1-(phenylcarbamoyl)-2-cyclohexylethyl |
| 608 | Me | N | 1-(N-methylphenylcarbamoyl)-2-cyclohexylethyl |
| 609 | Me | N | 1-(benzyloxycarbonyl)-2-(3-pyridyl)ethyl |
| 610 | Me | N | 1-(benzylaminomethyl)-2-(3-pyridyl)ethyl |
| 611 | Me | N | 1-(benzylcarbamoyl)-2-(4-pyridyl)ethyl |
| 612 | Me | N | 1-(4-pyridylmethylcarbamoyl)-2-(4-fluoro-phenyl) ethyl |
| 613 | Me | N | 1-(benzylcarbamoyl)-2-(7-aza-3-indolyl)ethyl |
| 614 | Me | N | 1-(benzyloxymethyl)-2-(2-indolyl)ethyl |
| 615 | Me | N | 1-(N-benzyl-N-methylaminomethyl)-2-(3-pyridyl)ethyl |
| 616 | Me | N | 1-(N-methylbenzylcarbamoyl)-2-(3-pyridyl)ethyl |
| 617 | Me | N | 2-hydroxy-2-(4-dimethylaminophenyl)ethyl |
| 618 | Me | N | 2-hydroxy-2-(2-quinolyl)ethyl |
| 619 | Me | N | 2-hydroxy-2-(3-quinolyl)ethyl |
| 620 | Me | N | 2-hydroxy-2-(4-quinolyl)ethyl |
| 621 | Me | N | 2-hydroxy-2-(3,5-difluorophenyl)ethyl |
| 622 | Me | N | 1-carboxy-2-cyclohexylethyl |
| 623 | Me | N | 2-hydroxy-2-(6-quinolyl)ethyl |
| 624 | Me | N | 2-(benzylamino)-2-phenylethyl |
| 625 | Me | N | 2-amino-2-(2-naphthyl)propyl |
| 626 | Me | N | 2-(phenylamino)ethyl |
| 627 | Me | N | diphenylmethyl |
| 628 | Me | N | 2,2-diphenylethyl |
| 629 | Me | N | 2-phenyl-2-(2-pyridyl)ethyl |
| 630 | Me | N | 2-phenyl-2-(3-pyridyl)ethyl |
| 631 | Me | N | 2-phenyl-2-(4-pyridyl)ethyl |
| 632 | Me | N | 2-phenoxy-2-phenylethyl |
| 633 | Me | N | 2-(benzyloxy)-2-phenylethyl |
| 634 | Et | N | 1-phenyl-3-pyrrolidinyl |
| 635 | Et | N | 1-(2-fluorophenyl)-3-pyrrolidinyl |
| 636 | Et | N | 1-(3-fluorophenyl)-3-pyrrolidinyl |
| 637 | Et | N | 1-(4-fluorophenyl)-3-pyrrolidinyl |
| 638 | Et | N | 1-(2-chlorophenyl)-3-pyrrolidinyl |
| 639 | Et | N | 1-(3-chlorophenyl)-3-pyrrolidinyl |
| 640 | Et | N | 1-(4-chlorophenyl)-3-pyrrolidinyl |
| 641 | Et | N | 1-(2-methylphenyl)-3-pyrrolidinyl |
| 642 | Et | N | 1-(3-methylphenyl)-3-pyrrolidinyl |
| 643 | Et | N | 1-(4-methylphenyl)-3-pyrrolidinyl |
| 644 | Et | N | 1-(2-methoxyphenyl)-3-pyrrolidinyl |
| 645 | Et | N | 1-(3-methoxyphenyl)-3-pyrrolidinyl |

TABLE 1-continued

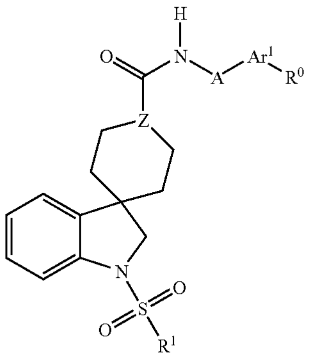

| No. | $R^1$ | Z | A—$Ar^1$—$R^0$ |
|---|---|---|---|
| 646 | Et | N | 1-(4-methoxyphenyl)-3-pyrrolidinyl |
| 647 | Et | N | 1-(2-trifluoromethylphenyl)-3-pyrrolidinyl |
| 648 | Et | N | 1-(3-trifluoromethylphenyl)-3-pyrrolidinyl |
| 649 | Et | N | 1-(4-trifluoromethylphenyl)-3-pyrrolidinyl |
| 650 | Et | N | 1-(3,5-difluorophenyl)-3-pyrrolidinyl |
| 651 | Et | N | 1-(2-difluoromethoxyphenyl)-3-pyrrolidinyl |
| 652 | Et | N | 1-(3-difluoromethoxyphenyl)-3-pyrrolidinyl |
| 653 | Et | N | 1-(4-difluoromethoxyphenyl)-3-pyrrolidinyl |
| 654 | Et | N | 1-(2-pyridyl)-3-pyrrolidinyl |
| 655 | Et | N | 1-(3-pyridyl)-3-pyrrolidinyl |
| 656 | Et | N | 1-(4-pyridyl)-3-pyrrolidinyl |
| 657 | Et | N | 1-(2-pyrimidinyl)-3-pyrrolidinyl |
| 658 | Et | N | 5-oxo-1-phenyl-3-pyrrolidinyl |
| 659 | Et | N | 1-phenyl-3-piperidyl |
| 660 | Et | N | 1-(2-fluorophenyl)-3-piperidyl |
| 661 | Et | N | 1-(3-fluorophenyl)-3-piperidyl |
| 662 | Et | N | 1-(4-fluorophenyl)-3-piperidyl |
| 663 | Et | N | 1-(2-chlorophenyl)-3-piperidyl |
| 664 | Et | N | 1-(3-chlorophenyl)-3-piperidyl |
| 665 | Et | N | 1-(4-chlorophenyl)-3-piperidyl |
| 666 | Et | N | 1-(2-methylphenyl)-3-piperidyl |
| 667 | Et | N | 1-(3-methylphenyl)-3-piperidyl |
| 668 | Et | N | 1-(4-methylphenyl)-3-piperidyl |
| 669 | Et | N | 1-(2-methoxyphenyl)-3-piperidyl |
| 670 | Et | N | 1-(3-methoxyphenyl)-3-piperidyl |
| 671 | Et | N | 1-(4-methoxyphenyl)-3-piperidyl |
| 672 | Et | N | 1-(2-trifluoromethylphenyl)-3-piperidyl |
| 673 | Et | N | 1-(3-trifluoromethylphenyl)-3-piperidyl |
| 674 | Et | N | 1-(4-trifluoromethylphenyl)-3-piperidyl |
| 675 | Et | N | 1-(3,5-difluorophenyl)-3-piperidyl |
| 676 | Et | N | 1-(2-difluoromethoxyphenyl)-3-piperidyl |
| 677 | Et | N | 1-(3-difluoromethoxyphenyl)-3-piperidyl |
| 678 | Et | N | 1-(4-difluoromethoxyphenyl)-3-piperidyl |
| 679 | Et | N | 1-(2-pyridyl)-3-piperidyl |
| 680 | Et | N | 1-(3-pyridyl)-3-piperidyl |
| 681 | Et | N | 1-(4-pyridyl)-3-piperidyl |
| 682 | Et | N | 1-phenyl-4-piperidyl |
| 683 | Et | N | 1-(2-fluorophenyl)-4-piperidyl |
| 684 | Et | N | 1-(3-fluorophenyl)-4-piperidyl |
| 685 | Et | N | 1-(4-fluorophenyl)-4-piperidyl |
| 686 | Et | N | 1-(2-chlorophenyl)-4-piperidyl |
| 687 | Et | N | 1-(3-chlorophenyl)-4-piperidyl |
| 688 | Et | N | 1-(4-chlorophenyl)-4-piperidyl |
| 689 | Et | N | 1-(2-methylphenyl)-4-piperidyl |
| 690 | Et | N | 1-(3-methylphenyl)-4-piperidyl |
| 691 | Et | N | 1-(4-methylphenyl)-4-piperidyl |
| 692 | Et | N | 1-(2-methoxyphenyl)-4-piperidyl |
| 693 | Et | N | 1-(3-methoxyphenyl)-4-piperidyl |
| 694 | Et | N | 1-(4-methoxyphenyl)-4-piperidyl |
| 695 | Et | N | 1-(2-trifluoromethylphenyl)-4-piperidyl |
| 696 | Et | N | 1-(3-trifluoromethylphenyl)-4-piperidyl |
| 697 | Et | N | 1-(4-trifluoromethylphenyl)-4-piperidyl |
| 698 | Et | N | 1-(3,5-difluorophenyl)-4-piperidyl |
| 699 | Et | N | 1-(2-difluoromethoxyphenyl)-4-piperidyl |
| 700 | Et | N | 1-(3-difluoromethoxyphenyl)-4-piperidyl |
| 701 | Et | N | 1-(4-difluoromethoxyphenyl)-4-piperidyl |
| 702 | Et | N | 1-(2-pyridyl)-4-piperidyl |
| 703 | Et | N | 1-(3-pyridyl)-4-piperidyl |
| 704 | Et | N | 1-(4-pyridyl)-4-piperidyl |

TABLE 1-continued

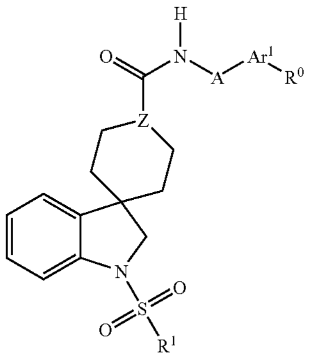

| No. | $R^1$ | Z | A—$Ar^1$—$R^0$ |
|---|---|---|---|
| 705 | Et | N | 3-hydroxymethyl-1-phenyl-4-piperidyl |
| 706 | Et | N | 3-methoxycarbonyl-1-phenyl-4-piperidyl |
| 707 | Et | N | 3-ethoxycarbonyl-1-phenyl-4-piperidyl |
| 708 | Et | N | 3-isopropoxycarbonyl-1-phenyl-4-piperidyl |
| 709 | Et | N | 4-phenylcyclohexyl |
| 710 | Et | N | 4-(2-fluorophenyl)cyclohexyl |
| 711 | Et | N | 4-(3-fluorophenyl)cyclohexyl |
| 712 | Et | N | 4-(4-fluorophenyl)cyclohexyl |
| 713 | Et | N | 4-(2-chlorophenyl)cyclohexyl |
| 714 | Et | N | 4-(3-chlorophenyl)cyclohexyl |
| 715 | Et | N | 4-(4-chlorophenyl)cyclohexyl |
| 716 | Et | N | 4-(2-methylphenyl)cyclohexyl |
| 717 | Et | N | 4-(3-methylphenyl)cyclohexyl |
| 718 | Et | N | 4-(4-methylphenyl)cyclohexyl |
| 719 | Et | N | 4-(2-methoxyphenyl)cyclohexyl |
| 720 | Et | N | 4-(3-methoxyphenyl)cyclohexyl |
| 721 | Et | N | 4-(4-methoxyphenyl)cyclohexyl |
| 722 | Et | N | 4-(2-trifluoromethylphenyl)cyclohexyl |
| 723 | Et | N | 4-(3-trifluoromethylphenyl)cyclohexyl |
| 724 | Et | N | 4-(4-trifluoromethylphenyl)cyclohexyl |
| 725 | Et | N | 4-(3,5-difluorophenyl)cyclohexyl |
| 726 | Et | N | 4-(3-acetylphenyl)cyclohexyl |
| 727 | Et | N | 4-(3-cyanophenyl)cyclohexyl |
| 728 | Et | N | 4-(2-difluoromethoxyphenyl)cyclohexyl |
| 729 | Et | N | 4-(3-difluoromethoxyphenyl)cyclohexyl |
| 730 | Et | N | 4-(4-difluoromethoxyphenyl)cyclohexyl |
| 731 | Et | N | 4-(2-pyridyl)cyclohexyl |
| 732 | Et | N | 4-(3-pyridyl)cyclohexyl |
| 733 | Et | N | 4-(4-pyridyl)cyclohexyl |
| 734 | Et | N | 4-(4-fluoro-3-pyridyl)cyclohexyl |
| 735 | Et | N | 4-(3-quinolyl)cyclohexyl |
| 736 | Et | N | 4-(3-fluorophenyl)-4-hydroxycyclohexyl |
| 737 | Et | N | 3-phenylcyclohexyl |
| 738 | Et | N | 3-phenylcyclopentyl |
| 739 | Et | N | 6-phenyl-3-tetrahydropyranyl |
| 740 | Et | N | 6-(3-fluorophenyl)-3-tetrahydropyranyl |
| 741 | Et | N | 2-phenylcyclopropyl |
| 742 | Et | N | 2-(2-pyridyl)cyclopropyl |
| 743 | Et | N | 2-(3-pyridyl)cyclopropyl |
| 744 | Et | N | 2-(4-pyridyl)cyclopropyl |
| 745 | Et | N | 2-(3-fluorophenyl)cyclopropyl |
| 746 | Et | N | 2-indanyl |
| 747 | Et | N | 2-tetrahydronaphthyl |
| 748 | Et | N | 6-methoxy-2-tetrahydronaphthyl |
| 749 | Et | N | benzyl |
| 750 | Et | N | phenethyl |
| 751 | Et | N | 3-phenylpropyl |
| 752 | Et | N | 4-phenylbutyl |
| 753 | Et | N | 2-methoxyphenethyl |
| 754 | Et | N | 3-methoxyphenethyl |
| 755 | Et | N | 4-methoxyphenethyl |
| 756 | Et | N | 4-fluorophenethyl |
| 757 | Et | N | 4-bromophenethyl |
| 758 | Et | N | 4-chlorophenethyl |
| 759 | Et | N | 3-trifluoromethylphenethyl |
| 760 | Et | N | 3,4-dimethoxyphenethyl |
| 761 | Et | N | 3-propoxyphenethyl |
| 762 | Et | N | 3,5-difluorophenethyl |
| 763 | Et | N | 4-dimethylaminophenethyl |

TABLE 1-continued

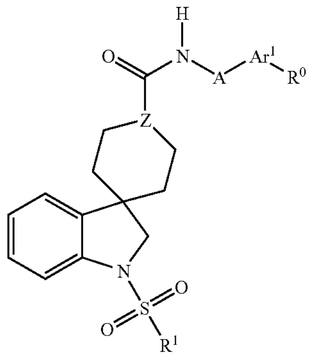

| No. | $R^1$ | Z | A—$Ar^1$—$R^0$ |
|---|---|---|---|
| 764 | Et | N | 3-difluoromethoxyphenethyl |
| 765 | Et | N | 2-methylphenethyl |
| 766 | Et | N | 4-acetylphenethyl |
| 767 | Et | N | 4-dimethylamino-2-methoxyphenethyl |
| 768 | Et | N | cyclohexylethyl |
| 769 | Et | N | 2-(2-pyridyl)ethyl |
| 770 | Et | N | 2-(3-pyridyl)ethyl |
| 771 | Et | N | 2-(4-pyridyl)ethyl |
| 772 | Et | N | 2-(2-quinolyl)ethyl |
| 773 | Et | N | 2-(3-quinolyl)ethyl |
| 774 | Et | N | 2-(4-quinolyl)ethyl |
| 775 | Et | N | 2-(6-quinolyl)ethyl |
| 776 | Et | N | 2-(2-indolyl)ethyl |
| 777 | Et | N | 2-(3-indolyl)ethyl |
| 778 | Et | N | 2-(7-aza-3-indolyl)ethyl |
| 779 | Et | N | 2-(benzimidazolyl)ethyl |
| 780 | Et | N | 2-(benzoxazolyl)ethyl |
| 781 | Et | N | 2-(benzothiazolyl)ethyl |
| 782 | Et | N | 2-(1-naphthyl)ethyl |
| 783 | Et | N | 2-(2-naphthyl)ethyl |
| 784 | Et | N | 1-(hydroxymethyl)-2-phenylethyl |
| 785 | Et | N | 1-(methoxycarbonyl)-2-phenylethyl |
| 786 | Et | N | 1-(ethoxycarbonyl)-2-phenylethyl |
| 787 | Et | N | 1-carboxy-2-phenylethyl |
| 788 | Et | N | 1-(benzyloxycarbonyl)-2-phenylethyl |
| 789 | Et | N | 1-(phenoxymethyl)-2-phenylethyl |
| 790 | Et | N | 1-(benzyloxymethyl)-2-phenylethyl |
| 791 | Et | N | 1-(benzylcarbamoyl)-2-phenylethyl |
| 792 | Et | N | 1-(N-methylbenzylcarbamoyl)-2-phenylethyl |
| 793 | Et | N | 1-(phenylcarbamoyl)-2-phenylethyl |
| 794 | Et | N | 1-(N-methylphenylcarbamoyl)-2-phenylethyl |
| 795 | Et | N | 1-(N-benzylaminomethyl)-2-phenylethyl |
| 796 | Et | N | 1-(N-benzyl-N-methylaminomethyl)-2-phenylethyl |
| 797 | Et | N | 1-(anilinomethyl)-2-phenylethyl |
| 798 | Et | N | 1-(N-methylanilinomethyl)-2-phenylethyl |
| 799 | Et | N | 1-(N-methylaminomethyl)-2-phenylethyl |
| 800 | Et | N | 1-(N-ethylaminomethyl)-2-phenylethyl |
| 801 | Et | N | 1-(N-isobutylaminomethyl)-2-phenylethyl |
| 802 | Et | N | 1-(N-cyclopropylmethylaminomethyl)-2-phenyl-ethyl |
| 803 | Et | N | 1-(aminomethyl)-2-phenylethyl |
| 804 | Et | N | 1-benzyl-2-(2-pyridylmethylamino)ethyl |
| 805 | Et | N | 1-benzyl-2-(3-pyridylmethylamino)ethyl |
| 806 | Et | N | 1-benzyl-2-(4-pyridylmethylamino)ethyl |
| 807 | Et | N | 2-phenyl-1-(2-pyridylmethylcarbamoyl)ethyl |
| 808 | Et | N | 2-phenyl-1-(3-pyridylmethylcarbamoyl)ethyl |
| 809 | Et | N | 2-phenyl-1-(4-pyridylmethylcarbamoyl)ethyl |
| 810 | Et | N | 2-hydroxy-2-phenylethyl |
| 811 | Et | N | benzoylmethyl |
| 812 | Et | N | 1-(benzyloxycarbonyl)-2-(3-indolyl)ethyl |
| 813 | Et | N | 1-(benzyloxycarbonyl)-2-cyclohexylethyl |
| 814 | Et | N | 1-(phenoxymethyl)-2-(3-indolyl)ethyl |
| 815 | Et | N | 2-(2-methoxyphenoxy)ethyl |
| 816 | Et | N | 1-(benzylcarbamoyl)-2-cyclohexylethyl |
| 817 | Et | N | 1-(N-methylbenzylcarbamoyl)-2-cyclohexylethyl |
| 818 | Et | N | 1-(phenylcarbamoyl)-2-cyclohexylethyl |
| 819 | Et | N | 1-(N-methylphenylcarbamoyl)-2-cyclohexylethyl |
| 820 | Et | N | 1-(benzyloxycarbonyl)-2-(3-pyridyl)ethyl |
| 821 | Et | N | 1-(benzylaminomethyl)-2-(3-pyridyl)ethyl |

TABLE 1-continued

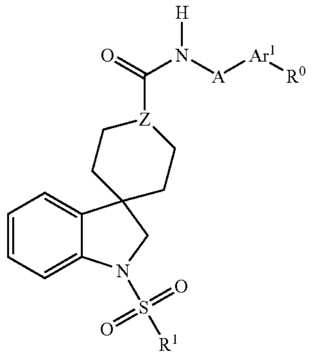

| No. | $R^1$ | Z | A—$Ar^1$—$R^0$ |
|---|---|---|---|
| 822 | Et | N | 1-(benzylcarbamoyl)-2-(4-pyridyl)ethyl |
| 823 | Et | N | 1-(4-pyridylmethylcarbamoyl)-2-(4-fluoro-phenyl)ethyl |
| 824 | Et | N | 1-(benzylcarbamoyl)-2-(7-aza-3-indolyl)ethyl |
| 825 | Et | N | 1-(benzyloxymethyl)-2-(2-indolyl)ethyl |
| 826 | Et | N | 1-(N-benzyl-N-methylaminomethyl)-2-(3-pyridyl)ethyl |
| 827 | Et | N | 1-(N-methylbenzylcarbamoyl)-2-(3-pyridyl)ethyl |
| 828 | Et | N | 2-hydroxy-2-(4-dimethylaminophenyl)ethyl |
| 829 | Et | N | 2-hydroxy-2-(2-quinolyl)ethyl |
| 830 | Et | N | 2-hydroxy-2-(3-quinolyl)ethyl |
| 831 | Et | N | 2-hydroxy-2-(4-quinolyl)ethyl |
| 832 | Et | N | 2-hydroxy-2-(3,5-difluorophenyl)ethyl |
| 833 | Et | N | 1-carboxy-2-cyclohexylethyl |
| 834 | Et | N | 2-hydroxy-2-(6-quinolyl)ethyl |
| 835 | Et | N | 2-(benzylamino)-2-phenylethyl |
| 836 | Et | N | 2-amino-2-(2-naphthyl)propyl |
| 837 | Et | N | 2-(phenylamino)ethyl |
| 838 | Et | N | diphenylmethyl |
| 839 | Et | N | 2,2-diphenylethyl |
| 840 | Et | N | 2-phenyl-2-(2-pyridyl)ethyl |
| 841 | Et | N | 2-phenyl-2-(3-pyridyl)ethyl |
| 842 | Et | N | 2-phenyl-2-(4-pyridyl)ethyl |
| 843 | Et | N | 2-phenoxy-2-phenylethyl |
| 844 | Et | N | 2-(benzyloxy)-2-phenylethyl |

TABLE 2

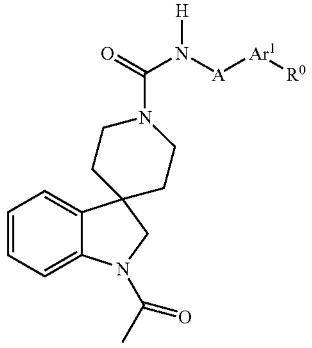

| No. | A—$Ar^1$—$R^0$ |
|---|---|
| 845 | 1-phenyl-3-pyrrolidinyl |
| 846 | 1-(2-fluorophenyl)-3-pyrrolidinyl |

TABLE 2-continued

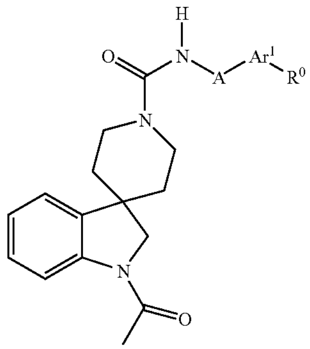

| No. | A—$Ar^1$—$R^0$ |
|---|---|
| 847 | 1-(3-fluorophenyl)-3-pyrrolidinyl |
| 848 | 1-(4-fluorophenyl)-3-pyrrolidinyl |
| 849 | 1-(2-chlorophenyl)-3-pyrrolidinyl |
| 850 | 1-(3-chlorophenyl)-3-pyrrolidinyl |
| 851 | 1-(4-chlorophenyl)-3-pyrrolidinyl |
| 852 | 1-(2-methylphenyl)-3-pyrrolidinyl |
| 853 | 1-(3-methylphenyl)-3-pyrrolidinyl |
| 854 | 1-(4-methylphenyl)-3-pyrrolidinyl |
| 855 | 1-(2-methoxphenyl)-3-pyrrolidinyl |
| 856 | 1-(3-methylphenyl)-3-pyrrolidinyl |
| 857 | 1-(4-methylphenyl)-3-pyrrolidinyl |
| 858 | 1-(2-trifluoromethylphenyl)-3-pyrrolidinyl |
| 859 | 1-(3-trifluoromethylphenyl)-3-pyrrolidinyl |
| 860 | 1-(4-trifluoromethylphenyl)-3-pyrrolidinyl |
| 861 | 1-(3,5-difluorophenyl)-3-pyrrolidinyl |
| 862 | 1-(2-difluoromethoxyphenyl)-3-pyrrolidinyl |
| 863 | 1-(3-difluoromethoxyphenyl)-3-pyrrolidinyl |
| 864 | 1-(4-difluoromethoxyphenyl)-3-pyrrolidinyl |
| 865 | 1-(2-pyridyl)-3-pyrrolidinyl |
| 866 | 1-(3-pyridyl)-3-pyrrolidinyl |
| 867 | 1-(4-pyridyl)-3-pyrrolidinyl |
| 868 | 1-(2-pyrimidinyl)-3-pyrrolidinyl |
| 869 | 5-oxo-1-phenyl-3-pyrrolidinyl |
| 870 | 1-phenyl-3-piperidyl |
| 871 | 1-(2-fluorophenyl)-3-piperidyl |
| 872 | 1-(3-fluorophenyl)-3-piperidyl |
| 873 | 1-(4-fluorophenyl)-3-piperidyl |
| 874 | 1-(2-chlorophenyl)-3-piperidyl |
| 875 | 1-(3-chlorophenyl)-3-piperidyl |
| 876 | 1-(4-chlorophenyl)-3-piperidyl |
| 877 | 1-(2-methylphenyl)-3-piperidyl |
| 878 | 1-(3-methylphenyl)-3-piperidyl |
| 879 | 1-(4-methylphenyl)-3-piperidyl |
| 880 | 1-(2-methoxyphenyl)-3-piperidyl |
| 881 | 1-(3-methoxyphenyl)-3-piperidyl |
| 882 | 1-(4-methoxyphenyl)-3-piperidyl |
| 883 | 1-(2-trifluoromethylphenyl)-3-piperidyl |
| 884 | 1-(3-trifluoromethylphenyl)-3-piperidyl |
| 885 | 1-(4-trifluoromethylphenyl)-3-piperidyl |
| 886 | 1-(3,5-difluorophenyl)-3-piperidyl |
| 887 | 1-(2-difluoromethoxyphenyl)-3-piperidyl |
| 888 | 1-(3-difluoromethoxyphenyl)-3-piperidyl |
| 889 | 1-(4-difluoromethoxyphenyl)-3-piperidyl |
| 890 | 1-(2-pyridyl)-3-piperidyl |
| 891 | 1-(3-pyridyl)-3-piperidyl |
| 892 | 1-(4-pyridyl)-3-piperidyl |
| 893 | 1-phenyl-4-piperidyl |
| 894 | 1-(2-fluorophenyl)-4-piperidyl |
| 895 | 1-(3-fluorophenyl)-4-piperidyl |
| 896 | 1-(4-fluorophenyl)-4-piperidyl |
| 897 | 1-(2-chlorophenyl)-4-piperidyl |
| 898 | 1-(3-chlorophenyl)-4-piperidyl |
| 899 | 1-(4-chlorophenyl)-4-piperidyl |
| 900 | 1-(2-methylphenyl)-4-piperidyl |
| 901 | 1-(3-methylphenyl)-4-piperidyl |
| 902 | 1-(4-methylphenyl)-4-piperidyl |
| 903 | 1-(2-methoxyphenyl)-4-piperidyl |
| 904 | 1-(3-methoxyphenyl)-4-piperidyl |
| 905 | 1-(4-methoxyphenyl)-4-piperidyl |

TABLE 2-continued

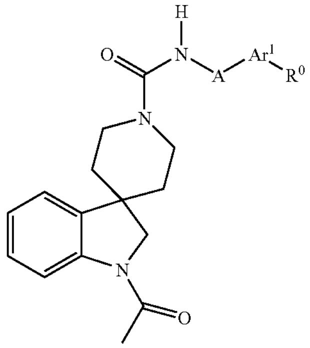

| No. | A—$Ar^1$—$R^0$ |
|---|---|
| 906 | 1-(2-trifluoromethylphenyl)-4-piperidyl |
| 907 | 1-(3-trifluoromethylphenyl)-4-piperidyl |
| 908 | 1-(4-trifluoromethylphenyl)-4-piperidyl |
| 909 | 1-(3,5-difluorophenyl)-4-piperidyl |
| 910 | 1-(2-difluoromethoxyphenyl)-4-piperidyl |
| 911 | 1-(3-difluoromethoxyphenyl)-4-piperidyl |
| 912 | 1-(4-difluoromethoxyphenyl)-4-piperidyl |
| 913 | 1-(2-pyridyl)-4-piperidyl |
| 914 | 1-(3-pyridyl)-4-piperidyl |
| 915 | 1-(4-pyridyl)-4-piperidyl |
| 916 | 3-hydroxymethyl-1-phenyl-4-piperidyl |
| 917 | 3-methoxycarbonyl-1-phenyl-4-piperidyl |
| 918 | 3-ethoxycarbonyl-1-phenyl-4-piperidyl |
| 919 | 3-isopropoxycarbonyl-1-phenyl-4-piperidyl |
| 920 | 4-phenylcyclohexyl |
| 921 | 4-(2-fluorophenyl)cyclohexyl |
| 922 | 4-(3-fluorophenyl)cyclohexyl |
| 923 | 4-(4-fluorophenyl)cyclohexyl |
| 924 | 4-(2-chlorophenyl)cyclohexyl |
| 925 | 4-(3-chlorophenyl)cyclohexyl |
| 926 | 4-(4-chlorophenyl)cyclohexyl |
| 927 | 4-(2-methylphenyl)cyclohexyl |
| 928 | 4-(3-methylphenyl)cyclohexyl |
| 929 | 4-(4-methylphenyl)cyclohexyl |
| 930 | 4-(2-methoxyphenyl)cyclohexyl |
| 931 | 4-(3-methoxyphenyl)cyclohexyl |
| 932 | 4-(4-methoxyphenyl)cyclohexyl |
| 933 | 4-(2-trifluoromethylphenyl)cyclohexyl |
| 934 | 4-(3-trifluoromethylphenyl)cyclohexyl |
| 935 | 4-(4-trifluoromethylphenyl)cyclohexyl |
| 936 | 4-(3,5-difluorophenyl)cyclohexyl |
| 937 | 4-(3-acetylphenyl)cyclohexyl |
| 938 | 4-(3-cyanophenyl)cyclohexyl |
| 939 | 4-(2-difluoromethoxyphenyl)cyclohexyl |
| 940 | 4-(3-difluoromethoxyphenyl)cyclohexyl |
| 941 | 4-(4-difluoromethoxyphenyl)cyclohexyl |
| 942 | 4-(2-pyridyl)cyclohexyl |
| 943 | 4-(3-pyridyl)cyclohexyl |
| 944 | 4-(4-pyridyl)cyclohexyl |
| 945 | 4-(4-fluoro-3-pyridyl)cyclohexyl |
| 946 | 4-(3-quinolyl)cyclohexyl |
| 947 | 4-(3-fluorophenyl)-4-hydroxycyclohexyl |
| 948 | 3-phenylcyclohexyl |
| 949 | 3-phenylcyclopentyl |
| 950 | 6-phenyl-3-tetrahydropyranyl |
| 951 | 6-(3-fluorophenyl)-3-tetrahydropyranyl |
| 952 | 2-phenylcyclopropyl |
| 953 | 2-(2-pyridyl)cyclopropyl |
| 954 | 2-(3-pyridyl)cyclopropyl |
| 955 | 2-(4-pyridyl)cyclopropyl |
| 956 | 2-(3-fluorophenyl)cyclopropyl |
| 957 | 2-indanyl |

TABLE 2-continued

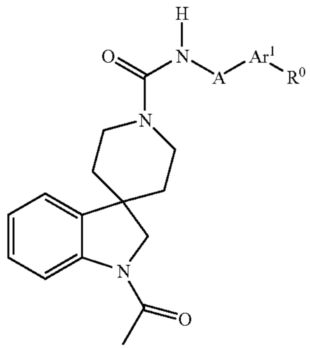

| No. | A—$Ar^1$—$R^0$ |
|---|---|
| 958 | 2-tetrahydronaphthyl |
| 959 | 6-methoxy-2-tetrahydronaphthyl |
| 960 | benzyl |
| 961 | phenethyl |
| 962 | 3-phenylpropyl |
| 963 | 4-phenylbutyl |
| 964 | 2-methoxyphenethyl |
| 965 | 3-methoxyphenethyl |
| 966 | 4-methoxyphenethyl |
| 967 | 4-fluorophenethyl |
| 968 | 4-bromophenethyl |
| 969 | 4-chlorophenethyl |
| 970 | 3-trifluoromethylphenethyl |
| 971 | 3,4-dimethoxyphenethyl |
| 972 | 3-propoxyphenethyl |
| 973 | 3,5-difluorophenethyl |
| 974 | 4-dimethylaminophenethyl |
| 975 | 3-difluoromethoxyphenethyl |
| 976 | 2-methylphenethyl |
| 977 | 4-acetylphenethyl |
| 978 | 4-dimethylamino-2-methoxyphenethyl |
| 979 | cyclohexylethyl |
| 980 | 2-(2-pyridyl)ethyl |
| 981 | 2-(3-pyridyl)ethyl |
| 982 | 2-(4-pyridyl)ethyl |
| 983 | 2-(2-quinolyl)ethyl |
| 984 | 2-(3-quinolyl)ethyl |
| 985 | 2-(4-quinolyl)ethyl |
| 986 | 2-(6-quinolyl)ethyl |
| 987 | 2-(2-indolyl)ethyl |
| 988 | 2-(3-indolyl)ethyl |
| 989 | 2-(7-aza-3-indolyl)ethyl |
| 990 | 2-(benzimidazolyl)ethyl |
| 991 | 2-(benzoxazolyl)ethyl |
| 992 | 2-(benzothiazolyl)ethyl |
| 993 | 2-(1-naphthyl)ethyl |
| 994 | 2-(2-naphthyl)ethyl |
| 995 | 1-(hydroxymethyl)-2-phenylethyl |
| 996 | 1-(methoxycarbonyl)-2-phenylethyl |
| 997 | 1-(ethoxycarbonyl)-2-phenylethyl |
| 998 | 1-carboxy-2-phenylethyl |
| 999 | 1-(benzyloxycarbonyl)-2-phenylethyl |
| 1000 | 1-(phenoxymethyl)-2-phenylethyl |
| 1001 | 1-(benzyloxymethyl)-2-phenylethyl |
| 1002 | 1-(benzylcarbamoyl)-2-phenylethyl |
| 1003 | 1-(N-methylbenzylcarbamoyl)-2-phenylethyl |
| 1004 | 1-(phenylcarbamoyl)-2-phenylethyl |
| 1005 | 1-(N-methylphenylcarbamoyl)-2-phenylethyl |
| 1006 | 1-(N-benzylaminomethyl)-2-phenylethyl |
| 1007 | 1-(N-benzyl-N-methylaminomethyl)-2-phenylethyl |
| 1008 | 1-(anilinomethyl)-2-phenylethyl |
| 1009 | 1-(N-methylanilinomethyl)-2-phenylethyl |
| 1010 | 1-(N-methylaminomethyl)-2-phenylethyl |
| 1011 | 1-(N-ethylaminomethyl)-2-phenylethyl |
| 1012 | 1-(N-isobutylaminomethyl)-2-phenylethyl |
| 1013 | 1-(N-cyclopropylmethylaminomethyl)-2-phenylethyl |
| 1014 | 1-(aminomethyl)-2-phenylethyl |
| 1015 | 1-benzyl-2-(2-pyridylmethylamino)ethyl |
| 1016 | 1-benzyl-2-(3-pyridylmethylamino)ethyl |

TABLE 2-continued

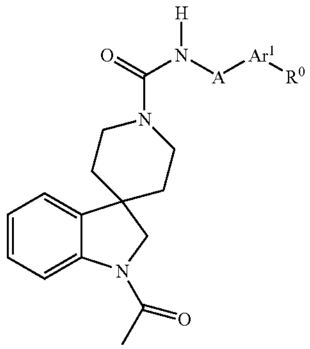

| No. | A—$Ar^1$—$R^0$ |
|---|---|
| 1017 | 1-benzyl-2-(4-pyridylmethylamino)ethyl |
| 1018 | 2-phenyl-1-(2-pyridylmethylcarbamoyl)ethyl |
| 1019 | 2-phenyl-1-(3-pyridylmethylcarbamoyl)ethyl |
| 1020 | 2-phenyl-1-(4-pyridylmethylcarbamoyl)ethyl |
| 1021 | 2-hydroxy-2-phenylethyl |
| 1022 | benzoylmethyl |
| 1023 | 1-(benzyloxycarbonyl)-2-(3-indolyl)ethyl |
| 1024 | 1-(benzyloxycarbonyl)-2-cyclohexylethyl |
| 1025 | 1-(phenoxymethyl)-2-(3-indolyl)ethyl |
| 1026 | 2-(2-methoxyphenoxy)ethyl |
| 1027 | 1-(benzylcarbamoyl)-2-cyclohexylethyl |
| 1028 | 1-(N-methylbenzylcarbamoyl)-2-cyclohexylethyl |
| 1029 | 1-(phenylcarbamoyl)-2-cyclohexylethyl |
| 1030 | 1-(N-methylphenylcarbamoyl)-2-cyclohexylethyl |
| 1031 | 1-(benzyloxycarbonyl)-2-(3-pyridyl)ethyl |
| 1032 | 1-(benzylaminomethyl)-2-(3-pyridyl)ethyl |
| 1033 | 1-(benzylcarbamoyl)-2-(4-pyridyl)ethyl |
| 1034 | 1-(4-pyridylmethylcarbamoyl)-2-(4-fluorophenyl)ethyl |
| 1035 | 1-(benzylcarbamoyl)-2-(7-aza-3-indolyl)ethyl |
| 1036 | 1-(benzyloxymethyl)-2-(2-indolyl)ethyl |
| 1037 | 1-(N-benzyl-N-methylaminomethyl)-2-(3-pyridyl)ethyl |
| 1038 | 1-(N-methylbenzylcarbamoyl)-2-(3-pyridyl)ethyl |
| 1039 | 2-hydroxy-2-(4-dimethylaminophenyl)ethyl |
| 1040 | 2-hydroxy-2-(2-quinolyl)ethyl |
| 1041 | 2-hydroxy-2-(3-quinolyl)ethyl |
| 1042 | 2-hydroxy-2-(4-quinolyl)ethyl |
| 1043 | 2-hydroxy-2-(3,5-difluorophenyl)ethyl |
| 1044 | 1-carboxy-2-cyclohexylethyl |
| 1045 | 2-hydroxy-2-(6-quinolyl)ethyl |
| 1046 | 2-(benzylamino)-2-phenylethyl |
| 1047 | 2-amino-2-(2-naphthyl)propyl |
| 1048 | 2-(phenylamino)ethyl |
| 1049 | diphenylmethyl |
| 1050 | 2,2-diphenylethyl |
| 1051 | 2-phenyl-2-(2-pyridyl)ethyl |
| 1052 | 2-phenyl-2-(3-pyridyl)ethyl |
| 1053 | 2-phenyl-2-(4-pyridyl)ethyl |
| 1054 | 2-phenoxy-2-phenylethyl |
| 1055 | 2-(benzyloxy)-2-phenylethyl |

TABLE 3

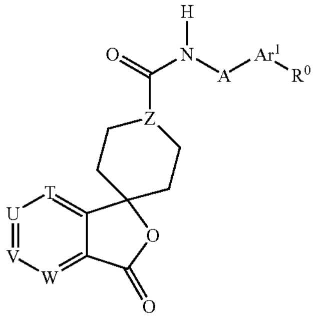

| No. | T | U | V | W | Z | A—$Ar^1$—$R^0$ |
|---|---|---|---|---|---|---|
| 1056 | CH | CH | CH | CH | CH | 1-phenyl-3-pyrrolidinyl |
| 1057 | CH | CH | CH | CH | CH | 1-(2-fluorophenyl)-3-pyrrolidinyl |
| 1058 | CH | CH | CH | CH | CH | 1-(3-fluorophenyl)-3-pyrrolidinyl |
| 1059 | CH | CH | CH | CH | CH | 1-(4-fluorophenyl)-3-pyrrolidinyl |
| 1060 | CH | CH | CH | CH | CH | 1-(2-chlorophenyl)-3-pyrrolidinyl |
| 1061 | CH | CH | CH | CH | CH | 1-(3-chlorophenyl)-3-pyrrolidinyl |
| 1062 | CH | CH | CH | CH | CH | 1-(4-chlorophenyl)-3-pyrrolidinyl |
| 1063 | CH | CH | CH | CH | CH | 1-(2-methylphenyl)-3-pyrrolidinyl |
| 1064 | CH | CH | CH | CH | CH | 1-(3-methylphenyl)-3-pyrrolidinyl |
| 1065 | CH | CH | CH | CH | CH | 1-(4-methylphenyl)-3-pyrrolidinyl |
| 1066 | CH | CH | CH | CH | CH | 1-(2-methoxyyphenyl)-3-pyrrolidinyl |
| 1067 | CH | CH | CH | CH | CH | 1-(3-methoxyyphenyl)-3-pyrrolidinyl |
| 1068 | CH | CH | CH | CH | CH | 1-(4-methoxyyphenyl)-3-pyrrolidinyl |
| 1069 | CH | CH | CH | CH | CH | 1-(2-trifluoromethylphenyl)-3-pyrrolidinyl |
| 1070 | CH | CH | CH | CH | CH | 1-(3-trifluoromethylphenyl)-3-pyrrolidinyl |
| 1071 | CH | CH | CH | CH | CH | 1-(4-trifluoromethylphenyl)-3-pyrrolidinyl |
| 1072 | CH | CH | CH | CH | CH | 1-(3,5-difluorophenyl)-3-pyrrolidinyl |
| 1073 | CH | CH | CH | CH | CH | 1-(2-difluoromethoxyphenyl)-3-pyrrolidinyl |
| 1074 | CH | CH | CH | CH | CH | 1-(3-difluoromethoxyphenyl)-3-pyrrolidinyl |
| 1075 | CH | CH | CH | CH | CH | 1-(4-difluoromethoxyphenyl)-3-pyrrolidinyl |
| 1076 | CH | CH | CH | CH | CH | 1-(2-pyridyl)-3-pyrrolidinyl |
| 1077 | CH | CH | CH | CH | CH | 1-(3-pyridyl)-3-pyrrolidinyl |
| 1078 | CH | CH | CH | CH | CH | 1-(4-pyridyl)-3-pyrrolidinyl |
| 1079 | CH | CH | CH | CH | CH | 1-(2-pyrimidinyl)-3-pyrrolidinyl |
| 1080 | CH | CH | CH | CH | CH | 5-oxo-1-phenyl-3-pyrrolidinyl |
| 1081 | CH | CH | CH | CH | CH | 1-phenyl-3-piperidyl |
| 1082 | CH | CH | CH | CH | CH | 1-(2-fluorophenyl)-3-piperidyl |
| 1083 | CH | CH | CH | CH | CH | 1-(3-fluorophenyl)-3-piperidyl |
| 1084 | CH | CH | CH | CH | CH | 1-(4-fluorophenyl)-3-piperidyl |
| 1085 | CH | CH | CH | CH | CH | 1-(2-chlorophenyl)-3-piperidyl |
| 1086 | CH | CH | CH | CH | CH | 1-(3-chlorophenyl)-3-piperidyl |
| 1087 | CH | CH | CH | CH | CH | 1-(4-chlorophenyl)-3-piperidyl |
| 1088 | CH | CH | CH | CH | CH | 1-(2-methylphenyl)-3-piperidyl |
| 1089 | CH | CH | CH | CH | CH | 1-(3-methylphenyl)-3-piperidyl |
| 1090 | CH | CH | CH | CH | CH | 1-(4-methylphenyl)-3-piperidyl |
| 1091 | CH | CH | CH | CH | CH | 1-(2-methoxyphenyl)-3-piperidyl |
| 1092 | CH | CH | CH | CH | CH | 1-(3-methoxyphenyl)-3-piperidyl |
| 1093 | CH | CH | CH | CH | CH | 1-(4-methoxyphenyl)-3-piperidyl |
| 1094 | CH | CH | CH | CH | CH | 1-(2-trifluoromethylphenyl)-3-piperidyl |
| 1095 | CH | CH | CH | CH | CH | 1-(3-trifluoromethylphenyl)-3-piperidyl |

TABLE 3-continued

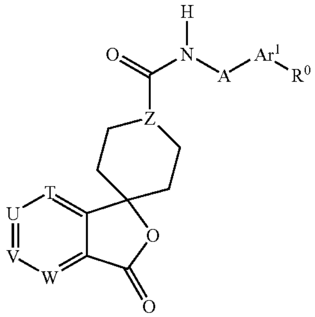

| No. | T | U | V | W | Z | A—Ar$^1$—R$^0$ |
|---|---|---|---|---|---|---|
| 1096 | CH | CH | CH | CH | CH | 1-(4-trifluoromethylphenyl)-3-piperidyl |
| 1097 | CH | CH | CH | CH | CH | 1-(3,5-difluorophenyl)-3-piperidyl |
| 1098 | CH | CH | CH | CH | CH | 1-(2-difluoromethoxyphenyl)-3-piperidyl |
| 1099 | CH | CH | CH | CH | CH | 1-(3-difluoromethoxyphenyl)-3-piperidyl |
| 1100 | CH | CH | CH | CH | CH | 1-(4-difluoromethoxyphenyl)-3-piperidyl |
| 1101 | CH | CH | CH | CH | CH | 1-(2-pyridyl)-3-piperidyl |
| 1102 | CH | CH | CH | CH | CH | 1-(3-pyridyl)-3-piperidyl |
| 1103 | CH | CH | CH | CH | CH | 1-(4-pyridyl)-3-piperidyl |
| 1104 | CH | CH | CH | CH | CH | 1-phenyl-4-piperidyl |
| 1105 | CH | CH | CH | CH | CH | 1-(2-fluorophenyl)-4-piperidyl |
| 1106 | CH | CH | CH | CH | CH | 1-(3-fluorophenyl)-4-piperidyl |
| 1107 | CH | CH | CH | CH | CH | 1-(4-fluorophenyl)-4-piperidyl |
| 1108 | CH | CH | CH | CH | CH | 1-(2-chlorophenyl)-4-piperidyl |
| 1109 | CH | CH | CH | CH | CH | 1-(3-chlorophenyl)-4-piperidyl |
| 1110 | CH | CH | CH | CH | CH | 1-(4-chlorophenyl)-4-piperidyl |
| 1111 | CH | CH | CH | CH | CH | 1-(2-methylphenyl)-4-piperidyl |
| 1112 | CH | CH | CH | CH | CH | 1-(3-methylphenyl)-4-piperidyl |
| 1113 | CH | CH | CH | CH | CH | 1-(4-methylphenyl)-4-piperidyl |
| 1114 | CH | CH | CH | CH | CH | 1-(2-methoxyphenyl)-4-piperidyl |
| 1115 | CH | CH | CH | CH | CH | 1-(3-methoxyphenyl)-4-piperidyl |
| 1116 | CH | CH | CH | CH | CH | 1-(4-methoxyphenyl)-4-piperidyl |
| 1117 | CH | CH | CH | CH | CH | 1-(2-trifluoromethylphenyl)-4-piperidyl |
| 1118 | CH | CH | CH | CH | CH | 1-(3-trifluoromethylphenyl)-4-piperidyl |
| 1119 | CH | CH | CH | CH | CH | 1-(4-trifluoromethylphenyl)-4-piperidyl |
| 1120 | CH | CH | CH | CH | CH | 1-(3,5-difluorophenyl)-4-piperidyl |
| 1121 | CH | CH | CH | CH | CH | 1-(2-difluoromethoxyphenyl)-4-piperidyl |
| 1122 | CH | CH | CH | CH | CH | 1-(3-difluoromethoxyphenyl)-4-piperidyl |
| 1123 | CH | CH | CH | CH | CH | 1-(4-difluoromethoxyphenyl)-4-piperidyl |
| 1124 | CH | CH | CH | CH | CH | 1-(2-pyridyl)-4-piperidyl |
| 1125 | CH | CH | CH | CH | CH | 1-(3-pyridyl)-4-piperidyl |
| 1126 | CH | CH | CH | CH | CH | 1-(4-pyridyl)-4-piperidyl |
| 1127 | CH | CH | CH | CH | CH | 3-hydroxymethyl-1-phenyl-4-piperidyl |
| 1128 | CH | CH | CH | CH | CH | 3-methoxycarbonyl-1-phenyl-4-piperidyl |
| 1129 | CH | CH | CH | CH | CH | 3-ethoxycarbonyl-1-phenyl-4-piperidyl |
| 1130 | CH | CH | CH | CH | CH | 3-isopropoxycarbonyl-1-phenyl-4-piperidyl |
| 1131 | CH | CH | CH | CH | CH | 4-phenylcyclohexyl |
| 1132 | CH | CH | CH | CH | CH | 4-(2-fluorophenyl)cyclohexyl |
| 1133 | CH | CH | CH | CH | CH | 4-(3-fluorophenyl)cyclohexyl |
| 1134 | CH | CH | CH | CH | CH | 4-(4-fluorophenyl)cyclohexyl |
| 1135 | CH | CH | CH | CH | CH | 4-(2-chlorophenyl)cyclohexyl |
| 1136 | CH | CH | CH | CH | CH | 4-(3-chlorophenyl)cyclohexyl |
| 1137 | CH | CH | CH | CH | CH | 4-(4-chlorophenyl)cyclohexyl |
| 1138 | CH | CH | CH | CH | CH | 4-(2-methylphenyl)cyclohexyl |
| 1139 | CH | CH | CH | CH | CH | 4-(3-methylphenyl)cyclohexyl |
| 1140 | CH | CH | CH | CH | CH | 4-(4-methylphenyl)cyclohexyl |
| 1141 | CH | CH | CH | CH | CH | 4-(2-methoxyphenyl)cyclohexyl |
| 1142 | CH | CH | CH | CH | CH | 4-(3-methoxyphenyl)cyclohexyl |

TABLE 3-continued

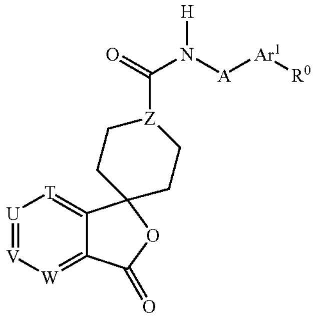

| No. | T | U | V | W | Z | A—$Ar^1$—$R^0$ |
|---|---|---|---|---|---|---|
| 1143 | CH | CH | CH | CH | CH | 4-(4-methoxyphenyl)cyclohexyl |
| 1144 | CH | CH | CH | CH | CH | 4-(2-trifluoromethylphenyl)cyclo-hexyl |
| 1145 | CH | CH | CH | CH | CH | 4-(3-trifluoromethylphenyl)cyclo-hexyl |
| 1146 | CH | CH | CH | CH | CH | 4-(4-trifluoromethylphenyl)cyclo-hexyl |
| 1147 | CH | CH | CH | CH | CH | 4-(3,5-difluorophenyl)cyclohexyl |
| 1148 | CH | CH | CH | CH | CH | 4-(3-acetylphenyl)cyclohexyl |
| 1149 | CH | CH | CH | CH | CH | 4-(3-cyanophenyl)cyclohexyl |
| 1150 | CH | CH | CH | CH | CH | 4-(2-difluoromethoxyphenyl)cyclo-hexyl |
| 1151 | CH | CH | CH | CH | CH | 4-(3-difluoromethoxyphenyl)cyclo-hexyl |
| 1152 | CH | CH | CH | CH | CH | 4-(4-difluoromethoxyphenyl)cyclo-hexyl |
| 1153 | CH | CH | CH | CH | CH | 4-(2-pyridyl)cyclohexyl |
| 1154 | CH | CH | CH | CH | CH | 4-(3-pyridyl)cyclohexyl |
| 1155 | CH | CH | CH | CH | CH | 4-(4-pyridyl)cyclohexyl |
| 1156 | CH | CH | CH | CH | CH | 4-(4-fluoro-3-pyridyl)cyclohexyl |
| 1157 | CH | CH | CH | CH | CH | 4-(3-quinolyl)cyclohexyl |
| 1158 | CH | CH | CH | CH | CH | 4-(3-fluorophenyl)-4-hydroxy-cyclohexyl |
| 1159 | CH | CH | CH | CH | CH | 3-phenylcyclohexyl |
| 1160 | CH | CH | CH | CH | CH | 3-phenylcyclopentyl |
| 1161 | CH | CH | CH | CH | CH | 6-phenyl-3-tetrhydropyranyl |
| 1162 | CH | CH | CH | CH | CH | 6-(3-fluorophenyl)-3-tetrhydro-pyranyl |
| 1163 | CH | CH | CH | CH | CH | 2-phenylcyclopropyl |
| 1164 | CH | CH | CH | CH | CH | 2-(2-pyridyl)cyclopropyl |
| 1165 | CH | CH | CH | CH | CH | 2-(3-pyridyl)cyclopropyl |
| 1166 | CH | CH | CH | CH | CH | 2-(4-pyridyl)cyclopropyl |
| 1167 | CH | CH | CH | CH | CH | 2-(3-fluorophenyl)cyclopropyl |
| 1168 | CH | CH | CH | CH | CH | 2-indanyl |
| 1169 | CH | CH | CH | CH | CH | 2-tetrahydronaphthyl |
| 1170 | CH | CH | CH | CH | CH | 6-methoxy-2-tetrahydronaphthyl |
| 1171 | CH | CH | CH | CH | CH | benzyl |
| 1172 | CH | CH | CH | CH | CH | phenethyl |
| 1173 | CH | CH | CH | CH | CH | 3-phenylpropyl |
| 1174 | CH | CH | CH | CH | CH | 4-phenylbutyl |
| 1175 | CH | CH | CH | CH | CH | 2-methoxyphenethyl |
| 1176 | CH | CH | CH | CH | CH | 3-methoxyphenethyl |
| 1177 | CH | CH | CH | CH | CH | 4-methoxyphenethyl |
| 1178 | CH | CH | CH | CH | CH | 4-fluorophenethyl |
| 1179 | CH | CH | CH | CH | CH | 4-bromophenethyl |
| 1180 | CH | CH | CH | CH | CH | 4-chlorophenethyl |
| 1181 | CH | CH | CH | CH | CH | 3-trifluoromethylphenethyl |
| 1182 | CH | CH | CH | CH | CH | 3,4-dimethoxyphenethyl |
| 1183 | CH | CH | CH | CH | CH | 3-propoxyphenethyl |
| 1184 | CH | CH | CH | CH | CH | 3,5-difluorophenethyl |
| 1185 | CH | CH | CH | CH | CH | 4-dimethylaminophenethyl |
| 1186 | CH | CH | CH | CH | CH | 3-difluoromethoxyphenethyl |
| 1187 | CH | CH | CH | CH | CH | 2-methylphenethyl |
| 1188 | CH | CH | CH | CH | CH | 4-acetylphenethyl |
| 1189 | CH | CH | CH | CH | CH | 4-dimethylamino-2-methoxyphenethyl |
| 1190 | CH | CH | CH | CH | CH | cyclohexylethyl |
| 1191 | CH | CH | CH | CH | CH | 2-(2-pyridyl)ethyl |
| 1192 | CH | CH | CH | CH | CH | 2-(3-pyridyl)ethyl |
| 1193 | CH | CH | CH | CH | CH | 2-(4-pyridyl)ethyl |
| 1194 | CH | CH | CH | CH | CH | 2-(2-quinolyl)ethyl |
| 1195 | CH | CH | CH | CH | CH | 2-(3-quinolyl)ethyl |

TABLE 3-continued

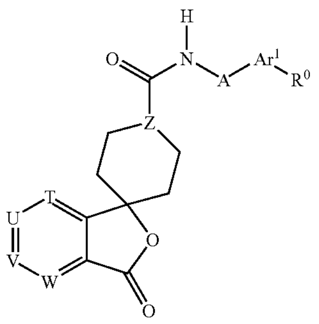

| No. | T | U | V | W | Z | A—Ar$^1$—R$^0$ |
|---|---|---|---|---|---|---|
| 1196 | CH | CH | CH | CH | CH | 2-(4-quinolyl)ethyl |
| 1197 | CH | CH | CH | CH | CH | 2-(6-quinolyl)ethyl |
| 1198 | CH | CH | CH | CH | CH | 2-(2-indolyl)ethyl |
| 1199 | CH | CH | CH | CH | CH | 2-(3-indolyl)ethyl |
| 1200 | CH | CH | CH | CH | CH | 2-(7-aza-3-indolyl)ethyl |
| 1201 | CH | CH | CH | CH | CH | 2-(benzimidazolyl)ethyl |
| 1202 | CH | CH | CH | CH | CH | 2-(benzoxazolyl)ethyl |
| 1203 | CH | CH | CH | CH | CH | 2-(benzothiazolyl)ethyl |
| 1204 | CH | CH | CH | CH | CH | 2-(1-naphthyl)ethyl |
| 1205 | CH | CH | CH | CH | CH | 2-(2-naphthyl)ethyl |
| 1206 | CH | CH | CH | CH | CH | 1-(hydroxymethyl)-2-phenylethyl |
| 1207 | CH | CH | CH | CH | CH | 1-(methoxycarbonyl)-2-phenylethyl |
| 1208 | CH | CH | CH | CH | CH | 1-(ethoxycarbonyl)-2-phenylethyl |
| 1209 | CH | CH | CH | CH | CH | 1-carboxy-2-phenylethyl |
| 1210 | CH | CH | CH | CH | CH | 1-(benzyloxycarbonyl)-2-phenyl-ethyl |
| 1211 | CH | CH | CH | CH | CH | 1-(phenoxymethyl)-2-phenylethyl |
| 1212 | CH | CH | CH | CH | CH | 1-(benzyloxymethyl)-2-phenylethyl |
| 1213 | CH | CH | CH | CH | CH | 1-(benzylcarbamoyl)-2-phenylethyl |
| 1214 | CH | CH | CH | CH | CH | 1-(N-methylbenzylcarbamoyl)-2-phenylethyl |
| 1215 | CH | CH | CH | CH | CH | 1-(phenylcarbamoyl)-2-phenylethyl |
| 1216 | CH | CH | CH | CH | CH | 1-(N-methylphenylcarbamoyl)-2-phenylethyl |
| 1217 | CH | CH | CH | CH | CH | 1-(N-benzylaminomethyl)-2-phenyl-ethyl |
| 1218 | CH | CH | CH | CH | CH | 1-(N-benzyl-N-methylaminomethyl)-2-phenylethyl |
| 1219 | CH | CH | CH | CH | CH | 1-(anilinomethyl)-2-phenylethyl |
| 1220 | CH | CH | CH | CH | CH | 1-(N-methylanilinomethyl)-2-phenylethyl |
| 1221 | CH | CH | CH | CH | CH | 1-(N-methylaminomethyl)-2-phenylethyl |
| 1222 | CH | CH | CH | CH | CH | 1-(N-ethylaminomethyl)-2-phenylethyl |
| 1223 | CH | CH | CH | CH | CH | 1-(N-isobutylaminomethyl)-2-phenylethyl |
| 1224 | CH | CH | CH | CH | CH | 1-(N-cyclopropylmethylamino-methyl)-2-phenylethyl |
| 1225 | CH | CH | CH | CH | CH | 1-(aminomethyl)-2-phenylethyl |
| 1226 | CH | CH | CH | CH | CH | 1-benzyl-2-(2-pyridylmethyl-amino)ethyl |
| 1227 | CH | CH | CH | CH | CH | 1-benzyl-2-(3-pyridylmethyl-amino)ethyl |
| 1228 | CH | CH | CH | CH | CH | 1-benzyl-2-(4-pyridylmethyl-amino)ethyl |
| 1229 | CH | CH | CH | CH | CH | 2-phenyl-1-(2-pyridylmethyl-carbamoyl)ethyl |
| 1230 | CH | CH | CH | CH | CH | 2-phenyl-1-(3-pyridylmethyl-carbamoyl)ethyl |
| 1231 | CH | CH | CH | CH | CH | 2-phenyl-1-(4-pyridylmethyl-carbamoyl)ethyl |
| 1232 | CH | CH | CH | CH | CH | 2-hydroxy-2-phenylethyl |
| 1233 | CH | CH | CH | CH | CH | benzoylmethyl |
| 1234 | CH | CH | CH | CH | CH | 1-(benzyloxycarbonyl)-2-(3-indolyl)ethyl |
| 1235 | CH | CH | CH | CH | CH | 1-(benzyloxycarbonyl)-2-cyclo-hexylethyl |
| 1236 | CH | CH | CH | CH | CH | 1-(phenoxymethyl)-2-(3-indolyl)ethyl |
| 1237 | CH | CH | CH | CH | CH | 2-(2-methoxyphenoxy)ethyl |

TABLE 3-continued

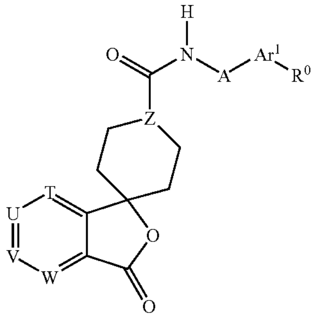

| No. | T | U | V | W | Z | A—$Ar^1$—$R^0$ |
|---|---|---|---|---|---|---|
| 1238 | CH | CH | CH | CH | CH | 1-(benzylcarbamoyl)-2-cyclohexyl-ethyl |
| 1239 | CH | CH | CH | CH | CH | 1-(N-methylbenzylcarbamoyl)-2-cyclohexylethyl |
| 1240 | CH | CH | CH | CH | CH | 1-(phenylcarbamoyl)-2-cyclohexyl-ethyl |
| 1241 | CH | CH | CH | CH | CH | 1-(N-methylphenylcarbamoyl)-2-cyclohexylethyl |
| 1242 | CH | CH | CH | CH | CH | 1-(benzyloxycarbonyl)-2-(3-pyridyl)ethyl |
| 1243 | CH | CH | CH | CH | CH | 1-(benzylaminomethyl)-2-(3-pyridyl)ethyl |
| 1244 | CH | CH | CH | CH | CH | 1-(benzylcarbamoyl)-2-(4-pyridyl)ethyl |
| 1245 | CH | CH | CH | CH | CH | 1-(4-pyridylmethylcarbamoyl)-2-(4-fluorophenyl)ethyl |
| 1246 | CH | CH | CH | CH | CH | 1-(benzylcarbamoyl)-2-(7-aza-3-indolyl)ethyl |
| 1247 | CH | CH | CH | CH | CH | 1-(benzyloxymethyl)-2-(2-indolyl)ethyl |
| 1248 | CH | CH | CH | CH | CH | 1-(N-benzyl-N-methylaminomethyl)-2-(3-pyridyl)ethyl |
| 1249 | CH | CH | CH | CH | CH | 1-(N-methylbenzylcarbamoyl)-2-(3-pyridyl)ethyl |
| 1250 | CH | CH | CH | CH | CH | 2-hydroxy-2-(4-dimethylamino-phenyl)ethyl |
| 1251 | CH | CH | CH | CH | CH | 2-hydroxy-2-(2-quinolyl)ethyl |
| 1252 | CH | CH | CH | CH | CH | 2-hydroxy-2-(3-quinolyl)ethyl |
| 1253 | CH | CH | CH | CH | CH | 2-hydroxy-2-(4-quinolyl)ethyl |
| 1254 | CH | CH | CH | CH | CH | 2-hydroxy-2-(3,5-difluoro-phenyl)ethyl |
| 1255 | CH | CH | CH | CH | CH | 1-carboxy-2-cyclohexylethyl |
| 1256 | CH | CH | CH | CH | CH | 2-hydroxy-2-(6-quinolyl)ethyl |
| 1257 | CH | CH | CH | CH | CH | 2-(benzylamino)-2-phenylethyl |
| 1258 | CH | CH | CH | CH | CH | 2-amino-2-(2-naphthyl)propyl |
| 1259 | CH | CH | CH | CH | CH | 2-(phenylamino)ethyl |
| 1260 | CH | CH | CH | CH | CH | diphenylmethyl |
| 1261 | CH | CH | CH | CH | CH | 2,2-diphenylethyl |
| 1262 | CH | CH | CH | CH | CH | 2-phenyl-2-(2-pyridyl)ethyl |
| 1263 | CH | CH | CH | CH | CH | 2-phenyl-2-(3-pyridyl)ethyl |
| 1264 | CH | CH | CH | CH | CH | 2-phenyl-2-(4-pyridyl)ethyl |
| 1265 | CH | CH | CH | CH | CH | 2-phenoxy-2-phenylethyl |
| 1266 | CH | CH | CH | CH | CH | 2-(benzyloxy)-2-phenylethyl |
| 1267 | CH | CH | CH | CH | N | 1-phenyl-3-pyrrolidinyl |
| 1268 | CH | CH | CH | CH | N | 1-(2-fluorophenyl)-3-pyrrolidinyl |
| 1269 | CH | CH | CH | CH | N | 1-(3-fluorophenyl)-3-pyrrolidinyl |
| 1270 | CH | CH | CH | CH | N | 1-(4-fluorophenyl)-3-pyrrolidinyl |
| 1271 | CH | CH | CH | CH | N | 1-(2-chlorophenyl)-3-pyrrolidinyl |
| 1272 | CH | CH | CH | CH | N | 1-(3-chlorophenyl)-3-pyrrolidinyl |
| 1273 | CH | CH | CH | CH | N | 1-(4-chlorophenyl)-3-pyrrolidinyl |
| 1274 | CH | CH | CH | CH | N | 1-(2-methylphenyl)-3-pyrrolidinyl |
| 1275 | CH | CH | CH | CH | N | 1-(3-methylphenyl)-3-pyrrolidinyl |
| 1276 | CH | CH | CH | CH | N | 1-(4-methylphenyl)-3-pyrrolidinyl |
| 1277 | CH | CH | CH | CH | N | 1-(2-methoxyphenyl)-3-pyrrolidinyl |
| 1278 | CH | CH | CH | CH | N | 1-(3-methoxyphenyl)-3-pyrrolidinyl |
| 1279 | CH | CH | CH | CH | N | 1-(4-methoxyphenyl)-3-pyrrolidinyl |
| 1280 | CH | CH | CH | CH | N | 1-(2-trifluoromethylphenyl)-3-pyrrolidinyl |
| 1281 | CH | CH | CH | CH | N | 1-(3-trifluromethylphenyl)-3-pyrrolidinyl |

TABLE 3-continued

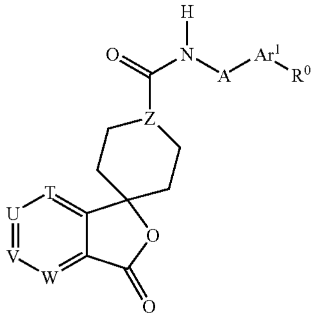

| No. | T | U | V | W | Z | A—$Ar^1$—$R^0$ |
|---|---|---|---|---|---|---|
| 1282 | CH | CH | CH | CH | N | 1-(4-trifluromethylphenyl)-3-pyrrolidinyl |
| 1283 | CH | CH | CH | CH | N | 1-(3,5-diflurophenyl)-3-pyrrolidinyl |
| 1284 | CH | CH | CH | CH | N | 1-(2-difluromethoxyphenyl)-3-pyrrolidinyl |
| 1285 | CH | CH | CH | CH | N | 1-(3-difluromethoxyphenyl)-3-pyrrolidinyl |
| 1286 | CH | CH | CH | CH | N | 1-(4-difluromethoxyphenyl)-3-pyrrolidinyl |
| 1287 | CH | CH | CH | CH | N | 1-(2-pyridyl)-3-pyrrolidinyl |
| 1288 | CH | CH | CH | CH | N | 1-(3-pyridyl)-3-pyrrolidinyl |
| 1289 | CH | CH | CH | CH | N | 1-(4-pyridyl)-3-pyrrolidinyl |
| 1290 | CH | CH | CH | CH | N | 1-(2-pyrimidinyl)-3-pyrrolidinyl |
| 1291 | CH | CH | CH | CH | N | 5-oxo-1-phenyl-3-pyrrolidinyl |
| 1292 | CH | CH | CH | CH | N | 1-phenyl-3-piperidyl |
| 1293 | CH | CH | CH | CH | N | 1-(2-fluorophenyl)-3-piperidyl |
| 1294 | CH | CH | CH | CH | N | 1-(3-fluorophenyl)-3-piperidyl |
| 1295 | CH | CH | CH | CH | N | 1-(4-fluorophenyl)-3-piperidyl |
| 1296 | CH | CH | CH | CH | N | 1-(2-chlorophenyl)-3-piperidyl |
| 1297 | CH | CH | CH | CH | N | 1-(3-chlorophenyl)-3-piperidyl |
| 1298 | CH | CH | CH | CH | N | 1-(4-chlorophenyl)-3-piperidyl |
| 1299 | CH | CH | CH | CH | N | 1-(2-methylphenyl)-3-piperidyl |
| 1300 | CH | CH | CH | CH | N | 1-(3-methylphenyl)-3-piperidyl |
| 1301 | CH | CH | CH | CH | N | 1-(4-methylphenyl)-3-piperidyl |
| 1302 | CH | CH | CH | CH | N | 1-(2-methoxyphenyl)-3-piperidyl |
| 1303 | CH | CH | CH | CH | N | 1-(3-methoxyphenyl)-3-piperidyl |
| 1304 | CH | CH | CH | CH | N | 1-(4-methoxyphenyl)-3-piperidyl |
| 1305 | CH | CH | CH | CH | N | 1-(2-trifluoromethylphenyl)-3-piperidyl |
| 1306 | CH | CH | CH | CH | N | 1-(3-trifluoromethylphenyl)-3-piperidyl |
| 1307 | CH | CH | CH | CH | N | 1-(4-trifluoromethylphenyl)-3-piperidyl |
| 1308 | CH | CH | CH | CH | N | 1-(3,5-difluorophenyl)-3-piperidyl |
| 1309 | CH | CH | CH | CH | N | 1-(2-difluoromethoxyphenyl)-3-piperidyl |
| 1310 | CH | CH | CH | CH | N | 1-(3-difluoromethoxyphenyl)-3-piperidyl |
| 1311 | CH | CH | CH | CH | N | 1-(4-difluoromethoxyphenyl)-3-piperidyl |
| 1312 | CH | CH | CH | CH | N | 1-(2-pyridyl)-3-piperidyl |
| 1313 | CH | CH | CH | CH | N | 1-(3-pyridyl)-3-piperidyl |
| 1314 | CH | CH | CH | CH | N | 1-(4-pyridyl)-3-piperidyl |
| 1315 | CH | CH | CH | CH | N | 1-phenyl-4-piperidyl |
| 1316 | CH | CH | CH | CH | N | 1-(2-fluorophenyl)-4-piperidyl |
| 1317 | CH | CH | CH | CH | N | 1-(3-fluorophenyl)-4-piperidyl |
| 1318 | CH | CH | CH | CH | N | 1-(4-fluorophenyl)-4-piperidyl |
| 1319 | CH | CH | CH | CH | N | 1-(2-chlorophenyl)-4-piperidyl |
| 1320 | CH | CH | CH | CH | N | 1-(3-chlorophenyl)-4-piperidyl |
| 1321 | CH | CH | CH | CH | N | 1-(4-chlorophenylj-4-piperidyl |
| 1322 | CH | CH | CH | CH | N | 1-(2-methylphenyl)-4-piperidyl |
| 1323 | CH | CH | CH | CH | N | 1-(3-methylphenyl)-4-piperidyl |
| 1324 | CH | CH | CH | CH | N | 1-(4-methylphenyl)-4-piperidyl |
| 1325 | CH | CH | CH | CH | N | 1-(2-methoxyphenyl)-4-piperidyl |
| 1326 | CH | CH | CH | CH | N | 1-(3-methoxyphenyl)-4-piperidyl |
| 1327 | CH | CH | CH | CH | N | 1-(4-methoxyphenyl)-4-piperidyl |
| 1328 | CH | CH | CH | CH | N | 1-(2-trifluoromethylphenyl)-4-piperidyl |
| 1329 | CH | CH | CH | CH | N | 1-(3-trifluoromethylphenyl)-4-piperidyl |

TABLE 3-continued

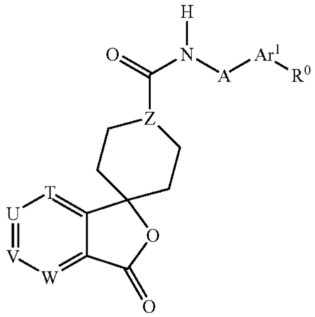

| No. | T | U | V | W | Z | A—$Ar^1$—$R^0$ |
|---|---|---|---|---|---|---|
| 1330 | CH | CH | CH | CH | N | 1-(4-trifluoromethylphenyl)-4-piperidyl |
| 1331 | CH | CH | CH | CH | N | 1-(3,5-difluorophenyl)-4-piperidyl |
| 1332 | CH | CH | CH | CH | N | 1-(2-difluoromethoxyphenyl)-4-piperidyl |
| 1333 | CH | CH | CH | CH | N | 1-(3-difluoromethoxyphenyl)-4-piperidyl |
| 1334 | CH | CH | CH | CH | N | 1-(4-difluoromethoxyphenyl)-4-piperidyl |
| 1335 | CH | CH | CH | CH | N | 1-(2-pyridyl)-4-piperidyl |
| 1336 | CH | CH | CH | CH | N | 1-(3-pyridyl)-4-piperidyl |
| 1337 | CH | CH | CH | CH | N | 1-(4-pyridyl)-4-piperidyl |
| 1338 | CH | CH | CH | CH | N | 3-hydroxymethyl-1-phenyl-4-piperidyl |
| 1339 | CH | CH | CH | CH | N | 3-methoxycarbonyl-1-phenyl-4-piperidyl |
| 1340 | CH | CH | CH | CH | N | 3-ethoxycarbonyl-1-phenyl-4-piperidyl |
| 1341 | CH | CH | CH | CH | N | 3-isopropoxycarbonyl-1-phenyl-4-piperidyl |
| 1342 | CH | CH | CH | CH | N | 4-phenylcyclohexyl |
| 1343 | CH | CH | CH | CH | N | 4-(2-fluorophenyl)cyclohexyl |
| 1344 | CH | CH | CH | CH | N | 4-(3-fluorophenyl)cyclohexyl |
| 1345 | CH | CH | CH | CH | N | 4-(4-fluorophenyl)cyclohexyl |
| 1346 | CH | CH | CH | CH | N | 4-(2-chlorophenyl)cyclohexyl |
| 1347 | CH | CH | CH | CH | N | 4-(3-chlorophenyl)cyclohexyl |
| 1348 | CH | CH | CH | CH | N | 4-(4-chlorophenyl)cyclohexyl |
| 1349 | CH | CH | CH | CH | N | 4-(2-methylphenyl)cyclohexyl |
| 1350 | CH | CH | CH | CH | N | 4-(3-methylphenyl)cyclohexyl |
| 1351 | CH | CH | CH | CH | N | 4-(4-methylphenyl)cyclohexyl |
| 1352 | CH | CH | CH | CH | N | 4-(2-methoxyphenyl)cyclohexyl |
| 1353 | CH | CH | CH | CH | N | 4-(3-methoxyphenyl)cyclohexyl |
| 1354 | CH | CH | CH | CH | N | 4-(4-methoxyphenyl)cyclohexyl |
| 1355 | CH | CH | CH | CH | N | 4-(2-trifluoromethylphenyl)cyclohexyl |
| 1356 | CH | CH | CH | CH | N | 4-(3-trifluoromethylphenyl)cyclohexyl |
| 1357 | CH | CH | CH | CH | N | 4-(4-trifluoromethylphenyl)cyclohexyl |
| 1358 | CH | CH | CH | CH | N | 4-(3,5-difluorophenyl)cyclohexyl |
| 1359 | CH | CH | CH | CH | N | 4-(3-acetylphenyl)cyclohexyl |
| 1360 | CH | CH | CH | CH | N | 4-(3-cyanophenyl)cyclohexyl |
| 1361 | CH | CH | CH | CH | N | 4-(2-difluoromethoxyphenyl)cyclohexyl |
| 1362 | CH | CH | CH | CH | N | 4-(3-difluoromethoxyphenyl)cyclohexyl |
| 1363 | CH | CH | CH | CH | N | 4-(4-difluoromethoxyphenyl)cyclohexyl |
| 1364 | CH | CH | CH | CH | N | 4-(2-pyridyl)cyclohexyl |
| 1365 | CH | CH | CH | CH | N | 4-(3-pyridyl)cyclohexyl |
| 1366 | CH | CH | CH | CH | N | 4-(4-pyridyl)cyclohexyl |
| 1367 | CH | CH | CH | CH | N | 4-(4-fluoro-3-pyridyl)cyclohexyl |
| 1368 | CH | CH | CH | CH | N | 4-(3-quinolyl)cyclohexyl |
| 1369 | CH | CH | CH | CH | N | 4-(3-fluorophenyl)-4-hydroxycyclohexyl |
| 1370 | CH | CH | CH | CH | N | 3-phenylcyclohexyl |
| 1371 | CH | CH | CH | CH | N | 3-phenylcyclopentyl |
| 1372 | CH | CH | CH | CH | N | 6-phenyl-3-tetrahydropyranyl |
| 1373 | CH | CH | CH | CH | N | 6-(3-fluorophenyl)-3-tetrahydropyranyl |

TABLE 3-continued

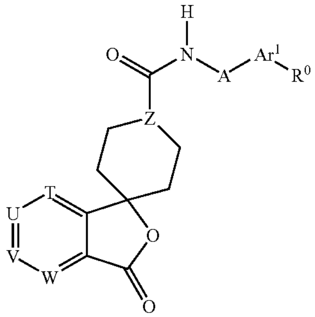

| No. | T | U | V | W | Z | A—Ar$^1$—R$^0$ |
|---|---|---|---|---|---|---|
| 1374 | CH | CH | CH | CH | N | 2-phenylcyclopropyl |
| 1375 | CH | CH | CH | CH | N | 2-(2-pyridyl)cyclopropyl |
| 1376 | CH | CH | CH | CH | N | 2-(3-pyridyl)cyclopropyl |
| 1377 | CH | CH | CH | CH | N | 2-(4-pyridyl)cyclopropyl |
| 1378 | CH | CH | CH | CH | N | 2-(3-fluorophenyl)cyclopropyl |
| 1379 | CH | CH | CH | CH | N | 2-indanyl |
| 1380 | CH | CH | CH | CH | N | 2-tetrahydronaphthyl |
| 1381 | CH | CH | CH | CH | N | 6-methoxy-2-tetrahydronaphthyl |
| 1382 | CH | CH | CH | CH | N | benzyl |
| 1383 | CH | CH | CH | CH | N | phenethyl |
| 1384 | CH | CH | CH | CH | N | 3-phenylpropyl |
| 1385 | CH | CH | CH | CH | N | 4-phenylbutyl |
| 1386 | CH | CH | CH | CH | N | 2-methoxyphenethyl |
| 1387 | CH | CH | CH | CH | N | 3-methoxyphenethyl |
| 1388 | CH | CH | CH | CH | N | 4-methoxyphenethyl |
| 1389 | CH | CH | CH | CH | N | 4-fluorophenethyl |
| 1390 | CH | CH | CH | CH | N | 4-bromophenethyl |
| 1391 | CH | CH | CH | CH | N | 4-chlorophenethyl |
| 1392 | CH | CH | CH | CH | N | 3-trifluoromethylphenethyl |
| 1393 | CH | CH | CH | CH | N | 3,4-dimethoxyphenethyl |
| 1394 | CH | CH | CH | CH | N | 3-propoxyphenethyl |
| 1395 | CH | CH | CH | CH | N | 3,5-difluorophenethyl |
| 1396 | CH | CH | CH | CH | N | 4-dimethylaminophenethyl |
| 1397 | CH | CH | CH | CH | N | 3-difluoromethoxyphenethyl |
| 1398 | CH | CH | CH | CH | N | 2-methylphenethyl |
| 1399 | CH | CH | CH | CH | N | 4-acetylphenethyl |
| 1400 | CH | CH | CH | CH | N | 4-dimethylamino-2-methoxy-phenethyl |
| 1401 | CH | CH | CH | CH | N | cyclohexylethyl |
| 1402 | CH | CH | CH | CH | N | 2-(2-pyridyl)ethyl |
| 1403 | CH | CH | CH | CH | N | 2-(3-pyridyl)ethyl |
| 1404 | CH | CH | CH | CH | N | 2-(4-pyridyl)ethyl |
| 1405 | CH | CH | CH | CH | N | 2-(2-quinolyl)ethyl |
| 1406 | CH | CH | CH | CH | N | 2-(3-quinolyl)ethyl |
| 1407 | CH | CH | CH | CH | N | 2-(4-quinolyl)ethyl |
| 1408 | CH | CH | CH | CH | N | 2-(6-quinolyl)ethyl |
| 1409 | CH | CH | CH | CH | N | 2-(2-indolyl)ethyl |
| 1410 | CH | CH | CH | CH | N | 2-(3-indolyl)ethyl |
| 1411 | CH | CH | CH | CH | N | 2-(7-aza-3-indolyl)ethyl |
| 1412 | CH | CH | CH | CH | N | 2-(benzimidazolyl)ethyl |
| 1413 | CH | CH | CH | CH | N | 2-(benzoxazolyl)ethyl |
| 1414 | CH | CH | CH | CH | N | 2-(benzothiazolyl)ethyl |
| 1415 | CH | CH | CH | CH | N | 2-(1-naphthyl)ethyl |
| 1416 | CH | CH | CH | CH | N | 2-(2-naphthyl)ethyl |
| 1417 | CH | CH | CH | CH | N | 1-(hydroxymethyl)-2-phenylethyl |
| 1418 | CH | CH | CH | CH | N | 1-(methoxycarbonyl)-2-phenyl-ethyl |
| 1419 | CH | CH | CH | CH | N | 1-(ethoxycarbonyl)-2-phenylethyl |
| 1420 | CH | CH | CH | CH | N | 1-carboxy-2-phenylethyl |
| 1421 | CH | CH | CH | CH | N | 1-(benzyloxycarbonyl)-2-phenyl-ethyl |
| 1422 | CH | CH | CH | CH | N | 1-(phenoxymethyl)-2-phenylethyl |
| 1423 | CH | CH | CH | CH | N | 1-(benzyloxymethyl)-2-phenylethyl |
| 1424 | CH | CH | CH | CH | N | 1-(benzylcarbamoyl)-2-phenylethyl |
| 1425 | CH | CH | CH | CH | N | 1-(N-methylbenzylcarbamoyl)-2-phenylethyl |
| 1426 | CH | CH | CH | CH | N | 1-(phenylcarbamoyl)-2-phenylethyl |
| 1427 | CH | CH | CH | CH | N | 1-(N-methylphenylcarbamoyl)-2-phenylethyl |
| 1428 | CH | CH | CH | CH | N | 1-(N-benzylaminomethyl)-2-phenylethyl |

TABLE 3-continued

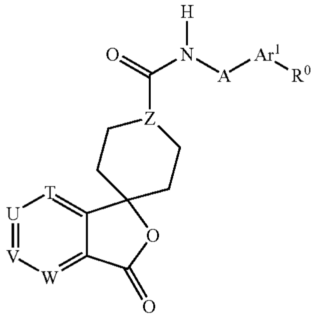

| No. | T | U | V | W | Z | A—$Ar^1$—$R^0$ |
|---|---|---|---|---|---|---|
| 1429 | CH | CH | CH | CH | N | 1-(N-benzyl-N-methylamino-methyl)-2-phenylethyl |
| 1430 | CH | CH | CH | CH | N | 1-(anilinomethyl)-2-phenylethyl |
| 1431 | CH | CH | CH | CH | N | 1-(N-methylanilinomethyl)-2-phenylethyl |
| 1432 | CH | CH | CH | CH | N | 1-(N-methylaminomethyl)-2-phenylethyl |
| 1433 | CH | CH | CH | CH | N | 1-(N-ethylaminomethyl)-2-phenylethyl |
| 1434 | CH | CH | CH | CH | N | 1-(N-isobutylaminomethyl)-2-phenylethyl |
| 1435 | CH | CH | CH | CH | N | 1-(N-cyclopropylmethylamino-methyl)-2-phenylethyl |
| 1436 | CH | CH | CH | CH | N | 1-(aminomethyl)-2-phenylethyl |
| 1437 | CH | CH | CH | CH | N | 1-benzyl-2-(2-pyridylmethyl-amino)ethyl |
| 1438 | CH | CH | CH | CH | N | 1-benzyl-2-(3-pyridylmethyl-amino)ethyl |
| 1439 | CH | CH | CH | CH | N | 1-benzyl-2-(4-pyridylmethyl-amino)ethyl |
| 1440 | CH | CH | CH | CH | N | 2-phenyl-1-(2-pyridylmethyl-carbamoyl)ethyl |
| 1441 | CH | CH | CH | CH | N | 2-phenyl-1-(3-pyridylmethyl-carbamoyl)ethyl |
| 1442 | CH | CH | CH | CH | N | 2-phenyl-1-(4-pyridylmethyl-carbamoyl)ethyl |
| 1443 | CH | CH | CH | CH | N | 2-hydroxy-2-phenylethyl |
| 1444 | CH | CH | CH | CH | N | benzoylmethyl |
| 1445 | CH | CH | CH | CH | N | 1-(benzyloxycarbonyl)-2-(3-indolyl)ethyl |
| 1446 | CH | CH | CH | CH | N | 1-(benzyloxycarbonyl)-2-cyclohexylethyl |
| 1447 | CH | CH | CH | CH | N | 1-(phenoxymethyl)-2-(3-indolyl)ethyl |
| 1448 | CH | CH | CH | CH | N | 2-(2-methoxyphenoxy)ethyl |
| 1449 | CH | CH | CH | CH | N | 1-(benzylcarbamoyl)-2-cyclohexyl-ethyl |
| 1450 | CH | CH | CH | CH | N | 1-(N-methylbenzylcarbamoyl)-2-cyclohexylethyl |
| 1451 | CH | CH | CH | CH | N | 1-(phenylcarbamoyl)-2-cyclohexyl-ethyl |
| 1452 | CH | CH | CH | CH | N | 1-(N-methylphenylcarbamoyl)-2-cyclohexylethyl |
| 1453 | CH | CH | CH | CH | N | 1-(benzyloxycarbonyl)-2-(3-pyridyl)ethyl |
| 1454 | CH | CH | CH | CH | N | 1-(benzylaminomethyl)-2-(3-pyridyl)ethyl |
| 1455 | CH | CH | CH | CH | N | 1-(benzylcarbamoyl)-2-(4-pyridyl)ethyl |
| 1456 | CH | CH | CH | CH | N | 1-(4-pyridylmethylcarbamoyl)-2-(4-fluorophenyl)ethyl |
| 1457 | CH | CH | CH | CH | N | 1-(benzylcarbamoyl)-2-(7-aza-3-indolyl)ethyl |
| 1458 | CH | CH | CH | CH | N | 1-(benzyloxymethyl)-2-(2-indolyl)ethyl |
| 1459 | CH | CH | CH | CH | N | 1-(N-benzyl-N-methylaminomethyl)-2-(3-pyridyl)ethyl |
| 1460 | CH | CH | CH | CH | N | 1-(N-methylbenzylcarbamoyl)-2-(3-pyridyl)ethyl |
| 1461 | CH | CH | CH | CH | N | 2-hydroxy-2-(4-dimethylamino-phenyl)ethyl |

TABLE 3-continued

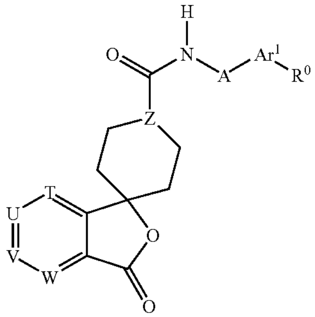

| No. | T | U | V | W | Z | A—$Ar^1$—$R^0$ |
|---|---|---|---|---|---|---|
| 1462 | CH | CH | CH | CH | N | 2-hydroxy-2-(2-quinolyl)ethyl |
| 1463 | CH | CH | CH | CH | N | 2-hydroxy-2-(3-quinolyl)ethyl |
| 1464 | CH | CH | CH | CH | N | 2-hydroxy-2-(4-quinolyl)ethyl |
| 1465 | CH | CH | CH | CH | N | 2-hydroxy-2-(3,5-difluoro-phenyl)ethyl |
| 1466 | CH | CH | CH | CH | N | 1-carboxy-2-cyclohexylethyl |
| 1467 | CH | CH | CH | CH | N | 2-hydroxy-2-(6-quinolyl)ethyl |
| 1468 | CH | CH | CH | CH | N | 2-(benzylamino)-2-phenylethyl |
| 1469 | CH | CH | CH | CH | N | 2-amino-2-(2-naphthyl)propyl |
| 1470 | CH | CH | CH | CH | N | 2-(phenylamino)ethyl |
| 1471 | CH | CH | CH | CH | N | diphenylmethyl |
| 1472 | CH | CH | CH | CH | N | 2,2-diphenylethyl |
| 1473 | CH | CH | CH | CH | N | 2-phenyl-2-(2-pyridyl)ethyl |
| 1474 | CH | CH | CH | CH | N | 2-phenyl-2-(3-pyridyl)ethyl |
| 1475 | CH | CH | CH | CH | N | 2-phenyl-2-(4-pyridyl)ethyl |
| 1476 | CH | CH | CH | CH | N | 2-phenoxy-2-phenylethyl |
| 1477 | CH | CH | CH | CH | N | 2-(benzyloxy)-2-phenylethyl |
| 1478 | N | CH | CH | CH | CH | 1-phenyl-3-pyrrolidinyl |
| 1479 | N | CH | CH | CH | CH | 1-(2-fluorophenyl)-3-pyrrolidinyl |
| 1480 | N | CH | CH | CH | CH | 1-(3-fluorophenyl)-3-pyrrolidinyl |
| 1481 | N | CH | CH | CH | CH | 1-(4-fluorophenyl)-3-pyrrolidinyl |
| 1482 | N | CH | CH | CH | CH | 1-(2-chlorophenyl)-3-pyrrolidinyl |
| 1483 | N | CH | CH | CH | CH | 1-(3-chlorophenyl)-3-pyrrolidinyl |
| 1484 | N | CH | CH | CH | CH | 1-(4-chlorophenyl)-3-pyrrolidinyl |
| 1485 | N | CH | CH | CH | CH | 1-(2-methylphenyl)-3-pyrrolidinyl |
| 1486 | N | CH | CH | CH | CH | 1-(3-methylphenyl)-3-pyrrolidinyl |
| 1487 | N | CH | CH | CH | CH | 1-(4-methylphenyl)-3-pyrrolidinyl |
| 1488 | N | CH | CH | CH | CH | 1-(2-methoxyphenyl)-3-pyrrolidinyl |
| 1489 | N | CH | CH | CH | CH | 1-(3-methoxyphenyl)-3-pyrrolidinyl |
| 1490 | N | CH | CH | CH | CH | 1-(4-methoxyphenyl)-3-pyrrolidinyl |
| 1491 | N | CH | CH | CH | CH | 1-(2-trifluoromethylphenyl)-3-pyrrolidinyl |
| 1492 | N | CH | CH | CH | CH | 1-(3-trifluoromethylphenyl)-3-pyrrolidinyl |
| 1493 | N | CH | CH | CH | CH | 1-(4-trifluoromethylphenyl)-3-pyrrolidinyl |
| 1494 | N | CH | CH | CH | CH | 1-(3,5-difluorophenyl)-3-pyrrolidinyl |
| 1495 | N | CH | CH | CH | CH | 1-(2-difluoromethoxyphenyl)-3-pyrrolidinyl |
| 1496 | N | CH | CH | CH | CH | 1-(3-difluoromethoxyphenyl)-3-pyrrolidinyl |
| 1497 | N | CH | CH | CH | CH | 1-(4-difluoromethoxyphenyl)-3-pyrrolidinyl |
| 1498 | N | CH | CH | CH | CH | 1-(2-pyridyl)-3-pyrrolidinyl |
| 1499 | N | CH | CH | CH | CH | 1-(3-pyridyl)-3-pyrrolidinyl |
| 1500 | N | CH | CH | CH | CH | 1-(4-pyridyl)-3-pyrrolidinyl |
| 1501 | N | CH | CH | CH | CH | 1-(2-pyrimidinyl)-3-pyrrolidinyl |
| 1502 | N | CH | CH | CH | CH | 5-oxo-1-phenyl-3-pyrrolidinyl |
| 1503 | N | CH | CH | CH | CH | 1-phenyl-3-piperidyl |
| 1504 | N | CH | CH | CH | CH | 1-(2-fluorophenyl)-3-piperidyl |
| 1505 | N | CH | CH | CH | CH | 1-(3-fluorophenyl)-3-piperidyl |
| 1506 | N | CH | CH | CH | CH | 1-(4-fluorophenyl)-3-piperidyl |
| 1507 | N | CH | CH | CH | CH | 1-(2-chlorophenyl)-3-piperidyl |
| 1508 | N | CH | CH | CH | CH | 1-(3-chlorophenyl)-3-piperidyl |
| 1509 | N | CH | CH | CH | CH | 1-(4-chlorophenyl)-3-piperidyl |
| 1510 | N | CH | CH | CH | CH | 1-(2-methylphenyl)-3-piperidyl |
| 1511 | N | CH | CH | CH | CH | 1-(3-methylphenyl)-3-piperidyl |

TABLE 3-continued

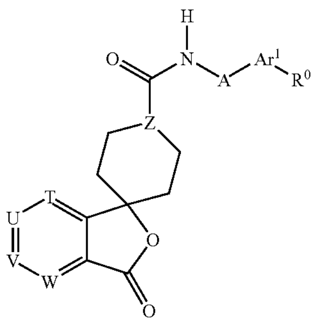

| No. | T | U | V | W | Z | A—$Ar^1$—$R^0$ |
|---|---|---|---|---|---|---|
| 1512 | N | CH | CH | CH | CH | 1-(4-methylphenyl)-3-piperidyl |
| 1513 | N | CH | CH | CH | CH | 1-(2-methoxyphenyl)-3-piperidyl |
| 1514 | N | CH | CH | CH | CH | 1-(3-methoxyphenyl)-3-piperidyl |
| 1515 | N | CH | CH | CH | CH | 1-(4-methoxyphenyl)-3-piperidyl |
| 1516 | N | CH | CH | CH | CH | 1-(2-trifluoromethylphenyl)-3-piperidyl |
| 1517 | N | CH | CH | CH | CH | 1-(3-trifluoromethylphenyl)-3-piperidyl |
| 1518 | N | CH | CH | CH | CH | 1-(4-trifluoromethylphenyl)-3-piperidyl |
| 1519 | N | CH | CH | CH | CH | 1-(3,5-difluorophenyl)-3-piperidyl |
| 1520 | N | CH | CH | CH | CH | 1-(2-difluoromethoxyphenyl)-3-piperidyl |
| 1521 | N | CH | CH | CH | CH | 1-(3-difluoromethoxyphenyl)-3-piperidyl |
| 1522 | N | CH | CH | CH | CH | 1-(4-difluoromethoxyphenyl)-3-piperidyl |
| 1523 | N | CH | CH | CH | CH | 1-(2-pyridyl)-3-piperidyl |
| 1524 | N | CH | CH | CH | CH | 1-(3-pyridyl)-3-piperidyl |
| 1525 | N | CH | CH | CH | CH | 1-(4-pyridyl)-3-piperidyl |
| 1526 | N | CH | CH | CH | CH | 1-phenyl-4-piperidyl |
| 1527 | N | CH | CH | CH | CH | 1-(2-fluorophenyl)-4-piperidyl |
| 1528 | N | CH | CH | CH | CH | 1-(3-fluorophenyl)-4-piperidyl |
| 1529 | N | CH | CH | CH | CH | 1-(4-fluorophenyl)-4-piperidyl |
| 1530 | N | CH | CH | CH | CH | 1-(2-chlorophenyl)-4-piperidyl |
| 1531 | N | CH | CH | CH | CH | 1-(3-chlorophenyl)-4-piperidyl |
| 1532 | N | CH | CH | CH | CH | 1-(4-chlorophenyl)-4-piperidyl |
| 1533 | N | CH | CH | CH | CH | 1-(2-methylphenyl)-4-piperidyl |
| 1534 | N | CH | CH | CH | CH | 1-(3-methylphenyl)-4-piperidyl |
| 1535 | N | CH | CH | CH | CH | 1-(4-methylphenyl)-4-piperidyl |
| 1536 | N | CH | CH | CH | CH | 1-(2-methoxyphenyl)-4-piperidyl |
| 1537 | N | CH | CH | CH | CH | 1-(3-methoxyphenyl)-4-piperidyl |
| 1538 | N | CH | CH | CH | CH | 1-(4-methoxyphenyl)-4-piperidyl |
| 1539 | N | CH | CH | CH | CH | 1-(2-trifluoromethylphenyl)-4-piperidyl |
| 1540 | N | CH | CH | CH | CH | 1-(3-trifluoromethylphenyl)-4-piperidyl |
| 1541 | N | CH | CH | CH | CH | 1-(4-trifluoromethylphenyl)-4-piperidyl |
| 1542 | N | CH | CH | CH | CH | 1-(3,5-difluorophenyl)-4-piperidyl |
| 1543 | N | CH | CH | CH | CH | 1-(2-difluoromethoxyphenyl)-4-piperidyl |
| 1544 | N | CH | CH | CH | CH | 1-(3-difluoromethoxyphenyl)-4-piperidyl |
| 1545 | N | CH | CH | CH | CH | 1-(4-difluoromethoxyphenyl)-4-piperidyl |
| 1546 | N | CH | CH | CH | CH | 1-(2-pyridyl)-4-piperidyl |
| 1547 | N | CH | CH | CH | CH | 1-(3-pyridyl)-4-piperidyl |
| 1548 | N | CH | CH | CH | CH | 1-(4-pyridyl)-4-piperidyl |
| 1549 | N | CH | CH | CH | CH | 3-hydroxymethyl-1-phenyl-4-piperidyl |
| 1550 | N | CH | CH | CH | CH | 3-methoxycarbonyl-1-phenyl-4-piperidyl |
| 1551 | N | CH | CH | CH | CH | 3-ethoxycarbonyl-1-phenyl-4-piperidyl |
| 1552 | N | CH | CH | CH | CH | 3-isopropoxycarbonyl-1-phenyl-4-piperidyl |
| 1553 | N | CH | CH | CH | CH | 4-phenylcyclohexyl |
| 1554 | N | CH | CH | CH | CH | 4-(2-fluorophenyl)cyclohexyl |

TABLE 3-continued

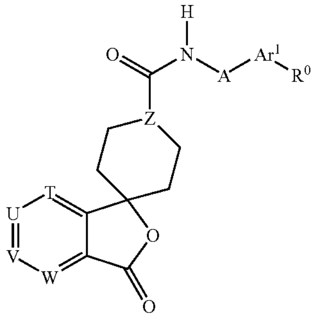

| No. | T | U | V | W | Z | A—$Ar^1$—$R^0$ |
|---|---|---|---|---|---|---|
| 1555 | N | CH | CH | CH | CH | 4-(3-fluorophenyl)cyclohexyl |
| 1556 | N | CH | CH | CH | CH | 4-(4-fluorophenyl)cyclohexyl |
| 1557 | N | CH | CH | CH | CH | 4-(2-chlorophenyl)cyclohexyl |
| 1558 | N | CH | CH | CH | CH | 4-(3-chlorophenyl)cyclohexyl |
| 1559 | N | CH | CH | CH | CH | 4-(4-chlorophenyl)cyclohexyl |
| 1560 | N | CH | CH | CH | CH | 4-(2-methylphenyl)cyclohexyl |
| 1561 | N | CH | CH | CH | CH | 4-(3-methylphenyl)cyclohexyl |
| 1562 | N | CH | CH | CH | CH | 4-(4-methylphenyl)cyclohexyl |
| 1563 | N | CH | CH | CH | CH | 4-(2-methoxyphenyl)cyclohexyl |
| 1564 | N | CH | CH | CH | CH | 4-(3-methoxyphenyl)cyclohexyl |
| 1565 | N | CH | CH | CH | CH | 4-(4-methoxyphenyl)cyclohexyl |
| 1566 | N | CH | CH | CH | CH | 4-(2-trifluoromethylphenyl)cyclohexyl |
| 1567 | N | CH | CH | CH | CH | 4-(3-trifluoromethylphenyl)cyclohexyl |
| 1568 | N | CH | CH | CH | CH | 4-(4-trifluoromethylphenyl)cyclohexyl |
| 1569 | N | CH | CH | CH | CH | 4-(3,5-difluorophenyl)cyclohexyl |
| 1570 | N | CH | CH | CH | CH | 4-(3-acetylphenyl)cyclohexyl |
| 1571 | N | CH | CH | CH | CH | 4-(3-cyanophenyl)cyclohexyl |
| 1572 | N | CH | CH | CH | CH | 4-(2-difluoromethoxyphenyl)cyclohexyl |
| 1573 | N | CH | CH | CH | CH | 4-(3-difluoromethoxyphenyl)cyclohexyl |
| 1574 | N | CH | CH | CH | CH | 4-(4-difluoromethoxyphenyl)cyclohexyl |
| 1575 | N | CH | CH | CH | CH | 4-(2-pyridyl)cyclohexyl |
| 1576 | N | CH | CH | CH | CH | 4-(3-pyridyl)cyclohexyl |
| 1577 | N | CH | CH | CH | CH | 4-(4-pyridyl)cyclohexyl |
| 1578 | N | CH | CH | CH | CH | 4-(4-fluoro-3-pyridyl)cyclohexyl |
| 1579 | N | CH | CH | CH | CH | 4-(3-quinolyl)cyclohexyl |
| 1580 | N | CH | CH | CH | CH | 4-(3-fluorophenyl)-4-hydroxycyclohexyl |
| 1581 | N | CH | CH | CH | CH | 3-phenylcyclohexyl |
| 1582 | N | CH | CH | CH | CH | 3-phenylcyclopentyl |
| 1583 | N | CH | CH | CH | CH | 6-phenyl-3-tetrahydropyranyl |
| 1584 | N | CH | CH | CH | CH | 6-(3-fluorophenyl)-3-tetrahydropyranyl |
| 1585 | N | CH | CH | CH | CH | 2-phenylcyclopropyl |
| 1586 | N | CH | CH | CH | CH | 2-(2-pyridyl)cyclopropyl |
| 1587 | N | CH | CH | CH | CH | 2-(3-pyridyl)cyclopropyl |
| 1588 | N | CH | CH | CH | CH | 2-(4-pyridyl)cyclopropyl |
| 1589 | N | CH | CH | CH | CH | 2-(3-fluorophenyl)cyclopropyl |
| 1590 | N | CH | CH | CH | CH | 2-indanyl |
| 1591 | N | CH | CH | CH | CH | 2-tetrahydronaphthyl |
| 1592 | N | CH | CH | CH | CH | 6-methoxy-2-tetrahydronaphthyl |
| 1593 | N | CH | CH | CH | CH | benzyl |
| 1594 | N | CH | CH | CH | CH | phenethyl |
| 1595 | N | CH | CH | CH | CH | 3-phenylpropyl |
| 1596 | N | CH | CH | CH | CH | 4-phenylbutyl |
| 1597 | N | CH | CH | CH | CH | 2-methoxyphenethyl |
| 1598 | N | CH | CH | CH | CH | 3-methoxyphenethyl |
| 1599 | N | CH | CH | CH | CH | 4-methoxyphenethyl |
| 1600 | N | CH | CH | CH | CH | 4-fluorophenethyl |
| 1601 | N | CH | CH | CH | CH | 4-bromophenethyl |
| 1602 | N | CH | CH | CH | CH | 4-chlorophenethyl |
| 1603 | N | CH | CH | CH | CH | 3-trifluoromethylphenethyl |
| 1604 | N | CH | CH | CH | CH | 3,4-dimethoxyphenethyl |
| 1605 | N | CH | CH | CH | CH | 3-propoxyphenethyl |
| 1606 | N | CH | CH | CH | CH | 3,5-difluorophenethyl |
| 1607 | N | CH | CH | CH | CH | 4-dimethylaminophenethyl |

TABLE 3-continued

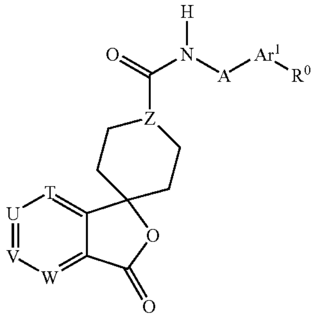

| No. | T | U | V | W | Z | A—$Ar^1$—$R^0$ |
|---|---|---|---|---|---|---|
| 1608 | N | CH | CH | CH | CH | 3-difluoromethoxyphenethyl |
| 1609 | N | CH | CH | CH | CH | 2-methylphenethyl |
| 1610 | N | CH | CH | CH | CH | 4-acetylphenethyl |
| 1611 | N | CH | CH | CH | CH | 4-dimethylamino-2-methoxy-phenethyl |
| 1612 | N | CH | CH | CH | CH | cyclohexylethyl |
| 1613 | N | CH | CH | CH | CH | 2-(2-pyridyl)ethyl |
| 1614 | N | CH | CH | CH | CH | 2-(3-pyridyl)ethyl |
| 1615 | N | CH | CH | CH | CH | 2-(4-pyridyl)ethyl |
| 1616 | N | CH | CH | CH | CH | 2-(2-quinolyl)ethyl |
| 1617 | N | CH | CH | CH | CH | 2-(3-quinolyl)ethyl |
| 1618 | N | CH | CH | CH | CH | 2-(4-quinolyl)ethyl |
| 1619 | N | CH | CH | CH | CH | 2-(6-quinolyl)ethyl |
| 1620 | N | CH | CH | CH | CH | 2-(2-indolyl)ethyl |
| 1621 | N | CH | CH | CH | CH | 2-(3-indolyl)ethyl |
| 1622 | N | CH | CH | CH | CH | 2-(7-aza-3-indolyl)ethyl |
| 1623 | N | CH | CH | CH | CH | 2-(benzimidazolyl)ethyl |
| 1624 | N | CH | CH | CH | CH | 2-(benzoxazolyl)ethyl |
| 1625 | N | CH | CH | CH | CH | 2-(benzothiazolyl)ethyl |
| 1626 | N | CH | CH | CH | CH | 2-(1-naphthyl)ethyl |
| 1627 | N | CH | CH | CH | CH | 2-(2-naphthyl)ethyl |
| 1628 | N | CH | CH | CH | CH | 1-(hydroxymethyl)-2-phenylethyl |
| 1629 | N | CH | CH | CH | CH | 1-(methoxycarbonyl)-2-phenyl-ethyl |
| 1630 | N | CH | CH | CH | CH | 1-(ethoxycarbonyl)-2-phenylethyl |
| 1631 | N | CH | CH | CH | CH | 1-carboxy-2-phenylethyl |
| 1632 | N | CH | CH | CH | CH | 1-(benzyloxycarbonyl)-2-phenylethyl |
| 1633 | N | CH | CH | CH | CH | 1-(phenoxymethyl)-2-phenylethyl |
| 1634 | N | CH | CH | CH | CH | 1-(benzyloxymethyl)-2-phenyl-ethyl |
| 1635 | N | CH | CH | CH | CH | 1-(benzylcarbamoyl)-2-phenyl-ethyl |
| 1636 | N | CH | CH | CH | CH | 1-(N-methylbenzylcarbamoyl)-2-phenylethyl |
| 1637 | N | CH | CH | CH | CH | 1-(phenylcarbamoyl)-2-phenyl-ethyl |
| 1638 | N | CH | CH | CH | CH | 1-(N-methylphenylcarbamoyl)-2-phenylethyl |
| 1639 | N | CH | CH | CH | CH | 1-(N-benzylaminomethyl)-2-phenylethyl |
| 1640 | N | CH | CH | CH | CH | 1-(N-benzyl-N-methylamino-methyl)-2-phenylethyl |
| 1641 | N | CH | CH | CH | CH | 1-(anilinomethyl)-2-phenylethyl |
| 1642 | N | CH | CH | CH | CH | 1-(N-methylanilinomethyl)-2-phenylethyl |
| 1643 | N | CH | CH | CH | CH | 1-(N-methylaminomethyl)-2-phenyl-ethyl |
| 1644 | N | CH | CH | CH | CH | 1-(N-ethylaminomethyl)-2-phenyl-ethyl |
| 1645 | N | CH | CH | CH | CH | 1-(N-isobutylaminomethyl)-2-phenylethyl |
| 1646 | N | CH | CH | CH | CH | 1-(N-cyclopropylmethylamino-methyl)-2-phenylethyl |
| 1647 | N | CH | CH | CH | CH | 1-(aminomethyl)-2-phenylethyl |
| 1648 | N | CH | CH | CH | CH | 1-benzyl-2-(2-pyridylmethyl-amino)ethyl |
| 1649 | N | CH | CH | CH | CH | 1-benzyl-2-(3-pyridylmethyl-amino)ethyl |
| 1650 | N | CH | CH | CH | CH | 1-benzyl-2-(4-pyridylmethyl-amino)ethyl |

TABLE 3-continued

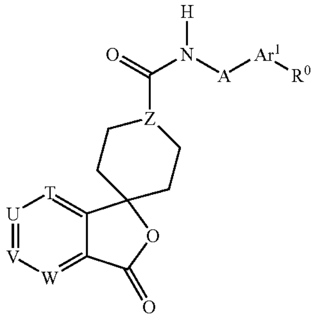

| No. | T | U | V | W | Z | A—$Ar^1$—$R^0$ |
|---|---|---|---|---|---|---|
| 1651 | N | CH | CH | CH | CH | 2-phenyl-1-(2-pyridylmethyl-carbamoyl)ethyl |
| 1652 | N | CH | CH | CH | CH | 2-phenyl-1-(3-pyridylmethyl-carbamoyl)ethyl |
| 1653 | N | CH | CH | CH | CH | 2-phenyl-1-(4-pyridylmethyl-carbamoyl)ethyl |
| 1654 | N | CH | CH | CH | CH | 2-hydroxy-2-phenylethyl |
| 1655 | N | CH | CH | CH | CH | benzoylmethyl |
| 1656 | N | CH | CH | CH | CH | 1-(benzyloxycarbonyl)-2-(3-indolyl)ethyl |
| 1657 | N | CH | CH | CH | CH | 1-(benzyloxycarbonyl)-2-cyclo-hexylethyl |
| 1658 | N | CH | CH | CH | CH | 1-(phenoxymethyl)-2-(3-indolyl)ethyl |
| 1659 | N | CH | CH | CH | CH | 2-(2-methoxyphenoxy)ethyl |
| 1660 | N | CH | CH | CH | CH | 1-(benzylcarbamoyl)-2-cyclo-hexylethyl |
| 1661 | N | CH | CH | CH | CH | 1-(N-methylbenzylcarbamoyl)-2-cyclohexylethyl |
| 1662 | N | CH | CH | CH | CH | 1-(phenylcarbamoyl)-2-cyclohexyl-ethyl |
| 1663 | N | CH | CH | CH | CH | 1-(N-methylphenylcarbamoyl)-2-cyclohexylethyl |
| 1664 | N | CH | CH | CH | CH | 1-(benzyloxycarbonyl)-2-(3-pyridyl)ethyl |
| 1665 | N | CH | CH | CH | CH | 1-(benzylaminomethyl)-2-(3-pyridyl)ethyl |
| 1666 | N | CH | CH | CH | CH | 1-(benzylcarbamoyl)-2-(4-pyridyl)ethyl |
| 1667 | N | CH | CH | CH | CH | 1-(4-pyridylmethylcarbamoyl)-2-(4-fluorophenyl)ethyl |
| 1668 | N | CH | CH | CH | CH | 1-(benzylcarbamoyl)-2-(7-aza-3-indolyl)ethyl |
| 1669 | N | CH | CH | CH | CH | 1-(benzyloxymethyl)-2-(2-indolyl)ethyl |
| 1670 | N | CH | CH | CH | CH | 1-(N-benzyl-N-methylaminomethyl)-2-(3-pyridyl)ethyl |
| 1671 | N | CH | CH | CH | CH | 1-(N-methylbenzylcarbamoyl)-2-(3-pyridyl)ethyl |
| 1672 | N | CH | CH | CH | CH | 2-hydroxy-2-(4-dimethylamino-phenyl)ethyl |
| 1673 | N | CH | CH | CH | CH | 2-hydroxy-2-(2-quinolyl)ethyl |
| 1674 | N | CH | CH | CH | CH | 2-hydroxy-2-(3-quinolyl)ethyl |
| 1675 | N | CH | CH | CH | CH | 2-hydroxy-2-(4-quinolyl)ethyl |
| 1676 | N | CH | CH | CH | CH | 2-hydroxy-2-(3,5-difluoro-phenyl)ethyl |
| 1677 | N | CH | CH | CH | CH | 1-carboxy-2-cyclohexylethyl |
| 1678 | N | CH | CH | CH | CH | 2-hydroxy-2-(6-quinolyl)ethyl |
| 1679 | N | CH | CH | CH | CH | 2-(benzylamino)-2-phenylethyl |
| 1680 | N | CH | CH | CH | CH | 2-amino-2-(2-naphthyl)propyl |
| 1681 | N | CH | CH | CH | CH | 2-(phenylamino)ethyl |
| 1682 | N | CH | CH | CH | CH | diphenylmethyl |
| 1683 | N | CH | CH | CH | CH | 2,2-diphenylethyl |
| 1684 | N | CH | CH | CH | CH | 2-phenyl-2-(2-pyridyl)ethyl |
| 1685 | N | CH | CH | CH | CH | 2-phenyl-2-(3-pyridyl)ethyl |
| 1686 | N | CH | CH | CH | CH | 2-phenyl-2-(4-pyridyl)ethyl |
| 1687 | N | CH | CH | CH | CH | 2-phenoxy-2-phenylethyl |
| 1688 | N | CH | CH | CH | CH | 2-(benzyloxy)-2-phenylethyl |
| 1689 | N | CH | CH | CH | N | 1-phenyl-3-pyrrolidinyl |
| 1690 | N | CH | CH | CH | N | 1-(2-fluorophenyl)-3-pyrrolidinyl |
| 1691 | N | CH | CH | CH | N | 1-(3-fluorophenyl)-3-pyrrolidinyl |

TABLE 3-continued

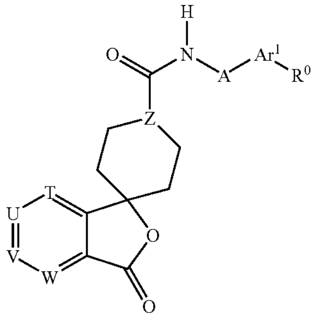

| No. | T | U | V | W | Z | A—$Ar^1$—$R^0$ |
|---|---|---|---|---|---|---|
| 1692 | N | CH | CH | CH | N | 1-(4-fluorophenyl)-3-pyrrolidinyl |
| 1693 | N | CH | CH | CH | N | 1-(2-chlorophenyl)-3-pyrrolidinyl |
| 1694 | N | CH | CH | CH | N | 1-(3-chlorophenyl)-3-pyrrolidinyl |
| 1695 | N | CH | CH | CH | N | 1-(4-chlorophenyl)-3-pyrrolidinyl |
| 1696 | N | CH | CH | CH | N | 1-(2-methylphenyl)-3-pyrrolidinyl |
| 1697 | N | CH | CH | CH | N | 1-(3-methylphenyl)-3-pyrrolidinyl |
| 1698 | N | CH | CH | CH | N | 1-(4-methylphenyl)-3-pyrrolidinyl |
| 1699 | N | CH | CH | CH | N | 1-(2-methoxyphenyl)-3-pyrrolidinyl |
| 1700 | N | CH | CH | CH | N | 1-(3-methoxyphenyl)-3-pyrrolidinyl |
| 1701 | N | CH | CH | CH | N | 1-(4-methoxyphenyl)-3-pyrrolidinyl |
| 1702 | N | CH | CH | CH | N | 1-(2-trifluoromethylphenyl)-3-pyrrolidinyl |
| 1703 | N | CH | CH | CH | N | 1-(3-trifluoromethylphenyl)-3-pyrrolidinyl |
| 1704 | N | CH | CH | CH | N | 1-(4-trifluoromethylphenyl)-3-pyrrolidinyl |
| 1705 | N | CH | CH | CH | N | 1-(3,5-difluorophenyl)-3-pyrrolidinyl |
| 1706 | N | CH | CH | CH | N | 1-(2-difluoromethoxyphenyl)-3-pyrrolidinyl |
| 1707 | N | CH | CH | CH | N | 1-(3-difluoromethoxyphenyl)-3-pyrrolidinyl |
| 1708 | N | CH | CH | CH | N | 1-(4-difluoromethoxyphenyl)-3-pyrrolidinyl |
| 1709 | N | CH | CH | CH | N | 1-(2-pyridyl)-3-pyrrolidinyl |
| 1710 | N | CH | CH | CH | N | 1-(3-pyridyl)-3-pyrrolidinyl |
| 1711 | N | CH | CH | CH | N | 1-(4-pyridyl)-3-pyrrolidinyl |
| 1712 | N | CH | CH | CH | N | 1-(2-pyrimidinyl)-3-pyrrolidinl |
| 1713 | N | CH | CH | CH | N | 5-oxo-1-phenyl-3-pyrrolidinyl |
| 1714 | N | CH | CH | CH | N | 1-phenyl-3-piperidyl |
| 1715 | N | CH | CH | CH | N | 1-(2-fluorophenyl)-3-piperidyl |
| 1716 | N | CH | CH | CH | N | 1-(3-fluorophenyl)-3-piperidyl |
| 1717 | N | CH | CH | CH | N | 1-(4-fluorophenyl)-3-piperidyl |
| 1718 | N | CH | CH | CH | N | 1-(2-chlorophenyl)-3-piperidyl |
| 1719 | N | CH | CH | CH | N | 1-(3-chlorophenyl)-3-piperidyl |
| 1720 | N | CH | CH | CH | N | 1-(4-chlorophenyl)-3-piperidyl |
| 1721 | N | CH | CH | CH | N | 1-(2-methylphenyl)-3-piperidyl |
| 1722 | N | CH | CH | CH | N | 1-(3-methylphenyl)-3-piperidyl |
| 1723 | N | CH | CH | CH | N | 1-(4-methylphenyl)-3-piperidyl |
| 1724 | N | CH | CH | CH | N | 1-(2-methoxyphenyl)-3-piperidyl |
| 1725 | N | CH | CH | CH | N | 1-(3-methoxyphenyl)-3-piperidyl |
| 1726 | N | CH | CH | CH | N | 1-(4-methoxyphenyl)-3-piperidyl |
| 1727 | N | CH | CH | CH | N | 1-(2-trifuoromethylphenyl)-3-piperidyl |
| 1728 | N | CH | CH | CH | N | 1-(3-trifuoromethylphenyl)-3-piperidyl |
| 1729 | N | CH | CH | CH | N | 1-(4-trifuoromethylphenyl)-3-piperidyl |
| 1730 | N | CH | CH | CH | N | 1-(3,5-difluorophenyl)-3-piperidyl |
| 1731 | N | CH | CH | CH | N | 1-(2-difluoromethoxyphenyl)-3-piperidyl |
| 1732 | N | CH | CH | CH | N | 1-(3-difluoromethoxyphenyl)-3-piperidyl |
| 1733 | N | CH | CH | CH | N | 1-(4-difluoromethoxyphenyl)-3-piperidiyl |
| 1734 | N | CH | CH | CH | N | 1-(2-pyridyl)-3-piperidyl |
| 1735 | N | CH | CH | CH | N | 1-(3-pyridyl)-3-piperidyl |
| 1736 | N | CH | CH | CH | N | 1-(4-pyridyl)-3-piperidyl |

TABLE 3-continued

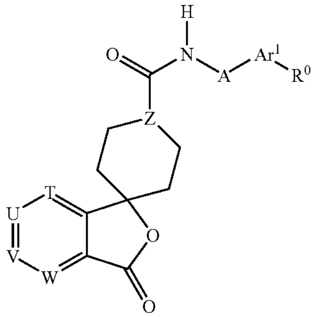

| No. | T | U | V | W | Z | A—Ar$^1$—R$^0$ |
|---|---|---|---|---|---|---|
| 1737 | N | CH | CH | CH | N | 1-phenyl-4-piperidyl |
| 1738 | N | CH | CH | CH | N | 1-(2-fluorophenyl)-4-piperidyl |
| 1739 | N | CH | CH | CH | N | 1-(3-fluorophenyl)-4-piperidyl |
| 1740 | N | CH | CH | CH | N | 1-(4-fluorophenyl)-4-piperidyl |
| 1741 | N | CH | CH | CH | N | 1-(2-chlorophenyl)-4-piperidyl |
| 1742 | N | CH | CH | CH | N | 1-(3-chlorophenyl)-4-piperidyl |
| 1743 | N | CH | CH | CH | N | 1-(4-chlorophenyl)-4-piperidyl |
| 1744 | N | CH | CH | CH | N | 1-(2-methylphenyl)-4-piperidyl |
| 1745 | N | CH | CH | CH | N | 1-(3-methylphenyl)-4-piperidyl |
| 1746 | N | CH | CH | CH | N | 1-(4-methylphenyl)-4-piperidyl |
| 1747 | N | CH | CH | CH | N | 1-(2-methoxyphenyl)-4-piperidyl |
| 1748 | N | CH | CH | CH | N | 1-(3-methoxyphenyl)-4-piperidyl |
| 1749 | N | CH | CH | CH | N | 1-(4-methoxyphenyl)-4-piperidyl |
| 1750 | N | CH | CH | CH | N | 1-(2-trifluoromethylphenyl)-4-piperidyl |
| 1751 | N | CH | CH | CH | N | 1-(3-trifluoromethylphenyl)-4-piperidyl |
| 1752 | N | CH | CH | CH | N | 1-(4-trifluoromethylphenyl)-4-piperidyl |
| 1753 | N | CH | CH | CH | N | 1-(3,5-difluorophenyl)-4-piperidyl |
| 1754 | N | CH | CH | CH | N | 1-(2-difluoromethoxyphenyl)-4-piperidyl |
| 1755 | N | CH | CH | CH | N | 1-(3-difluoromethoxyphenyl)-4-piperidyl |
| 1756 | N | CH | CH | CH | N | 1-(4-difluoromethoxyphenyl)-4-piperidyl |
| 1757 | N | CH | CH | CH | N | 1-(2-pyridyl)-4-piperidyl |
| 1758 | N | CH | CH | CH | N | 1-(3-pyridyl)-4-piperidyl |
| 1759 | N | CH | CH | CH | N | 1-(4-pyridyl)-4-piperidyl |
| 1760 | N | CH | CH | CH | N | 3-hydroxymethyl-1-phenyl-4-piperidyl |
| 1761 | N | CH | CH | CH | N | 3-methoxycarbonyl-1-phenyl-4-piperidyl |
| 1762 | N | CH | CH | CH | N | 3-ethoxycarbonyl-1-phenyl-4-piperidyl |
| 1763 | N | CH | CH | CH | N | 3-isopropoxycarbonyl-1-phenyl-4-piperidyl |
| 1764 | N | CH | CH | CH | N | 4-phenylcyclohexyl |
| 1765 | N | CH | CH | CH | N | 4-(2-fluorophenyl)cyclohexyl |
| 1766 | N | CH | CH | CH | N | 4-(3-fluorophenyl)cyclohexyl |
| 1767 | N | CH | CH | CH | N | 4-(4-fluorophenyl)cyclohexyl |
| 1768 | N | CH | CH | CH | N | 4-(2-chlorophenyl)cyclohexyl |
| 1769 | N | CH | CH | CH | N | 4-(3-chlorophenyl)cyclohexyl |
| 1770 | N | CH | CH | CH | N | 4-(4-chlorophenyl)cyclohexyl |
| 1771 | N | CH | CH | CH | N | 4-(2-methylphenyl)cyclohexyl |
| 1772 | N | CH | CH | CH | N | 4-(3-methylphenyl)cyclohexyl |
| 1773 | N | CH | CH | CH | N | 4-(4-methylphenyl)cyclohexyl |
| 1774 | N | CH | CH | CH | N | 4-(2-methoxyphenyl)cyclohexyl |
| 1775 | N | CH | CH | CH | N | 4-(3-methoxyphenyl)cyclohexyl |
| 1776 | N | CH | CH | CH | N | 4-(4-methoxyphenyl)cyclohexyl |
| 1777 | N | CH | CH | CH | N | 4-(2-trifluoromethylphenyl)cyclohexyl |
| 1778 | N | CH | CH | CH | N | 4-(3-trifluoromethylphenyl)cyclohexyl |
| 1779 | N | CH | CH | CH | N | 4-(4-trifluoromethylphenyl)cyclohexyl |
| 1780 | N | CH | CH | CH | N | 4-(3,5-difluorophenyl)cyclohexyl |
| 1781 | N | CH | CH | CH | N | 4-(3-acetylphenyl)cyclohexyl |
| 1782 | N | CH | CH | CH | N | 4-(3-cyanophenyl)cyclohexyl |

TABLE 3-continued

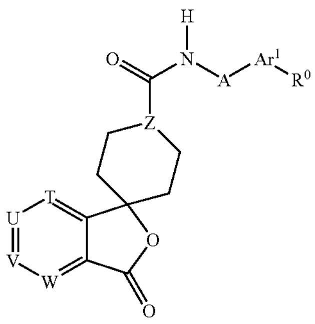

| No. | T | U | V | W | Z | A—$Ar^1$—$R^0$ |
|---|---|---|---|---|---|---|
| 1783 | N | CH | CH | CH | N | 4-(2-difluoromethoxyphenyl)cyclohexyl |
| 1784 | N | CH | CH | CH | N | 4-(3-difluoromethoxyphenyl)cyclohexyl |
| 1785 | N | CH | CH | CH | N | 4-(4-difluoromethoxyphenyl)cyclohexyl |
| 1786 | N | CH | CH | CH | N | 4-(2-pyridyl)cyclohexyl |
| 1787 | N | CH | CH | CH | N | 4-(3-pyridyl)cyclohexyl |
| 1788 | N | CH | CH | CH | N | 4-(4-pyridyl)cyclohexyl |
| 1789 | N | CH | CH | CH | N | 4-(4-fluoro-3-pyridyl)cyclohexyl |
| 1790 | N | CH | CH | CH | N | 4-(3-quinolyl)cyclohexyl |
| 1791 | N | CH | CH | CH | N | 4-(3-fluorophenyl)-4-hydroxycyclohexyl |
| 1792 | N | CH | CH | CH | N | 3-phenylcyclohexyl |
| 1793 | N | CH | CH | CH | N | 3-phenylcyclopentyl |
| 1794 | N | CH | CH | CH | N | 6-phenyl-3-tetrahydropyranyl |
| 1795 | N | CH | CH | CH | N | 6-(3-fluorophenyl)-3-tetrahydropyranyl |
| 1796 | N | CH | CH | CH | N | 2-phenylcyclopropyl |
| 1797 | N | CH | CH | CH | N | 2-(2-pyridyl)cyclopropyl |
| 1798 | N | CH | CH | CH | N | 2-(3-pyridyl)cyclopropyl |
| 1799 | N | CH | CH | CH | N | 2-(4-pyridyl)cyclopropyl |
| 1800 | N | CH | CH | CH | N | 2-(3-fluorophenyl)cyclopropyl |
| 1801 | N | CH | CH | CH | N | 2-indanyl |
| 1802 | N | CH | CH | CH | N | 2-tetrahydronaphthyl |
| 1803 | N | CH | CH | CH | N | 6-methoxy-2-tetrahydronaphthyl |
| 1804 | N | CH | CH | CH | N | benzyl |
| 1805 | N | CH | CH | CH | N | phenethyl |
| 1806 | N | CH | CH | CH | N | 3-phenylpropyl |
| 1807 | N | CH | CH | CH | N | 4-phenylbutyl |
| 1808 | N | CH | CH | CH | N | 2-methoxyphenethyl |
| 1809 | N | CH | CH | CH | N | 3-methoxyphenethyl |
| 1810 | N | CH | CH | CH | N | 4-methoxyphenethyl |
| 1811 | N | CH | CH | CH | N | 4-fluorophenethyl |
| 1812 | N | CH | CH | CH | N | 4-bromophenethyl |
| 1813 | N | CH | CH | CH | N | 4-chlorophenethyl |
| 1814 | N | CH | CH | CH | N | 3-trifluoromethylphenethyl |
| 1815 | N | CH | CH | CH | N | 3,4-dimethoxyphenethyl |
| 1816 | N | CH | CH | CH | N | 3-propoxyphenethyl |
| 1817 | N | CH | CH | CH | N | 3,5-difluorophenethyl |
| 1818 | N | CH | CH | CH | N | 4-dimethylaminophenethyl |
| 1819 | N | CH | CH | CH | N | 3-difluoromethoxyphenethyl |
| 1820 | N | CH | CH | CH | N | 2-methylphenethyl |
| 1821 | N | CH | CH | CH | N | 4-acetylphenethyl |
| 1822 | N | CH | CH | CH | N | 4-dimethylamino-2-methoxyphenethyl |
| 1823 | N | CH | CH | CH | N | cyclohexylethyl |
| 1824 | N | CH | CH | CH | N | 2-(2-pyridyl)ethyl |
| 1825 | N | CH | CH | CH | N | 2-(3-pyridyl)ethyl |
| 1826 | N | CH | CH | CH | N | 2-(4-pyridyl)ethyl |
| 1827 | N | CH | CH | CH | N | 2-(2-quinolyl)ethyl |
| 1828 | N | CH | CH | CH | N | 2-(3-quinolyl)ethyl |
| 1829 | N | CH | CH | CH | N | 2-(4-quinolyl)ethyl |
| 1830 | N | CH | CH | CH | N | 2-(6-quinolyl)ethyl |
| 1831 | N | CH | CH | CH | N | 2-(2-indolyl)ethyl |
| 1832 | N | CH | CH | CH | N | 2-(3-indolyl)ethyl |
| 1833 | N | CH | CH | CH | N | 2-(7-aza-3-indolyl)ethyl |
| 1834 | N | CH | CH | CH | N | 2-(benzimidazolyl)ethyl |
| 1835 | N | CH | CH | CH | N | 2-(benzoxazolyl)ethyl |
| 1836 | N | CH | CH | CH | N | 2-(benzothiazolyl)ethyl |
| 1837 | N | CH | CH | CH | N | 2-(1-naphthyl)ethyl |

TABLE 3-continued

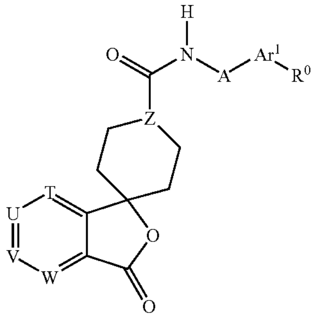

| No. | T | U | V | W | Z | A—$Ar^1$—$R^0$ |
|---|---|---|---|---|---|---|
| 1838 | N | CH | CH | CH | N | 2-(2-naphthyl)ethyl |
| 1839 | N | CH | CH | CH | N | 1-(hydroxymethyl)-2-phenylethyl |
| 1840 | N | CH | CH | CH | N | 1-(methoxycarbonyl)-2-phenylethyl |
| 1841 | N | CH | CH | CH | N | 1-(ethoxycarbonyl)-2-phenylethyl |
| 1842 | N | CH | CH | CH | N | 1-carboxy-2-phenylethyl |
| 1843 | N | CH | CH | CH | N | 1-(benzyloxycarbonyl)-2-phenyl-ethyl |
| 1844 | N | CH | CH | CH | N | 1-(phenoxymethyl)-2-phenylethyl |
| 1845 | N | CH | CH | CH | N | 1-(benzyloxymethyl)-2-phenylethyl |
| 1846 | N | CH | CH | CH | N | 1-(benzylcarbamoyl)-2-phenylethyl |
| 1847 | N | CH | CH | CH | N | 1-(N-methylbenzylcarbamoyl)-2-phenylethyl |
| 1848 | N | CH | CH | CH | N | 1-(phenylcarbamoyl)-2-phenylethyl |
| 1849 | N | CH | CH | CH | N | 1-(N-methylphenylcarbamoyl)-2-phenylethyl |
| 1850 | N | CH | CH | CH | N | 1-(N-benzylaminomethyl)-2-phenylethyl |
| 1851 | N | CH | CH | CH | N | 1-(N-benzyl-N-methylaminomethyl)-2-phenylethyl |
| 1852 | N | CH | CH | CH | N | 1-(anilinomethyl)-2-phenylethyl |
| 1853 | N | CH | CH | CH | N | 1-(N-methylanilinomethyl)-2-phenylethyl |
| 1854 | N | CH | CH | CH | N | 1-(N-methylaminomethyl)-2-phenylethyl |
| 1855 | N | CH | CH | CH | N | 1-(N-ethylaminomethyl)-2-phenylethyl |
| 1856 | N | CH | CH | CH | N | 1-(N-isobutylaminomethyl)-2-phenylethyl |
| 1857 | N | CH | CH | CH | N | 1-(N-cyclopropylmethylamino-methyl)-2-phenylethyl |
| 1858 | N | CH | CH | CH | N | 1-(aminomethyl)-2-phenylethyl |
| 1859 | N | CH | CH | CH | N | 1-benzyl-2-(2-pyridylmethyl-amino)ethyl |
| 1860 | N | CH | CH | CH | N | 1-benzyl-2-(3-pyridylmethyl-amino)ethyl |
| 1861 | N | CH | CH | CH | N | 1-benzyl-2-(4-pyridylmethyl-amino)ethyl |
| 1862 | N | CH | CH | CH | N | 2-phenyl-1-(2-pyridylmethyl-carbamoyl)ethyl |
| 1863 | N | CH | CH | CH | N | 2-phenyl-1-(3-pyridylmethyl-carbamoyl)ethyl |
| 1864 | N | CH | CH | CH | N | 2-phenyl-1-(4-pyridylmethyl-carbamoyl)ethyl |
| 1865 | N | CH | CH | CH | N | 2-hydroxy-2-phenylethyl |
| 1866 | N | CH | CH | CH | N | benzoylmethyl |
| 1867 | N | CH | CH | CH | N | 1-(benzyloxycarbonyl)-2-(3-indolyl)ethyl |
| 1868 | N | CH | CH | CH | N | 1-(benzyloxycarbonyl)-2-cyclohexylethyl |
| 1869 | N | CH | CH | CH | N | 1-(phenoxymethyl)-2-(3-indolyl)ethyl |
| 1870 | N | CH | CH | CH | N | 2-(2-methoxyphenoxy)ethyl |
| 1871 | N | CH | CH | CH | N | 1-(benzylcarbamoyl)-2-cyclohexylethyl |
| 1872 | N | CH | CH | CH | N | 1-(N-methylbenzylcarbamoyl)-2-cyclohexylethyl |
| 1873 | N | CH | CH | CH | N | 1-(phenylcarbamoyl)-2-cyclohexylethyl |
| 1874 | N | CH | CH | CH | N | 1-(N-methylphenylcarbamoyl)-2-cyclohexylethyl |

TABLE 3-continued

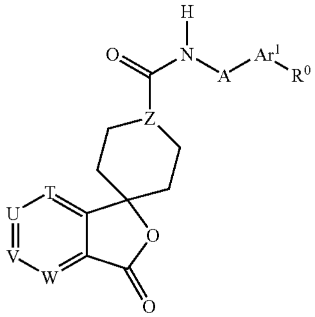

| No. | T | U | V | W | Z | A—Ar$^1$—R$^0$ |
|---|---|---|---|---|---|---|
| 1875 | N | CH | CH | CH | N | 1-(benzyloxycarbonyl)-2-(3-pyridyl)ethyl |
| 1876 | N | CH | CH | CH | N | 1-(benzylaminomethyl)-2-(3-pyridyl)ethyl |
| 1877 | N | CH | CH | CH | N | 1-(benzylcarbamoyl)-2-(4-pyridyl)ethyl |
| 1878 | N | CH | CH | CH | N | 1-(4-pyridylmethylcarbamoyl)-2-(4-fluorophenyl)ethyl |
| 1879 | N | CH | CH | CH | N | 1-(benzylcarbamoyl)-2-(7-aza-3-indolyl)ethyl |
| 1880 | N | CH | CH | CH | N | 1-(benzyloxymethyl)-2-(2-indolyl)ethyl |
| 1881 | N | CH | CH | CH | N | 1-(N-benzyl-N-methylaminomethyl)-2-(3-pyridyl)ethyl |
| 1882 | N | CH | CH | CH | N | 1-(N-methylbenzylcarbamoyl)-2-(3-pyridyl)ethyl |
| 1883 | N | CH | CH | CH | N | 2-hydroxy-2-(4-dimethylamino-phenyl)ethyl |
| 1884 | N | CH | CH | CH | N | 2-hydroxy-2-(2-quinolyl)ethyl |
| 1885 | N | CH | CH | CH | N | 2-hydroxy-2-(3-quinolyl)ethyl |
| 1886 | N | CH | CH | CH | N | 2-hydroxy-2-(4-quinolyl)ethyl |
| 1887 | N | CH | CH | CH | N | 2-hydroxy-2-(3,5-difluoro-phenyl)ethyl |
| 1888 | N | CH | CH | CH | N | 1-carboxy-2-cyclohexylethyl |
| 1889 | N | CH | CH | CH | N | 2-hydroxy-2-(6-quinolyl)ethyl |
| 1890 | N | CH | CH | CH | N | 2-(benzylamino)-2-phenylethyl |
| 1891 | N | CH | CH | CH | N | 2-amino-2-(2-naphthyl)propyl |
| 1892 | N | CH | CH | CH | N | 2-(phenylamino)ethyl |
| 1893 | N | CH | CH | CH | N | diphenylmethyl |
| 1894 | N | CH | CH | CH | N | 2,2-diphenylethyl |
| 1895 | N | CH | CH | CH | N | 2-phenyl-2-(2-pyridyl)ethyl |
| 1896 | N | CH | CH | CH | N | 2-phenyl-2-(3-pyridyl)ethyl |
| 1897 | N | CH | CH | CH | N | 2-phenyl-2-(4-pyridyl)ethyl |
| 1898 | N | CH | CH | CH | N | 2-phenoxy-2-phenylethyl |
| 1899 | N | CH | CH | CH | N | 2-(benzyloxy)-2-phenylethyl |
| 1900 | CH | N | CH | CH | CH | 1-phenyl-3-pyrrolidinyl |
| 1901 | CH | N | CH | CH | CH | 1-(2-fluorophenyl)-3-pyrrolidinyl |
| 1902 | CH | N | CH | CH | CH | 1-(3-fluorophenyl)-3-pyrrolidinyl |
| 1903 | CH | N | CH | CH | CH | 1-(4-fluorophenyl)-3-pyrrolidinyl |
| 1904 | CH | N | CH | CH | CH | 1-(2-chlorophenyl)-3-pyrrolidinyl |
| 1905 | CH | N | CH | CH | CH | 1-(3-chlorophenyl)-3-pyrrolidinyl |
| 1906 | CH | N | CH | CH | CH | 1-(4-chlorophenyl)-3-pyrrolidinyl |
| 1907 | CH | N | CH | CH | CH | 1-(2-methylphenyl)-3-pyrrolidinyl |
| 1908 | CH | N | CH | CH | CH | 1-(3-methylphenyl)-3-pyrrolidinyl |
| 1909 | CH | N | CH | CH | CH | 1-(4-methylphenyl)-3-pyrrolidinyl |
| 1910 | CH | N | CH | CH | CH | 1-(2-methoxyphenyl)-3-pyrrolidinyl |
| 1911 | CH | N | CH | CH | CH | 1-(3-methoxyphenyl)-3-pyrrolidinyl |
| 1912 | CH | N | CH | CH | CH | 1-(4-methoxyphenyl)-3-pyrrolidinyl |
| 1913 | CH | N | CH | CH | CH | 1-(2-trifluoromethylphenyl)-3-pyrrolidinyl |
| 1914 | CH | N | CH | CH | CH | 1-(3-trifluoromethylphenyl)-3-pyrrolidinyl |
| 1915 | CH | N | CH | CH | CH | 1-(4-trifluoromethylphenyl)-3-pyrrolidinyl |
| 1916 | CH | N | CH | CH | CH | 1-(3,5-difluorophenyl)-3-pyrrolidinyl |
| 1917 | CH | N | CH | CH | CH | 1-(2-difluoromethoxyphenyl)-3-pyrrolidinyl |
| 1918 | CH | N | CH | CH | CH | 1-(3-difluoromethoxyphenyl)-3-pyrrolidinyl |

TABLE 3-continued

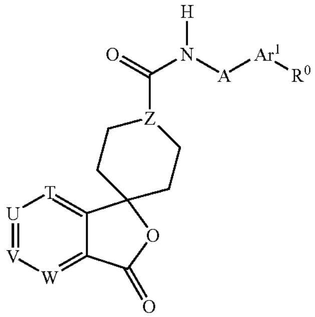

| No. | T | U | V | W | Z | A—Ar$^1$—R$^0$ |
|---|---|---|---|---|---|---|
| 1919 | CH | N | CH | CH | CH | 1-(4-difluoromethoxyphenyl)-3-pyrrolidinyl |
| 1920 | CH | N | CH | CH | CH | 1-(2-pyridyl)-3-pyrrolidinyl |
| 1921 | CH | N | CH | CH | CH | 1-(3-pyridyl)-3-pyrrolidinyl |
| 1922 | CH | N | CH | CH | CH | 1-(4-pyridyl)-3-pyrrolidinyl |
| 1923 | CH | N | CH | CH | CH | 1-(2-pyrimidinyl)-3-pyrrolidinyl |
| 1924 | CH | N | CH | CH | CH | 5-oxo-1-phenyl-3-pyrrolidinyl |
| 1925 | CH | N | CH | CH | CH | 1-phenyl-3-piperidyl |
| 1926 | CH | N | CH | CH | CH | 1-(2-fluorophenyl)-3-piperidyl |
| 1927 | CH | N | CH | CH | CH | 1-(3-fluorophenyl)-3-piperidyl |
| 1928 | CH | N | CH | CH | CH | 1-(4-fluorophenyl)-3-piperidyl |
| 1929 | CH | N | CH | CH | CH | 1-(2-chlorophenyl)-3-piperidyl |
| 1930 | CH | N | CH | CH | CH | 1-(3-chlorophenyl)-3-piperidyl |
| 1931 | CH | N | CH | CH | CH | 1-(4-chlorophenyl)-3-piperidyl |
| 1932 | CH | N | CH | CH | CH | 1-(2-methylphenyl)-3-piperidyl |
| 1933 | CH | N | CH | CH | CH | 1-(3-methylphenyl)-3-piperidyl |
| 1934 | CH | N | CH | CH | CH | 1-(4-methylphenyl)-3-piperidyl |
| 1935 | CH | N | CH | CH | CH | 1-(2-methoxyphenyl)-3-piperidyl |
| 1936 | CH | N | CH | CH | CH | 1-(3-methoxyphenyl)-3-piperidyl |
| 1937 | CH | N | CH | CH | CH | 1-(4-methoxyphenyl)-3-piperidyl |
| 1938 | CH | N | CH | CH | CH | 1-(2-trifluoromethylphenyl)-3-piperidyl |
| 1939 | CH | N | CH | CH | CH | 1-(3-trifluoromethylphenyl)-3-piperidyl |
| 1940 | CH | N | CH | CH | CH | 1-(4-trifluoromethylphenyl)-3-piperidyl |
| 1941 | CH | N | CH | CH | CH | 1-(3,5-difluorophenyl)-3-piperidyl |
| 1942 | CH | N | CH | CH | CH | 1-(2-difluoromethoxyphenyl)-3-piperidyl |
| 1943 | CH | N | CH | CH | CH | 1-(3-difluoromethoxyphenyl)-3-piperidyl |
| 1944 | CH | N | CH | CH | CH | 1-(4-difluoromethoxyphenyl)-3-piperidyl |
| 1945 | CH | N | CH | CH | CH | 1-(2-pyridyl)-3-piperidyl |
| 1946 | CH | N | CH | CH | CH | 1-(3-pyridyl)-3-piperidyl |
| 1947 | CH | N | CH | CH | CH | 1-(4-pyridyl)-3-piperidyl |
| 1948 | CH | N | CH | CH | CH | 1-phenyl-4-piperidyl |
| 1949 | CH | N | CH | CH | CH | 1-(2-fluorophenyl)-4-piperidyl |
| 1950 | CH | N | CH | CH | CH | 1-(3-fluorophenyl)-4-piperidyl |
| 1951 | CH | N | CH | CH | CH | 1-(4-fluorophenyl)-4-piperidyl |
| 1952 | CH | N | CH | CH | CH | 1-(2-chlorophenyl)-4-piperidyl |
| 1953 | CH | N | CH | CH | CH | 1-(3-chlorophenyl)-4-piperidyl |
| 1954 | CH | N | CH | CH | CH | 1-(4-chlorophenyl)-4-piperidyl |
| 1955 | CH | N | CH | CH | CH | 1-(2-methylphenyl)-4-piperidyl |
| 1956 | CH | N | CH | CH | CH | 1-(3-methylphenyl)-4-piperidyl |
| 1957 | CH | N | CH | CH | CH | 1-(4-methylphenyl)-4-piperidyl |
| 1958 | CH | N | CH | CH | CH | 1-(2-methoxyphenyl)-4-piperidyl |
| 1959 | CH | N | CH | CH | CH | 1-(3-methoxyphenyl)-4-piperidyl |
| 1960 | CH | N | CH | CH | CH | 1-(4-methoxyphenyl)-4-piperidyl |
| 1961 | CH | N | CH | CH | CH | 1-(2-trifluoromethylphenyl)-4-piperidyl |
| 1962 | CH | N | CH | CH | CH | 1-(3-trifluoromethylphenyl)-4-piperidyl |
| 1963 | CH | N | CH | CH | CH | 1-(4-trifluoromethylphenyl)-4-piperidyl |
| 1964 | CH | N | CH | CH | CH | 1-(3,5-difluorophenyl)-4-piperidyl |
| 1965 | CH | N | CH | CH | CH | 1-(2-difluoromethoxyphenyl)-4-piperidyl |
| 1966 | CH | N | CH | CH | CH | 1-(3-difluoromethoxyphenyl)-4-piperidyl |

TABLE 3-continued

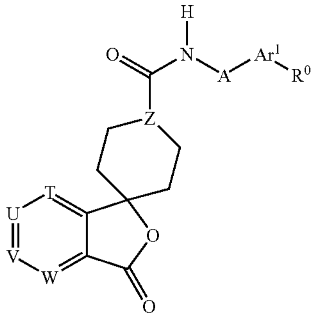

| No. | T | U | V | W | Z | A—$Ar^1$—$R^0$ |
|---|---|---|---|---|---|---|
| 1967 | CH | N | CH | CH | CH | 1-(4-difluoromethoxyphenyl)-4-piperidyl |
| 1968 | CH | N | CH | CH | CH | 1-(2-pyridyl)-4-piperidyl |
| 1969 | CH | N | CH | CH | CH | 1-(3-pyridyl)-4-piperidyl |
| 1970 | CH | N | CH | CH | CH | 1-(4-pyridyl)-4-piperidyl |
| 1971 | CH | N | CH | CH | CH | 3-hydroxymethyl-1-phenyl-4-piperidyl |
| 1972 | CH | N | CH | CH | CH | 3-methoxycarbonyl-1-phenyl-4-piperidyl |
| 1973 | CH | N | CH | CH | CH | 3-ethoxycarbonyl-1-phenyl-4-piperidyl |
| 1974 | CH | N | CH | CH | CH | 3-isopropoxycarbonyl-1-phenyl-4-piperidyl |
| 1975 | CH | N | CH | CH | CH | 4-phenylcyclohexyl |
| 1976 | CH | N | CH | CH | CH | 4-(2-fluorophenyl)cyclohexyl |
| 1977 | CH | N | CH | CH | CH | 4-(3-fluorophenyl)cyclohexyl |
| 1978 | CH | N | CH | CH | CH | 4-(4-fluorophenyl)cyclohexyl |
| 1979 | CH | N | CH | CH | CH | 4-(2-chlorophenyl)cyclohexyl |
| 1980 | CH | N | CH | CH | CH | 4-(3-chlorophenyl)cyclohexyl |
| 1981 | CH | N | CH | CH | CH | 4-(4-chlorophenyl)cyclohexyl |
| 1982 | CH | N | CH | CH | CH | 4-(2-methylphenyl)cyclohexyl |
| 1983 | CH | N | CH | CH | CH | 4-(3-methylphenyl)cyclohexyl |
| 1984 | CH | N | CH | CH | CH | 4-(4-methylphenyl)cyclohexyl |
| 1985 | CH | N | CH | CH | CH | 4-(2-methoxyphenyl)cyclohexyl |
| 1986 | CH | N | CH | CH | CH | 4-(3-methoxyphenyl)cyclohexyl |
| 1987 | CH | N | CH | CH | CH | 4-(4-methoxyphenyl)cyclohexyl |
| 1988 | CH | N | CH | CH | CH | 4-(2-trifluoromethylphenyl)cyclohexyl |
| 1989 | CH | N | CH | CH | CH | 4-(3-trifluoromethylphenyl)cyclohexyl |
| 1990 | CH | N | CH | CH | CH | 4-(4-trifluoromethylphenyl)cyclohexyl |
| 1991 | CH | N | CH | CH | CH | 4-(3,5-difluorophenyl)cyclohexyl |
| 1992 | CH | N | CH | CH | CH | 4-(3-acetylphenyl)cyclohexyl |
| 1993 | CH | N | CH | CH | CH | 4-(3-cyanophenyl)cyclohexyl |
| 1994 | CH | N | CH | CH | CH | 4-(2-difluoromethoxyphenyl)cyclohexyl |
| 1995 | CH | N | CH | CH | CH | 4-(3-difluoromethoxyphenyl)cyclohexyl |
| 1996 | CH | N | CH | CH | CH | 4-(4-difluoromethoxyphenyl)cyclohexyl |
| 1997 | CH | N | CH | CH | CH | 4-(2-pyridyl)cyclohexyl |
| 1998 | CH | N | CH | CH | CH | 4-(3-pyridyl)cyclohexyl |
| 1999 | CH | N | CH | CH | CH | 4-(4-pyridyl)cyclohexyl |
| 2000 | CH | N | CH | CH | CH | 4-(4-fluoro-3-pyridyl)cyclohexyl |
| 2001 | CH | N | CH | CH | CH | 4-(3-quinolyl)cyclohexyl |
| 2002 | CH | N | CH | CH | CH | 4-(3-fluorophenyl)-4-hydroxy-cyclohexyl |
| 2003 | CH | N | CH | CH | CH | 3-phenylcyclohexyl |
| 2004 | CH | N | CH | CH | CH | 3-phenylcyclopentyl |
| 2005 | CH | N | CH | CH | CH | 6-phenyl-3-tetrahydropyranyl |
| 2006 | CH | N | CH | CH | CH | 6-(3-fluorophenyl)-3-tetrahydropyranyl |
| 2007 | CH | N | CH | CH | CH | 2-phenylcyclopropyl |
| 2008 | CH | N | CH | CH | CH | 2-(2-pyridyl)cyclopropyl |
| 2009 | CH | N | CH | CH | CH | 2-(3-pyridyl)cyclopropyl |
| 2010 | CH | N | CH | CH | CH | 2-(4-pyridyl)cyclopropyl |
| 2011 | CH | N | CH | CH | CH | 2-(3-fluorophenyl)cyclopropyl |
| 2012 | CH | N | CH | CH | CH | 2-indanyl |
| 2013 | CH | N | CH | CH | CH | 2-tetrahydronaphthyl |
| 2014 | CH | N | CH | CH | CH | 6-methoxy-2-tetrahydronaphthyl |

TABLE 3-continued

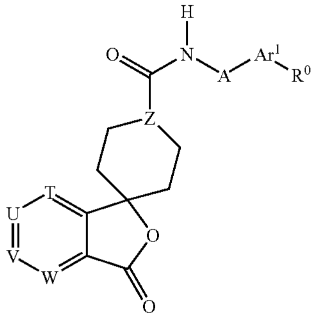

| No. | T | U | V | W | Z | A—$Ar^1$—$R^0$ |
|---|---|---|---|---|---|---|
| 2015 | CH | N | CH | CH | CH | benzyl |
| 2016 | CH | N | CH | CH | CH | phenethyl |
| 2017 | CH | N | CH | CH | CH | 3-phenylpropyl |
| 2018 | CH | N | CH | CH | CH | 4-phenylbutyl |
| 2019 | CH | N | CH | CH | CH | 2-methoxyphenethyl |
| 2020 | CH | N | CH | CH | CH | 3-methoxyphenethyl |
| 2021 | CH | N | CH | CH | CH | 4-methoxyphenethyl |
| 2022 | CH | N | CH | CH | CH | 4-fluorophenethyl |
| 2023 | CH | N | CH | CH | CH | 4-bromophenethyl |
| 2024 | CH | N | CH | CH | CH | 4-chlorophenethyl |
| 2025 | CH | N | CH | CH | CH | 3-trifluoromethylphenethyl |
| 2026 | CH | N | CH | CH | CH | 3,4-dimethoxyphenethyl |
| 2027 | CH | N | CH | CH | CH | 3-propoxyphenethyl |
| 2028 | CH | N | CH | CH | CH | 3,5-difluorophenethyl |
| 2029 | CH | N | CH | CH | CH | 4-dimethylaminophenethyl |
| 2030 | CH | N | CH | CH | CH | 3-difluoromethoxyphenethyl |
| 2031 | CH | N | CH | CH | CH | 2-methylphenethyl |
| 2032 | CH | N | CH | CH | CH | 4-acetylphenethyl |
| 2033 | CH | N | CH | CH | CH | 4-dimethylamino-2-methoxyphenethyl |
| 2034 | CH | N | CH | CH | CH | cyclohexylethyl |
| 2035 | CH | N | CH | CH | CH | 2-(2-pyridyl)ethyl |
| 2036 | CH | N | CH | CH | CH | 2-(3-pyridyl)ethyl |
| 2037 | CH | N | CH | CH | CH | 2-(4-pyridyl)ethyl |
| 2038 | CH | N | CH | CH | CH | 2-(2-quinolyl)ethyl |
| 2039 | CH | N | CH | CH | CH | 2-(3-quinolyl)ethyl |
| 2040 | CH | N | CH | CH | CH | 2-(4-quinolyl)ethyl |
| 2041 | CH | N | CH | CH | CH | 2-(6-quinolyl)ethyl |
| 2042 | CH | N | CH | CH | CH | 2-(2-indolyl)ethyl |
| 2043 | CH | N | CH | CH | CH | 2-(3-indolyl)ethyl |
| 2044 | CH | N | CH | CH | CH | 2-(7-aza-3-indolyl)ethyl |
| 2045 | CH | N | CH | CH | CH | 2-(benzimidazolyl)ethyl |
| 2046 | CH | N | CH | CH | CH | 2-(benzoxazolyl)ethyl |
| 2047 | CH | N | CH | CH | CH | 2-(benzothiazolyl)ethyl |
| 2048 | CH | N | CH | CH | CH | 2-(1-naphthyl)ethyl |
| 2049 | CH | N | CH | CH | CH | 2-(2-naphthyl)ethyl |
| 2050 | CH | N | CH | CH | CH | 1-(hydroxymethyl)-2-phenylethyl |
| 2051 | CH | N | CH | CH | CH | 1-(methoxycarbonyl)-2-phenylethyl |
| 2052 | CH | N | CH | CH | CH | 1-(ethoxycarbonyl)-2-phenylethyl |
| 2053 | CH | N | CH | CH | CH | 1-carboxy-2-phenylethyl |
| 2054 | CH | N | CH | CH | CH | 1-(benzyloxycarbonyl)-2-phenylethyl |
| 2055 | CH | N | CH | CH | CH | 1-(phenoxymethyl)-2-phenylethyl |
| 2056 | CH | N | CH | CH | CH | 1-(benzyloxymethyl)-2-phenylethyl |
| 2057 | CH | N | CH | CH | CH | 1-(benzylcarbamoyl)-2-phenylethyl |
| 2058 | CH | N | CH | CH | CH | 1-(N-methylbenzylcarbamoyl)-2-phenylethyl |
| 2059 | CH | N | CH | CH | CH | 1-(phenylcarbamoyl)-2-phenylethyl |
| 2060 | CH | N | CH | CH | CH | 1-(N-methylphenylcarbamoyl)-2-phenylethyl |
| 2061 | CH | N | CH | CH | CH | 1-(N-benzylaminomethyl)-2-phenylethyl |
| 2062 | CH | N | CH | CH | CH | 1-(N-benzyl-N-methylaminomethyl)-2-phenylethyl |
| 2063 | CH | N | CH | CH | CH | 1-(anilinomethyl)-2-phenylethyl |
| 2064 | CH | N | CH | CH | CH | 1-(N-methylanilinomethyl)-2-phenylethyl |
| 2065 | CH | N | CH | CH | CH | 1-(N-methylaminomethyl)-2-phenylethyl |
| 2066 | CH | N | CH | CH | CH | 1-(N-ethylaminomethyl)-2-phenylethyl |

TABLE 3-continued

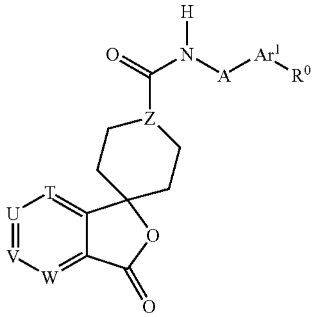

| No. | T | U | V | W | Z | A—Ar¹—R⁰ |
|---|---|---|---|---|---|---|
| 2067 | CH | N | CH | CH | CH | 1-(N-isobutylaminomethyl)-2-phenylethyl |
| 2068 | CH | N | CH | CH | CH | 1-(N-cyclopropylmethylamino-methyl)-2-phenylethyl |
| 2069 | CH | N | CH | CH | CH | 1-(aminomethyl)-2-phenylethyl |
| 2070 | CH | N | CH | CH | CH | 1-benzyl-2-(2-pyridylmethyl-2-amino)ethyl |
| 2071 | CH | N | CH | CH | CH | 1-benzyl-2-(3-pyridylmethyl-2-amino)ethyl |
| 2072 | CH | N | CH | CH | CH | 1-benzyl-2-(4-pyridylmethyl-2-amino)ethyl |
| 2073 | CH | N | CH | CH | CH | 2-phenyl-1-(2-pyridylmethyl-carbamoyl)ethyl |
| 2074 | CH | N | CH | CH | CH | 2-phenyl-1-(3-pyridylmethyl-carbamoyl)ethyl |
| 2075 | CH | N | CH | CH | CH | 2-phenyl-1-(4-pyridylmethyl-carbamoyl)ethyl |
| 2076 | CH | N | CH | CH | CH | 2-hydroxy-2-phenylethyl |
| 2077 | CH | N | CH | CH | CH | benzoylmethyl |
| 2078 | CH | N | CH | CH | CH | 1-(benzyloxycarbonyl)-2-(3-indolyl)ethyl |
| 2079 | CH | N | CH | CH | CH | 1-(benzyloxycarbonyl)-2-cyclohexylethyl |
| 2080 | CH | N | CH | CH | CH | 1-(phenoxymethyl)-2-(3-indolyl)ethyl |
| 2081 | CH | N | CH | CH | CH | 2-(2-methoxyphenoxy)ethyl |
| 2082 | CH | N | CH | CH | CH | 1-(benzylcarbamoyl)-2-cyclohexyl-ethyl |
| 2083 | CH | N | CH | CH | CH | 1-(N-methylbenzylcarbamoyl)-2-cyclohexylethyl |
| 2084 | CH | N | CH | CH | CH | 1-(phenylcarbamoyl)-2-cyclohexyl-ethyl |
| 2085 | CH | N | CH | CH | CH | 1-(N-methylphenylcarbamoyl)-2-cyclohexylethyl |
| 2086 | CH | N | CH | CH | CH | 1-(benzyloxycarbonyl)-2-(3-pyridyl)ethyl |
| 2087 | CH | N | CH | CH | CH | 1-(benzylaminomethyl)-2-(3-pyridyl)ethyl |
| 2088 | CH | N | CH | CH | CH | 1-(benzylcarbamoyl)-2-(4-pyridyl)ethyl |
| 2089 | CH | N | CH | CH | CH | 1-(4-pyridylmethylcarbamoyl)-2-(4-fluorophenyl)ethyl |
| 2090 | CH | N | CH | CH | CH | 1-(benzylcarbamoyl)-2-(7-aza-3-indolyl)ethyl |
| 2091 | CH | N | CH | CH | CH | 1-(benzyloxymethyl)-2-(2-indolyl)ethyl |
| 2092 | CH | N | CH | CH | CH | 1-(N-benzyl-N-methylaminomethyl)-2-(3-pyridyl)ethyl |
| 2093 | CH | N | CH | CH | CH | 1-(N-methylbenzylcarbamoyl)-2-(3-pyridyl)ethyl |
| 2094 | CH | N | CH | CH | CH | 2-hydroxy-2-(4-dimethylamino-phenyl)ethyl |
| 2095 | CH | N | CH | CH | CH | 2-hydroxy-2-(2-quinolyl)ethyl |
| 2096 | CH | N | CH | CH | CH | 2-hydroxy-2-(3-quinolyl)ethyl |
| 2097 | CH | N | CH | CH | CH | 2-hydroxy-2-(4-quinolyl)ethyl |
| 2098 | CH | N | CH | CH | CH | 2-hydroxy-2-(3,5-difluoro-phenyl)ethyl |
| 2099 | CH | N | CH | CH | CH | 1-carboxy-2-cyclohexylethyl |
| 2100 | CH | N | CH | CH | CH | 2-hydroxy-2-(6-quinolyl)ethyl |
| 2101 | CH | N | CH | CH | CH | 2-(benzylamino)-2-phenylethyl |
| 2102 | CH | N | CH | CH | CH | 2-amino-2-(2-naphthyl)propyl |
| 2103 | CH | N | CH | CH | CH | 2-(phenylamino)ethyl |

TABLE 3-continued

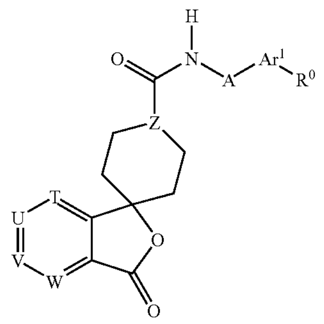

| No. | T | U | V | W | Z | A—Ar$^1$—R$^0$ |
|---|---|---|---|---|---|---|
| 2104 | CH | N | CH | CH | CH | diphenylmethyl |
| 2105 | CH | N | CH | CH | CH | 2,2-diphenylethyl |
| 2106 | CH | N | CH | CH | CH | 2-phenyl-2-(2-pyridyl)ethyl |
| 2107 | CH | N | CH | CH | CH | 2-phenyl-2-(3-pyridyl)ethyl |
| 2108 | CH | N | CH | CH | CH | 2-phenyl-2-(4-pyridyl)ethyl |
| 2109 | CH | N | CH | CH | CH | 2-phenoxy-2-phenylethyl |
| 2110 | CH | N | CH | CH | CH | 2-(benzyloxy)-2-phenylethyl |
| 2111 | CH | N | CH | CH | N | 1-phenyl-3-pyrrolidinyl |
| 2112 | CH | N | CH | CH | N | 1-(2-fluorophenyl)-3-pyrrolidinyl |
| 2113 | CH | N | CH | CH | N | 1-(3-fluorophenyl)-3-pyrrolidinyl |
| 2114 | CH | N | CH | CH | N | 1-(4-fluorophenyl)-3-pyrrolidinyl |
| 2115 | CH | N | CH | CH | N | 1-(2-chlorophenyl)-3-pyrrolidinyl |
| 2116 | CH | N | CH | CH | N | 1-(3-chlorophenyl)-3-pyrrolidinyl |
| 2117 | CH | N | CH | CH | N | 1-(4-chlorophenyl)-3-pyrrolidinyl |
| 2118 | CH | N | CH | CH | N | 1-(2-methylphenyl)-3-pyrrolidinyl |
| 2119 | CH | N | CH | CH | N | 1-(3-methylphenyl)-3-pyrrolidinyl |
| 2120 | CH | N | CH | CH | N | 1-(4-methylphenyl)-3-pyrrolidinyl |
| 2121 | CH | N | CH | CH | N | 1-(2-methoxyphenyl)-3-pyrrolidinyl |
| 2122 | CH | N | CH | CH | N | 1-(3-methoxyphenyl)-3-pyrrolidinyl |
| 2123 | CH | N | CH | CH | N | 1-(4-methoxyphenyl)-3-pyrrolidinyl |
| 2124 | CH | N | CH | CH | N | 1-(2-trifluoromethylphenyl)-3-pyrrolidinyl |
| 2125 | CH | N | CH | CH | N | 1-(3-trifluoromethylphenyl)-3-pyrrolidinyl |
| 2126 | CH | N | CH | CH | N | 1-(4-trifluoromethylphenyl)-3-pyrrolidinyl |
| 2127 | CH | N | CH | CH | N | 1-(3,5-difluorophenyl)-3-pyrrolidinyl |
| 2128 | CH | N | CH | CH | N | 1-(2-difluoromethoxyphenyl)-3-pyrrolidinyl |
| 2129 | CH | N | CH | CH | N | 1-(3-difluoromethoxyphenyl)-3-pyrrolidinyl |
| 2130 | CH | N | CH | CH | N | 1-(4-difluoromethoxyphenyl)-3-pyrrolidinyl |
| 2131 | CH | N | CH | CH | N | 1-(2-pyridyl)-3-pyrrolidinyl |
| 2132 | CH | N | CH | CH | N | 1-(3-pyridyl)-3-pyrrolidinyl |
| 2133 | CH | N | CH | CH | N | 1-(4-pyridyl)-3-pyrrolidinyl |
| 2134 | CH | N | CH | CH | N | 1-(2-pyrimidinyl)-3-pyrrolidinyl |
| 2135 | CH | N | CH | CH | N | 5-oxo-1-phenyl-3-pyrrolidinyl |
| 2136 | CH | N | CH | CH | N | 1-phenyl-3-piperidyl |
| 2137 | CH | N | CH | CH | N | 1-(2-fluorophenyl)-3-piperidyl |
| 2138 | CH | N | CH | CH | N | 1-(3-fluorophenyl)-3-piperidyl |
| 2139 | CH | N | CH | CH | N | 1-(4-fluorophenyl)-3-piperidyl |
| 2140 | CH | N | CH | CH | N | 1-(2-chlorophenyl)-3-piperidyl |
| 2141 | CH | N | CH | CH | N | 1-(3-chlorophenyl)-3-piperidyl |
| 2142 | CH | N | CH | CH | N | 1-(4-chlorophenyl)-3-piperidyl |
| 2143 | CH | N | CH | CH | N | 1-(2-methylphenyl)-3-piperidyl |
| 2144 | CH | N | CH | CH | N | 1-(3-methylphenyl)-3-piperidyl |
| 2145 | CH | N | CH | CH | N | 1-(4-methylphenyl)-3-piperidyl |
| 2146 | CH | N | CH | CH | N | 1-(2-methoxyphenyl)-3-piperidyl |
| 2147 | CH | N | CH | CH | N | 1-(3-methoxyphenyl)-3-piperidyl |
| 2148 | CH | N | CH | CH | N | 1-(4-methoxyphenyl)-3-piperidyl |
| 2149 | CH | N | CH | CH | N | 1-(2-trifluoromethylphenyl)-3-piperidyl |
| 2150 | CH | N | CH | CH | N | 1-(3-trifluoromethylphenyl)-3-piperidyl |
| 2151 | CH | N | CH | CH | N | 1-(4-trifluoromethylphenyl)-3-piperidyl |
| 2152 | CH | N | CH | CH | N | 1-(3,5-difluorophenyl)-3-piperidyl |
| 2153 | CH | N | CH | CH | N | 1-(2-difluoromethoxyphenyl)-3-piperidyl |

TABLE 3-continued

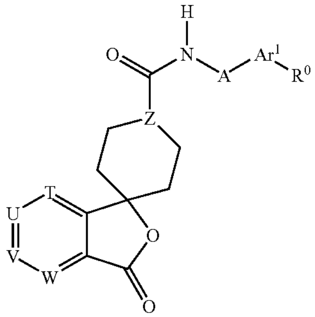

| No. | T | U | V | W | Z | A—$Ar^1$—$R^0$ |
|---|---|---|---|---|---|---|
| 2154 | CH | N | CH | CH | N | 1-(3-difluoromethoxyphenyl)-3-piperidyl |
| 2155 | CH | N | CH | CH | N | 1-(4-difluoromethoxyphenyl)-3-piperidyl |
| 2156 | CH | N | CH | CH | N | 1-(2-pyridyl)-3-piperidyl |
| 2157 | CH | N | CH | CH | N | 1-(3-pyridyl)-3-piperidyl |
| 2158 | CH | N | CH | CH | N | 1-(4-pyridyl)-3-piperidyl |
| 2159 | CH | N | CH | CH | N | 1-phenyl-4-piperidyl |
| 2160 | CH | N | CH | CH | N | 1-(2-fluorophenyl)-4-piperidyl |
| 2161 | CH | N | CH | CH | N | 1-(3-fluorophenyl)-4-piperidyl |
| 2162 | CH | N | CH | CH | N | 1-(4-fluorophenyl)-4-piperidyl |
| 2163 | CH | N | CH | CH | N | 1-(2-chlorophenyl)-4-piperidyl |
| 2164 | CH | N | CH | CH | N | 1-(3-chlorophenyl)-4-piperidyl |
| 2165 | CH | N | CH | CH | N | 1-(4-chlorophenyl)-4-piperidyl |
| 2166 | CH | N | CH | CH | N | 1-(2-methylphenyl)-4-piperidyl |
| 2167 | CH | N | CH | CH | N | 1-(3-methylphenyl)-4-piperidyl |
| 2168 | CH | N | CH | CH | N | 1-(4-methylphenyl)-4-piperidyl |
| 2169 | CH | N | CH | CH | N | 1-(2-methoxyphenyl)-4-piperidyl |
| 2170 | CH | N | CH | CH | N | 1-(3-methoxyphenyl)-4-piperidyl |
| 2171 | CH | N | CH | CH | N | 1-(4-methoxyphenyl)-4-piperidyl |
| 2172 | CH | N | CH | CH | N | 1-(2-trifluoromethylphenyl)-4-piperidyl |
| 2173 | CH | N | CH | CH | N | 1-(3-trifluoromethylphenyl)-4-piperidyl |
| 2174 | CH | N | CH | CH | N | 1-(4-trifluoromethylphenyl)-4-piperidyl |
| 2175 | CH | N | CH | CH | N | 1-(3,5-difluorophenyl)-4-piperidyl |
| 2176 | CH | N | CH | CH | N | 1-(2-difluoromethoxyphenyl)-4-piperidyl |
| 2177 | CH | N | CH | CH | N | 1-(3-difluoromethoxyphenyl)-4-piperidyl |
| 2178 | CH | N | CH | CH | N | 1-(4-difluoromethoxyphenyl)-4-piperidyl |
| 2179 | CH | N | CH | CH | N | 1-(2-pyridyl)-4-piperidyl |
| 2180 | CH | N | CH | CH | N | 1-(3-pyridyl)-4-piperidyl |
| 2181 | CH | N | CH | CH | N | 1-(4-pyridyl)-4-piperidyl |
| 2182 | CH | N | CH | CH | N | 3-hydroxymethyl-1-phenyl-4-piperidyl |
| 2183 | CH | N | CH | CH | N | 3-methoxycarbonyl-1-phenyl-4-piperidyl |
| 2184 | CH | N | CH | CH | N | 3-ethoxycarbonyl-1-phenyl-4-piperidyl |
| 2185 | CH | N | CH | CH | N | 3-isopropoxycarbonyl-1-phenyl-4-piperidyl |
| 2186 | CH | N | CH | CH | N | 4-phenylcyclohexyl |
| 2187 | CH | N | CH | CH | N | 4-(2-fluorophenyl)cyclohexyl |
| 2188 | CH | N | CH | CH | N | 4-(3-fluorophenyl)cyclohexyl |
| 2189 | CH | N | CH | CH | N | 4-(4-fluorophenyl)cyclohexyl |
| 2190 | CH | N | CH | CH | N | 4-(2-chlorophenyl)cyclohexyl |
| 2191 | CH | N | CH | CH | N | 4-(3-chlorophenyl)cyclohexyl |
| 2192 | CH | N | CH | CH | N | 4-(4-chlorophenyl)cyclohexyl |
| 2193 | CH | N | CH | CH | N | 4-(2-methylphenyl)cyclohexyl |
| 2194 | CH | N | CH | CH | N | 4-(3-methylphenyl)cyclohexyl |
| 2195 | CH | N | CH | CH | N | 4-(4-methylphenyl)cyclohexyl |
| 2196 | CH | N | CH | CH | N | 4-(2-methoxyphenyl)cyclohexyl |
| 2197 | CH | N | CH | CH | N | 4-(3-methoxyphenyl)cyclohexyl |
| 2198 | CH | N | CH | CH | N | 4-(4-methoxyphenyl)cyclohexyl |
| 2199 | CH | N | CH | CH | N | 4-(2-trifluoromethylphenyl)cyclohexyl |
| 2200 | CH | N | CH | CH | N | 4-(3-trifluoromethylphenyl)cyclohexyl |

TABLE 3-continued

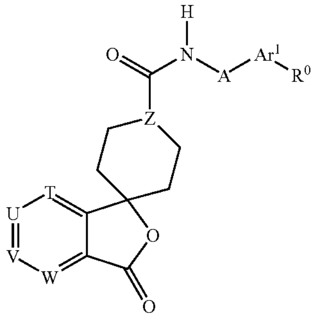

| No. | T | U | V | W | Z | A—$Ar^1$—$R^0$ |
|---|---|---|---|---|---|---|
| 2201 | CH | N | CH | CH | N | 4-(4-trifluoromethylphenyl)cyclo-hexyl |
| 2202 | CH | N | CH | CH | N | 4-(3,5-difluorophenyl)cyclohexyl |
| 2203 | CH | N | CH | CH | N | 4-(3-acetylphenyl)cyclohexyl |
| 2204 | CH | N | CH | CH | N | 4-(3-cyanophenyl)cyclohexyl |
| 2205 | CH | N | CH | CH | N | 4-(2-difluoromethoxyphenyl)cyclo-hexyl |
| 2206 | CH | N | CH | CH | N | 4-(3-difluoromethoxyphenyl)cyclo-hexyl |
| 2207 | CH | N | CH | CH | N | 4-(4-difluoromethoxyphenyl)cyclo-hexyl |
| 2208 | CH | N | CH | CH | N | 4-(2-pyridyl)cyclohexyl |
| 2209 | CH | N | CH | CH | N | 4-(3-pyridyl)cyclohexyl |
| 2210 | CH | N | CH | CH | N | 4-(4-pyridyl)cyclohexyl |
| 2211 | CH | N | CH | CH | N | 4-(4-fluoro-3-pyridyl)cyclohexyl |
| 2212 | CH | N | CH | CH | N | 4-(3-quinolyl)cyclohexyl |
| 2213 | CH | N | CH | CH | N | 4-(3-fluorophenyl)-4-hydroxycyclo-hexyl |
| 2214 | CH | N | CH | CH | N | 3-phenylcyclohexyl |
| 2215 | CH | N | CH | CH | N | 3-phenylcyclopentyl |
| 2216 | CH | N | CH | CH | N | 6-phenyl-3-tetrahydropyranyl |
| 2217 | CH | N | CH | CH | N | 6-(3-fluorophenyl)-3-tetrahydropyranyl |
| 2218 | CH | N | CH | CH | N | 2-phenylcyclopropyl |
| 2219 | CH | N | CH | CH | N | 2-(2-pyridyl)cyclopropyl |
| 2220 | CH | N | CH | CH | N | 2-(3-pyridyl)cyclopropyl |
| 2221 | CH | N | CH | CH | N | 2-(4-pyridyl)cyclopropyl |
| 2222 | CH | N | CH | CH | N | 2-(3-fluorophenyl)cyclopropyl |
| 2223 | CH | N | CH | CH | N | 2-indanyl |
| 2224 | CH | N | CH | CH | N | 2-tetrahydronaphthyl |
| 2225 | CH | N | CH | CH | N | 6-methoxy-2-tetrahydronaphthyl |
| 2226 | CH | N | CH | CH | N | benzyl |
| 2227 | CH | N | CH | CH | N | phenethyl |
| 2228 | CH | N | CH | CH | N | 3-phenylpropyl |
| 2229 | CH | N | CH | CH | N | 4-phenylbutyl |
| 2230 | CH | N | CH | CH | N | 2-methoxyphenethyl |
| 2231 | CH | N | CH | CH | N | 3-methoxyphenethyl |
| 2232 | CH | N | CH | CH | N | 4-methoxyphenethyl |
| 2233 | CH | N | CH | CH | N | 4-fluorophenethyl |
| 2234 | CH | N | CH | CH | N | 4-bromophenethyl |
| 2235 | CH | N | CH | CH | N | 4-chlorophenethyl |
| 2236 | CH | N | CH | CH | N | 3-trifiluoromethylphenethyl |
| 2237 | CH | N | CH | CH | N | 3,4-dimethoxyphenethyl |
| 2238 | CH | N | CH | CH | N | 3-propoxyphenethyl |
| 2239 | CH | N | CH | CH | N | 3,5-difluorophenethyl |
| 2240 | CH | N | CH | CH | N | 4-dimethylaminophenethyl |
| 2241 | CH | N | CH | CH | N | 3-difluoromethoxyphenethyl |
| 2242 | CH | N | CH | CH | N | 2-methylphenethyl |
| 2243 | CH | N | CH | CH | N | 4-acetylphenethyl |
| 2244 | CH | N | CH | CH | N | 4-dimethylamino-2-methoxyphenethyl |
| 2245 | CH | N | CH | CH | N | cyclohexylethyl |
| 2246 | CH | N | CH | CH | N | 2-(2-pyridyl)ethyl |
| 2247 | CH | N | CH | CH | N | 2-(3-pyridyl)ethyl |
| 2248 | CH | N | CH | CH | N | 2-(4-pyridyl)ethyl |
| 2249 | CH | N | CH | CH | N | 2-(2-quinolyl)ethyl |
| 2250 | CH | N | CH | CH | N | 2-(3-quinolyl)ethyl |
| 2251 | CH | N | CH | CH | N | 2-(4-quinolyl)ethyl |
| 2252 | CH | N | CH | CH | N | 2-(6-quinolyl)ethyl |
| 2253 | CH | N | CH | CH | N | 2-(2-indolyl)ethyl |
| 2254 | CH | N | CH | CH | N | 2-(3-indolyl)ethyl |
| 2255 | CH | N | CH | CH | N | 2-(7-aza-3-indolyl)ethyl |

TABLE 3-continued

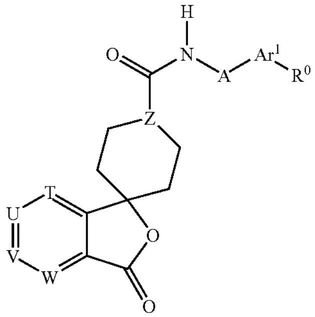

| No. | T | U | V | W | Z | A—$Ar^1$—$R^0$ |
|---|---|---|---|---|---|---|
| 2256 | CH | N | CH | CH | N | 2-(benzimidazolyl)ethyl |
| 2257 | CH | N | CH | CH | N | 2-(benzoxazolyl)ethyl |
| 2258 | CH | N | CH | CH | N | 2-(benzothiazolyl)ethyl |
| 2259 | CH | N | CH | CH | N | 2-(1-naphthyl)ethyl |
| 2260 | CH | N | CH | CH | N | 2-(2-naphthyl)ethyl |
| 2261 | CH | N | CH | CH | N | 1-(hydroxymethyl)-2-phenylethyl |
| 2262 | CH | N | CH | CH | N | 1-(methoxycarbonyl)-2-phenylethyl |
| 2263 | CH | N | CH | CH | N | 1-(ethoxycarbonyl)-2-phenylethyl |
| 2264 | CH | N | CH | CH | N | 1-carboxy-2-phenylethyl |
| 2265 | CH | N | CH | CH | N | 1-(benzyloxycarbonyl)-2-phenylethyl |
| 2266 | CH | N | CH | CH | N | 1-(phenoxymethyl)-2-phenylethyl |
| 2267 | CH | N | CH | CH | N | 1-(benzyloxymethyl)-2-phenylethyl |
| 2268 | CH | N | CH | CH | N | 1-(benzylcarbamoyl)-2-phenylethyl |
| 2269 | CH | N | CH | CH | N | 1-(N-methylbenzylcarbamoyl)-2-phenylethyl |
| 2270 | CH | N | CH | CH | N | 1-(phenylcarbamoyl)-2-phenylethyl |
| 2271 | CH | N | CH | CH | N | 1-(N-methylphenylcarbamoyl)-2-phenylethyl |
| 2272 | CH | N | CH | CH | N | 1-(N-benzylaminomethyl)-2-phenylethyl |
| 2273 | CH | N | CH | CH | N | 1-(N-benzyl-N-methylaminomethyl)-2-phenylethyl |
| 2274 | CH | N | CH | CH | N | 1-(anilinomethyl)-2-phenylethyl |
| 2275 | CH | N | CH | CH | N | 1-(N-methylanilinomethyl)-2-phenylethyl |
| 2276 | CH | N | CH | CH | N | 1-(N-methylaminomethyl)-2-phenylethyl |
| 2277 | CH | N | CH | CH | N | 1-(N-ethylaminomethyl)-2-phenylethyl |
| 2278 | CH | N | CH | CH | N | 1-(N-isobutylaminomethyl)-2-phenylethyl |
| 2279 | CH | N | CH | CH | N | 1-(N-cyclopropylmethylaminomethyl)-2-phenylethyl |
| 2280 | CH | N | CH | CH | N | 1-(aminomethyl)-2-phenylethyl |
| 2281 | CH | N | CH | CH | N | 1-benzyl-2-(2-pyridylmethylamino)ethyl |
| 2282 | CH | N | CH | CH | N | 1-benzyl-2-(3-pyridylmethylamino)ethyl |
| 2283 | CH | N | CH | CH | N | 1-benzyl-2-(4-pyridylmethylamino)ethyl |
| 2284 | CH | N | CH | CH | N | 2-phenyl-1-(2-pyridylmethylcarbamoyl)ethyl |
| 2285 | CH | N | CH | CH | N | 2-phenyl-1-(3-pyridylmethylcarbamoyl)ethyl |
| 2286 | CH | N | CH | CH | N | 2-phenyl-1-(4-pyridylmethylcarbamoyl)ethyl |
| 2287 | CH | N | CH | CH | N | 2-hydroxy-2-phenylethyl |
| 2288 | CH | N | CH | CH | N | benzoylmethyl |
| 2289 | CH | N | CH | CH | N | 1-(benzyloxycarbonyl)-2-(3-indolyl)ethyl |
| 2290 | CH | N | CH | CH | N | 1-(benzyloxycarbonyl)-2-cyclohexylethyl |
| 2291 | CH | N | CH | CH | N | 1-(phenoxymethyl)-2-(3-indolyl)ethyl |
| 2292 | CH | N | CH | CH | N | 2-(2-methoxyphenoxy)ethyl |
| 2293 | CH | N | CH | CH | N | 1-(benzylcarbamoyl)-2-cyclohexylethyl |
| 2294 | CH | N | CH | CH | N | 1-(N-methylbenzylcarbamoyl)-2-cyclohexylethyl |

TABLE 3-continued

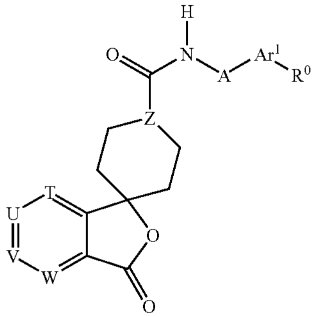

| No. | T | U | V | W | Z | A—$Ar^1$—$R^0$ |
|---|---|---|---|---|---|---|
| 2295 | CH | N | CH | CH | N | 1-(phenylcarbamoyl)-2-cyclohexylethyl |
| 2296 | CH | N | CH | CH | N | 1-(N-methylphenylcarbamoyl)-2-cyclohexylethyl |
| 2297 | CH | N | CH | CH | N | 1-(benzyloxycarbonyl)-2-(3-pyridyl)ethyl |
| 2298 | CH | N | CH | CH | N | 1-(benzylaminomethyl)-2-(3-pyridyl)ethyl |
| 2299 | CH | N | CH | CH | N | 1-(benzylcarbamoyl)-2-(4-pyridyl)ethyl |
| 2300 | CH | N | CH | CH | N | 1-(4-pyridylmethylcarbamoyl)-2-(4-fluorophenyl)ethyl |
| 2301 | CH | N | CH | CH | N | 1-(benzylcarbamoyl)-2-(7-aza-3-indolyl)ethyl |
| 2302 | CH | N | CH | CH | N | 1-(benzyloxymethyl)-2-(2-indolyl)ethyl |
| 2303 | CH | N | CH | CH | N | 1-(N-benzyl-N-methylaminomethyl)-2-(3-pyridyl)ethyl |
| 2304 | CH | N | CH | CH | N | 1-(N-methylbenzylcarbamoyl)-2-(3-pyridyl)ethyl |
| 2305 | CH | N | CH | CH | N | 2-hydroxy-2-(4-dimethylamino-phenyl)ethyl |
| 2306 | CH | N | CH | CH | N | 2-hydroxy-2-(2-quinolyl)ethyl |
| 2307 | CH | N | CH | CH | N | 2-hydroxy-2-(3-quinolyl)ethyl |
| 2308 | CH | N | CH | CH | N | 2-hydroxy-2-(4-quinolyl)ethyl |
| 2309 | CH | N | CH | CH | N | 2-hydroxy-2-(3,5-difluoro-phenyl)ethyl |
| 2310 | CH | N | CH | CH | N | 1-carboxy-2-cyclohexylethyl |
| 2311 | CH | N | CH | CH | N | 2-hydroxy-2-(6-quinolyl)ethyl |
| 2312 | CH | N | CH | CH | N | 2-(benzylamino)-2-phenylethyl |
| 2313 | CH | N | CH | CH | N | 2-amino-2-(2-naphthyl)propyl |
| 2314 | CH | N | CH | CH | N | 2-(phenylamino)ethyl |
| 2315 | CH | N | CH | CH | N | diphenylmethyl |
| 2316 | CH | N | CH | CH | N | 2,2-diphenylethyl |
| 2317 | CH | N | CH | CH | N | 2-phenyl-2-(2-pyridyl)ethyl |
| 2318 | CH | N | CH | CH | N | 2-phenyl-2-(3-pyridyl)ethyl |
| 2319 | CH | N | CH | CH | N | 2-phenyl-2-(4-pyridyl)ethyl |
| 2320 | CH | N | CH | CH | N | 2-phenoxy-2-phenylethyl |
| 2321 | CH | N | CH | CH | N | 2-(benzyloxy)-2-phenylethyl |
| 2322 | CH | CH | N | CH | CH | 1-phenyl-3-pyrrolidinyl |
| 2323 | CH | CH | N | CH | CH | 1-(2-fluorophenyl)-3-pyrrolidinyl |
| 2324 | CH | CH | N | CH | CH | 1-(3-fluorophenyl)-3-pyrrolidinyl |
| 2325 | CH | CH | N | CH | CH | 1-(4-fluorophenyl)-3-pyrrolidinyl |
| 2326 | CH | CH | N | CH | CH | 1-(2-chlorophenyl)-3-pyrrolidinyl |
| 2327 | CH | CH | N | CH | CH | 1-(3-chlorophenyl)-3-pyrrolidinyl |
| 2328 | CH | CH | N | CH | CH | 1-(4-chlorophenyl)-3-pyrrolidinyl |
| 2329 | CH | CH | N | CH | CH | 1-(2-methylphenyl)-3-pyrrolidinyl |
| 2330 | CH | CH | N | CH | CH | 1-(3-methylphenyl)-3-pyrrolidinyl |
| 2331 | CH | CH | N | CH | CH | 1-(4-methylphenyl)-3-pyrrolidinyl |
| 2332 | CH | CH | N | CH | CH | 1-(2-methoxyphenyl)-3-pyrrolidinyl |
| 2333 | CH | CH | N | CH | CH | 1-(3-methoxyphenyl)-3-pyrrolidinyl |
| 2334 | CH | CH | N | CH | CH | 1-(4-methoxyphenyl)-3-pyrrolidinyl |
| 2335 | CH | CH | N | CH | CH | 1-(2-trifluoromethylphenyl)-3-pyrrolidinyl |
| 2336 | CH | CH | N | CH | CH | 1-(3-trifluoromethylphenyl)-3-pyrrolidinyl |
| 2337 | CH | CH | N | CH | CH | 1-(4-trifluoromethylphenyl)-3-pyrrolidinyl |
| 2338 | CH | CH | N | CH | CH | 1-(3,5-difluorophenyl)-3-pyrrolidinyl |

TABLE 3-continued

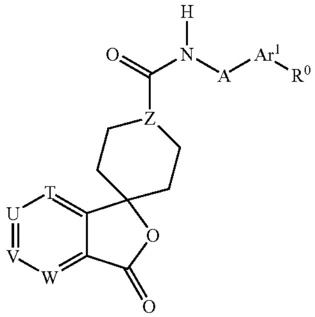

| No. | T | U | V | W | Z | A—$Ar^1$—$R^0$ |
|---|---|---|---|---|---|---|
| 2339 | CH | CH | N | CH | CH | 1-(2-difluoromethoxyphenyl)-3-pyrrolidinyl |
| 2340 | CH | CH | N | CH | CH | 1-(3-difluoromethoxyphenyl)-3-pyrrolidinyl |
| 2341 | CH | CH | N | CH | CH | 1-(4-difluoromethoxyphenyl)-3-pyrrolidinyl |
| 2342 | CH | CH | N | CH | CH | 1-(2-pyridyl)-3-pyrrolidinyl |
| 2343 | CH | CH | N | CH | CH | 1-(3-pyridyl)-3-pyrrolidinyl |
| 2344 | CH | CH | N | CH | CH | 1-(4-pyridyl)-3-pyrrolidinyl |
| 2345 | CH | CH | N | CH | CH | 1-(2-pyrimidinyl)-3-pyrrolidinyl |
| 2346 | CH | CH | N | CH | CH | 5-oxo-1-phenyl-3-pyrrolidinyl |
| 2347 | CH | CH | N | CH | CH | 1-phenyl-3-piperidyl |
| 2348 | CH | CH | N | CH | CH | 1-(2-fluorophenyl)-3-piperidyl |
| 2349 | CH | CH | N | CH | CH | 1-(3-fluorophenyl)-3-piperidyl |
| 2350 | CH | CH | N | CH | CH | 1-(4-fluorophenyl)-3-piperidyl |
| 2351 | CH | CH | N | CH | CH | 1-(2-chlorophenyl)-3-piperidyl |
| 2352 | CH | CH | N | CH | CH | 1-(3-chlorophenyl)-3-piperidyl |
| 2353 | CH | CH | N | CH | CH | 1-(4-chlorophenyl)-3-piperidyl |
| 2354 | CH | CH | N | CH | CH | 1-(2-methylphenyl)-3-piperidyl |
| 2355 | CH | CH | N | CH | CH | 1-(3-methylphenyl)-3-piperidyl |
| 2356 | CH | CH | N | CH | CH | 1-(4-methylphenyl)-3-piperidyl |
| 2357 | CH | CH | N | CH | CH | 1-(2-methoxyphenyl)-3-piperidyl |
| 2358 | CH | CH | N | CH | CH | 1-(3-methoxyphenyl)-3-piperidyl |
| 2359 | CH | CH | N | CH | CH | 1-(4-methoxyphenyl)-3-piperidyl |
| 2360 | CH | CH | N | CH | CH | 1-(2-trifluoromethylphenyl)-3-piperidyl |
| 2361 | CH | CH | N | CH | CH | 1-(3-trifluoromethylphenyl)-3-piperidyl |
| 2362 | CH | CH | N | CH | CH | 1-(4-trifluoromethylphenyl)-3-piperidyl |
| 2363 | CH | CH | N | CH | CH | 1-(3,5-difluorophenyl)-3-piperidyl |
| 2364 | CH | CH | N | CH | CH | 1-(2-difluoromethoxyphenyl)-3-piperidyl |
| 2365 | CH | CH | N | CH | CH | 1-(3-difluoromethoxyphenyl)-3-piperidyl |
| 2366 | CH | CH | N | CH | CH | 1-(4-difluoromethoxyphenyl)-3-piperidyl |
| 2367 | CH | CH | N | CH | CH | 1-(2-pyridyl)-3-piperidyl |
| 2368 | CH | CH | N | CH | CH | 1-(3-pyridyl)-3-piperidyl |
| 2369 | CH | CH | N | CH | CH | 1-(4-pyridyl)-3-piperidyl |
| 2370 | CH | CH | N | CH | CH | 1-phenyl-4-piperidyl |
| 2371 | CH | CH | N | CH | CH | 1-(2-fluorophenyl)-4-piperidyl |
| 2372 | CH | CH | N | CH | CH | 1-(3-fluorophenyl)-4-piperidyl |
| 2373 | CH | CH | N | CH | CH | 1-(4-fluorophenyl)-4-piperidyl |
| 2374 | CH | CH | N | CH | CH | 1-(2-chlorophenyl)-4-piperidyl |
| 2375 | CH | CH | N | CH | CH | 1-(3-chlorophenyl)-4-piperidyl |
| 2376 | CH | CH | N | CH | CH | 1-(4-chlorophenyl)-4-piperidyl |
| 2377 | CH | CH | N | CH | CH | 1-(2-methylphenyl)-4-piperidyl |
| 2378 | CH | CH | N | CH | CH | 1-(3-methylphenyl)-4-piperidyl |
| 2379 | CH | CH | N | CH | CH | 1-(4-methylphenyl)-4-piperidyl |
| 2380 | CH | CH | N | CH | CH | 1-(2-methoxyphenyl)-4-piperidyl |
| 2381 | CH | CH | N | CH | CH | 1-(3-methoxyphenyl)-4-piperidyl |
| 2382 | CH | CH | N | CH | CH | 1-(4-methoxyphenyl)-4-piperidyl |
| 2383 | CH | CH | N | CH | CH | 1-(2-trifluoromethylphenyl)-4-piperidyl |
| 2384 | CH | CH | N | CH | CH | 1-(3-trifluoromethylphenyl)-4-piperidyl |
| 2385 | CH | CH | N | CH | CH | 1-(4-trifluoromethylphenyl)-4-piperidyl |
| 2386 | CH | CH | N | CH | CH | 1-(3,5-difluorophenyl)-4-piperidyl |

TABLE 3-continued

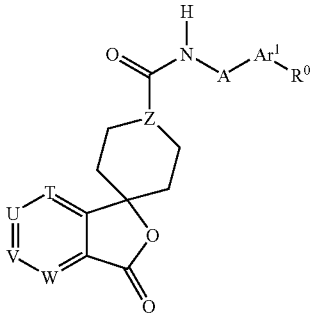

| No. | T | U | V | W | Z | A—Ar$^1$—R$^0$ |
|---|---|---|---|---|---|---|
| 2387 | CH | CH | N | CH | CH | 1-(2-difluoromethoxyphenyl)-4-piperidyl |
| 2388 | CH | CH | N | CH | CH | 1-(3-difluoromethoxyphenyl)-4-piperidyl |
| 2389 | CH | CH | N | CH | CH | 1-(4-difluoromethoxyphenyl)-4-piperidyl |
| 2390 | CH | CH | N | CH | CH | 1-(2-pyridyl)-4-piperidyl |
| 2391 | CH | CH | N | CH | CH | 1-(3-pyridyl)-4-piperidyl |
| 2392 | CH | CH | N | CH | CH | 1-(4-pyridyl)-4-piperidyl |
| 2393 | CH | CH | N | CH | CH | 3-hydroxymethyl-1-phenyl-4-piperidyl |
| 2394 | CH | CH | N | CH | CH | 3-methoxycarbonyl-1-phenyl-4-piperidyl |
| 2395 | CH | CH | N | CH | CH | 3-ethoxycarbonyl-1-phenyl-4-piperidyl |
| 2396 | CH | CH | N | CH | CH | 3-isopropoxycarbonyl-1-phenyl-4-piperidyl |
| 2397 | CH | CH | N | CH | CH | 4-phenylcyclohexyl |
| 2398 | CH | CH | N | CH | CH | 4-(2-fluorophenyl)cyclohexyl |
| 2399 | CH | CH | N | CH | CH | 4-(3-fluorophenyl)cyclohexyl |
| 2400 | CH | CH | N | CH | CH | 4-(4-fluorophenyl)cyclohexyl |
| 2401 | CH | CH | N | CH | CH | 4-(2-chlorophenyl)cyclohexyl |
| 2402 | CH | CH | N | CH | CH | 4-(3-chlorophenyl)cyclohexyl |
| 2403 | CH | CH | N | CH | CH | 4-(4-chlorophenyl)cyclohexyl |
| 2404 | CH | CH | N | CH | CH | 4-(2-methylphenyl)cyclohexyl |
| 2405 | CH | CH | N | CH | CH | 4-(3-methylphenyl)cyclohexyl |
| 2406 | CH | CH | N | CH | CH | 4-(4-methylphenyl)cyclohexyl |
| 2407 | CH | CH | N | CH | CH | 4-(2-methoxyphenyl)cyclohexyl |
| 2408 | CH | CH | N | CH | CH | 4-(3-methoxyphenyl)cyclohexyl |
| 2409 | CH | CH | N | CH | CH | 4-(4-methoxyphenyl)cyclohexyl |
| 2410 | CH | CH | N | CH | CH | 4-(2-trifluoromethylphenyl)cyclohexyl |
| 2411 | CH | CH | N | CH | CH | 4-(3-trifluoromethylphenyl)cyclohexyl |
| 2412 | CH | CH | N | CH | CH | 4-(4-trifluoromethylphenyl)cyclohexyl |
| 2413 | CH | CH | N | CH | CH | 4-(3,5-difluorophenyl)cyclohexyl |
| 2414 | CH | CH | N | CH | CH | 4-(3-acetylphenyl)cyclohexyl |
| 2415 | CH | CH | N | CH | CH | 4-(3-cyanophenyl)cyclohexyl |
| 2416 | CH | CH | N | CH | CH | 4-(2-difluoromethoxyphenyl)cyclohexyl |
| 2417 | CH | CH | N | CH | CH | 4-(3-difluoromethoxyphenyl)cyclohexyl |
| 2418 | CH | CH | N | CH | CH | 4-(4-difluoromethoxyphenyl)cyclohexyl |
| 2419 | CH | CH | N | CH | CH | 4-(2-pyridyl)cyclohexyl |
| 2420 | CH | CH | N | CH | CH | 4-(3-pyridyl)cyclohexyl |
| 2421 | CH | CH | N | CH | CH | 4-(4-pyridyl)cyclohexyl |
| 2422 | CH | CH | N | CH | CH | 4-(4-fluoro-3-pyridyl)cyclohexyl |
| 2423 | CH | CH | N | CH | CH | 4-(3-quinolyl)cyclohexyl |
| 2424 | CH | CH | N | CH | CH | 4-(3-fluorophenyl)-4-hydroxycyclohexyl |
| 2425 | CH | CH | N | CH | CH | 3-phenylcyclohexyl |
| 2426 | CH | CH | N | CH | CH | 3-phenylcyclopentyl |
| 2427 | CH | CH | N | CH | CH | 6-phenyl-3-tetrhydropyranyl |
| 2428 | CH | CH | N | CH | CH | 6-(3-fluorophenyl)-3-tetrhydropyranyl |
| 2429 | CH | CH | N | CH | CH | 2-phenylcyclopropyl |
| 2430 | CH | CH | N | CH | CH | 2-(2-pyridyl)cyclopropyl |
| 2431 | CH | CH | N | CH | CH | 2-(3-pyridyl)cyclopropyl |
| 2432 | CH | CH | N | CH | CH | 2-(4-pyridyl)cyclopropyl |
| 2433 | CH | CH | N | CH | CH | 2-(3-fluorophenyl)cyclopropyl |

TABLE 3-continued

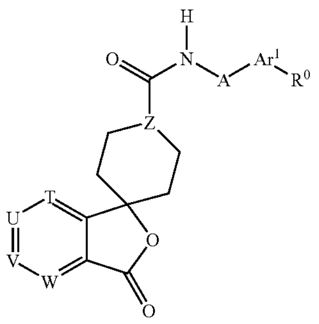

| No. | T | U | V | W | Z | A—$Ar^1$—$R^0$ |
|---|---|---|---|---|---|---|
| 2434 | CH | CH | N | CH | CH | 2-indanyl |
| 2435 | CH | CH | N | CH | CH | 2-tetrahydronaphthyl |
| 2436 | CH | CH | N | CH | CH | 6-methoxy-2-tetrahydronaphthyl |
| 2437 | CH | CH | N | CH | CH | benzyl |
| 2438 | CH | CH | N | CH | CH | phenethyl |
| 2439 | CH | CH | N | CH | CH | 3-phenylpropyl |
| 2440 | CH | CH | N | CH | CH | 4-phenylbutyl |
| 2441 | CH | CH | N | CH | CH | 2-methoxyphenethyl |
| 2442 | CH | CH | N | CH | CH | 3-methoxyphenethyl |
| 2443 | CH | CH | N | CH | CH | 4-methoxyphenethyl |
| 2444 | CH | CH | N | CH | CH | 4-fluorophenethyl |
| 2445 | CH | CH | N | CH | CH | 4-bromophenethyl |
| 2446 | CH | CH | N | CH | CH | 4-chlorophenethyl |
| 2447 | CH | CH | N | CH | CH | 3-trifluoromethylphenethyl |
| 2448 | CH | CH | N | CH | CH | 3,4-dimethoxyphenethyl |
| 2449 | CH | CH | N | CH | CH | 3-propoxyphenethyl |
| 2450 | CH | CH | N | CH | CH | 3,5-difluorophenethyl |
| 2451 | CH | CH | N | CH | CH | 4-dimethylaminophenethyl |
| 2452 | CH | CH | N | CH | CH | 3-difluoromethoxyphenethyl |
| 2453 | CH | CH | N | CH | CH | 2-methylphenethyl |
| 2454 | CH | CH | N | CH | CH | 4-acetylphenethyl |
| 2455 | CH | CH | N | CH | CH | 4-dimethylamino-2-methoxyphenethyl |
| 2456 | CH | CH | N | CH | CH | cyclohexylethyl |
| 2457 | CH | CH | N | CH | CH | 2-(2-pyridyl)ethyl |
| 2458 | CH | CH | N | CH | CH | 2-(3-pyridyl)ethyl |
| 2459 | CH | CH | N | CH | CH | 2-(4-pyridyl)ethyl |
| 2460 | CH | CH | N | CH | CH | 2-(2-quinolyl)ethyl |
| 2461 | CH | CH | N | CH | CH | 2-(3-quinolyl)ethyl |
| 2462 | CH | CH | N | CH | CH | 2-(4-quinolyl)ethyl |
| 2463 | CH | CH | N | CH | CH | 2-(6-quinolyl)ethyl |
| 2464 | CH | CH | N | CH | CH | 2-(2-indolyl)ethyl |
| 2465 | CH | CH | N | CH | CH | 2-(3-indolyl)ethyl |
| 2466 | CH | CH | N | CH | CH | 2-(7-aza-3-indolyl)ethyl |
| 2467 | CH | CH | N | CH | CH | 2-(benzimidazolyl)ethyl |
| 2468 | CH | CH | N | CH | CH | 2-(benzoxazolyl)ethyl |
| 2469 | CH | CH | N | CH | CH | 2-(benzothiazolyl)ethyl |
| 2470 | CH | CH | N | CH | CH | 2-(1-naphthyl)ethyl |
| 2471 | CH | CH | N | CH | CH | 2-(2-naphthyl)ethyl |
| 2472 | CH | CH | N | CH | CH | 1-(hydroxymethyl)-2-phenylethyl |
| 2473 | CH | CH | N | CH | CH | 1-(methoxycarbonyl)-2-phenylethyl |
| 2474 | CH | CH | N | CH | CH | 1-(ethoxycarbonyl)-2-phenylethyl |
| 2475 | CH | CH | N | CH | CH | 1-carboxy-2-phenylethyl |
| 2476 | CH | CH | N | CH | CH | 1-(benzyloxycarbonyl)-2-phenyl-ethyl |
| 2477 | CH | CH | N | CH | CH | 1-(phenoxymethyl)-2-phenylethyl |
| 2478 | CH | CH | N | CH | CH | 1-(benzyloxymethyl)-2-phenylethyl |
| 2479 | CH | CH | N | CH | CH | 1-(benzylcarbamoyl)-2-phenylethyl |
| 2480 | CH | CH | N | CH | CH | 1-(N-methylbenzylcarbamoyl)-2-phenylethyl |
| 2481 | CH | CH | N | CH | CH | 1-(phenylcarbamoyl)-2-phenylethyl |
| 2482 | CH | CH | N | CH | CH | 1-(N-methylphenylcarbamoyl)-2-phenylethyl |
| 2483 | CH | CH | N | CH | CH | 1-(N-benzylaminomethyl)-2-phenyl-ethyl |
| 2484 | CH | CH | N | CH | CH | 1-(N-benzyl-N-methylaminomethyl)-2-phenylethyl |
| 2485 | CH | CH | N | CH | CH | 1-(anilinomethyl)-2-phenylethyl |
| 2486 | CH | CH | N | CH | CH | 1-(N-methylanilinomethyl)-2-phenylethyl |
| 2487 | CH | CH | N | CH | CH | 1-(N-methylaminomethyl)-2-phenylethyl |

TABLE 3-continued

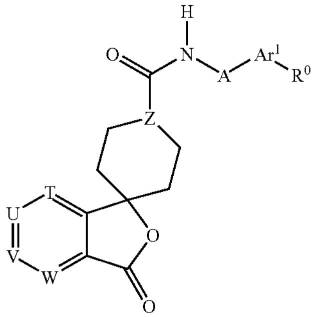

| No. | T | U | V | W | Z | A—Ar$^1$—R$^0$ |
|---|---|---|---|---|---|---|
| 2488 | CH | CH | N | CH | CH | 1-(N-ethylaminomethyl)-2-phenylethyl |
| 2489 | CH | CH | N | CH | CH | 1-(N-isobutylaminomethyl)-2-phenylethyl |
| 2490 | CH | CH | N | CH | CH | 1-(N-cyclopropylmethylamino-methyl)-2-phenylethyl |
| 2491 | CH | CH | N | CH | CH | 1-(aminomethyl)-2-phenylethyl |
| 2492 | CH | CH | N | CH | CH | 1-benzyl-2-(2-pyridylmethyl-amino)ethyl |
| 2493 | CH | CH | N | CH | CH | 1-benzyl-2-(3-pyridylmethyl-amino)ethyl |
| 2494 | CH | CH | N | CH | CH | 1-benzyl-2-(4-pyridylmethyl-amino)ethyl |
| 2495 | CH | CH | N | CH | CH | 2-phenyl-1-(2-pyridylmethyl-carbamoyl)ethyl |
| 2496 | CH | CH | N | CH | CH | 2-phenyl-1-(3-pyridylmethyl-carbamoyl)ethyl |
| 2497 | CH | CH | N | CH | CH | 2-phenyl-1-(4-pyridylmethyl-carbamoyl)ethyl |
| 2498 | CH | CH | N | CH | CH | 2-hydroxy-2-phenylethyl |
| 2499 | CH | CH | N | CH | CH | benzoylmethyl |
| 2500 | CH | CH | N | CH | CH | 1-(benzyloxycarbonyl)-2-(3-indolyl)ethyl |
| 2501 | CH | CH | N | CH | CH | 1-(benzyloxycarbonyl)-2-cyclo-hexylethyl |
| 2502 | CH | CH | N | CH | CH | 1-(phenoxymethyl)-2-(3-indolyl)ethyl |
| 2503 | CH | CH | N | CH | CH | 2-(2-methoxyphenoxy)ethyl |
| 2504 | CH | CH | N | CH | CH | 1-(benzylcarbamoyl)-2-cyclohexyl-ethyl |
| 2505 | CH | CH | N | CH | CH | 1-(N-methylbenzylcarbamoyl)-2-cyclohexylethyl |
| 2506 | CH | CH | N | CH | CH | 1-(phenylcarbamoyl)-2-cyclohexyl-ethyl |
| 2507 | CH | CH | N | CH | CH | 1-(N-methylphenylcarbamoyl)-2-cyclohexylethyl |
| 2508 | CH | CH | N | CH | CH | 1-(benzyloxycarbonyl)-2-(3-pyridyl)ethyl |
| 2509 | CH | CH | N | CH | CH | 1-(benzylaminomethyl)-2-(3-pyridyl)ethyl |
| 2510 | CH | CH | N | CH | CH | 1-(benzylcarbamoyl)-2-(4-pyridyl)ethyl |
| 2511 | CH | CH | N | CH | CH | 1-(4-pyridylmethylcarbamoyl)-2-(4-fluorophenyl)ethyl |
| 2512 | CH | CH | N | CH | CH | 1-(benzylcarbamoyl)-2-(7-aza-3-indolyl)ethyl |
| 2513 | CH | CH | N | CH | CH | 1-(benzyloxymethyl)-2-(2-indolyl)ethyl |
| 2514 | CH | CH | N | CH | CH | 1-(N-benzyl-N-methylaminomethyl)-2-(3-pyridyl)ethyl |
| 2515 | CH | CH | N | CH | CH | 1-(N-methylbenzylcarbamoyl)-2-(3-pyridyl)ethyl |
| 2516 | CH | CH | N | CH | CH | 2-hydroxy-2-(4-dimethylamino-phenyl)ethyl |
| 2517 | CH | CH | N | CH | CH | 2-hydroxy-2-(2-quinolyl)ethyl |
| 2518 | CH | CH | N | CH | CH | 2-hydroxy-2-(3-quinolyl)ethyl |
| 2519 | CH | CH | N | CH | CH | 2-hydroxy-2-(4-quinolyl)ethyl |
| 2520 | CH | CH | N | CH | CH | 2-hydroxy-2-(3,5-difluoro-phenyl)ethyl |
| 2521 | CH | CH | N | CH | CH | 1-carboxy-2-cyclohexylethyl |
| 2522 | CH | CH | N | CH | CH | 2-hydroxy-2-(6-quinolyl)ethyl |

TABLE 3-continued

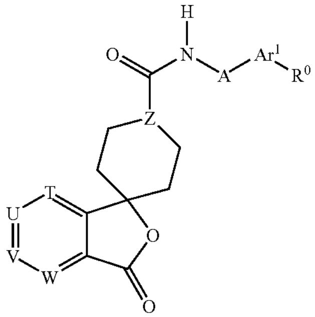

| No. | T | U | V | W | Z | A—Ar$^1$—R$^0$ |
|---|---|---|---|---|---|---|
| 2523 | CH | CH | N | CH | CH | 2-(benzylamino)-2-phenylethyl |
| 2524 | CH | CH | N | CH | CH | 2-amino-2-(2-naphthyl)propyl |
| 2525 | CH | CH | N | CH | CH | 2-(phenylamino)ethyl |
| 2526 | CH | CH | N | CH | CH | diphenylmethyl |
| 2527 | CH | CH | N | CH | CH | 2,2-diphenylethyl |
| 2528 | CH | CH | N | CH | CH | 2-phenyl-2-(2-pyridyl)ethyl |
| 2529 | CH | CH | N | CH | CH | 2-phenyl-2-(3-pyridyl)ethyl |
| 2530 | CH | CH | N | CH | CH | 2-phenyl-2-(4-pyridyl)ethyl |
| 2531 | CH | CH | N | CH | CH | 2-phenoxy-2-phenylethyl |
| 2532 | CH | CH | N | CH | CH | 2-(benzyloxy)-2-phenylethyl |
| 2533 | CH | CH | N | CH | N | 1-phenyl-3-pyrrolidinyl |
| 2534 | CH | CH | N | CH | N | 1-(2-fluorophenyl)-3-pyrrolidinyl |
| 2535 | CH | CH | N | CH | N | 1-(3-fluorophenyl)-3-pyrrolidinyl |
| 2536 | CH | CH | N | CH | N | 1-(4-fluorophenyl)-3-pyrrolidinyl |
| 2537 | CH | CH | N | CH | N | 1-(2-chlorophenyl)-3-pyrrolidinvl |
| 2538 | CH | CH | N | CH | N | 1-(3-chlorophenyl)-3-pyrrolidinyl |
| 2539 | CH | CH | N | CH | N | 1-(4-chlorophenyl)-3-pyrrolidinyl |
| 2540 | CH | CH | N | CH | N | 1-(2-methylphenyl)-3-pyrrolidinyl |
| 2541 | CH | CH | N | CH | N | 1-(3-methylphenyl)-3-pyrrolidinyl |
| 2542 | CH | CH | N | CH | N | 1-(4-methylphenyl)-3-pyrrolidinyl |
| 2543 | CH | CH | N | CH | N | 1-(2-methoxyphenyl)-3-pyrrolidinyl |
| 2544 | CH | CH | N | CH | N | 1-(3-methoxyphenyl)-3-pyrrolidinyl |
| 2545 | CH | CH | N | CH | N | 1-(4-methoxyphenyl)-3-pyrrolidinyl |
| 2546 | CH | CH | N | CH | N | 1-(2-trifluoromethylphenyl)-3-pyrrolidinyl |
| 2547 | CH | CH | N | CH | N | 1-(3-trifluoromethylphenyl)-3-pyrrolidinyl |
| 2548 | CH | CH | N | CH | N | 1-(4-trifluoromethylphenyl)-3-pyrrolidinyl |
| 2549 | CH | CH | N | CH | N | 1-(3,5-diflurophenyl)-3-pyrrolidinyl |
| 2550 | CH | CH | N | CH | N | 1-(2-difluromethoxyphenyl)-3-pyrrolidinyl |
| 2551 | CH | CH | N | CH | N | 1-(3-difluromethoxyphenyl)-3-pyrrolidinyl |
| 2552 | CH | CH | N | CH | N | 1-(4-difluromethoxyphenyl)-3-pyrrolidinyl |
| 2553 | CH | CH | N | CH | N | 1-(2-pyridyl)-3-pyrrolidinyl |
| 2554 | CH | CH | N | CH | N | 1-(3-pyridyl)-3-pyrrolidinyl |
| 2555 | CH | CH | N | CH | N | 1-(4-pyridyl)-3-pyrrolidinyl |
| 2556 | CH | CH | N | CH | N | 1-(2-pyrimidinyl)-3-pyrrolidinyl |
| 2557 | CH | CH | N | CH | N | 5-oxo-1-phenyl-3-pyrrolidinyl |
| 2558 | CH | CH | N | CH | N | 1-phenyl-3-piperidyl |
| 2559 | CH | CH | N | CH | N | 1-(2-fluorophenyl)-3-piperidyl |
| 2560 | CH | CH | N | CH | N | 1-(3-fluorophenyl)-3-piperidyl |
| 2561 | CH | CH | N | CH | N | 1-(4-fluorophenyl)-3-piperidyl |
| 2562 | CH | CH | N | CH | N | 1-(2-chlorophenyl)-3-piperidyl |
| 2563 | CH | CH | N | CH | N | 1-(3-chlorophenyl)-3-piperidyl |
| 2564 | CH | CH | N | CH | N | 1-(4-chlorophenyl)-3-piperidyl |
| 2565 | CH | CH | N | CH | N | 1-(2-methylphenyl)-3-piperidyl |
| 2566 | CH | CH | N | CH | N | 1-(3-methylphenyl)-3-piperidyl |
| 2567 | CH | CH | N | CH | N | 1-(4-methylphenyl)-3-piperidyl |
| 2568 | CH | CH | N | CH | N | 1-(2-methoxyphenyl)-3-piperidyl |
| 2569 | CH | CH | N | CH | N | 1-(3-methoxyphenyl)-3-piperidyl |
| 2570 | CH | CH | N | CH | N | 1-(4-methoxyphenyl)-3-piperidyl |
| 2571 | CH | CH | N | CH | N | 1-(2-trifluoromethylphenyl)-3-piperidyl |
| 2572 | CH | CH | N | CH | N | 1-(3-trifluoromethylphenyl)-3-piperidyl |
| 2573 | CH | CH | N | CH | N | 1-(4-trifluoromethylphenyl)-3-piperidyl |

TABLE 3-continued

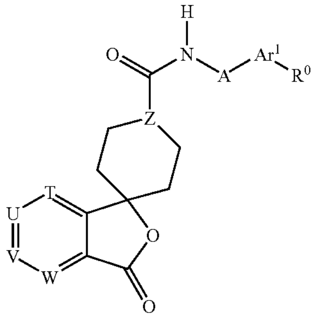

| No. | T | U | V | W | Z | A—$Ar^1$—$R^0$ |
|---|---|---|---|---|---|---|
| 2574 | CH | CH | N | CH | N | 1-(3,5-difluorophenyl)-3-piperidyl |
| 2575 | CH | CH | N | CH | N | 1-(2-difluoromethoxyphenyl)-3-piperidyl |
| 2576 | CH | CH | N | CH | N | 1-(3-difluoromethoxyphenyl)-3-piperidyl |
| 2577 | CH | CH | N | CH | N | 1-(4-difluoromethoxyphenyl)-3-piperidyl |
| 2578 | CH | CH | N | CH | N | 1-(2-pyridyl)-3-piperidyl |
| 2579 | CH | CH | N | CH | N | 1-(3-pyridyl)-3-piperidyl |
| 2580 | CH | CH | N | CH | N | 1-(4-pyridyl)-3-piperidyl |
| 2581 | CH | CH | N | CH | N | 1-phenyl-4-piperidyl |
| 2582 | CH | CH | N | CH | N | 1-(2-fluorophenyl)-4-piperidyl |
| 2583 | CH | CH | N | CH | N | 1-(3-fluorophenyl)-4-piperidyl |
| 2584 | CH | CH | N | CH | N | 1-(4-fluorophenyl)-4-piperidyl |
| 2585 | CH | CH | N | CH | N | 1-(2-chlorophenyl)-4-piperidyl |
| 2586 | CH | CH | N | CH | N | 1-(3-chlorophenyl)-4-piperidyl |
| 2587 | CH | CH | N | CH | N | 1-(4-chlorophenyl)-4-piperidyl |
| 2588 | CH | CH | N | CH | N | 1-(2-methylphenyl)-4-piperidyl |
| 2589 | CH | CH | N | CH | N | 1-(3-methylphenyl)-4-piperidyl |
| 2590 | CH | CH | N | CH | N | 1-(4-methylphenyl)-4-piperidyl |
| 2591 | CH | CH | N | CH | N | 1-(2-methoxyphenyl)-4-piperidyl |
| 2592 | CH | CH | N | CH | N | 1-(3-methoxyphenyl)-4-piperidyl |
| 2593 | CH | CH | N | CH | N | 1-(4-methoxyphenyl)-4-piperidyl |
| 2594 | CH | CH | N | CH | N | 1-(2-trifluoromethylphenyl)-4-piperidyl |
| 2595 | CH | CH | N | CH | N | 1-(3-trifluoromethylphenyl)-4-piperidyl |
| 2596 | CH | CH | N | CH | N | 1-(4-trifluoromethylphenyl)-4-piperidyl |
| 2597 | CH | CH | N | CH | N | 1-(3,5-difluorophenyl)-4-piperidyl |
| 2598 | CH | CH | N | CH | N | 1-(2-difluoromethoxyphenyl)-4-piperidyl |
| 2599 | CH | CH | N | CH | N | 1-(3-difluoromethoxyphenyl)-4-piperidyl |
| 2600 | CH | CH | N | CH | N | 1-(4-difluoromethoxyphenyl)-4-piperidyl |
| 2601 | CH | CH | N | CH | N | 1-(2-pyridyl)-4-piperidyl |
| 2602 | CH | CH | N | CH | N | 1-(3-pyridyl)-4-piperidyl |
| 2603 | CH | CH | N | CH | N | 1-(4-pyridyl)-4-piperidyl |
| 2604 | CH | CH | N | CH | N | 3-hydroxymethyl-1-phenyl-4-piperidyl |
| 2605 | CH | CH | N | CH | N | 3-methoxycarbonyl-1-phenyl-4-piperidyl |
| 2606 | CH | CH | N | CH | N | 3-ethoxycarbonyl-1-phenyl-4-piperidyl |
| 2607 | CH | CH | N | CH | N | 3-isopropoxycarbonyl-1-phenyl-4-piperidyl |
| 2608 | CH | CH | N | CH | N | 4-phenylcyclohexyl |
| 2609 | CH | CH | N | CH | N | 4-(2-fluorophenyl)cyclohexyl |
| 2610 | CH | CH | N | CH | N | 4-(3-fluorophenyl)cyclohexyl |
| 2611 | CH | CH | N | CH | N | 4-(4-fluorophenyl)cyclohexyl |
| 2612 | CH | CH | N | CH | N | 4-(2-chlorophenyl)cyclohexyl |
| 2613 | CH | CH | N | CH | N | 4-(3-chlorophenyl)cyclohexyl |
| 2614 | CH | CH | N | CH | N | 4-(4-chlorophenyl)cyclohexyl |
| 2615 | CH | CH | N | CH | N | 4-(2-methylphenyl)cyclohexyl |
| 2616 | CH | CH | N | CH | N | 4-(3-methylphenyl)cyclohexyl |
| 2617 | CH | CH | N | CH | N | 4-(4-methylphenyl)cyclohexyl |
| 2618 | CH | CH | N | CH | N | 4-(2-methoxyphenyl)cyclohexyl |
| 2619 | CH | CH | N | CH | N | 4-(3-methoxyphenyl)cyclohexyl |
| 2620 | CH | CH | N | CH | N | 4-(4-methoxyphenyl)cyclohexyl |

TABLE 3-continued

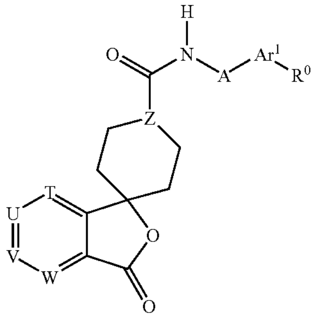

| No. | T | U | V | W | Z | A—$Ar^1$—$R^0$ |
|---|---|---|---|---|---|---|
| 2621 | CH | CH | N | CH | N | 4-(2-trifluoromethylphenyl)cyclo-hexyl |
| 2622 | CH | CH | N | CH | N | 4-(3-trifluoromethylphenyl)cyclo-hexyl |
| 2623 | CH | CH | N | CH | N | 4-(4-trifluoromethylphenyl)cyclo-hexyl |
| 2624 | CH | CH | N | CH | N | 4-(3,5-difluorophenyl)cyclohexyl |
| 2625 | CH | CH | N | CH | N | 4-(3-acetylphenyl)cyclohexyl |
| 2626 | CH | CH | N | CH | N | 4-(3-cyanophenyl)cyclohexyl |
| 2627 | CH | CH | N | CH | N | 4-(2-difluoromethoxyphenyl)cyclo-hexyl |
| 2628 | CH | CH | N | CH | N | 4-(3-difluoromethoxyphenyl)cyclo-hexyl |
| 2629 | CH | CH | N | CH | N | 4-(4-difluoromethoxyphenyl)cyclo-hexyl |
| 2630 | CH | CH | N | CH | N | 4-(2-pyridyl)cyclohexyl |
| 2631 | CH | CH | N | CH | N | 4-(3-pyridyl)cyclohexyl |
| 2632 | CH | CH | N | CH | N | 4-(4-pyridyl)cyclohexyl |
| 2633 | CH | CH | N | CH | N | 4-(4-fluoro-3-pyridyl)cyclohexyl |
| 2634 | CH | CH | N | CH | N | 4-(3-quinolyl)cyclohexyl |
| 2635 | CH | CH | N | CH | N | 4-(3-fluorophenyl)-4-hydroxy-cyclohexyl |
| 2636 | CH | CH | N | CH | N | 3-phenylcyclohexyl |
| 2637 | CH | CH | N | CH | N | 3-phenylcyclopentyl |
| 2638 | CH | CH | N | CH | N | 6-phenyl-3-tetrahydropyranyl |
| 2639 | CH | CH | N | CH | N | 6-(3-fluorophenyl)-3-tetrahydro-pyranyl |
| 2640 | CH | CH | N | CH | N | 2-phenylcyclopropyl |
| 2641 | CH | CH | N | CH | N | 2-(2-pyridyl)cyclopropyl |
| 2642 | CH | CH | N | CH | N | 2-(3-pyridyl)cyclopropyl |
| 2643 | CH | CH | N | CH | N | 2-(4-pyridyl)cyclopropyl |
| 2644 | CH | CH | N | CH | N | 2-(3-fluorophenyl)cyclopropyl |
| 2645 | CH | CH | N | CH | N | 2-indanyl |
| 2646 | CH | CH | N | CH | N | 2-tetrahydronaphthyl |
| 2647 | CH | CH | N | CH | N | 6-methoxy-2-tetrahydronaphthyl |
| 2648 | CH | CH | N | CH | N | benzyl |
| 2649 | CH | CH | N | CH | N | phenethyl |
| 2650 | CH | CH | N | CH | N | 3-phenylpropyl |
| 2651 | CH | CH | N | CH | N | 4-phenylbutyl |
| 2652 | CH | CH | N | CH | N | 2-methoxyphenethyl |
| 2653 | CH | CH | N | CH | N | 3-methoxyphenethyl |
| 2654 | CH | CH | N | CH | N | 4-methoxyphenethyl |
| 2655 | CH | CH | N | CH | N | 4-fluorophenethyl |
| 2656 | CH | CH | N | CH | N | 4-bromophenethyl |
| 2657 | CH | CH | N | CH | N | 4-chlorophenethyl |
| 2658 | CH | CH | N | CH | N | 3-trifluoromethylphenethyl |
| 2659 | CH | CH | N | CH | N | 3,4-dimethoxyphenethyl |
| 2660 | CH | CH | N | CH | N | 3-propoxyphenethyl |
| 2661 | CH | CH | N | CH | N | 3,5-difluorophenethyl |
| 2662 | CH | CH | N | CH | N | 4-dimethylaminophenethyl |
| 2663 | CH | CH | N | CH | N | 3-difluoromethoxyphenethyl |
| 2664 | CH | CH | N | CH | N | 2-methylphenethyl |
| 2665 | CH | CH | N | CH | N | 4-acetylphenethyl |
| 2666 | CH | CH | N | CH | N | 4-dimethylamino-2-methoxyphenethyl |
| 2667 | CH | CH | N | CH | N | cyclohexylethyl |
| 2668 | CH | CH | N | CH | N | 2-(2-pyridyl)ethyl |
| 2669 | CH | CH | N | CH | N | 2-(3-pyridyl)ethyl |
| 2670 | CH | CH | N | CH | N | 2-(4-pyridyl)ethyl |
| 2671 | CH | CH | N | CH | N | 2-(2-quinolyl)ethyl |
| 2672 | CH | CH | N | CH | N | 2-(3-quinolyl)ethyl |
| 2673 | CH | CH | N | CH | N | 2-(4-quinolyl)ethyl |

TABLE 3-continued

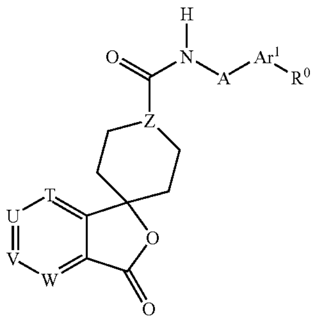

| No. | T | U | V | W | Z | A—Ar$^1$—R$^0$ |
|---|---|---|---|---|---|---|
| 2674 | CH | CH | N | CH | N | 2-(6-quinolyl)ethyl |
| 2675 | CH | CH | N | CH | N | 2-(2-indolyl)ethyl |
| 2676 | CH | CH | N | CH | N | 2-(3-indolyl)ethyl |
| 2677 | CH | CH | N | CH | N | 2-(7-aza-3-indolyl)ethyl |
| 2678 | CH | CH | N | CH | N | 2-(benzimidazolyl)ethyl |
| 2679 | CH | CH | N | CH | N | 2-(benzoxazolyl)ethyl |
| 2680 | CH | CH | N | CH | N | 2-(benzothiazolyl)ethyl |
| 2681 | CH | CH | N | CH | N | 2-(1-naphthyl)ethyl |
| 2682 | CH | CH | N | CH | N | 2-(2-naphthyl)ethyl |
| 2683 | CH | CH | N | CH | N | 1-(hydroxymethyl)-2-phenylethyl |
| 2684 | CH | CH | N | CH | N | 1-(methoxycarbonyl)-2-phenylethyl |
| 2685 | CH | CH | N | CH | N | 1-(ethoxycarbonyl)-2-phenylethyl |
| 2686 | CH | CH | N | CH | N | 1-carboxy-2-phenylethyl |
| 2687 | CH | CH | N | CH | N | 1-(benzyloxycarbonyl)-2-phenyl-ethyl |
| 2688 | CH | CH | N | CH | N | 1-(phenoxymethyl)-2-phenylethyl |
| 2689 | CH | CH | N | CH | N | 1-(benzyloxymethyl)-2-phenylethyl |
| 2690 | CH | CH | N | CH | N | 1-(benzylcarbamoyl)-2-phenylethyl |
| 2691 | CH | CH | N | CH | N | 1-(N-methylbenzylcarbamoyl)-2-phenylethyl |
| 2692 | CH | CH | N | CH | N | 1-(phenylcarbamoyl)-2-phenylethyl |
| 2693 | CH | CH | N | CH | N | 1-(N-methylphenylcarbamoyl)-2-phenylethyl |
| 2694 | CH | CH | N | CH | N | 1-(N-benzylaminomethyl)-2-phenylethyl |
| 2695 | CH | CH | N | CH | N | 1-(N-benzyl-N-methylamino-methyl)-2-phenylethyl |
| 2696 | CH | CH | N | CH | N | 1-(anilinomethyl)-2-phenylethyl |
| 2697 | CH | CH | N | CH | N | 1-(N-methylanilinomethyl)-2-phenylethyl |
| 2698 | CH | CH | N | CH | N | 1-(N-methylaminomethyl)-2-phenylethyl |
| 2699 | CH | CH | N | CH | N | 1-(N-ethylaminomethyl)-2-phenylethyl |
| 2700 | CH | CH | N | CH | N | 1-(N-isobutylaminomethyl)-2-phenylethyl |
| 2701 | CH | CH | N | CH | N | 1-(N-cyclopropylmethylamino-methyl)-2-phenylethyl |
| 2702 | CH | CH | N | CH | N | 1-(aminomethyl)-2-phenylethyl |
| 2703 | CH | CH | N | CH | N | 1-benzyl-2-(2-pyridylmethyl-amino)ethyl |
| 2704 | CH | CH | N | CH | N | 1-benzyl-2-(3-pyridylmethyl-amino)ethyl |
| 2705 | CH | CH | N | CH | N | 1-benzyl-2-(4-pyridylmethyl-amino)ethyl |
| 2706 | CH | CH | N | CH | N | 2-phenyl-1-(2-pyridylmethyl-carbamoyl)ethyl |
| 2707 | CH | CH | N | CH | N | 2-phenyl-1-(3-pyridylmethyl-carbamoyl)ethyl |
| 2708 | CH | CH | N | CH | N | 2-phenyl-1-(4-pyridylmethyl-carbamoyl)ethyl |
| 2709 | CH | CH | N | CH | N | 2-hydroxy-2-phenylethyl |
| 2710 | CH | CH | N | CH | N | benzoylmethyl |
| 2711 | CH | CH | N | CH | N | 1-(benzyloxycarbonyl)-2-(3-indolyl)ethyl |
| 2712 | CH | CH | N | CH | N | 1-(benzyloxycarbonyl)-2-cyclohexylethyl |
| 2713 | CH | CH | N | CH | N | 1-(phenoxymethyl)-2-(3-indolyl)ethyl |
| 2714 | CH | CH | N | CH | N | 2-(2-methoxyphenoxy)ethyl |

TABLE 3-continued

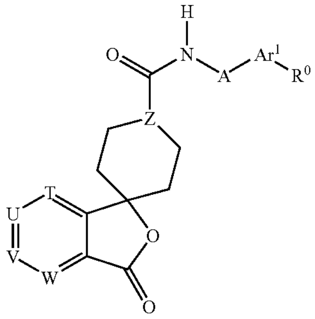

| No. | T | U | V | W | Z | A—$Ar^1$—$R^0$ |
|---|---|---|---|---|---|---|
| 2715 | CH | CH | N | CH | N | 1-(benzylcarbamoyl)-2-cyclohexylethyl |
| 2716 | CH | CH | N | CH | N | 1-(N-methylbenzylcarbamoyl)-2-cyclohexylethyl |
| 2717 | CH | CH | N | CH | N | 1-(phenylcarbamoyl)-2-cyclohexyl-ethyl |
| 2718 | CH | CH | N | CH | N | 1-(N-methylphenylcarbamoyl)-2-cyclohexylethyl |
| 2719 | CH | CH | N | CH | N | 1-(benzyloxycarbonyl)-2-(3-pyridyl)ethyl |
| 2720 | CH | CH | N | CH | N | 1-(benzylaminomethyl)-2-(3-pyridyl)ethyl |
| 2721 | CH | CH | N | CH | N | 1-(benzylcarbamoyl)-2-4-pyridyl)ethyl |
| 2722 | CH | CH | N | CH | N | 1-(4-pyridylmethylcarbamoyl)-2-(4-fluorophenyl)ethyl |
| 2723 | CH | CH | N | CH | N | 1-(benzylcarbamoyl)-2-(7-aza-3-indolyl)ethyl |
| 2724 | CH | CH | N | CH | N | 1-(benzyloxymethyl)-2-(2-indolyl)ethyl |
| 2725 | CH | CH | N | CH | N | 1-(N-benzyl-N-methylaminomethyl)-2-(3-pyridyl)ethyl |
| 2726 | CH | CH | N | CH | N | 1-(N-methylbenzylcarbamoyl)-2-(3-pyridyl)ethyl |
| 2727 | CH | CH | N | CH | N | 2-hydroxy-2-(4-dimethylamino-phenyl)ethyl |
| 2728 | CH | CH | N | CH | N | 2-hydroxy-2-(2-quinolyl)ethyl |
| 2729 | CH | CH | N | CH | N | 2-hydroxy-2-(3-quinolyl)ethyl |
| 2730 | CH | CH | N | CH | N | 2-hydroxy-2-(4-quinolyl)ethyl |
| 2731 | CH | CH | N | CH | N | 2-hydroxy-2-(3,5-difluorophenyl)ethyl |
| 2732 | CH | CH | N | CH | N | 1-carboxy-2-cyclohexylethyl |
| 2733 | CH | CH | N | CH | N | 2-hydroxy-2-(6-quinolyl)ethyl |
| 2734 | CH | CH | N | CH | N | 2-(benzylamino)-2-phenylethyl |
| 2735 | CH | CH | N | CH | N | 2-amino-2-(2-naphthyl)propyl |
| 2736 | CH | CH | N | CH | N | 2-(phenylamino)ethyl |
| 2737 | CH | CH | N | CH | N | diphenylmethyl |
| 2738 | CH | CH | N | CH | N | 2,2-diphenylethyl |
| 2739 | CH | CH | N | CH | N | 2-phenyl-2-(2-pyridyl)ethyl |
| 2740 | CH | CH | N | CH | N | 2-phenyl-2-(3-pyridyl)ethyl |
| 2741 | CH | CH | N | CH | N | 2-phenyl-2-(4-pyridyl)ethyl |
| 2742 | CH | CH | N | CH | N | 2-phenoxy-2-phenylethyl |
| 2743 | CH | CH | N | CH | N | 2-(benzyloxy)-2-phenylethyl |
| 2744 | CH | CH | CH | N | CH | 1-phenyl-3-pyrrolidinyl |
| 2745 | CH | CH | CH | N | CH | 1-(2-fluorophenyl)-3-pyrrolidinyl |
| 2746 | CH | CH | CH | N | CH | 1-(3-fluorophenyl)-3-pyrrolidinyl |
| 2747 | CH | CH | CH | N | CH | 1-(4-fluorophenyl)-3-pyrrolidinyl |
| 2748 | CH | CH | CH | N | CH | 1-(2-chlorophenyl)-3-pyrrolidinyl |
| 2749 | CH | CH | CH | N | CH | 1-(3-chlorophenyl)-3-pyrrolidinyl |
| 2750 | CH | CH | CH | N | CH | 1-(4-chlorophenyl)-3-pyrrolidinyl |
| 2751 | CH | CH | CH | N | CH | 1-(2-methylphenyl)-3-pyrrolidinyl |
| 2752 | CH | CH | CH | N | CH | 1-(3-methylphenyl)-3-pyrrolidinyl |
| 2753 | CH | CH | CH | N | CH | 1-(4-methylphenyl)-3-pyrrolidinyl |
| 2754 | CH | CH | CH | N | CH | 1-(2-methoxyphenyl)-3-pyrrolidinyl |
| 2755 | CH | CH | CH | N | CH | 1-(3-methoxyphenyl)-3-pyrrolidinyl |
| 2756 | CH | CH | CH | N | CH | 1-(4-methoxyphenyl)-3-pyrrolidinyl |
| 2757 | CH | CH | CH | N | CH | 1-(2-trifluoromethylphenyl)-3-pyrrolidinyl |

TABLE 3-continued

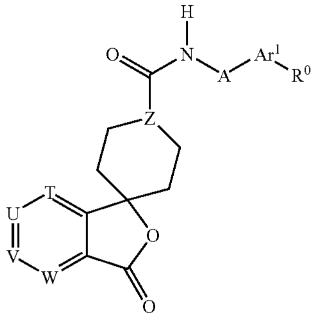

| No. | T | U | V | W | Z | A—Ar$^1$—R$^0$ |
|---|---|---|---|---|---|---|
| 2758 | CH | CH | CH | N | CH | 1-(3-trifluoromethylphenyl)-3-pyrrolidinyl |
| 2759 | CH | CH | CH | N | CH | 1-(4-trifluoromethylphenyl)-3-pyrrolidinyl |
| 2760 | CH | CH | CH | N | CH | 1-(3,5-difluorophenyl)-3-pyrrolidinyl |
| 2761 | CH | CH | CH | N | CH | 1-(2-difluoromethoxyphenyl)-3-pyrrolidinyl |
| 2762 | CH | CH | CH | N | CH | 1-(3-difluoromethoxyphenyl)-3-pyrrolidinyl |
| 2763 | CH | CH | CH | N | CH | 1-(4-difluoromethoxyphenyl)-3-pyrrolidinyl |
| 2764 | CH | CH | CH | N | CH | 1-(2-pyridyl)-3-pyrrolidinyl |
| 2765 | CH | CH | CH | N | CH | 1-(3-pyridyl)-3-pyrrolidinyl |
| 2766 | CH | CH | CH | N | CH | 1-(4-pyridyl)-3-pyrrolidinyl |
| 2767 | CH | CH | CH | N | CH | 1-(2-pyrimidinyl)-3-pyrrolidinyl |
| 2768 | CH | CH | CH | N | CH | 5-oxo-1-phenyl-3-pyrrolidinyl |
| 2769 | CH | CH | CH | N | CH | 1-phenyl-3-piperidyl |
| 2770 | CH | CH | CH | N | CH | 1-(2-fluorophenyl)-3-piperidyl |
| 2771 | CH | CH | CH | N | CH | 1-(3-fluorophenyl)-3-piperidyl |
| 2772 | CH | CH | CH | N | CH | 1-(4-fluorophenyl)-3-piperidyl |
| 2773 | CH | CH | CH | N | CH | 1-(2-chlorophenyl)-3-piperidyl |
| 2774 | CH | CH | CH | N | CH | 1-(3-chlorophenyl)-3-piperidyl |
| 2775 | CH | CH | CH | N | CH | 1-(4-chlorophenyl)-3-piperidyl |
| 2776 | CH | CH | CH | N | CH | 1-(2-methylphenyl)-3-piperidyl |
| 2777 | CH | CH | CH | N | CH | 1-(3-methylphenyl)-3-piperidyl |
| 2778 | CH | CH | CH | N | CH | 1-(4-methylphenyl)-3-piperidyl |
| 2779 | CH | CH | CH | N | CH | 1-(2-methoxyphenyl)-3-piperidyl |
| 2780 | CH | CH | CH | N | CH | 1-(3-methoxyphenyl)-3-piperidyl |
| 2781 | CH | CH | CH | N | CH | 1-(4-methoxyphenyl)-3-piperidyl |
| 2782 | CH | CH | CH | N | CH | 1-(2-trifluoromethylphenyl)-3-piperidyl |
| 2783 | CH | CH | CH | N | CH | 1-(3-trifluoromethylphenyl)-3-piperidyl |
| 2784 | CH | CH | CH | N | CH | 1-(4-trifluoromethylphenyl)-3-piperidyl |
| 2785 | CH | CH | CH | N | CH | 1-(3,5-difluorophenyl)-3-piperidyl |
| 2786 | CH | CH | CH | N | CH | 1-(2-difluoromethoxyphenyl)-3-piperidyl |
| 2787 | CH | CH | CH | N | CH | 1-(3-difluoromethoxyphenyl)-3-piperidyl |
| 2788 | CH | CH | CH | N | CH | 1-(4-difluoromethoxyphenyl)-3-piperidyl |
| 2789 | CH | CH | CH | N | CH | 1-(2-pyridyl)-3-piperidyl |
| 2790 | CH | CH | CH | N | CH | 1-(3-pyridyl)-3-piperidyl |
| 2791 | CH | CH | CH | N | CH | 1-(4-pyridyl)-3-piperidyl |
| 2792 | CH | CH | CH | N | CH | 1-phenyl-4-piperidyl |
| 2793 | CH | CH | CH | N | CH | 1-(2-fluorophenyl)-4-piperidyl |
| 2794 | CH | CH | CH | N | CH | 1-(3-fluorophenyl)-4-piperidyl |
| 2795 | CH | CH | CH | N | CH | 1-(4-fluorophenyl)-4-piperidyl |
| 2796 | CH | CH | CH | N | CH | 1-(2-chlorophenyl)-4-piperidyl |
| 2797 | CH | CH | CH | N | CH | 1-(3-chlorophenyl)-4-piperidyl |
| 2798 | CH | CH | CH | N | CH | 1-(4-chlorophenyl)-4-piperidyl |
| 2799 | CH | CH | CH | N | CH | 1-(2-methylphenyl)-4-piperidyl |
| 2800 | CH | CH | CH | N | CH | 1-(3-methylphenyl)-4-piperidyl |
| 2801 | CH | CH | CH | N | CH | 1-(4-methylphenyl)-4-piperidyl |
| 2802 | CH | CH | CH | N | CH | 1-(2-methoxyphenyl)-4-piperidyl |
| 2803 | CH | CH | CH | N | CH | 1-(3-methoxyphenyl)-4-piperidyl |
| 2804 | CH | CH | CH | N | CH | 1-(4-methoxyphenyl)-4-piperidyl |

TABLE 3-continued

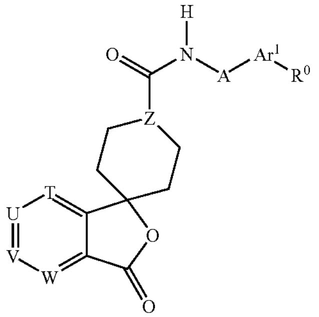

| No. | T | U | V | W | Z | A—Ar$^1$—R$^0$ |
|---|---|---|---|---|---|---|
| 2805 | CH | CH | CH | N | CH | 1-(2-trifluoromethylphenyl)-4-piperidyl |
| 2806 | CH | CH | CH | N | CH | 1-(3-trifluoromethylphenyl)-4-piperidyl |
| 2807 | CH | CH | CH | N | CH | 1-(4-trifluoromethylphenyl)-4-piperidyl |
| 2808 | CH | CH | CH | N | CH | 1-(3,5-difluorophenyl)-4-piperidyl |
| 2809 | CH | CH | CH | N | CH | 1-(2-difluoromethoxyphenyl)-4-piperidyl |
| 2810 | CH | CH | CH | N | CH | 1-(3-difluoromethoxyphenyl)-4-piperidyl |
| 2811 | CH | CH | CH | N | CH | 1-(4-difluoromethoxyphenyl)-4-piperidyl |
| 2812 | CH | CH | CH | N | CH | 1-(2-pyridyl)-4-piperidyl |
| 2813 | CH | CH | CH | N | CH | 1-(3-pyridyl)-4-piperidyl |
| 2814 | CH | CH | CH | N | CH | 1-(4-pyridyl)-4-piperidyl |
| 2815 | CH | CH | CH | N | CH | 3-hydroxymethyl-1-phenyl-4-piperidyl |
| 2816 | CH | CH | CH | N | CH | 3-methoxycarbonyl-1-phenyl-4-piperidyl |
| 2817 | CH | CH | CH | N | CH | 3-ethoxycarbonyl-1-phenyl-4-piperidyl |
| 2818 | CH | CH | CH | N | CH | 3-isopropoxycarbonyl-1-phenyl-4-piperidyl |
| 2819 | CH | CH | CH | N | CH | 4-phenylcyclohexyl |
| 2820 | CH | CH | CH | N | CH | 4-(2-fluorophenyl)cyclohexyl |
| 2821 | CH | CH | CH | N | CH | 4-(3-fluorophenyl)cyclohexyl |
| 2822 | CH | CH | CH | N | CH | 4-(4-fluorophenyl)cyclohexyl |
| 2823 | CH | CH | CH | N | CH | 4-(2-chlorophenyl)cyclohexyl |
| 2824 | CH | CH | CH | N | CH | 4-(3-chlorophenyl)cyclohexyl |
| 2825 | CH | CH | CH | N | CH | 4-(4-chlorophenyl)cyclohexyl |
| 2826 | CH | CH | CH | N | CH | 4-(2-methylphenyl)cyclohexyl |
| 2827 | CH | CH | CH | N | CH | 4-(3-methylphenyl)cyclohexyl |
| 2828 | CH | CH | CH | N | CH | 4-(4-methylphenyl)cyclohexyl |
| 2829 | CH | CH | CH | N | CH | 4-(2-methoxyphenyl)cyclohexyl |
| 2830 | CH | CH | CH | N | CH | 4-(3-methoxyphenyl)cyclohexyl |
| 2831 | CH | CH | CH | N | CH | 4-(4-methoxyphenyl)cyclohexyl |
| 2832 | CH | CH | CH | N | CH | 4-(2-trifluoromethylphenyl)cyclohexyl |
| 2833 | CH | CH | CH | N | CH | 4-(3-trifluoromethylphenyl)cyclohexyl |
| 2834 | CH | CH | CH | N | CH | 4-(4-trifluoromethylphenyl)cyclohexyl |
| 2835 | CH | CH | CH | N | CH | 4-(3,5-difluorophenyl)cyclohexyl |
| 2836 | CH | CH | CH | N | CH | 4-(3-acetylphenyl)cyclohexyl |
| 2837 | CH | CH | CH | N | CH | 4-(3-cyanophenyl)cyclohexyl |
| 2838 | CH | CH | CH | N | CH | 4-(2-difluoromethoxyphenyl)cyclohexyl |
| 2839 | CH | CH | CH | N | CH | 4-(3-difluoromethoxyphenyl)cyclohexyl |
| 2840 | CH | CH | CH | N | CH | 4-(4-difluoromethoxyphenyl)cyclohexyl |
| 2841 | CH | CH | CH | N | CH | 4-(2-pyridyl)cyclohexyl |
| 2842 | CH | CH | CH | N | CH | 4-(3-pyridyl)cyclohexyl |
| 2843 | CH | CH | CH | N | CH | 4-(4-pyridyl)cyclohexyl |
| 2844 | CH | CH | CH | N | CH | 4-(4-fluoro-3-pyridyl)cyclohexyl |
| 2845 | CH | CH | CH | N | CH | 4-(3-quinolyl)cyclohexyl |
| 2846 | CH | CH | CH | N | CH | 4-(3-fluorophenyl)-4-hydroxycyclohexyl |
| 2847 | CH | CH | CH | N | CH | 3-phenylcyclohexyl |
| 2848 | CH | CH | CH | N | CH | 3-phenylcyclopentyl |

TABLE 3-continued

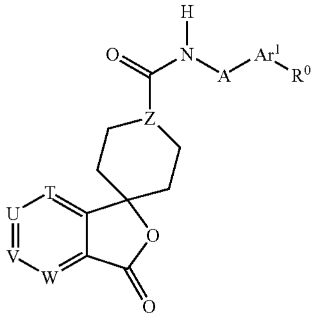

| No. | T | U | V | W | Z | A—$Ar^1$—$R^0$ |
|---|---|---|---|---|---|---|
| 2849 | CH | CH | CH | N | CH | 6-phenyl-3-tetrahydropyranyl |
| 2850 | CH | CH | CH | N | CH | 6-(3-fluorophenyl)-3-tetrahydro-pyranyl |
| 2851 | CH | CH | CH | N | CH | 2-phenylcyclopropyl |
| 2852 | CH | CH | CH | N | CH | 2-(2-pyridyl)cyclopropyl |
| 2853 | CH | CH | CH | N | CH | 2-(3-pyridyl)cyclopropyl |
| 2854 | CH | CH | CH | N | CH | 2-(4-pyridyl)cyclopropyl |
| 2855 | CH | CH | CH | N | CH | 2-(3-fluorophenyl)cyclopropyl |
| 2856 | CH | CH | CH | N | CH | 2-indanyl |
| 2857 | CH | CH | CH | N | CH | 2-tetrahydronaphthyl |
| 2858 | CH | CH | CH | N | CH | 6-methoxy-2-tetrahydronaphthyl |
| 2859 | CH | CH | CH | N | CH | benzyl |
| 2860 | CH | CH | CH | N | CH | phenethyl |
| 2861 | CH | CH | CH | N | CH | 3-phenylpropyl |
| 2862 | CH | CH | CH | N | CH | 4-phenylbutyl |
| 2863 | CH | CH | CH | N | CH | 2-methoxyphenethyl |
| 2864 | CH | CH | CH | N | CH | 3-methoxyphenethyl |
| 2865 | CH | CH | CH | N | CH | 4-methoxyphenethyl |
| 2866 | CH | CH | CH | N | CH | 4-fluorophenethyl |
| 2867 | CH | CH | CH | N | CH | 4-bromophenethyl |
| 2868 | CH | CH | CH | N | CH | 4-chlorophenethyl |
| 2869 | CH | CH | CH | N | CH | 3-trifluoromethylphenethyl |
| 2870 | CH | CH | CH | N | CH | 3,4-dimethoxyphenethyl |
| 2871 | CH | CH | CH | N | CH | 3-propoxyphenethyl |
| 2872 | CH | CH | CH | N | CH | 3,5-difluorophenethyl |
| 2873 | CH | CH | CH | N | CH | 4-dimethylaminophenethyl |
| 2874 | CH | CH | CH | N | CH | 3-difluoromethoxyphenethyl |
| 2875 | CH | CH | CH | N | CH | 2-methylphenethyl |
| 2876 | CH | CH | CH | N | CH | 4-acetylphenethyl |
| 2877 | CH | CH | CH | N | CH | 4-dimethylamino-2-methoxy-phenethyl |
| 2878 | CH | CH | CH | N | CH | cyclohexylethyl |
| 2879 | CH | CH | CH | N | CH | 2-(2-pyridyl)ethyl |
| 2880 | CH | CH | CH | N | CH | 2-(3-pyridyl)ethyl |
| 2881 | CH | CH | CH | N | CH | 2-(4-pyridyl)ethyl |
| 2882 | CH | CH | CH | N | CH | 2-(2-quinolyl)ethyl |
| 2883 | CH | CH | CH | N | CH | 2-(3-quinolyl)ethyl |
| 2884 | CH | CH | CH | N | CH | 2-(4-quinolyl)ethyl |
| 2885 | CH | CH | CH | N | CH | 2-(6-quinolyl)ethyl |
| 2886 | CH | CH | CH | N | CH | 2-(2-indolyl)ethyl |
| 2887 | CH | CH | CH | N | CH | 2-(3-indolyl)ethyl |
| 2888 | CH | CH | CH | N | CH | 2-(7-aza-3-indolyl)ethyl |
| 2889 | CH | CH | CH | N | CH | 2-(benzimidazolyl)ethyl |
| 2890 | CH | CH | CH | N | CH | 2-(benzoxazolyl)ethyl |
| 2891 | CH | CH | CH | N | CH | 2-(benzothiazolyl)ethyl |
| 2892 | CH | CH | CH | N | CH | 2-(1-naphthyl)ethyl |
| 2893 | CH | CH | CH | N | CH | 2-(2-naphthyl)ethyl |
| 2894 | CH | CH | CH | N | CH | 1-(hydroxymethyl)-2-phenylethyl |
| 2895 | CH | CH | CH | N | CH | 1-(methoxycarbonyl)-2-phenylethyl |
| 2896 | CH | CH | CH | N | CH | 1-(ethoxycarbonyl)-2-phenylethyl |
| 2897 | CH | CH | CH | N | CH | 1-carboxy-2-phenylethyl |
| 2898 | CH | CH | CH | N | CH | 1-(benzyloxycarbonyl)-2-phenylethyl |
| 2899 | CH | CH | CH | N | CH | 1-(phenoxymethyl)-2-phenylethyl |
| 2900 | CH | CH | CH | N | CH | 1-(benzyloxymethyl)-2-phenyl-ethyl |
| 2901 | CH | CH | CH | N | CH | 1-(benzylcarbamoyl)-2-phenylethyl |
| 2902 | CH | CH | CH | N | CH | 1-(N-methylbenzylcarbamoyl)-2-phenylethyl |
| 2903 | CH | CH | CH | N | CH | 1-(phenylcarbamoyl)-2-phenyl-ethyl |

TABLE 3-continued

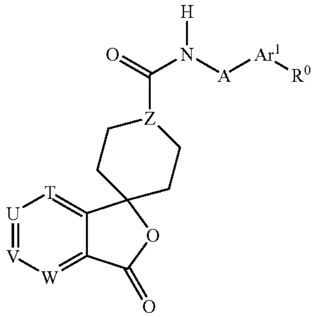

| No. | T | U | V | W | Z | A—$Ar^1$—$R^0$ |
|---|---|---|---|---|---|---|
| 2904 | CH | CH | CH | N | CH | 1-(N-methylphenylcarbamoyl)-2-phenylethyl |
| 2905 | CH | CH | CH | N | CH | 1-(N-benzylaminomethyl)-2-phenylethyl |
| 2906 | CH | CH | CH | N | CH | 1-(N-benzyl-N-methylamino-methyl)-2-phenylethyl |
| 2907 | CH | CH | CH | N | CH | 1-(anilinomethyl)-2-phenylethyl |
| 2908 | CH | CH | CH | N | CH | 1-(N-methylanilinomethyl)-2-phenylethyl |
| 2909 | CH | CH | CH | N | CH | 1-(N-methylaminomethyl)-2-phenyl-ethyl |
| 2910 | CH | CH | CH | N | CH | 1-(N-ethylaminomethyl)-2-phenyl-ethyl |
| 2911 | CH | CH | CH | N | CH | 1-(N-isobutylaminomethyl)-2-phenylethyl |
| 2912 | CH | CH | CH | N | CH | 1-(N-cyclopropylmethylamino-methyl)-2-phenylethyl |
| 2913 | CH | CH | CH | N | CH | 1-(aminomethyl)-2-phenylethyl |
| 2914 | CH | CH | CH | N | CH | 1-benzyl-2-(2-pyridylmethyl-amino)ethyl |
| 2915 | CH | CH | CH | N | CH | 1-benzyl-2-(3-pyridylmethyl-amino)ethyl |
| 2916 | CH | CH | CH | N | CH | 1-benzyl-2-(4-pyridylmethyl-amino)ethyl |
| 2917 | CH | CH | CH | N | CH | 2-phenyl-1-(2-pyridylmethyl-carbamoyl)ethyl |
| 2918 | CH | CH | CH | N | CH | 2-phenyl-1-(3-pyridylmethyl-carbamoyl)ethyl |
| 2919 | CH | CH | CH | N | CH | 2-phenyl-1-(4-pyridylmethyl-carbamoyl)ethyl |
| 2920 | CH | CH | CH | N | CH | 2-hydroxy-2-phenylethyl |
| 2921 | CH | CH | CH | N | CH | benzoylmethyl |
| 2922 | CH | CH | CH | N | CH | 1-(benzyloxycarbonyl)-2-(3-indolyl)ethyl |
| 2923 | CH | CH | CH | N | CH | 1-(benzyloxycarbonyl)-2-cyclo-hexylethyl |
| 2924 | CH | CH | CH | N | CH | 1-(phenoxymethyl)-2-(3-indolyl)ethyl |
| 2925 | CH | CH | CH | N | CH | 2-(2-methoxyphenoxy)ethyl |
| 2926 | CH | CH | CH | N | CH | 1-(benzylcarbamoyl)-2-cyclo-hexylethyl |
| 2927 | CH | CH | CH | N | CH | 1-(N-methylbenzylcarbamoyl)-2-cyclohexylethyl |
| 2928 | CH | CH | CH | N | CH | 1-(phenylcarbamoyl)-2-cyclohexylethyl |
| 2929 | CH | CH | CH | N | CH | 1-(N-methylphenylcarbamoyl)-2-cyclohexylethyl |
| 2930 | CH | CH | CH | N | CH | 1-(benzyloxycarbonyl)-2-(3-pyridyl)ethyl |
| 2931 | CH | CH | CH | N | CH | 1-(benzylaminomethyl)-2-(3-pyridyl)ethyl |
| 2932 | CH | CH | CH | N | CH | 1-(benzylcarbamoyl)-2-(4-pyridyl)ethyl |
| 2933 | CH | CH | CH | N | CH | 1-(4-pyridylmethylcarbamoyl)-2-(4-fluorophenyl)ethyl |
| 2934 | CH | CH | CH | N | CH | 1-(benzylcarbamoyl)-2-(7-aza-3-indolyl)ethyl |
| 2935 | CH | CH | CH | N | CH | 1-(benzyloxymethyl)-2-(2-indolyl)ethyl |
| 2936 | CH | CH | CH | N | CH | 1-(N-benzyl-N-methylaminomethyl)-2-(3-pyridyl)ethyl |

TABLE 3-continued

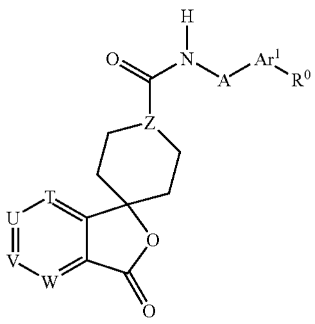

| No. | T | U | V | W | Z | A—Ar$^1$—R$^0$ |
|---|---|---|---|---|---|---|
| 2937 | CH | CH | CH | N | CH | 1-(N-methylbenzylcarbamoyl)-2-(3-pyridyl)ethyl |
| 2938 | CH | CH | CH | N | CH | 2-hydroxy-2-(4-dimethylamino-phenyl)ethyl |
| 2939 | CH | CH | CH | N | CH | 2-hydroxy-2-(2-quinolyl)ethyl |
| 2940 | CH | CH | CH | N | CH | 2-hydroxy-2-(3-quinolyl)ethyl |
| 2941 | CH | CH | CH | N | CH | 2-hydroxy-2-(4-quinolyl)ethyl |
| 2942 | CH | CH | CH | N | CH | 2-hydroxy-2-(3,5-difluoro-phenyl)ethyl |
| 2943 | CH | CH | CH | N | CH | 1-carboxy-2-cyclohexylethyl |
| 2944 | CH | CH | CH | N | CH | 2-hydroxy-2-(6-quinolyl)ethyl |
| 2945 | CH | CH | CH | N | CH | 2-(benzylamino)-2-phenylethyl |
| 2946 | CH | CH | CH | N | CH | 2-amino-2-(2-naphthyl)propyl |
| 2947 | CH | CH | CH | N | CH | 2-(phenylamino)ethyl |
| 2948 | CH | CH | CH | N | CH | diphenylmethyl |
| 2949 | CH | CH | CH | N | CH | 2,2-diphenylethyl |
| 2950 | CH | CH | CH | N | CH | 2-phenyl-2-(2-pyridyl)ethyl |
| 2951 | CH | CH | CH | N | CH | 2-phenyl-2-(3-pyridyl)ethyl |
| 2952 | CH | CH | CH | N | CH | 2-phenyl-2-(4-pyridyl)ethyl |
| 2953 | CH | CH | CH | N | CH | 2-phenoxy-2-phenylethyl |
| 2954 | CH | CH | CH | N | CH | 2-(benzyloxy)-2-phenylethyl |
| 2955 | CH | CH | CH | N | N | 1-phenyl-3-pyrrolidinyl |
| 2956 | CH | CH | CH | N | N | 1-(2-fluorophenyl)-3-pyrrolidinyl |
| 2957 | CH | CH | CH | N | N | 1-(3-fluorophenyl)-3-pyrrolidinyl |
| 2958 | CH | CH | CH | N | N | 1-(4-fluorophenyl)-3-pyrrolidinyl |
| 2959 | CH | CH | CH | N | N | 1-(2-chlorophenyl)-3-pyrrolidinyl |
| 2960 | CH | CH | CH | N | N | 1-(3-chlorophenyl)-3-pyrrolidinyl |
| 2961 | CH | CH | CH | N | N | 1-(4-chlorophenyl)-3-pyrrolidinyl |
| 2962 | CH | CH | CH | N | N | 1-(2-methylphenyl)-3-pyrrolidinyl |
| 2963 | CH | CH | CH | N | N | 1-(3-methylphenyl)-3-pyrrolidinyl |
| 2964 | CH | CH | CH | N | N | 1-(4-methylphenyl)-3-pyrrolidinyl |
| 2965 | CH | CH | CH | N | N | 1-(2-methoxyphenyl)-3-pyrrolidinyl |
| 2966 | CH | CH | CH | N | N | 1-(3-methoxyphenyl)-3-pyrrolidinyl |
| 2967 | CH | CH | CH | N | N | 1-(4-methoxyphenyl)-3-pyrrolidinyl |
| 2968 | CH | CH | CH | N | N | 1-(2-trifluoromethylphenyl)-3-pyrrolidinyl |
| 2969 | CH | CH | CH | N | N | 1-(3-trifluoromethylphenyl)-3-pyrrolidinyl |
| 2970 | CH | CH | CH | N | N | 1-(4-trifluoromethylphenyl)-3-pyrrolidinyl |
| 2971 | CH | CH | CH | N | N | 1-(3,5-difluorophenyl)-3-pyrrolidinyl |
| 2972 | CH | CH | CH | N | N | 1-(2-difluoromethoxyphenyl)-3-pyrrolidinyl |
| 2973 | CH | CH | CH | N | N | 1-(3-difluoromethoxyphenyl)-3-pyrrolidinyl |
| 2974 | CH | CH | CH | N | N | 1-(4-difluoromethoxyphenyl)-3-pyrrolidinyl |
| 2975 | CH | CH | CH | N | N | 1-(2-pyridyl)-3-pyrrolidinyl |
| 2976 | CH | CH | CH | N | N | 1-(3-pyridyl)-3-pyrrolidinyl |
| 2977 | CH | CH | CH | N | N | 1-(4-pyridyl)-3-pyrrolidinyl |
| 2978 | CH | CH | CH | N | N | 1-(2-pyrimidinyl)-3-pyrrolidinyl |
| 2979 | CH | CH | CH | N | N | 5-oxo-1-phenyl-3-pyrrolidinyl |
| 2980 | CH | CH | CH | N | N | 1-phenyl-3-piperidyl |
| 2981 | CH | CH | CH | N | N | 1-(2-fluorophenyl)-3-piperidyl |
| 2982 | CH | CH | CH | N | N | 1-(3-fluorophenyl)-3-piperidyl |
| 2983 | CH | CH | CH | N | N | 1-(4-fluorophenyl)-3-piperidyl |
| 2984 | CH | CH | CH | N | N | 1-(2-chlorophenyl)-3-piperidyl |
| 2985 | CH | CH | CH | N | N | 1-(3-chlorophenyl)-3-piperidyl |
| 2986 | CH | CH | CH | N | N | 1-(4-chlorophenyl)-3-piperidyl |
| 2987 | CH | CH | CH | N | N | 1-(2-methylphenyl)-3-piperidyl |

TABLE 3-continued

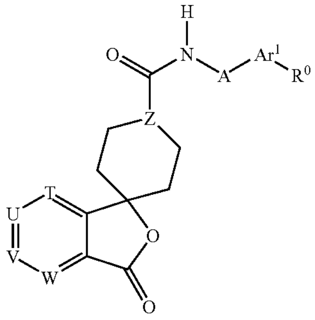

| No. | T | U | V | W | Z | A—$Ar^1$—$R^0$ |
|---|---|---|---|---|---|---|
| 2988 | CH | CH | CH | N | N | 1-(3-methylphenyl)-3-piperidyl |
| 2989 | CH | CH | CH | N | N | 1-(4-methylphenyl)-3-piperidyl |
| 2990 | CH | CH | CH | N | N | 1-(2-methoxyphenyl)-3-piperidyl |
| 2991 | CH | CH | CH | N | N | 1-(3-methoxyphenyl)-3-piperidyl |
| 2992 | CH | CH | CH | N | N | 1-(4-methoxyphenyl)-3-piperidyl |
| 2993 | CH | CH | CH | N | N | 1-(2-trifuoromethylphenyl)-3-piperidyl |
| 2994 | CH | CH | CH | N | N | 1-(3-trifuoromethylphenyl)-3-piperidyl |
| 2995 | CH | CH | CH | N | N | 1-(4-trifuoromethylphenyl)-3-piperidyl |
| 2996 | CH | CH | CH | N | N | 1-(3,5-difluorophenyl)-3-piperidyl |
| 2997 | CH | CH | CH | N | N | 1-(2-difluoromethoxyphenyl)-3-piperidyl |
| 2998 | CH | CH | CH | N | N | 1-(3-difluoromethoxyphenyl)-3-piperidyl |
| 2999 | CH | CH | CH | N | N | 1-(4-difluoromethoxyphenyl)-3-piperidiyl |
| 3000 | CH | CH | CH | N | N | 1-(2-pyridyl)-3-piperidyl |
| 3001 | CH | CH | CH | N | N | 1-(3-pyridyl)-3-piperidyl |
| 3002 | CH | CH | CH | N | N | 1-(4-pyridyl)-3-piperidyl |
| 3003 | CH | CH | CH | N | N | 1-phenyl-4-piperidyl |
| 3004 | CH | CH | CH | N | N | 1-(2-fluorophenyl)-4-piperidyl |
| 3005 | CH | CH | CH | N | N | 1-(3-fluorophenyl)-4-piperidyl |
| 3006 | CH | CH | CH | N | N | 1-(4-fluorophenyl)-4-piperidyl |
| 3007 | CH | CH | CH | N | N | 1-(2-chlorophenyl)-4-piperidyl |
| 3008 | CH | CH | CH | N | N | 1-(3-chlorophenyl)-4-piperidyl |
| 3009 | CH | CH | CH | N | N | 1-(4-chlorophenyl)-4-piperidyl |
| 3010 | CH | CH | CH | N | N | 1-(2-methylphenyl)-4-piperidyl |
| 3011 | CH | CH | CH | N | N | 1-(3-methylphenyl)-4-piperidyl |
| 3012 | CH | CH | CH | N | N | 1-(4-methylphenyl)-4-piperidyl |
| 3013 | CH | CH | CH | N | N | 1-(2-methoxyphenyl)-4-piperidyl |
| 3014 | CH | CH | CH | N | N | 1-(3-methoxyphenyl)-4-piperidyl |
| 3015 | CH | CH | CH | N | N | 1-(4-methoxyphenyl)-4-piperidyl |
| 3016 | CH | CH | CH | N | N | 1-(2-trifluoromethylphenyl)-4-piperidyl |
| 3017 | CH | CH | CH | N | N | 1-(3-trifluoromethylphenyl)-4-piperidyl |
| 3018 | CH | CH | CH | N | N | 1-(4-trifluoromethylphenyl)-4-piperidyl |
| 3019 | CH | CH | CH | N | N | 1-(3,5-difluorophenyl)-4-piperidyl |
| 3020 | CH | CH | CH | N | N | 1-(2-difluoromethoxyphenyl)-4-piperidyl |
| 3021 | CH | CH | CH | N | N | 1-(3-difluoromethoxyphenyl)-4-piperidyl |
| 3022 | CH | CH | CH | N | N | 1-(4-difluoromethoxyphenyl)-4-piperidyl |
| 3023 | CH | CH | CH | N | N | 1-(2-pyridyl)-4-piperidyl |
| 3024 | CH | CH | CH | N | N | 1-(3-pyridyl)-4-piperidyl |
| 3025 | CH | CH | CH | N | N | 1-(4-pyridyl)-4-piperidyl |
| 3026 | CH | CH | CH | N | N | 3-hydroxymethyl-1-phenyl-4-piperidyl |
| 3027 | CH | CH | CH | N | N | 3-methoxycarbonyl-1-phenyl-4-piperidyl |
| 3028 | CH | CH | CH | N | N | 3-ethoxycarbonyl-1-phenyl-4-piperidyl |
| 3029 | CH | CH | CH | N | N | 3-isopropoxycarbonyl-1-phenyl-4-piperidyl |
| 3030 | CH | CH | CH | N | N | 4-phenylcyclohexyl |

TABLE 3-continued

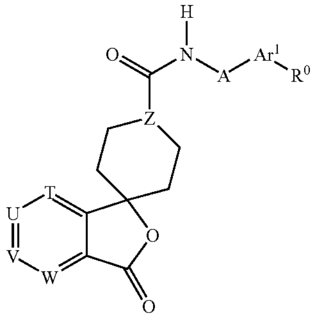

| No. | T | U | V | W | Z | A—$Ar^1$—$R^0$ |
|---|---|---|---|---|---|---|
| 3031 | CH | CH | CH | N | N | 4-(2-fluorophenyl)cyclohexyl |
| 3032 | CH | CH | CH | N | N | 4-(3-fluorophenyl)cyclohexyl |
| 3033 | CH | CH | CH | N | N | 4-(4-fluorophenyl)cyclohexyl |
| 3034 | CH | CH | CH | N | N | 4-(2-chlorophenyl)cyclohexyl |
| 3035 | CH | CH | CH | N | N | 4-(3-chlorophenyl)cyclohexyl |
| 3036 | CH | CH | CH | N | N | 4-(4-chlorophenyl)cyclohexyl |
| 3037 | CH | CH | CH | N | N | 4-(2-methylphenyl)cyclohexyl |
| 3038 | CH | CH | CH | N | N | 4-(3-methylphenyl)cyclohexyl |
| 3039 | CH | CH | CH | N | N | 4-(4-methylphenyl)cyclohexyl |
| 3040 | CH | CH | CH | N | N | 4-(2-methoxyphenyl)cyclohexyl |
| 3041 | CH | CH | CH | N | N | 4-(3-methoxyphenyl)cyclohexyl |
| 3042 | CH | CH | CH | N | N | 4-(4-methoxyphenyl)cyclohexyl |
| 3043 | CH | CH | CH | N | N | 4-(2-trifluoromethylphenyl)cyclohexyl |
| 3044 | CH | CH | CH | N | N | 4-(3-trifluoromethylphenyl)cyclohexyl |
| 3045 | CH | CH | CH | N | N | 4-(4-trifluoromethylphenyl)cyclohexyl |
| 3046 | CH | CH | CH | N | N | 4-(3,5-difluorophenyl)cyclohexyl |
| 3047 | CH | CH | CH | N | N | 4-(3-acetylphenyl)cyclohexyl |
| 3048 | CH | CH | CH | N | N | 4-(3-cyanophenyl)cyclohexyl |
| 3049 | CH | CH | CH | N | N | 4-(2-difluoromethoxyphenyl)cyclohexyl |
| 3050 | CH | CH | CH | N | N | 4-(3-difluoromethoxyphenyl)cyclohexyl |
| 3051 | CH | CH | CH | N | N | 4-(4-difluoromethoxyphenyl)cyclohexyl |
| 3052 | CH | CH | CH | N | N | 4-(2-pyridyl)cyclohexyl |
| 3053 | CH | CH | CH | N | N | 4-(3-pyridyl)cyclohexyl |
| 3054 | CH | CH | CH | N | N | 4-(4-pyridyl)cyclohexyl |
| 3055 | CH | CH | CH | N | N | 4-(4-fluoro-3-pyridyl)cyclohexyl |
| 3056 | CH | CH | CH | N | N | 4-(3-quinolyl)cyclohexyl |
| 3057 | CH | CH | CH | N | N | 4-(3-fluorophenyl)-4-hydroxycyclohexyl |
| 3058 | CH | CH | CH | N | N | 3-phenylcyclohexyl |
| 3059 | CH | CH | CH | N | N | 3-phenylcyclopentyl |
| 3060 | CH | CH | CH | N | N | 6-phenyl-3-tetrahydropyranyl |
| 3061 | CH | CH | CH | N | N | 6-(3-fluorophenyl)-3-tetrahydropyranyl |
| 3062 | CH | CH | CH | N | N | 2-phenylcyclopropyl |
| 3063 | CH | CH | CH | N | N | 2-(2-pyridyl)cyclopropyl |
| 3064 | CH | CH | CH | N | N | 2-(3-pyridyl)cyclopropyl |
| 3065 | CH | CH | CH | N | N | 2-(4-pyridyl)cyclopropyl |
| 3066 | CH | CH | CH | N | N | 2-(3-fluorophenyl)cyclopropyl |
| 3067 | CH | CH | CH | N | N | 2-indanyl |
| 3068 | CH | CH | CH | N | N | 2-tetrahydronaphthyl |
| 3069 | CH | CH | CH | N | N | 6-methoxy-2-tetrahydronaphthyl |
| 3070 | CH | CH | CH | N | N | benzyl |
| 3071 | CH | CH | CH | N | N | phenethyl |
| 3072 | CH | CH | CH | N | N | 3-phenylpropyl |
| 3073 | CH | CH | CH | N | N | 4-phenylbutyl |
| 3074 | CH | CH | CH | N | N | 2-methoxyphenethyl |
| 3075 | CH | CH | CH | N | N | 3-methoxyphenethyl |
| 3076 | CH | CH | CH | N | N | 4-methoxyphenethyl |
| 3077 | CH | CH | CH | N | N | 4-fluorophenethyl |
| 3078 | CH | CH | CH | N | N | 4-bromophenethyl |
| 3079 | CH | CH | CH | N | N | 4-chlorophenethyl |
| 3080 | CH | CH | CH | N | N | 3-trifluoromethylphenethyl |
| 3081 | CH | CH | CH | N | N | 3,4-dimethoxyphenethyl |
| 3082 | CH | CH | CH | N | N | 3-propoxyphenethyl |
| 3083 | CH | CH | CH | N | N | 3,5-difluorophenethyl |

TABLE 3-continued

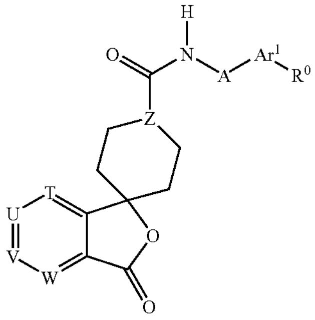

| No. | T | U | V | W | Z | A—$Ar^1$—$R^0$ |
|---|---|---|---|---|---|---|
| 3084 | CH | CH | CH | N | N | 4-dimethylaminophenethyl |
| 3085 | CH | CH | CH | N | N | 3-difluoromethoxyphenethyl |
| 3086 | CH | CH | CH | N | N | 2-methylphenethyl |
| 3087 | CH | CH | CH | N | N | 4-acetylphenethyl |
| 3088 | CH | CH | CH | N | N | 4-dimethylamino-2-methoxyphenethyl |
| 3089 | CH | CH | CH | N | N | cyclohexylethyl |
| 3090 | CH | CH | CH | N | N | 2-(2-pyridyl)ethyl |
| 3091 | CH | CH | CH | N | N | 2-(3-pyridyl)ethyl |
| 3092 | CH | CH | CH | N | N | 2-(4-pyridyl)ethyl |
| 3093 | CH | CH | CH | N | N | 2-(2-quinolyl)ethyl |
| 3094 | CH | CH | CH | N | N | 2-(3-quinolyl)ethyl |
| 3095 | CH | CH | CH | N | N | 2-(4-quinolyl)ethyl |
| 3096 | CH | CH | CH | N | N | 2-(6-quinolyl)ethyl |
| 3097 | CH | CH | CH | N | N | 2-(2-indolyl)ethyl |
| 3098 | CH | CH | CH | N | N | 2-(3-indolyl)ethyl |
| 3099 | CH | CH | CH | N | N | 2-(7-aza-3-indolyl)ethyl |
| 3100 | CH | CH | CH | N | N | 2-(benzimidazolyl)ethyl |
| 3101 | CH | CH | CH | N | N | 2-(benzoxazolyl)ethyl |
| 3102 | CH | CH | CH | N | N | 2-(benzothiazolyl)ethyl |
| 3103 | CH | CH | CH | N | N | 2-(1-naphthyl)ethyl |
| 3104 | CH | CH | CH | N | N | 2-(2-naphthyl)ethyl |
| 3105 | CH | CH | CH | N | N | 1-(hydroxymethyl)-2-phenylethyl |
| 3106 | CH | CH | CH | N | N | 1-(methoxycarbonyl)-2-phenylethyl |
| 3107 | CH | CH | CH | N | N | 1-(ethoxycarbonyl)-2-phenylethyl |
| 3108 | CH | CH | CH | N | N | 1-carboxy-2-phenylethyl |
| 3109 | CH | CH | CH | N | N | 1-(benzyloxycarbonyl)-2-phenylethyl |
| 3110 | CH | CH | CH | N | N | 1-(phenoxymethyl)-2-phenylethyl |
| 3111 | CH | CH | CH | N | N | 1-(benzyloxymethyl)-2-phenylethyl |
| 3112 | CH | CH | CH | N | N | 1-(benzylcarbamoyl)-2-phenylethyl |
| 3113 | CH | CH | CH | N | N | 1-(N-methylbenzylcarbamoyl)-2-phenylethyl |
| 3114 | CH | CH | CH | N | N | 1-(phenylcarbamoyl)-2-phenylethyl |
| 3115 | CH | CH | CH | N | N | 1-(N-methylphenylcarbamoyl)-2-phenylethyl |
| 3116 | CH | CH | CH | N | N | 1-(N-benzylaminomethyl)-2-phenylethyl |
| 3117 | CH | CH | CH | N | N | 1-(N-benzyl-N-methylaminomethyl)-2-phenylethyl |
| 3118 | CH | CH | CH | N | N | 1-(anilinomethyl)-2-phenylethyl |
| 3119 | CH | CH | CH | N | N | 1-(N-methylanilinomethyl)-2-phenylethyl |
| 3120 | CH | CH | CH | N | N | 1-(N-methylaminomethyl)-2-phenylethyl |
| 3121 | CH | CH | CH | N | N | 1-(N-ethylaminomethyl)-2-phenylethyl |
| 3122 | CH | CH | CH | N | N | 1-(N-isobutylaminomethyl)-2-phenylethyl |
| 3123 | CH | CH | CH | N | N | 1-(N-cyclopropylmethylamino-methyl)-2-phenylethyl |
| 3124 | CH | CH | CH | N | N | 1-(aminomethyl)-2-phenylethyl |
| 3125 | CH | CH | CH | N | N | 1-benzyl-2-(2-pyridylmethyl-amino)ethyl |
| 3126 | CH | CH | CH | N | N | 1-benzyl-2-(3-pyridylmethyl-amino)ethyl |
| 3127 | CH | CH | CH | N | N | 1-benzyl-2-(4-pyridylmethyl-amino)ethyl |
| 3128 | CH | CH | CH | N | N | 2-phenyl-1-(2-pyridylmethyl-carbamoyl)ethyl |

TABLE 3-continued

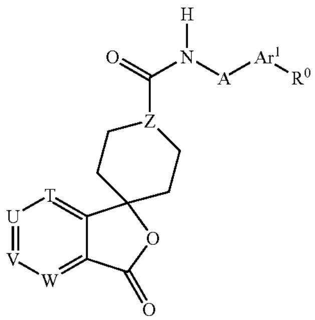

| No. | T | U | V | W | Z | A—Ar¹—R⁰ |
|---|---|---|---|---|---|---|
| 3129 | CH | CH | CH | N | N | 2-phenyl-1-(3-pyridylmethyl-carbamoyl)ethyl |
| 3130 | CH | CH | CH | N | N | 2-phenyl-1-(4-pyridylmethyl-carbamoyl)ethyl |
| 3131 | CH | CH | CH | N | N | 2-hydroxy-2-phenylethyl |
| 3132 | CH | CH | CH | N | N | benzoylmethyl |
| 3133 | CH | CH | CH | N | N | 1-(benzyloxycarbonyl)-2-(3-indolyl)ethyl |
| 3134 | CH | CH | CH | N | N | 1-(benzyloxycarbonyl)-2-cyclohexylethyl |
| 3135 | CH | CH | CH | N | N | 1-(phenoxymethyl)-2-(3-indolyl)ethyl |
| 3136 | CH | CH | CH | N | N | 2-(2-methoxyphenoxy)ethyl |
| 3137 | CH | CH | CH | N | N | 1-(benzylcarbamoyl)-2-cyclohexylethyl |
| 3138 | CH | CH | CH | N | N | 1-(N-methylbenzylcarbamoyl)-2-cyclohexylethyl |
| 3139 | CH | CH | CH | N | N | 1-(phenylcarbamoyl)-2-cyclohexylethyl |
| 3140 | CH | CH | CH | N | N | 1-(N-methylphenylcarbamoyl)-2-cyclohexylethyl |
| 3141 | CH | CH | CH | N | N | 1-(benzyloxycarbonyl)-2-(3-pyridyl)ethyl |
| 3142 | CH | CH | CH | N | N | 1-(benzylaminomethyl)-2-(3-pyridyl)ethyl |
| 3143 | CH | CH | CH | N | N | 1-(benzylcarbamoyl)-2-(4-pyridyl)ethyl |
| 3144 | CH | CH | CH | N | N | 1-(4-pyridylmethylcarbamoyl)-2-(4-fluorophenyl)ethyl |
| 3145 | CH | CH | CH | N | N | 1-(benzylcarbamoyl)-2-(7-aza-3-indolyl)ethyl |
| 3146 | CH | CH | CH | N | N | 1-(benzyloxymethyl)-2-(2-indolyl)ethyl |
| 3147 | CH | CH | CH | N | N | 1-(N-benzyl-N-methylaminomethyl)-2-(3-pyridyl)ethyl |
| 3148 | CH | CH | CH | N | N | 1-(N-methylbenzylcarbamoyl)-2-(3-pyridyl)ethyl |
| 3149 | CH | CH | CH | N | N | 2-hydroxy-2-(4-dimethylamino-phenyl)ethyl |
| 3150 | CH | CH | CH | N | N | 2-hydroxy-2-(2-quinolyl)ethyl |
| 3151 | CH | CH | CH | N | N | 2-hydroxy-2-(3-quinolyl)ethyl |
| 3152 | CH | CH | CH | N | N | 2-hydroxy-2-(4-quinolyl)ethyl |
| 3153 | CH | CH | CH | N | N | 3-hydroxy-2-(3,5-difluoro-phenyl)ethyl |
| 3154 | CH | CH | CH | N | N | 1-carboxy-2-cyclohexylethyl |
| 3155 | CH | CH | CH | N | N | 2-hydroxy-2-(6-quinolyl)ethyl |
| 3156 | CH | CH | CH | N | N | 2-(benzylamino)-2-phenylethyl |
| 3157 | CH | CH | CH | N | N | 2-amino-2-(2-naphthyl)propyl |
| 3158 | CH | CH | CH | N | N | 2-(phenylamino)ethyl |
| 3159 | CH | CH | CH | N | N | diphenylmethyl |
| 3160 | CH | CH | CH | N | N | 2,2-diphenylethyl |
| 3161 | CH | CH | CH | N | N | 2-phenyl-2-(2-pyridyl)ethyl |
| 3162 | CH | CH | CH | N | N | 2-phenyl-2-(3-pyridyl)ethyl |
| 3163 | CH | CH | CH | N | N | 2-phenyl-2-(4-pyridyl)ethyl |
| 3164 | CH | CH | CH | N | N | 2-phenoxy-2-phenylethyl |
| 3165 | CH | CH | CH | N | N | 2-(benzyloxy)-2-phenylethyl |

TABLE 4

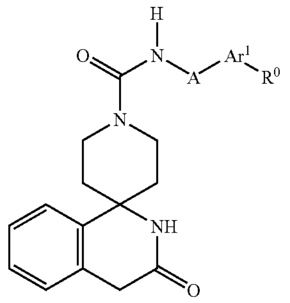

| No. | A—$Ar^1$—$R^0$ |
|---|---|
| 3157' | 1-phenyl-3-pyrrolidinyl |
| 3158' | 1-(2-fluorophenyl)-3-pyrrolidinyl |
| 3159' | 1-(3-fluorophenyl)-3-pyrrolidinyl |
| 3160' | 1-(4-fluorophenyl)-3-pyrrolidinyl |
| 3161' | 1-(2-chlorophenyl)-3-pyrrolidinyl |
| 3162' | 1-(3-chlorophenyl)-3-pyrrolidinyl |
| 3163' | 1-(4-chlorophenyl)-3-pyrrolidinyl |
| 3164' | 1-(2-methylphenyl)-3-pyrrolidinyl |
| 3165' | 1-(3-methyiphenyl)-3-pyrrolidinyl |
| 3166 | 1-(4-methylphenyl)-3-pyrrolidinyl |
| 3167 | 1-(2-methoxyphenyl)-3-pyrrolidinyl |
| 3168 | 1-(3-methoxyphenyl)-3-pyrrolidinyl |
| 3169 | 1-(4-methoxyphenyl)-3-pyrrolidinyl |
| 3170 | 1-(2-trifluoromethylphenyl)-3-pyrrolidinyl |
| 3171 | 1-(3-trifluoromethylphenyl)-3-pyrrolidinyl |
| 3172 | 1-(4-trifluoromethylphenyl)-3-pyrrolidinyl |
| 3173 | 1-(3,5-difluorophenyl)-3-pyrrolidinyl |
| 3174 | 1-(2-difluoromethoxyphenyl)-3-pyrrolidinyl |
| 3175 | 1-(3-difluoromethoxyphenyl)-3-pyrrolidinyl |
| 3176 | 1-(4-difluoromethoxyphenyl)-3-pyrrolidinyl |
| 3177 | 1-(2-pyridyl)-3-pyrrolidinyl |
| 3178 | 1-(3-pyridyl)-3-pyrrolidinyl |
| 3179 | 1-(4-pyridyl)-3-pyrrolidinyl |
| 3180 | 1-(2-pyrimidinyl)-3-pyrrolidinyl |
| 3181 | 5-oxo-1-phenyl-3-pyrrolidinyl |
| 3182 | 1-phenyl-3-piperidyl |
| 3183 | 1-(2-fluorophenyl)-3-piperidyl |
| 3184 | 1-(3-fluorophenyl)-3-piperidyl |
| 3185 | 1-(4-fluorophenyl)-3-piperidyl |
| 3186 | 1-(2-chlorophenyl)-3-piperidyl |
| 3187 | 1-(3-chlorophenyl)-3-piperidyl |
| 3188 | 1-(4-chlorophenyl)-3-piperidyl |
| 3189 | 1-(2-methylphenyl)-3-piperidyl |
| 3190 | 1-(3-methylphenyl)-3-piperidyl |
| 3191 | 1-(4-methylphenyl)-3-piperidyl |
| 3192 | 1-(2-methoxyphenyl)-3-piperidyl |
| 3193 | 1-(3-methoxyphenyl)-3-piperidyl |
| 3194 | 1-(4-methoxyphenyl)-3-piperidyl |
| 3195 | 1-(2-trifluoromethylphenyl)-3-piperidyl |
| 3196 | 1-(3-trifluoromethylphenyl)-3-piperidyl |
| 3197 | 1-(4-trifluoromethylphenyl)-3-piperidyl |
| 3198 | 1-(3,5-difluorophenyl)-3-piperidyl |
| 3199 | 1-(2-difluoromethoxyphenyl)-3-piperidyl |
| 3200 | 1-(3-difluoromethoxyphenyl)-3-piperidyl |
| 3201 | 1-(4-difluoromethoxyphenyl)-3-piperidyl |
| 3202 | 1-(2-pyridyl)-3-piperidyl |
| 3203 | 1-(3-pyridyl)-3-piperidyl |
| 3204 | 1-(4-pyridyl)-3-piperidyl |
| 3205 | 1-phenyl-4-piperidyl |
| 3206 | 1-(2-fluorophenyl)-4-piperidyl |
| 3207 | 1-(3-fluorophenyl)-4-piperidyl |
| 3208 | 1-(4-fluorophenyl)-4-piperidyl |
| 3209 | 1-(2-chlorophenyl)-4-piperidyl |
| 3210 | 1-(3-chlorophenyl)-4-piperidyl |
| 3211 | 1-(4-chlorophenyl)-4-piperidyl |
| 3212 | 1-(2-methylphenyl)-4-piperidyl |
| 3213 | 1-(3-methylphenyl)-4-piperidyl |
| 3214 | 1-(4-methylphenyl)-4-piperidyl |
| 3215 | 1-(2-methoxyphenyl)-4-piperidyl |
| 3216 | 1-(3-methoxyphenyl)-4-piperidyl |
| 3217 | 1-(4-methoxyphenyl)-4-piperidyl |

TABLE 4-continued

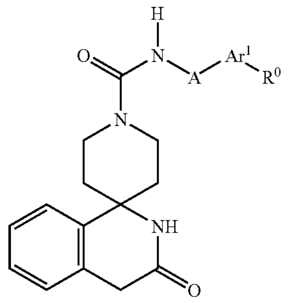

| No. | A—$Ar^1$—$R^0$ |
|---|---|
| 3218 | 1-(2-trifluoromethylphenyl)-4-piperidyl |
| 3219 | 1-(3-trifluoromethylphenyl)-4-piperidyl |
| 3220 | 1-(4-trifluoromethylphenyl)-4-piperidyl |
| 3221 | 1-(3,5-difluorophenyl)-4-piperidyl |
| 3222 | 1-(2-difluoromethoxyphenyl)-4-piperidyl |
| 3223 | 1-(3-difluoromethoxyphenyl)-4-piperidyl |
| 3224 | 1-(4-difluoromethoxyphenyl)-4-piperidyl |
| 3225 | 1-(2-pyridyl)-4-piperidyl |
| 3226 | 1-(3-pyridyl)-4-piperidyl |
| 3227 | 1-(4-pyridyl)-4-piperidyl |
| 3228 | 3-hydroxymethyl-1-phenyl-4-piperidyl |
| 3229 | 3-methoxycarbonyl-1-phenyl-4-piperidyl |
| 3230 | 3-ethoxycarbonyl-1-phenyl-4-piperidyl |
| 3231 | 3-isopropoxycarbonyl-1-phenyl-4-piperidyl |
| 3232 | 4-phenylcyclohexyl |
| 3233 | 4-(2-fluorophenyl)cyclohexyl |
| 3234 | 4-(3-fluorophenyl)cyclohexyl |
| 3235 | 4-(4-fluorophenyl)cyclohexyl |
| 3236 | 4-(2-chlorophenyl)cyclohexyl |
| 3237 | 4-(3-chlorophenyl)cyclohexyl |
| 3238 | 4-(4-chlorophenyl)cyclohexyl |
| 3239 | 4-(2-methylphenyl)cyclohexyl |
| 3240 | 4-(3-methylphenyl)cyclohexyl |
| 3241 | 4-(4-methylphenyl)cyclohexyl |
| 3242 | 4-(2-methoxyphenyl)cyclohexyl |
| 3243 | 4-(3-methoxyphenyl)cyclohexyl |
| 3244 | 4-(4-methoxyphenyl)cyclohexyl |
| 3245 | 4-(2-trifluoromethylphenyl)cyclohexyl |
| 3246 | 4-(3-trifluoromethylphenyl)cyclohexyl |
| 3247 | 4-(4-trifluoromethylphenyl)cyclohexyl |
| 3248 | 4-(3,5-difluorophenyl)cyclohexyl |
| 3249 | 4-(3-acetylphenyl)cyclohexyl |
| 3250 | 4-(3-cyanophenyl)cyclohexyl |
| 3251 | 4-(2-difluoromethoxyphenyl)cyclohexyl |
| 3252 | 4-(3-difluoromethoxyphenyl)cyclohexyl |
| 3253 | 4-(4-difluoromethoxyphenyl)cyclohexyl |
| 3254 | 4-(2-pyridyl)cyclohexyl |
| 3255 | 4-(3-pyridyl)cyclohexyl |
| 3256 | 4-(4-pyridyl)cyclohexyl |
| 3257 | 4-(4-fluoro-3-pyridyl)cyclohexyl |
| 3258 | 4-(3-quinolyl)cyclohexyl |
| 3259 | 4-(3-fluorophenyl)-4-hydroxycyclohexyl |
| 3260 | 3-phenylcyclohexyl |
| 3261 | 3-phenylcyclopentyl |
| 3262 | 6-phenyl-3-tetrahydropyranyl |
| 3263 | 6-(3-fluorophenyl)-3-tetrahydropyranyl |
| 3264 | 2-phenylcyclopropyl |
| 3265 | 2-(2-pyridyl)cyclopropyl |
| 3266 | 2-(3-pyridyl)cyclopropyl |
| 3267 | 2-(4-pyridyl)cyclopropyl |
| 3268 | 2-(3-fluorophenyl)cyclopropyl |
| 3269 | 2-indanyl |
| 3270 | 2-tetrahydronaphthyl |
| 3271 | 6-methoxy-2-tetrahydronaphthyl |
| 3272 | benzyl |
| 3273 | phenethyl |
| 3274 | 3-phenylpropyl |
| 3275 | 4-phenylbutyl |
| 3276 | 2-methoxyphenethyl |
| 3277 | 3-methoxyphenethyl |
| 3278 | 4-methoxyphenethyl |

TABLE 4-continued

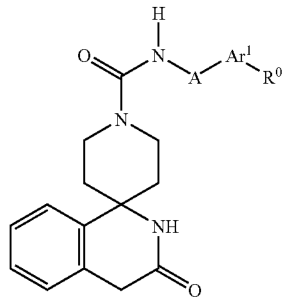

| No. | A—$Ar^1$—$R^0$ |
|---|---|
| 3279 | 4-fluorophenethyl |
| 3280 | 4-bromophenethyl |
| 3281 | 4-chlorophenethyl |
| 3282 | 3-trifluoromethylphenethyl |
| 3283 | 3,4-dimethoxyphenethyl |
| 3284 | 3-propoxyphenethyl |
| 3285 | 3,5-difluorophenethyl |
| 3286 | 4-dimethylaminophenethyl |
| 3287 | 3-difluoromethoxyphenethyl |
| 3288 | 2-methylphenethyl |
| 3289 | 4-acetylphenethyl |
| 3290 | 4-dimethylamino-2-methoxyphenethyl |
| 3291 | cyclohexylethyl |
| 3292 | 2-(2-pyridyl)ethyl |
| 3293 | 2-(3-pyridyl)ethyl |
| 3294 | 2-(4-pyridyl)ethyl |
| 3295 | 2-(2-quinolyl)ethyl |
| 3296 | 2-(3-quinolyl)ethyl |
| 3297 | 2-(4-quinolyl)ethyl |
| 3298 | 2-(6-quinolyl)ethyl |
| 3299 | 2-(2-indolyl)ethyl |
| 3300 | 2-(3-indolyl)ethyl |
| 3301 | 2-(7-aza-3-indolyl)ethyl |
| 3302 | 2-(benzimidazolyl)ethyl |
| 3303 | 2-(benzoxazolyl)ethyl |
| 3304 | 2-(benzothiazolyl)ethyl |
| 3305 | 2-(1-naphthyl)ethyl |
| 3306 | 2-(2-naphthyl)ethyl |
| 3307 | 1-(hydroxymethyl)-2-phenylethyl |
| 3308 | 1-(methoxycarbonyl)-2-phenylethyl |
| 3309 | 1-(ethoxycarbonyl)-2-phenylethyl |
| 3310 | 1-carboxy-2-phenylethyl |
| 3311 | 1-(benzyloxycarbonyl)-2-phenylethyl |
| 3312 | 1-(phenoxymethyl)-2-phenylethyl |
| 3313 | 1-(benzyloxymethyl)-2-phenylethyl |
| 3314 | 1-(benzylcarbamoyl)-2-phenylethyl |
| 3315 | 1-(N-methylbenzylcarbamoyl)-2-phenylethyl |
| 3316 | 1-(phenylcarbamoyl)-2-phenylethyl |
| 3317 | 1-(N-methylphenylcarbamoyl)-2-phenylethyl |
| 3318 | 1-(N-benzylaminomethyl)-2-phenylethyl |
| 3319 | 1-(N-benzyl-N-methylaminomethyl)-2-phenylethyl |
| 3320 | 1-(anilinomethyl)-2-phenylethyl |
| 3321 | 1-(N-methylanilinomethyl)-2-phenylethyl |
| 3322 | 1-(N-methylaminomethyl)-2-phenylethyl |
| 3323 | 1-(N-ethylaminomethyl)-2-phenylethyl |
| 3324 | 1-(N-isobutylaminomethyl)-2-phenylethyl |
| 3325 | 1-(N-cyclopropylmethylaminomethyl)-2-phenylethyl |
| 3326 | 1-(aminomethyl)-2-phenylethyl |
| 3327 | 1-benzyl-2-(2-pyridylmethylamino)ethyl |
| 3328 | 1-benzyl-2-(3-pyridylmethylamino)ethyl |
| 3329 | 1-benzyl-2-(4-pyridylmethylaniino)ethyl |
| 3330 | 2-phenyl-1-(2-pyridylmethylcarbamoyl)ethyl |
| 3331 | 2-phenyl-1-(3-pyridylmethylcarbamoyl)ethyl |
| 3332 | 2-phenyl-1-(4-pyridylmethylcarbamoyl)ethyl |
| 3333 | 2-hydroxy-2-phenylethyl |
| 3334 | benzoylmethyl |
| 3335 | 1-(benzyloxycarbonyl)-2-(3-indolyl)ethyl |
| 3336 | 1-(benzyloxycarbonyl)-2-cyclohexylethyl |
| 3337 | 1-(phenoxymethyl)-2-(3-indolyl)ethyl |
| 3338 | 2-(2-methoxyphenoxyy)ethyl |
| 3339 | 1-(benzylcarbamoyl)-2-cyclohexylethyl |

TABLE 4-continued

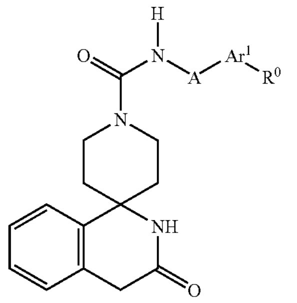

| No. | A—$Ar^1$—$R^0$ |
|---|---|
| 3340 | 1-(N-methylbenzylcarbamoyl)-2-cyclohexylethyl |
| 3341 | 1-(phenylcarbamoyl)-2-cyclohexylethyl |
| 3342 | 1-(N-methylphenylcarbamoyl)-2-cyclohexylethyl |
| 3343 | 1-(benzyloxycarbonyl)-2-(3-pyridyl)ethyl |
| 3344 | 1-(benzylaminomethyl)-2-(3-pyridyl)ethyl |
| 3345 | 1-(benzylcarbamoyl)-2-(4-pyridyl)ethyl |
| 3346 | 1-(4-pyridylmethylcarbamoyl)-2-(4-fluorophenyl)ethyl |
| 3347 | 1-(benzylcarbamoyl)-2-(7-aza-3-indolyl)ethyl |
| 3348 | 1-(benzyloxymethyl)-2-(2-indolyl)ethyl |
| 3349 | 1-(N-benzyl-N-methylaminomethyl)-2-(3-pyridyl)ethyl |
| 3350 | 1-(N-methylbenzylcarbamoyl)-2-(3-pyridyl)ethyl |
| 3351 | 2-hydroxy-2-(4-dimethylaminophenyl)ethyl |
| 3352 | 2-hydroxy-2-(2-quinolyl)ethyl |
| 3353 | 2-hydroxy-2-(3-quinolyl)ethyl |
| 3354 | 2-hydroxy-2-(4-quinolyl)ethyl |
| 3355 | 2-hydroxy-2-(3,5-difluorophenyl)ethyl |
| 3356 | 1-carboxy-2-cyclohexylethyl |
| 3357 | 2-hydroxy-2-(6-quinolyl)ethyl |
| 3358 | 2-(benzylamino)-2-phenylethyl |
| 3359 | 2-amino-2-(2-naphthyl)propyl |
| 3360 | 2-(phenylamino)ethyl |
| 3361 | diphenylmethyl |
| 3362 | 2,2-diphenylethyl |
| 3363 | 2-phenyl-2-(2-pyridyl)ethyl |
| 3364 | 2-phenyl-2-(3-pyridyl)ethyl |
| 3365 | 2-phenyl-2-(4-pyridyl)ethyl |
| 3366 | 2-phenoxy-2-phenylethyl |
| 3367 | 2-(benzyloxy)-2-phenylethyl |

Among the above compounds, the preferred examples are trans-3'-oxo-N-(trans-4-phenylcyclohexyl)spiro[cyclohexane-1,1'(3'H)-isobenzofuran]-4-carboxamide, trans-N-[(3S)-1-(2-fluorophenyl)-3-pyrrolidinyl]-3'-oxospiro[cyclohexane-1,1'(3'H)-isobenzofuran]-4-carboxamide, trans-N-[(3S)-1-(3-fluorophenyl)-3-pyrrolidinyl]-3'-oxospiro[cyclohexane-1,1'(3'H)-isobenzofuran]-4-carboxamide, trans-N-[(3S)-1-(4-fluorophenyl)-3-pyrrolidinyl]-3'-oxospiro[cyclohexane-1,1'(3'H)-isobenzofuran]-4-carboxamide, trans-N-[1-(2-fluorophenyl)-4-piperidyl]-3'-oxospiro[cyclohexane-1,1'(3'H)-isobenzofuran]-4-carboxamide, trans-N-[1-(3-fluorophenyl)-4-piperidyl]-3'-oxospiro[cyclohexane-1,1'(3'H)-isobenzofuran]-4-carboxamide, trans-N-[1-(4-fluorophenyl)-4-piperidyl]-3'-oxospiro[cyclohexane-1,1'(3'H)-isobenzofuran]-4-carboxamide, trans-3'-oxo-N-(1,2,3,4-tetrahydro-2-naphthyl)spiro[cyclohexane-1,1'(3'H)-isobenzofuran]-4-carboxamide, trans-N-[1-(3-fluorophenyl)-4-piperidyl]-3-oxospiro[4-azaisobenzofuran-1(3H),1'-cyclohexane]-4'-carboxamide, trans-N-[1-(3-fluorophenyl)-4-piperidyl]-3-oxospiro[5-azaisobenzofuran-1(3H),1'-cyclohexane]-4'-carboxamide, trans-N-[1-(3-fluorophenyl)-4-piperidyl]-3-oxospiro[6-azaisobenzofuran-1(3H),1'-cyclohexane]-4'-carboxamide, trans-N-[1-(3-fluorophenyl)-4-piperidyl]-3-oxospiro[7-azaisobenzofuran-1(3H),1'-cyclohexane]-4'-carboxamide, trans-N-(6-methoxy-1,2,3,4-tetrahydro-2-naphthyl)-3-oxospiro[5-azaisobenzofuran-1(3H),1'-cyclohexane]-4'-carboxamide, trans-3'-oxo-N-[(3S)-5-oxo-1-phenyl-3-pyrrolidinyl]spiro-[cyclohexane-1,1'(3'H)-isobenzofuran]-4-carboxamide, trans-N-[(3S)-1-(2-fluorophenyl)-3-pyrrolidinyl]-3-oxospiro[6-azaisobenzofuran-1(3H),1'-cyclohexane]-4'-carboxamide, trans-N-[(3S)-1-(3-fluorophenyl)-3-pyrrolidinyl]-3-oxospiro[6-azaisobenzofuran-1(3H),1'-cyclohexane]-4'-carboxamide, trans-3-oxo-N-(trans-4-phenylcyclohexyl)spiro[5-azaisobenzofuran-1(3H),1'-cyclohexane]-4'-carboxamide, trans-3-oxo-N-(trans-4-phenylcyclohexyl)spiro[6-azaisobenzofuran-1(3H),1'-cyclohexane]-4'-carboxamide, trans-3-oxo-N-(trans-4-phenylcyclohexyl)spiro[7-azaisobenzofuran-1(3H),1'-cyclohexane]-4'-carboxamide, trans-3-oxo-N-[(3S)-1-phenyl-3-pyrrolidinyl]spiro[6-azaisobenzofuran-1(3H),1'-cyclohexane]-4'-carboxamide, trans-3-oxo-N-[(3S)-1-(3-trifluoromethylphenyl)-3-pyrrolidinyl]spiro[6-azaisobenzofuran-1(3H),1'-cyclohexane]-4'-carboxamide, trans-3-oxo-N-[(3S)-1-(2-pyridyl)-3-pyrrolidinyl]spiro[5-azaisobenzofuran-1(3H),1'-cyclohexane]-4'-carboxamide, trans-3-oxo-N-[(3S)-1-(3-pyridyl)-3-pyrrolidinyl]spiro[5-azaisobenzofuran-1(3H),1'-cyclohexane]-4'-carboxamide, trans-N-[trans-4-(4-fluorophenyl)cyclohexyl]-3-oxospiro[6-azaisobenzofuran-1(3H),1'-cyclohexane]-4'-carboxamide, trans-N-[trans-4-(3-fluorophenyl)cyclohexyl]-3-oxospiro[6-azaisobenzofuran-1(3H),1'-cyclohexane]-4'-carboxamide, trans-N-[trans-4-(3-fluorophenyl)cyclohexyl]-3-oxospiro[4-azaisobenzofuran-1(3H),1'-cyclohexane]-4'-carboxamide, trans-N-[trans-4-(3-fluorophenyl)cyclohexyl]-3-oxospiro[7-azaisobenzofuran-1(3H),1'-cyclohexane]-4'-carboxamide, trans-N-[(3S)-1-(3,5-difluorophenyl)-3-pyrrolidinyl]-3-oxo-spiro[6-azaisobenzofuran-1(3H),1'-cyclohexane]-4'-carboxamide, trans-N-[1-(3,5-difluorophenyl)-4-piperidyl]-3-oxospiro[6-azaisobenzofuran-1(3H),1'-cyclohexane]-4'-carboxamide, trans-N-[3-(3-fluorophenyl)-tetrahydropyran-6-yl]-3-oxospiro[6-azaisobenzofuran-1(3H),1'-cyclohexane]-4'-carboxamide, trans-N-[trans-4-(2-fluorophenyl)cyclohexyl]-3-oxospiro[6-azaisobenzofuran-1(3H),1'-cyclohexane]-4'-carboxamide, trans-N-[(S)-1-benzyl-2-(benzylamino)ethyl]-3'-oxospiro-[cyclohexane-1,1'(3'H)-isobenzofuran]-4-carboxamide, trans-N-benzhydryl-3'-oxospiro[cyclohexane-1,1'(3'H)-isobenzofuran]-4-carboxamide, trans-1-methanesulfonyl-N-(1-phenyl-4-piperidyl)spiro-[indoline-3,1'-cyclohexane]-4'-carboxamide, trans-N-(2-indanyl)-1-methanesulfonylspiro[indoline-3,1'-cyclohexane]-4'-carboxamide, trans-N-[1-(3-fluorophenyl)-4-piperidyl]-1-methanesulfonyl-spiro[indoline-3,1'-cyclohexane]-4'-carboxamide, trans-1-methanesulfonyl-N-[1-(2-pyridyl)-4-piperidyl]spiro-[indoline-3,1'-cyclohexane]-4'-carboxamide, trans-1-methanesulfonyl-N-(1-phenyl-3-piperidyl)spiro-[indoline-3,1'-cyclohexane]-4'-carboxamide, trans-N-[1-(3,5-difluorophenyl)-3-piperidyl]-1-methanesulfonylspiro[indoline-3,1'-cyclohexane]-4'-carboxamide, trans-1-methanesulfonyl-N-[1-(2-pyridyl)-3-piperidyl]spiro-[indoline-3,1'-cyclohexane]-4'-carboxamide, trans-1-methanesulfonyl-N-[(3S)-1-phenyl-3-pyrrolidinyl]-spiro[indoline-3,1'-cyclohexane]-4'-carboxamide, trans-1-methanesulfonyl-N-[(3R)-1-phenyl-3-pyrrolidinyl]-spiro[indoline-3,1'-cyclohexane]-4'-carboxamide, trans-1-methanesulfonyl-N-(2-phenylcyclopropyl)spiro-[indoline-3,1'-cyclohexane]-4'-carboxamide, trans-1-methanesulfonyl-N-[2-(3-pyridyl)cyclopropyl]spiro-[indoline-3,1'-cyclohexane]-4'-carboxamide, trans-N-[(S)-1-benzyl-2-(benzylamino)ethyl]-1-methanesulfonylspiro[indoline-3,1'-cyclohexane]-4'-carboxamide, trans-N-[1-benzylcarbamoyl-2-(4-pyridyl)ethyl]-1-methane-sulfonylspiro[indoline-3,1'-cyclohexane]-4'-carboxamide, trans-N-[2-(4-fluorophenyl)-1-[(4-pyridylmethyl)carbamoyl]-ethyl]-1-methanesulfonylspiro[indoline-3,1'-cyclohexane]-4'-carboxamide, trans-N-(2-hydroxy-2-phenylethyl)-1-methanesulfonyl-spiro-[indoline-3,1'-cyclohexane]-4'-carboxamide, trans-N-(benzoylmethyl)-1-methanesulfonylspiro[indoline-3,1'-cyclohexane]-4'-carboxamide, trans-N-[(S)-1-benzyl-2-(N-benzylmethylamino)ethyl]-1-methanesulfonylspiro[indoline-3,1'-cyclohexane]-4'-carboxamide, trans-N-[(S)-1-(N-benzylmethylcarbamoyl)-2-phenylethyl]-1-methanesulfonylspiro[indoline-3,1'-cyclohexane]-4'-carboxamide, trans-N-[(S)-1-(N-benzylmethylcarbamoyl)-2-(3-pyridyl)-ethyl]-1-methanesulfonylspiro[indoline-3,1'-cyclohexane]-4'-carboxamide, trans-N-(4-dimethylaminophenethyl)-1-methanesulfonyl-spiro-[indoline-3,1'-cyclohexane]-4'-carboxamide, trans-1-methanesulfonyl-N-[2-(3-quinolyl)ethyl]spiro-[indoline-3,1'-cyclohexane]-4'-carboxamide, trans-N-[2-(4-dimethylaminophenyl)-2-hydroxyethyl]-1-methanesulfonylspiro[indoline-3,1'-cyclohexane]-4'-carboxamide, trans-N-[2-hydroxy-2-(3-quinolyl)ethyl]-1-methanesulfonyl-spiro[indoline-3,1'-cyclohexane]-4'-carboxamide, trans-N-[2-(3,5-difluorophenyl)-2-hydroxyethyl]-1-methane-sulfonylspiro[indoline-3,1'-cyclohexane]-4'-carboxamide, trans-N-[(S)-1-benzyl-2-[(3-pyridylmethyl)amino]ethyl]-1-methanesulfonylspiro[indoline-3,1'-cyclohexane]-4'-carboxamide, trans-N-[(S)-1-benzyl-2-[(2-pyridylmethyl)amino]ethyl]-1-methanesulfonylspiro[indoline-3,1'-cyclohexane]-4'-carboxamide, trans-N-[(S)-2-anilino-1-benzylethyl]-1-methanesulfonyl-spiro[indoline-3,1'-cyclohexane]-4'-carboxamide, trans-N-[(S)-1-benzyl-2-(isobutylamino)ethyl]-1-methanesulfonylspiro[indoline-3,1'-cyclohexane]-4'-carboxamide, trans-1-methanesulfonyl-N-[2-phenyl-1-(methoxycarbonyl)-ethyl]spiro[indoline-3,1'-cyclohexane]-4'-carboxamide, trans-N-(1-hydroxymethyl-2-phenylethyl)-1-methanesulfonyl-spiro[indoline-3,1'-cyclohexane]-4'-carboxamide, 1-methanesulfonyl-N-(1-phenyl-4-piperidyl)spiro[indoline-3,4'-piperidine]-1'-carboxamide, 3-oxo-N-(1-phenyl-3-piperidyl)spiro[isobenzofuran-1(3H), 4'-piperidine]-1'-carboxamide, 3-oxo-N-[(3S)-1-phenyl-3-pyrrolidinyl]spiro[isobenzofuran-1(3H),4'-piperidine]-1'-carboxamide, N-[1-benzylcarbamoyl-2-cyclohexylethyl]-3,4-dihydro-3-oxospiro[isoquinoline-1(2H),4'-piperidine]-1'-carboxamide, N-[(S)-1-benzyloxymethyl-2-cyclohexylethyl]-3,4-dihydro-3-oxospiro[isoquinoline-1(2H),4'-piperidine]-1'-carboxamide, N-[(S)-1-benzylcarbamoyl-2-phenylethyl]-3,4-dihydro-3-oxospiro[isoquinoline-1(2H),4'-piperidine]-1'-carboxamide, N-[(S)-1-benzyl-2-(benzylamino)ethyl]-3,4-dihydro-3-oxospiro[isoquinoline-1(2H),4'-piperidine]-1'-carboxamide, N-(2-indanyl)-1-methanesulfonylspiro[indoline-3,4'-piperidine]-1'-carboxamide, 1-methanesulfonyl-N-phenethylspiro[indoline-3,4'-piperidine]-1'-carboxamide, 1-methanesulfonyl-N-(3-phenylpropyl)spiro[indoline-3,4'-piperidine]-1'-carboxamide, 1-methanesulfonyl-N-(4-phenylbutyl)spiro[indoline-3,4'-piperidine]-1'-carboxamide, N-(4-bromophenethyl)-1-methanesulfonylspiro[indoline-3, 4'-piperidine]-1'-carboxamide, N-(3,4-dimethoxyphenethyl)-1-methanesulfonylspiro[indoline-3,4'-piperidine]-1'-carboxamide, 1-methanesulfonyl-N-(3-methoxyphenethyl)spiro[indoline-3,4'-piperidine]-1'-carboxamide, N-(4-dimethylamino-2-methoxyphenethyl)-1-methanesulfonyl-spiro[indoline-3,4'-piperidine]-1'-carboxamide, N-[(S)-1-benzyloxycarbonyl-2-(3-indolyl)ethyl]-3,4-dihydro-3-oxospiro[isoquinoline-1(2H),4'-piperidine]-1'-carboxamide, N-[(R)-1-benzyloxycarbonyl-2-(3-indolyl)ethyl]-3,4-dihydro-3-oxospiro[isoquinoline-1(2H),4'-piperidine]-1'-carboxamide, N-[(S)-1-benzyloxycarbonyl-2-cyclohexylethyl]-3,4-dihydro-3-oxospiro[isoquinoline-1(2H),4'-piperidine]-1'-carboxamide, 3,4-dihydro-N-(3-methoxyphenethyl)-3-oxospiro[isoquinoline-1(2H),4'-piperidine]-1'-carboxamide, trans-N-[1-(3-trifluoromethylphenyl)-4-piperidyl]-3-oxospiro[6-azaisobenzofuran-1(3H),1'-cyclohexane]-4'-carboxamide, trans-N-[trans-2-(3-fluorophenyl)cyclopropyl]-3'-oxospiro-[cyclohexane-1,1'(3'H)-isobenzofuran]-4-carboxamide, trans-N-[trans-2-(4-fluorophenyl)cyclopropyl]-3'-oxospiro-[cyclohexane-1,1'(3'H)-isobenzofuran]-4-carboxamide, trans-N-[1-(2-fluorophenyl)-4-piperidyl]-3-oxospiro[6-azaisobenzofuran-1(3H),1'-cyclohexane]-4'-carboxamide, trans-3'-oxo-N-[5-oxo-1-(2-fluorophenyl)-3-pyrrolidinyl]-spiro[cyclohexane-1,1'(3'H)-isobenzofuran]-4-carboxamide, trans-3'-oxo-N-[5-oxo-1-(3-fluorophenyl)-3-pyrrolidinyl]-spiro[cyclohexane-1,1'(3'H)-isobenzofuran]-4-carboxamide, trans-3-oxo-N-[5-oxo-1-(3-fluorophenyl)-3-pyrrolidinyl]-spiro[6-azaisobenzofuran-1(3H),1'-cyclohexane]-4'-carboxamide, trans-N-[trans-4-(3-trifluoromethylphenyl)cyclohexyl]-3-oxospiro[6-azaisobenzofuran-1(3H),1'-cyclohexane]-4'-carboxamide, trans-3'-oxo-N-[2-oxo-1-phenyl-4-piperidyl]spiro[cyclohexane-1,1'(3'H)-isobenzofuran]-4-carboxamide, trans-3'-oxo-N-[2-oxo-1-(3-fluorophenyl)-4-piperidyl] spiro-[cyclohexane-1,1'(3'H)-isobenzofuran]-4-carboxamide, trans-N-[trans-2-(2-fluorophenyl)cyclopropyl]-3'-oxospiro-[cyclohexane-1,1'(3'H)-isobenzofuran]-4-carboxamide, trans-N-[trans-2-(3-fluorophenyl)cyclopropyl]-3-oxospiro [6-azaisobenzofuran-1(3H),1'-cyclohexane]-4'-carboxamide or trans-N-[trans-2-(4-fluorophenyl)cyclopropyl]-3-oxospiro [6-azaisobenzofuran-1(3H),1'-cyclohexane]-4'-carboxamide, and the like.

The processes for producing the compounds of the present invention are illustrated below.

The compounds (I) of the present invention can be prepared, for example, by the following production processes or the methods shown in Examples, but Manufacturing methods of the compounds (I) of the present invention are not limited to these embodiments.

Production Process 1

A compound of the formula (II):

(II)

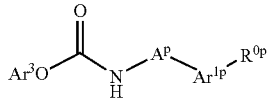

(wherein $A^p$ is a straight-chain hydrocarbon having 1 to 6 carbon atoms, which is optionally substituted by a substituent selected from the group consisting of di-lower alkylamino, lower alkoxy, lower alkoxycarbonyl, lower alkylene, aryl, heteroaryl, —$R^{ap}$, optionally protected oxo, optionally protected amino, optionally protected lower alkylamino and optionally protected hydroxy, and is optionally intervened by oxygen or nitrogen atom;

$Ar^{1p}$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, di-lower alkylamino, lower alkylthio, lower alkanoyl, lower alkoxycarbonyl, -$Q^p$-$Ar^{2p}$, optionally protected oxo, optionally protected hydroxy-lower alkyl, optionally protected lower alkylamino and optionally protected carboxyl;

$Ar^{2p}$ is aryl or heteroaryl, any of which is optionally substituted by a substituent selected from the group consisting of halogen, cyano, lower alkyl, halo-lower alkyl, lower alkoxy, halo-lower alkoxy, di-lower alkylamino, lower alkanoyl, aryl, optionally protected hydroxy-lower alkyl, optionally protected hydroxy and optionally protected lower alkylamino;

$Ar^3$ is phenyl which is optionally substituted by halogen or nitro;

$Q^p$ is a single bond or optionally protected carbonyl;

$R^{ap}$ is lower alkyl which is optionally substituted by a substituent selected from the group consisting of di-lower alkylamino, optionally protected amino, optionally protected lower alkylamino, optionally protected hydroxy, and cyclo-lower alkyl, aryl and heteroaryl, the last three groups being optionally substituted by fluorine;

$R^{0p}$ is hydrogen, or lower alkylene attached to an arbitrary, bondable position of $A^P$) is reacted with a compound of the formula (III):

(III)

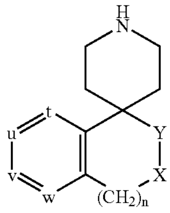

(wherein t, u, v and w are independently methine or nitrogen atom, said methine being optionally substituted by a substituent selected from the group consisting of halogen, lower alkyl, lower alkoxy and optionally protected hydroxy, and at least two of t, u, v and w are said methine group; n, X and Y have the same meaning as defined above), to provide a compound of the formula (IV-1):

(IV-1)

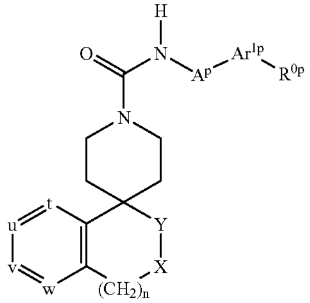

(wherein $A^P$, $Ar^{1p}$, n, $R^{0p}$, t, u, v, w, X and Y have the same meaning as defined above), optionally followed by removal of the protecting group(s) from the compound (IV-1), thereby a compound of the formula (I-1):

(I-1)

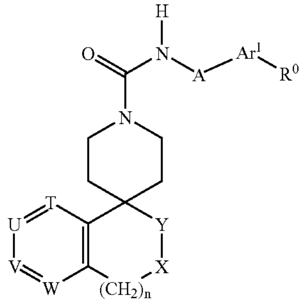

(wherein A, $Ar^1$, n, $R^0$, T, U, V, W, X and Y have the same meaning as defined above) can be prepared.

The present process is a process for preparing a compound of the formula (I) wherein Z is nitrogen atom, that is, a compound of the formula (I-1).

In the above reaction, when a reactant has an amino, hydroxy, carboxyl, oxo, carbonyl or the like which does not participate in the reaction, the reaction may be carried out after protecting said amino, hydroxy, carboxyl, oxo or carbonyl with an amino-protecting group, a hydroxy-protecting group, a carboxyl-protecting group, or an oxo- or carbonyl-protecting group, and said protecting groups may be removed after completion of the reaction.

The "amino-protecting group" includes, for example, aralkyl (e.g. benzyl, p-methoxybenzyl, 3,4-dimethoxybenzyl, o-nitrobenzyl, p-nitrobenzyl, benzhydryl, trityl); lower alkanoyl (e.g. formyl, acetyl, propionyl, butyryl, pivaloyl); benzoyl; arylalkanoyl (e.g. phenylacetyl, phenoxyacetyl); lower alkoxycarbonyl (e.g. methoxycarbonyl, ethoxycarbonyl, propyloxycarbonyl, tert-butoxycarbonyl); aralkyloxycarbonyl (e.g. benzyloxycarbonyl, p-nitrobenzyloxycarbonyl, phenethyloxycarbonyl); lower alkylsilyl (e.g. trimethylsilyl, tert-butyldimethylsilyl); among which the preferred examples are acetyl, pivaloyl, benzoyl, ethoxycarbonyl, tert-butoxycarbonyl, and the like.

The "hydroxy-protecting group" includes, for example, lower alkyl (e.g. methyl, ethyl, propyl, isopropyl, tert-butyl); lower alkylsilyl (e.g. trimethylsilyl, tert-butyldimethylsilyl); lower alkoxymethyl (e.g. methoxymethyl, 2-methoxyethoxymethyl); tetrahydropyranyl; trimethylsilylethoxymethyl; aralkyl (e.g. benzyl, p-methoxybenzyl, 2,3-dimethoxybenzyl, o-nitrobenzyl, p-nitrobenzyl, trityl); acyl (e.g. formyl, acetyl); among which the preferred examples are methyl, methoxymethyl, tetrahydropyranyl, trityl, trimethylsilylethoxymethyl, tert-butyldimethylsilyl, acetyl, and the like.

The "carboxyl-protecting group" includes, for example, lower alkyl (e.g. methyl, ethyl, propyl, isopropyl, tert-butyl); halo-lower alkyl (e.g. 2,2,2-trichloroethyl); lower alkenyl (e.g. 2-propenyl); aralkyl (e.g. benzyl, p-methoxybenzyl, p-nitrobenzyl, benzhydryl, trityl), among which the preferred examples are methyl, ethyl, tert-butyl, 2-propenyl, benzyl, p-methoxybenzyl, benzhydryl, and the like.

The "oxo- or carbonyl-protecting group" includes, for example, acetal (e.g. ethylene ketal, trimethylene ketal, dimethyl ketal), ketal, and the like.

The reaction between a compound of the formula (II) and a compound of the formula (III) is usually carried out by employing equivalent to excess moles, preferably equivalent to 1.5 moles of the compound of the formula (III) based on 1 mole of the compound (II).

The reaction is usually carried out in an inert solvent, and preferable examples of such inert solvent are methylene chloride, chloroform, tetrahydrofuran, dimethylformamide, dimethylsulfoxide, etc., or a mixture thereof and the like.

It is preferable to carry out the above reaction in the presence of a base, and examples of such base are organic bases (e.g. triethylamine, diisopropylethylamine, pyridine, 4-dimethylaminopyridine) or inorganic bases (e.g. sodium hydroxide, potassium hydroxide).

The amount of the said base employed is usually equivalent to excess moles, preferably 1 to 5 moles based on 1 mole of a compound of the formula (II).

The reaction temperature is usually from −30° C. to 200° C., preferably from 20° C. to 100° C.

The reaction time is usually from 5 minutes to 7 days, preferably from 30 minutes to 24 hours.

Usual workup procedures are applied after completion of the reaction to obtain a crude product of a compound of the formula (IV-1). The resulting compound of the formula (IV-1) is, with or without purification according to the common method, subjected to, if desired, proper combination of removal of the protecting group(s) for amino, hydroxy, carboxyl, oxo and carbonyl, thereby a compound of the formula (I-1) can be prepared.

Although the method for the removal of said protecting groups depends upon the kinds of the protecting groups, the stability of a desired compound (I-1), etc., it is carried out by, for example, a solvolysis using an acid or a base, that is, for example a method wherein 0.01 mole to a large excess of an acid, preferably trifluoroacetic acid, formic acid, hydrochloric acid and the like, or equivalent moles to a large excess of base, preferably potassium hydroxide, calcium hydroxide and the like is acted; a chemical reduction using a metal hydride complex; or a catalytic reduction using a palladium-carbon catalyst, a Raney-nickel catalyst, etc., according to, for example, a method described in the literature (Protective Groups in Organic Synthesis, T. W. Greene, John Wiley & Sons, (1981)) or its similar methods.

Production Process 2

A compound of the formula (V):

(V)

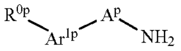

(wherein $A^p$, $Ar^{1p}$ and $R^{0p}$ have the same meaning as defined above) is reacted with a carboxylic acid of the formula (VI):

(VI)

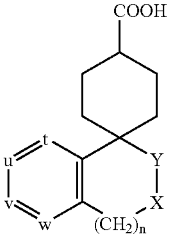

(wherein n, t, u, v, w, X and Y have the same meaning as defined above) or a reactive derivative thereof to provide a compound of the formula (IV-2):

(IV-2)

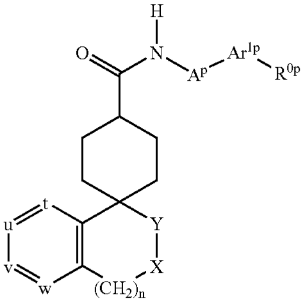

(wherein $A^p$, $Ar^{1p}$, n, $R^{0p}$, t, u, v, w, X and Y have the same meaning as defined above), optionally followed by removal of the protecting group (s) from the compound (IV-2), thereby a compound of the formula (I-2):

(I-2)

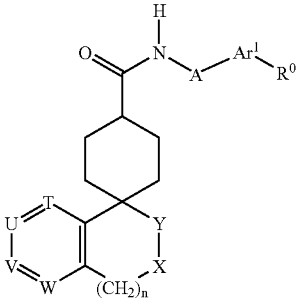

(wherein A, $Ar^1$, n, $R^0$, T, U, V, W, X and Y have the same meaning as defined above) can be prepared.

The present process is a process for preparing a compound of the formula (I) wherein Z is methine group, that is, a compound of the formula (I-2).

The reaction between a compound of the formula (V) and a carboxylic acid of the formula (VI) is usually carried out by employing 0.5 to excess moles, preferably 1 mole to 1.5 moles of the carboxylic acid of the formula (VI) based on 1 mole of the compound of the formula (V).

The reaction is usually carried out in an inert solvent, and the preferable examples of such inert solvent are methylene chloride, chloroform, tetrahydrofuran, dimethylformamide, pyridine, etc., or a mixture thereof and the like.

It is preferable to carry out the above reaction in the presence of a condensing agent, and examples of such condensing agent are, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium-hexafluorophosphate, benzotriazol-1-yloxy-tris-pyrrolidinophosphonium-hexafluorophosphate, bromotris-(dimethylamino)phosphonium-hexafluorophosphate, diphenylphosphoryl azide, 1,1'-carbonyldiimidazole, and the like.

The amount of said condensing agent employed may be usually 1 mole to excess mole, preferably 1 to 1.5 moles based on 1 mole of a compound of the formula (VI).

The reaction temperature is usually from −50° C. to 100° C., preferably from −20° C. to 50° C.

The reaction time is usually from 30 minutes to 7 days, preferably from 1 hour to 24 hours.

A compound of the formula (I-2) is also produced by reacting a compound of the formula (V) with an activated derivative of the carboxylic acid of the formula (VI) instead of the carboxylic acid of the formula (VI).

Examples of the activated derivatives of carboxylic acid of the formula (VI) include acid halides, mixed anhydrides, activated esters, activated amides, and the like.

The acid halides of carboxylic acid of the formula (VI) may be obtained by reacting a carboxylic acid of the formula (VI) with a halogenating agent according to the conventional method. The halogenating agent includes, for example, thionyl chloride, phosphorus trichloride, phosphorus pentachloride, phosphorus oxychloride, phosphorus tribromide, oxalyl chloride, phosgene, and the like.

The mixed anhydrides of carboxylic acid of the formula (VI) may be obtained by reacting a carboxylic acid of the formula (VI) with an alkyl chlorocarbonate such as ethyl chlorocarbonate, etc.; an aliphatic carboxylic acid chloride such as pivaloyl chloride, etc., and the like according to the conventional method.

The activated esters of carboxylic acid of the formula (VI) may be obtained by reacting a carboxylic acid of the formula (VI) with an N-hydroxy compound such as N-hydroxysuccinimide, N-hydroxyphthalimide, 1-hydroxybenzotriazole, etc.; a phenol compound such as 4-nitrophenol, 2,4-dinitrophenol, 2,4,5-trichlorophenol, pentachlorophenol, etc., and the like in the presence of a condensing agent such as N,N'-dicyclohexylcarbodiimide, 1-(3-dimethylaminopropyl)-3-ethylcarbodiimide, etc. according to the conventional method.

The activated amides of carboxylic acid of the formula (VI) may be obtained by reacting a carboxylic acid of the formula (VI) with, for example, 1,1'-carbonyldiimidazole, 1,1'-carbonylbis(2-methylimidazole) according to the conventional method.

The reaction between a compound of the formula (V) and an activated derivative of carboxylic acid of the formula (VI) is usually carried out by employing 0.5 to excess moles, preferably 1 to 1.5 moles of the activated derivative of carboxylic acid of the formula (VI) based on 1 mole of the compound of the formula (V).

The reaction is usually carried out in an inert solvent, and the preferable examples of such inert solvent are methylene chloride, chloroform, tetrahydrofuran, dimethylformamide, pyridine, etc., or a mixture thereof and the like.

Although the above reaction proceeds in the absence of a base, it is preferred to carry out the reaction in the presence of a base to promote the reaction smoothly.

Examples of such a base are organic bases (e.g. triethylamine, diisopropylethylamine, pyridine, 4-dimethylaminopyridine) or inorganic bases (e.g. sodium hydroxide, potassium hydroxide, sodium carbonate, potassium carbonate, sodium hydrogen carbonate).

The preferable amount of said base is usually 1 to excess moles based on 1 mole of a compound of the formula (V). Also, when the base is a liquid, such base can also be used as a solvent.

The reaction temperature is usually from −50° C. to 100° C., preferably from −20° C. to 50° C.

The reaction time is usually from 5 minutes to 7 days, preferably from 30 minutes to 24 hours.

A compound of the formula (I-2) can be produced by working up the resulting product in the usual way after removal of the said protecting group(s) when the product has a protecting group after completion of the reaction, or by working up the resulting product directly in the usual way when the protecting group is absent.

The removal of the protecting group(s) and the workup procedure may be carried out according to the method described in the above Production Process 1.

The compound of the formula (I-1) or (I-2) may be readily isolated and purified by the conventional separation technique, and examples of such technique are solvent extraction, recrystallization, column chromatography, preparative thin layer chromatography and the like.

These compounds can be converted into the pharmaceutically acceptable salts or esters by the conventional method, and on the contrary, the conversion of the salts or esters into free compounds can also be carried out according to the conventional method.

Compounds of the formula (II), (III), (V) or (VI) is commercially available, or can be prepared according to the methods described in the literatures (Japanese Patent Unexamined Publication No. 94/263737-A, U.S. Pat. No. 3,301,857, J. Org. Chem, 40, p. 1427 (1975), International Patent Publication W095/28389 and the like), or analogous methods thereto or the methods shown below or in Examples, optionally in combination.

Production Process A

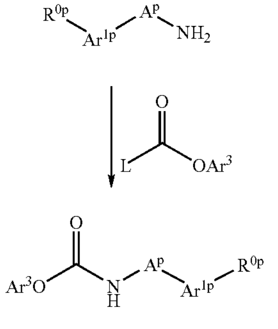

(V)

1

(II)

In the above reaction scheme, L is halogen; $A^p$, $Ar^{1p}$, $Ar^3$ and $R^{0p}$ have the same meaning as defined above.

The present process is a process for preparing a compound of the formula (II). According to the present process, the compound of the formula (II) can be prepared by reacting a compound of the formula (V) with a compound of the formula 1.

The reaction between the compound of the formula (V) and the compound of the formula 1 is usually carried out by employing 0.5 to excess moles, preferably equivalent to 1.5 moles of the compound of the formula 1, based on 1 mole of the compound (V).

The reaction is usually carried out in an inert solvent, and the preferable examples of such inert solvent are methylene chloride, chloroform, tetrahydrofuran, ethyl ether, benzene, toluene, dimethylformamide, etc., or a mixture thereof and the like.

The above reaction is preferably carried out in the presence of a base, and examples of such base are organic bases (e.g. triethylamine, diisopropylethylamine, pyridine, 4-dimethylaminopyridine) or inorganic bases (e.g. sodium hydroxide, potassium hydroxide, sodium carbonate, potassium carbonate, sodium hydrogen carbonate).

The preferable amount of said base is usually equivalent to excess moles based on 1 mole of a compound of the formula (V). Also, when the base is a liquid, such base can also be used as a solvent.

The reaction temperature is usually from −78° C. to 100° C., preferably from −20° C. to 50° C.

The reaction time is usually from 5 minutes to 7 days, preferably from 30 minutes to 24 hours.

A compound of the formula 1 is commercially available, or can be prepared according to the known methods or the methods in Examples, or analogous methods thereto, optionally in combination.

The utility of compounds of the present invention as a medicament is proved by showing NPY antagonistic activities in the following pharmacological test.

Pharmacological Test (NPY Binding Inhibition Test)

A sequence coding for human NPY Y5 receptor (c.f. International patent publication number W096/16542) was cloned into expression vectors pcDNA3, pRc/RSV (made by Invitrogen Inc.) and pCI-neo (made by Promega Inc.). The expression vectors thus obtained were transfected to host cells COS-7, CHO and LM(tk-) (American Type Culture Collection) by cationic lipid method (Proceedings of the National Academy of Sciences of the United States of America, vol. 84: p. 7413(1987)) to give NPY Y5 receptor expression cells.

A membrane sample prepared from the cells which expressed NPY Y5 receptor was incubated together with a test compound and $[^{125}I]$peptideYY (made by NEN) (20,000 cpm) in an assay buffer (25 mM Tris buffer, pH 7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH7.4) containing 0.3% BSA. The radioactivity of the cake on the glass filter was measured. Non-specific binding was measured in the presence of 1 μM peptide YY, and 50% Inhibitory Concentration ($IC_{50}$) of the test compound against specific peptideYY binding was determined (Endocrinology, vol. 131: p. 2090(1992)). The results are shown in Table 1.

TABLE 1

| NPY receptors binding inhibition | |
|---|---|
| compounds | $IC_{50}$ (nM) |
| Example 1 | 2.5 |
| Example 5 | 1.7 |
| Example 27 | 3.6 |
| Example 32 | 1.7 |
| Example 36 | 0.80 |
| Example 41 | 1.2 |
| Example 45 | 0.69 |
| Example 46 | 2.0 |

As shown above, the compounds of this invention potently inhibited peptideYY (NPY analogue) binding to NPY Y5 receptors.

The compounds of the formula (I) can be administered orally or parenterally and, by formulating into a suitable administrable form, may be administered as a therapeutic agent for various diseases related to NPY, for example, cardiovascular disorders such as hypertension, nephropathy, heart disease, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, etc., metabolic diseases such as obesity, diabetes, hormone abnormality, hypercholesterolemia, hyperlipidemia, etc., sexual and reproductive dysfunctions, gastro-intestinal disorders such as gastro-intestinal motility disorder, respiratory disorders, inflammatory diseases or glaucoma, and the like, particularly preferably bulimia, obesity, diabetes, and the like. In clinical use, the compounds of this invention may be administered after being formulated, together with pharmaceutically acceptable additives, into an appropriate preparation according to the mode of administration. As for such additives, those which are usually used in the field of pharmaceutical formulation, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin, etc. may be used.

The formulations prepared by mixing the compound of the present invention with said additives include, for example, solid preparations (e.g. tablets, capsules, granules, powder, suppositories); or liquid preparations (e.g. syrups, elixirs, injections). Such preparations may be formulated according to the techniques well-known in the art of pharmaceutical formulation. Liquid preparations may be in the form of preparations which are dissolved or suspended in water or other appropriate media when used. In the case of injectable preparations in particular, they may be dissolved or suspended in physiological saline or glucose solution if necessary, optionally together with a buffer or a preservative.

All the said preparations may contain 1.0 to 100 wt. %, preferably 1.0 to 60 wt. % of compounds of the present invention and may also contain other therapeutically effective compounds.

The compounds of the present invention can be used in combination with other agents useful for treating metabolic disorders and/or eating disorders. The individual component of such combinations can be administered separately at different times or concurrently in divided or single combination forms during the course of therapy. The present invention is therefore to be understood as embracing all such regimes of simultaneous or divided administration and the term "administration" is to be interpreted accordingly. The scope of combinations of the compounds of this invention with other agents useful for treating metabolic disorders and/or eating disorders includes in principle any combination of any pharmaceutical composition useful for treating metabolic disorders and/or eating disorders.

When compounds of the present invention are used clinically, for example, a daily dose for an adult is 0.01 to 100 mg/kg, preferably 0.03 to 3 mg/kg with simultaneous or divided administration when administered orally, and 0.001 to 10 mg/kg, preferably 0.001 to 0.1 mg/kg with simultaneous or divided administration when administered parenterally, though the dose and the frequency of administration may vary depending upon the sex, age, body weight, degree of symptoms, and type and range of the desired treatment effects.

An ordinarily skilled physician, veterinarian or clinician can readily determine and prescribe the effective amount of the drug required to prevent, suppress or arrest the progress of diseases.

BEST MODE FOR CARRYING OUT THE INVENTION

The present invention is further described in detail with reference to the following Examples, but the invention should in no way be restricted thereby.

EXAMPLE 1

Preparation of trans-3'-oxo-N-(trans-4-phenylcyclohexyl)-spiro[cyclohexane-1,1'(3'H)-isobenzofuran]-4-carboxamide 4-Phenylcyclohexylamine hydrochloride (64 mg) and 1-(3-dimethylaminopropyl)-3-ethylcarbodiimide hydrochloride (115 mg) were added to a solution of trans-3'-oxospiro[cyclohexane-1,1'(3'H)-isobenzofuran]-4-caboxylic acid (74 mg) in pyridine (2 mL). The mixture was stirred at room temperature for 24 hours and the reaction mixture was partitioned between water and ethyl acetate. The organic layer was dried over magnesium sulfate and the solvent was removed by evaporation. The residue was purified by preparative thin-layer chromatography (hexane/ethyl acetate=1/1) to give the title compound (50.7 mg) as a white solid.

$^{1}$H-NMR (300 MHz, $CDCl_3$, δppm): 1.72–1.89 (2H, m), 1.56–1.82 (4H, m), 1.92–2.20 (8H, m), 2.28–2.40 (2H, m), 2.45–2.58 (2H, m), 3.82–3.96 (1H, m), 5.44 (1H, br d), 7.17–7.33 (5H, m), 7.52 (1H, d, J=7.8 Hz), 7.58–7.69 (2H, m), 7.88 (1H, d, J=7.5 Hz).

Compounds of Examples 2 to 76 were obtained by following the same procedure as in Example 1, except that trans-3'-oxospiro[cyclohexan-1,1'(3'H)-isobenzofuran]-4-carboxylic acid and 4-phenylcyclohexylamine hydrochloride used in Example 1 were replaced with the corresponding starting materials of each desired compound.

EXAMPLE 2

Trans-N-[(3S)-1-(2-fluorophenyl)-3-pyrrolidinyl]-3'-oxo-spiro[cyclohexane-1,1'(3'H)-isobenzofuran]-4-carboxamide $^1$H-NMR(300 MHz, DMSO-$d_6$, δppm):1.69–1.77(2H, m), 1.83–2.18(8H, m), 2.47–2.53(1H, m), 3.17–3.23(1H, m), 3.28–3.34(1H, m), 3.43–3.47 (1H, m), 3.55–3.62(1H, m), 4.35–4.38(1H, m), 6.65–6.76(2H, m), 6.97–7.08(2H, m), 7.58–7.64(2H, m), 7.77(1H, d, J=7.3 Hz), 7.83(1H, d, J=7.6 Hz), 8.17(1H, d, J=6.9 Hz).

EXAMPLE 3

Trans-N-[(3S)-1-(3-fluorophenyl)-3-pyrrolidinyl]-3'-oxo-spiro[cyclohexane-1,1'(3'H)-isobenzofuran]-4-carboxamide $^1$H-NMR(300 MHz, $CDCl_3$, δppm):1.74–1.80(2H, m), 2.00–2.15(5H, m), 2.23–2.38(3H, m), 2.48–2.52(1H, m), 3.20(1H, dd, J=9.9,3.6 Hz), 3.35–3.47(2H, m), 3.59–3.65 (1H, m), 4.66–4.68(1H, m), 5.73–5.77 (1H, m), 6.23–6.45 (3H, m), 7.17(1H, dt, J=8.2,6.9 Hz), 7.49–7.58 (2H, m), 7.63–7.69(1H, m), 7.87(1H, dd, J=7.6, 0.8 Hz).

EXAMPLE 4

Trans-N-[(3S)-1-(4-fluorophenyl)-3-pyrrolidinyl]-3'-oxo-spiro[cyclohexane-1,1'(3'H)-isobenzofuran]-4-carboxamide $^1$H-NMR(300 MHz, $CDCl_3$, δppm):1.74–1.82(2H, m), 1.99–2.39(8H, m), 2.48–2.52(1H, m), 3.19(1H, dd, J=9.9, 3.3 Hz), 3.26–3.34(1H, m), 3.41–3.48(1H, m), 3.56(1H, dd, J=9.9, 5.9 Hz), 4.65–4.72(1H, m), 5.77–5.80(1H, m), 6.48–6.54(2H, m), 6.93–7.00(2H, m), 7.49–7.58 (2H, m), 7.62–7.68(1H, m), 7.88(1H, dd, J=7.6, 0.9 Hz).

EXAMPLE 5

Trans-N-[1-(2-fluorophenyl)-4-piperidyl]-3'-oxo-spiro[cyclohexane-1,1'(3'H)-isobenzofuran]-4-carboxamide $^1$H-NMR(300 MHz, $CD_3OD$, δppm):1.80–1.92(2H, m), 1.99–2.37(10H, m), 2.60–2.70(1H, m), 3.71–3.89(4H, m), 4.04–4.20(1H, m), 7.37–7.50 (2H, m), 7.52–7.64(2H, m), 7.69–7.89(4H, m).

EXAMPLE 6

Trans-N-[1-(3-fluorophenyl)-4-piperidyl]-3'-oxo-spiro[cyclohexane-1,1'(3'H)-isobenzofuran]-4-carboxamide $^1$H-NMR(300 MHz, $CD_3OD$, δppm):1.78–1.92(2H, m), 1.98–2.38(10H, m), 2.59–2.69(1H, m), 3.67–3.88(4H, m), 4.07–4.20(1H, m), 7.28(1H, dt, J=7.6,1.5 Hz), 7.43–7.68 (4H, m), 7.70–7.79(2H, m), 7.84(1H, d, J=7.6 Hz).

EXAMPLE 7

Trans-N-[1-(4-fluorophenyl)-4-piperidyl]-3'-oxo-spiro[cyclohexane-1,1'(3'H)-isobenzofuran]-4-carboxamide $^1$H-NMR(300 MHz, $CD_3OD$, δppm):1.77–1.93(2H, m), 1.98–2.41(10H, m), 2.60–2.71(1H, m), 3.70–3.91(4H, m), 4.11–4.26(1H, m), 7.30–7.43 (2H, m), 7.55–7.66(1H, m), 7.71–7.81(2H, m), 7.81–7.94(3H, m).

EXAMPLE 8

Trans-3'-oxo-N-(1,2,3,4-tetrahydro-2-naphthyl)spiro[cyclo-hexane-1,1'(3'H)-isobenzofuran]-4-carboxamide $^1$H-NMR(300 MHz, $CDCl_3$, δppm):1.70–1.91(3H, m), 1.96–2.19(5H, m), 2.19–2.39(2H, m), 2.49(1H, q, J=5.0 Hz), 2.73(1H, dd, J=16.3, 7.9 Hz), 2.79–3.03(2H, m), 3.15(1H, dd, J=16.3, 5.0 Hz), 4.37–4.42(1H, m), 5.62(1H, br d, J=7.6 Hz), 6.99–7.21(4H, m), 7.46–7.70(3H, m), 7.86(1H, dd, J=7.6, 1.0 Hz).

EXAMPLE 9

Trans-N-[1-(3-fluorophenyl)-4-piperidyl]-3-oxospiro[4-azaisobenzofuran-1(3H),1'-cyclohexane]-4'-carboxamide $^1$H-NMR(300 MHz, $CDCl_3$, δppm):1.61(2H, dq, J=11.6, 4.0 Hz), 1.70–1.95 (2H, m), 1.95–2.23(6H, m), 2.23–2.45 (2H, m), 2.53(1H, quintet, J=5.1 Hz), 2.81–3.03(2H, m), 3.65(2H, brd, J=12.9 Hz), 3.90–4.07(1H, m), 5.72(1H, brd, J=7.7 Hz), 6.52(1H, dt, J=8.2, 2.3 Hz), 6.58(1H, dt, J=12.3, 2.3 Hz), 6.69(1H, dt, J=8.3, 2.3 Hz), 7.17(1H, q, J=7.9 Hz), 7.56(1H, dd, J=7.3, 4.6 Hz), 8.03(1H, d, J=7.9 Hz), 8.89(1H, d, J=4.6 Hz).

EXAMPLE 10

Trans-N-[1-(3-fluorophenyl)-4-piperidyl]-3-oxospiro[5-azaisobenzofuran-1(3H),1'-cyclohexane]-4'-carboxamide $^1$H-NMR(300 MHz, $CDCl_3$, δppm):1.59(2H, dq, J=11.5, 4.0 Hz), 1.70–2.60(8H, m), 2.80–3.03(2H, m), 3.55–3.79 (2H, m), 3.90–4.09(1H, m), 5.63(1H, brd, J=7.9 Hz), 6.30–6.81(3H, m), 7.10–7.24(1H, m), 7.59 (1H, dd, J=5.2, 1.2 Hz), 8.84(1H, d, J=5.2 Hz), 9.14(1H, s).

EXAMPLE 11

Trans-N-[1-(3-fluorophenyl)-4-piperidyl]-3-oxospiro[6-azaisobenzofuran-1(3H),1'-cyclohexane]-4'-carboxamide $^1$H-NMR(300 MHz, $CDCl_3$, δppm):1.50–1.70(2H, m), 1.70–1.96(2H, m), 1.96–2.27(6H, m), 2.27–2.61(3H, m), 2.82–3.02(2H, m), 3.57–3.78 (2H, m), 3.94–4.09(1H, m), 5.64(1H, brd, J=7.9 Hz), 6.44–6.78(3H, m), 7.10–7.23(1H, m), 7.77(1H, dd, J=5.0, 1.1 Hz), 8.86(1H, d, J=5.0 Hz), 9.04(1H, d, J=1.1 Hz).

EXAMPLE 12

Trans-N-[1-(3-fluorophenyl)-4-piperidyl]-3-oxospiro[7-azaisobenzofuran-1(3H),1'-cyclohexane]-4'-carboxamide $^1$H-NMR(300 MHz, $CDCl_3$, δppm):1.49–1.69(2H, m), 1.80–2.53(11H, m), 2.82–3.03(2H, m), 3.53–3.78(2H, m), 3.95–4.17(1H, m), 5.70(1H, br d, J=7.6 Hz), 6.43–6.76(3H, m), 7.11–7.24(1H, m), 7.49(1H, dd, J=7.8, 4.9 Hz), 8.15(1H, dd, J=7.8, 1.6 Hz), 8.84(1H, dd, J=4.9, 1.6 Hz).

EXAMPLE 13

Trans-N-(6-methoxy-1,2,3,4-tetrahydro-2-naphthyl)-3-oxospiro[5-azaisobenzofuran-1(3H),1'-cyclohexane]-4'-carboxamide $^1$H-NMR(300 MHz, $CDCl_3$, δppm):1.71–1.95(3H, m), 1.95–2.23(5H, m), 2.23–2.42(2H, m), 2.50(1H, q, J=5.0 Hz), 2.66(1H, dd, J=16.0, 7.8 Hz), 2.77–3.01(2H, m), 3.07(1H, dd, J=16.0, 5.0 Hz), 3.77(3H, s), 4.24–4.42(1H, m), 5.96 (1H, br d, J=7.7 Hz), 6.65(1H, d, J=2.5 Hz), 6.72(1H, dd, J=8.4, 2.5 Hz), 6.97(1H, d, J=8.5 Hz), 7.61(1H, d, J=5.0 Hz), 8.83(1H, d, J=5.0 Hz), 9.12(1H, s).

EXAMPLE 14

Trans-3'-oxo-N-[(3S)-5-oxo-1-phenyl-3-pyrrolidinyl]spiro[cyclohexane-1,1'(3'H)-isobenzofuran]-4-carboxamide $^1$H-NMR(300 MHz, DMSO-$d_6$, δppm):1.68–1.76(2H, m), 1.86–2.11(6H, m), 2.40–2.54(2H, m), 2.92(1H, dd, J=17.1, 8.2 Hz), 3.60–3.67(1H, m), 4.16(1H, dd, J=10.2, 7.0 Hz), 4.46–4.51(1H, m), 7.10–7.16(3H, m), 7.33–7.40(2H, m), 7.57–7.67(4H, m), 7.74–7.84(2H, m), 8.46(1H, d, J=6.7 Hz).

EXAMPLE 15

Trans-N-[(3S)-1-(2-fluorophenyl)-3-pyrrolidinyl]-3-oxospiro[6-azaisobenzofuran-1(3H),1'-cyclohexane]-4'-carboxamide $^1$H-NMR(300 MHz, $CDCl_3$, δppm):1.80–2.00(3H, m), 2.00–2.20(4H, m), 2.30–2.40(3H, m), 2.52(1H, quintet, J=5.2 Hz), 3.30–3.40(2H, m), 3.50–3.70(2H, m), 4.60–4.70 (1H, m), 5.94(1H, d, J=7.7 Hz), 6.65–6.80(2H, m), 6.95–7.10(2H, m), 7.70–7.80(1H, m), 8.86(1H, d, J=4.9 Hz), 9.04(1H, s).

EXAMPLE 16

Trans-N-[(3S)-1-(3-fluorophenyl)-3-pyrrolidinyl]-3-oxospiro[6-azaisobenzofuran-1(3H),1'-cyclohexane]-4'-carboxamide $^1$H-NMR(300 MHz, $CDCl_3$, δppm):1.75–1.90(2H, m), 2.00–2.20(5H, m), 2.30–2.40(3H, m), 2.51(1H, quintet, J=4.9 Hz), 3.20(1H, dd, J=10.2, 3.4 Hz), 3.30–3.50(2H, m), 3.61(1H, dd, J=10.0, 6.0 Hz), 4.60–4.70 (1H, m), 5.93(1H, d, J=7.2 Hz), 6.25(1H, dt, J=12.1, 2.3 Hz), 6.30–6.36 (1H, m), 6.36–6.45(1H, m), 7.15(1H, dt, J=8.2, 6.9 Hz), 7.70–7.80 (1H, m), 8.80–8.90(1H, m), 9.04(1H, s).

EXAMPLE 17

Trans-3-oxo-N-(trans-4-phenylcyclohexyl)spiro[5-azaisobenzofuran-1(3H),1'-cyclohexane]-4'-carboxamide $^1$H-NMR(300 MHz, $CDCl_3$, δppm):1.18–1.93(2H, m), 1.49–1.74(2H, m), 1.72–1.88(2H, m), 1.91–2.22(8H, m), 2.27–2.42(2H, m), 2.45–2.59 (2H, m), 3.79–3.97(1H, m), 5.33–5.48(1H, m), 7.12–7.35(5H, m), 7.58 (1H, d, J=5.4 Hz), 8.84(1H, d, J=5.4 Hz), 9.15(1H, s).

EXAMPLE 18

Trans-3-oxo-N-(trans-4-phenylcyclohexyl)spiro[6-azaisobenzofuran-1(3H),1'-cyclohexane]-4'-carboxamide $^1$H-NMR(300 MHz, $CDCl_3$, δppm):1.15–1.41(2H, m), 1.43–1.84(2H, m), 1.86–2.24(10H, m), 2.28–2.60(4H, m), 3.78–4.00(1H, m), 5.29–5.50 (1H, m), 7.08–7.37(5H, m), 7.76(1H, dd, J=4.8, 1.2 Hz), 8.86(1H, d, J=4.8 Hz), 9.04(1H, d, J=1.2 Hz).

EXAMPLE 19

Trans-3-oxo-N-(trans-4-phenylcyclohexyl)spiro[7-azaisobenzofuran-1(3H),1'-cyclohexane]-4'-carboxamide $^1$H-NMR(300 MHz, $CDCl_3$, δppm):1.18–1.43(2H, m), 1.43–1.77(2H, m), 1.77–2.62(14H, m), 3.80–4.00(1H, m), 5.34–5.51(1H, m), 7.09–7.48 (5H, m), 7.46(1H, dd, J=7.8, 4.8 Hz), 8.17(1H, dd, J=7.8, 1.5 Hz), 8.84 (1H, dd, J=4.8, 1.5 Hz).

EXAMPLE 20

Trans-3-oxo-N-[(3S)-1-phenyl-3-pyrrolidinyl]spiro[6-azaisobenzofuran-1(3H),1'-cyclohexane]-4'-carboxamide $^1$H-NMR(300 MHz, $CDCl_3$, δppm):1.75–1.88(2H, m), 1.95–2.20(6H, m), 2.30–2.54(4H, m), 3.20–3.62(4H, m), 4.62–4.72(1H, m), 5.70–5.80 (1H, m), 6.60(2H, d, J=8.7 Hz), 6.74(1H, t, J=7.4 Hz), 7.20–7.32(2H, m), 7.76(1H, d, J=5.0 Hz), 8.87(1H, d, J=5.0 Hz), 9.04(1H, s).

EXAMPLE 21

Trans-3-oxo-N-[(3S)-1-(3-trifluoromethylphenyl)-3-pyrrolidinyl]spiro[6-azaisobenzofuran-1(3H),1'-cyclohexane]-4'-carboxamide $^1$H-NMR(200 MHz, $CDCl_3$, δppm):1.75–2.57(11H, m), 3.18–3.71(4H, m), 4.62–4.78(1H, m), 5.68–5.80(1H, m), 6.68–6.80(2H, m), 6.90–7.00 (1H, m), 7.25–7.38(1H, m), 7.76(1H, d, J=5.0 Hz), 8.87(1H, d, J=5.0 Hz), 9.04(1H, s).

EXAMPLE 22

Trans-3-oxo-N-[(3S)-1-(2-pyridyl)-3-pyrrolidinyl]spiro[5-azaisobenzofuran-1(3H),1'-cyclohexane]-4'-carboxamide $^1$H-NMR(300 MHz, $CDCl_3$, δppm):1.70–1.90(2H, m), 2.00–2.20(5H, m), 2.20–2.40(3H, m), 2.51(1H, quintet, J=4.9 Hz), 3.00–3.10(2H, m), 3.42(1H, dd, J=10.9, 3.6 Hz), 3.77(1H, dd, J=10.9, 5.9 Hz), 4.60–4.70 (1H, m), 5.83(1H, d, J=7.3 Hz), 6.38(1H, d, J=8.6 Hz), 6.55–6.65(1H, m), 7.64(1H, ddd, J=9.0,7.0,2.0 Hz), 7.56(1H, dd, J=5.4, 1.6 Hz), 8.10–8.20(1H, m), 8.84(1H, d, J=5.4 Hz), 9.14(1H, s).

EXAMPLE 23

Trans-3-oxo-N-[(3S)-1-(3-pyridyl)-3-pyrrolidinyl] spiro[5-azaisobenzofuran-1(3H),1'-cyclohexane]-4'-carboxamide H-NMR(300 MHz, $CDCl_3$, δppm):1.70–1.90(2H, m), 2.00–2.20(5H, m), 2.25–2.45(3H, m), 2.54(1H, quintet, J=5.3 Hz), 3.23(1H, dd, J=9.9, 3.0 Hz), 3.30–3.50(2H, m), 3.63(1H, dd, J=9.7, 5.9 Hz), 4.60–4.70 (1H, m), 6.17(1H, d, J=7.2 Hz), 6.70–6.90(1H, m), 7.00–7.20(1H, m), 7.57(1H, dd, J=5.3, 0.9 Hz), 7.90–8.00(2H, m), 8.85(1H, d, J=5.3 Hz), 9.15(1H, s).

EXAMPLE 24

Trans-N-[trans-4-(4-fluorophenyl)cyclohexyl]-3-oxospiro[6-azaisobenzofuran-1(3H),1'-cyclohexane]-4'-carboxamide $^1$H-NMR(300 MHz, $CDCl_3$, δppm):1.13–1.41(2H, m), 1.41–1.68(2H, m), 1.72–2.26(10H, m), 2.26–2.60(4H, m), 3.78–4.00(1H, m), 5.32–5.51 (1H, m), 6.81–7.07(2H, m), 7.07–7.37(2H, m), 7.76(1H, dd, J=5.4, 1.2 Hz), 8.86(1H, d, J=5.4 Hz), 9.04(1H, d, J=1.2 Hz).

EXAMPLE 25

Trans-N-[trans-4-(3-fluorophenyl)cyclohexyl]-3-oxospiro[6-azaisobenzofuran-1(3H),1'-cyclohexane]-4'-carboxamide $^1$H-NMR(300 MHz, $CDCl_3$, δppm):1.19–1.41(2H, m), 1.49–1.73(2H, m), 1.73–2.27(10H, m), 2.39–2.70(4H, m), 3.79–4.00(1H, m), 5.32–5.48 (1H, m), 6.82–7.03(3H, m), 7.19–7.34(1H, m), 7.76(1H, dd, J=4.8, 0.9 Hz), 8.86(1H, d, J=4.8 Hz), 9.04(1H, d, J=0.9 Hz).

EXAMPLE 26

Trans-N-[trans-4-(3-fluorophenyl)cyclohexyl]-3-oxospiro[4-azaisobenzofuran-1(3H),1'-cyclohexane]-4'-carboxamide $^1$H-NMR(300 MHz, $CDCl_3$, δppm):1.19–1.41(2H, m), 1.49–1.73(2H, m), 1.73–2.25(10H, m), 2.25–2.42(2H, m), 2.42–2.60(2H, m), 3.77–3.96 (1H, m), 5.36–5.56(1H, m), 6.82–7.03(1H, m), 7.19–7.34(1H, m), 7.54 (1H, dd, J=7.8, 4.5 Hz), 8.03(1H, d, J=7.8 Hz), 8.88(1H, d, J=4.5 Hz).

EXAMPLE 27

Trans-N-[trans-4-(3-fluorophenyl)cyclohexyl]-3-oxospiro[7-azaisobenzofuran-1(3H),1'-cyclohexane]-4'-carboxamide $^1$H-NMR(300 MHz, $CDCl_3$, δppm):1.19–1.41(2H, m), 1.49–1.76(2H, m), 1.78–2.60(14H, m), 3.80–4.00(1H, m), 5.35–5.53(1H, m), 6.82–7.03 (3H, m), 7.18–7.35(1H, m), 7.46(1H, dd, J=7.8, 4.8 Hz), 8.17(1H, dd, J=7.8, 1.5 Hz), 8.84(1H, dd, J=4.8, 1.5 Hz).

EXAMPLE 28

Trans-N-[(3S)-1-(3,5-difluorophenyl)-3-pyrrolidinyl]-3-oxospiro[6-azaisobenzofuran-1(3H),1'-cyclohexane]-4'-carboxamide $^1$H-NMR(300 MHz, $CDCl_3$, δppm):1.80–1.90(2H, m), 1.95–2.20(5H, m), 2.30–2.45(3H, m), 2.53(1H, quintet, J=4.6 Hz), 3.10–3.20(1H, m), 3.30–3.50(2H, m), 3.60–3.70 (1H, m), 4.60–4.70(1H, m), 5.60–5.70 (1H, m), 6.50–6.60 (2H, m), 6.60–6.70(1H, m), 7.76(1H, d, J=4.9 Hz), 8.87(1H, d, J=4.9 Hz), 9.03(1H, s).

EXAMPLE 29

Trans-N-[1-(3,5-difluorophenyl)-4-piperidyl]-3-oxospiro[6-azaisobenzofuran-1(3H),1'-cyclohexane]-4'-carboxamide $^1$H-NMR(300 MHz, $CDCl_3$, δppm):1.45–1.61(2H, m), 1.78–1.90(2H, m), 2.00–2.21(6H, m), 2.31–2.45(2H, m), 2.45–2.55(1H, m), 2.88–3.00 (2H, m), 3.60–3.71(2H, m), 3.95–4.10(1H, m), 5.48(1H, br d, J=7.5 Hz), 6.18–6.29(1H, m), 6.29–6.43(2H, m), 7.77(1H, dd, J=5.0, 1.1 Hz), 8.86(1H, d, J=5.0 Hz), 9.03(1H, d, J=1.1 Hz).

EXAMPLE 30

Trans-N-[3-(3-fluorophenyl)-tetrahydropyran-6-yl]-3-oxospiro[6-azaisobenzofuran-1(3H),1'-cyclohexane]-4'-carboxamide $^1$H-NMR(300 MHz, $CDCl_3$, δppm):1.43–2.10(13H, m), 3.24(1H, t, J=10.5 Hz), 4.02–4.20(1H, m), 4.24(1H, d, J=10.5 Hz), 4.32(1H, d, J=10.5 Hz), 5.20–5.40(1H, m), 6.88–7.03(1H, m), 7.03–7.16(2H, m), 7.20–7.39(1H, m), 7.76(1H, dd, J=5.1, 1.2 Hz), 8.87(1H, d, J=5.1 Hz), 9.04 (1H, d, J=1.2 Hz).

EXAMPLE 31

Trans-N-[trans-4-(2-fluorophenyl)cyclohexyl]-3-oxospiro[6-azaisobenzofuran-1(3H),1'-cyclohexane]-4'-carboxamide $^1$H-NMR(300 MHz, $CDCl_3$, δppm):1.22–1.46(2H, m), 1.52–2.28(12H, m), 2.28–2.60(3H, m), 2.76–2.97(1H, m), 3.80–4.00(1H, m), 5.35–5.53 (1H, m), 6.92–7.41(4H, m), 7.76(1H, dd, J=4.8, 1.2 Hz), 8.86(1H, d, J=4.8 Hz), 9.04(1H, d, J=1.2 Hz).

EXAMPLE 32

Trans-N-[(S)-1-benzyl-2-(benzylamino)ethyl]-3'-oxospiro[cyclohexane-1,1'(3'H)-isobenzofuran]-4'-carboxamide $^1$H-NMR(300 MHz, $CDCl_3$, δppm):1.50–1.74(2H, m), 1.60–2.10(5H, m), 2.16–2.27(1H, m), 2.39–2.47(1H, m), 2.68–2.75(2H, m), 2.86(2H, d, J=6.6 Hz), 3.79(2H, s), 4.28–4.39(1H, m), 5.85(1H, d, J=8.4 Hz), 7.13–7.37(10H, m), 7.46(1H, d, J=8.1 Hz), 7.51(1H, d, J=7.8 Hz), 7.63(1H, t, J=7.8 Hz), 7.86(1H, d, J=7.8 Hz).

EXAMPLE 33

Trans-N-benzhydryl-3'-oxospiro[cyclohexane-1,1'(3'H)-isobenzofuran]-4-carboxamide $^1$H-NMR(200 MHz, $CDCl_3$, δppm):1.70–1.80(2H, m), 2.10–2.40(6H, m), 2.64(1H, quintet, J=4.9 Hz), 6.16(1H, d, J=7.6 Hz), 6.28(1H, d, J=7.6 Hz), 7.20–7.40(10H, m), 7.45–7.55(2H, m), 7.60–7.70(1H, m), 7.80–7.90(1H, m).

EXAMPLE 34

Trans-1-methanesulfonyl-N-(1-phenyl-4-piperidyl)spiro[indoline-3,1'-cyclohexane]-4'-carboxamide $^1$H-NMR(300 MHz, $CDCl_3$, δppm):1.50–1.70(4H, m), 1.71–1.83(2H, m), 1.95–2.15(6H, m), 2.30–2.40(1H, m), 2.82–2.96(2H, m), 2.89(3H, s), 3.60–3.68(2H, br d, J=12.9 Hz), 3.72(2H, s), 3.92–4.08(1H, m), 5.47(1H, d, J=7.7 Hz), 6.85(1H, t, J=7.3 Hz), 6.94(2H, d, J=8.5 Hz), 7.05(1H, t, J=7.3 Hz), 7.18–7.30(3H, m), 7.40(2H, t, J=7.3 Hz).

EXAMPLE 35

Trans-N-(2-indanyl)-1-methanesulfonylspiro[indoline-3,1'-cyclohexane]-4'-carboxamide $^1$H-NMR(300 MHz, $CDCl_3$, δppm):1.50–1.63(2H, m), 1.68–1.80(2H, m), 1.99–2.11(4H, m), 2.23–2.32(1H, m), 2.81(2H, dd, J=16.2, 4.2 Hz), 2.88(3H, s), 3.36(2H, dd, J=16.2, 7.2 Hz), 3.70(2H, s), 4.72–4.85 (1H, m), 5.68–5.77 (1H, m), 7.05(1H, t, J=7.2 Hz), 7.18–7.30(5H, m), 7.34–7.45 (2H, m).

EXAMPLE 36

Trans-N-[1-(3-fluorophenyl)-4-piperidyl]-1-methanesulfonyl-spiro[indoline-3,1'-cyclohexane]-4'-carboxamide $^1$H-NMR(300 MHz, $CDCl_3$, δppm):1.46–1.68(4H, m), 1.70–1.84(2H, m), 2.00–2.13(6H, m), 2.30–2.40(1H, m), 2.89(3H, s), 2.86–2.98(2H, m), 3.61–3.71(2H, m), 3.72(2H, s), 3.95–4.05(1H, m), 5.43(1H, d, J=7.7 Hz), 6.49(1H, dt, J=8.2, 2.3 Hz), 6.60(1H, dt, J=12.4, 2.3 Hz), 6.68 (1H, dd, J=8.2, 2.3 Hz), 7.05(1H, dt, J=7.6, 1.1 Hz), 7.17(1H, t, J=7.6 Hz), 7.22(1H, dt, J=7.6, 1.3 Hz), 7.40(1H, dd, J=7.6, 1.1 Hz), 7.42 (1H, dd, J=7.6, 1.1 Hz).

EXAMPLE 37

Trans-1-methanesulfonyl-N-[1-(2-pyridyl)-4-piperidyl]spiro[indoline-3,1'-cyclohexane]-4'-carboxamide $^1$H-NMR(300 MHz, $CDCl_3$, δppm):1.38–1.54(2H, m), 1.53–1.63(2H, m), 1.65–1.75(4H, m), 2.00–2.12(6H, m), 2.29–2.40(1H, m), 2.88(3H, s), 3.02(2H, ddd, J=13.8, 11.2, 2.5 Hz), 3.72(2H, s), 4.06(1H, m), 4.25 (2H, m), 5.44(1H, d, J=7.8 Hz), 6.56–6.66(1H, m), 6.68(1H, d, J=8.7 Hz), 7.05 (1H, dt, J=7.6, 1.0 Hz), 7.22(1H, dt, J=7.6, 1.2 Hz), 7.39 (1H, d, J=7.6 Hz), 7.42(1H, dd, J=7.6, 1.0 Hz), 7.47(1H, ddd, J=8.8, 7.1, 2.0 Hz), 8.13–8.24(1H, m).

EXAMPLE 38

Trans-1-methanesulfonyl-N-(1-phenyl-3-piperidyl)spiro[indoline-3,1'-cyclohexane]-4'-carboxamide $^1$H-NMR(300 MHz, $CDCl_3$, δppm):1.54–1.88(8H, m), 2.00–2.19(4H, m), 2.33–2.42(1H, m), 2.89(3H, s), 2.96–3.05(1H, m), 3.13–3.43(3H, m), 3.68–3.75(2H, m), 4.20–4.30(1H, m), 6.03–6.10(1H, m), 6.88(1H, t, J=7.2 Hz), 6.91–6.99(2H, m), 7.01–7.08(1H, m), 7.19–7.30(3H, m), 7.37–7.43(2H, m).

EXAMPLE 39

Trans-N-[1-(3,5-difluorophenyl)-3-piperidyl]-1-methane-sulfonylspiro[indoline-3,1'-cyclohexane]-4'-carboxamide $^1$H-NMR(300 MHz, $CDCl_3$, δppm):1.53–1.90(8H, m), 2.00–2.13(4H, m), 2.33–2.42(1H, m), 2.88(3H, s), 3.01–3.20(3H, m), 3.40–3.48(1H, m), 3.67–3.82(2H, m), 4.10–4.21(1H, m), 5.97–6.03(1H, m), 6.19–6.28 (1H, m), 6.35–6.45(2H, m), 7.05(1H, t, J=7.5 Hz), 7.22(1H, t, J=7.5 Hz), 7.38(1H, d, J=7.8 Hz), 7.42(1H, d, J=7.8 Hz).

EXAMPLE 40

Trans-1-methanesulfonyl-N-[1-(2-pyridyl)-3-piperidyl]spiro[indoline-3,1'-cyclohexane]-4'-carboxamide $^1$H-NMR(300 MHz, $CDCl_3$, δppm):1.50–1.90(8H, m), 1.95–2.32(4H, m), 2.31–2.40(1H, m), 2.88(3H, s), 3.43–3.50(1H, m), 3.70(2H, s), 3.55–3.74(3H, m), 4.08–4.16(1H, m), 6.30(1H, d, J=7.6 Hz), 6.61(1H, dd, J=7.1, 5.0 Hz), 6.73(1H, d, J=8.6 Hz), 7.03(1H, dt, J=7.5, 1.1 Hz), 7.21 (1H, dt, J=7.5, 1.1 Hz), 7.38(2H, d, J=8.6 Hz), 7.47(1H, ddd, J=8.6, 7.1, 2.0 Hz), 8.14(1H, dd, J=5.0, 2.0 Hz).

EXAMPLE 41

Trans-1-methanesulfonyl-N-[(3S)-1-phenyl-3-pyrrolidinyl]spiro[indoline-3,1'-cyclohexane]-4'-carboxamide $^1$H-NMR(300 MHz, $CDCl_3$, δppm):1.52–1.82(6H, m), 1.96–2.13(3H, m), 2.28–2.40(2H, m), 2.87(3H, m), 3.22(1H, dd, J=9.9, 3.3 Hz), 3.31–3.51(2H, m), 3.59(1H, dd, J=9.9, 5.7 Hz), 3.67–3.72(2H, m), 4.61–4.71(1H, m), 5.82–5.89 (1H, m), 6.60(2H, d, J=7.8 Hz), 6.73(1H, t, J=7.5 Hz), 7.04(1H, dd, J=7.5, 1.2 Hz), 7.20–7.29(3H, m), 7.40(2H, t, J=8.4 Hz).

EXAMPLE 42

Trans-1-methanesulfonyl-N-[(3R)-1-phenyl-3-pyrrolidinyl spiro[indoline-3,1'-cyclohexane]-4'-carboxamide $^1$H-NMR(300 MHz, $CDCl_3$, δppm):1.52–1.82(6H, m), 1.96–2.13(3H, m), 2.28–2.40(2H, m), 2.87(3H, m), 3.22(1H, dd, J=9.9, 3.3 Hz), 3.31–3.51(2H, m), 3.59(1H, dd, J=9.9, 5.7 Hz), 3.67–3.72(2H, m), 4.61–4.71(1H, m), 5.82–5.89 (1H, m), 6.60(2H, d, J=7.8 Hz), 6.73(1H, t, J=7.5 Hz), 7.04(1H, dd, J=7.5, 1.2 Hz), 7.20–7.29(3H, m), 7.40(2H, t, J=8.4 Hz).

EXAMPLE 43

Trans-1-methanesulfonyl-N-(2-phenylcyclopropyl) spiro[indoline-3,1'-cyclohexane]-4'-carboxamide $^1$H-NMR(300 MHz, $CDCl_3$, δppm):1.10–1.30(2H, m), 1.50–1.87(4H, m), 1.95–2.20(5H, m), 2.30–2.38(1H, m), 2.89(3H, s), 2.86–2.95(1H, m), 3.72(2H, s), 5.75–5.84(1H, m), 6.99–7.48(9H, m).

EXAMPLE 44

Trans-1-methanesulfonyl-N-[2-(3-pyridyl)cyclopropyl]spiro[indoline-3,1'-cyclohexane]-4'-carboxamide $^1$H-NMR(300 MHz, $CDCl_3$, δppm):1.20–1.34(2H, m), 1.52–1.89(4H, m), 2.00–2.20(5H, m), 2.34–2.43(1H, m), 2.89(3H, s), 2.87–2.94(1H, m), 3.72(2H, s), 5.86–5.95(1H, m), 7.05(1H, dt, J=7.5, 1.1 Hz), 7.19–7.30(2H, m), 7.37–7.47(2H, m), 7.51(1H, brd, J=7.9 Hz), 8.45(1H, dd, J=4.7 Hz, 1.7 Hz), 8.50(1H, d, J=2.1 Hz).

EXAMPLE 45

Trans-N-[(S)-1-benzyl-2-(benzylamino)ethyl]-1-methylsulfonylspiro[indoline-3,1'-cyclohexane]-4'-carboxamide $^1$H-NMR(300 MHz, $CDCl_3$, δppm):1.46–1.75(4H, m), 1.82–2.05(4H, m), 2.25–2.34(1H, m), 2.68–2.72(2H, m), 2.88(3H, s), 2.80–2.90(2H, m), 3.70(2H, s), 3.77(2H, s), 4.25–4.36(1H, m), 5.85(1H, d, J=7.5 Hz), 7.03(1H, t, J=7.5 Hz), 7.15–7.32(12H, m), 7.38(1H, d, J=7.5 Hz).

EXAMPLE 46

Trans-N-[1-benzylcarbamoyl-2-(4-pyridyl)ethyl]-1-methylsulfonylspiro[indoline-3,1'-cyclohexane]-4'-carboxamide $^1$H-NMR(300 MHz, $CDCl_3$, δppm):1.45–2.02(8H, m), 2.30–2.40(1H, m), 2.88(3H, s), 3.00–3.19(2H, m), 3.68(2H, s), 4.28–4.43(2H, m), 4.78 (1H, q, J=7.5 Hz), 6.40–6.52(2H, m), 6.98–7.40(11H, m), 8.46(2H, d, J=5.9 Hz).

EXAMPLE 47

Trans-N-[2-(4-fluorophenyl)-1-[(4-pyridyl-methyl) carbamoyl]ethyl]-1-methanesulfonylspiro[indoline-3,1'-cyclohexane]-4'-carboxamide $^1$H-NMR(300 MHz, $CDCl_3$, δppm):1.45–2.10(8H, m), 2.35–2.45(1H, m), 2.88(3H, s), 3.00–3.18(2H, m), 3.70(2H, s), 4.31(1H, dd, J=15.8, 6.0 Hz), 4.41(1H, dd, J=15.8, 6.0 Hz), 4.76(1H, q, J=7.9 Hz), 6.42(1H, d, J=7.9 Hz), 6.79(1H, t, J=6.0 Hz), 6.90–7.10(5H, m), 7.11–7.32(4H, m), 7.38(1H, d, J=8.0 Hz), 8.47(2H, d, J=5.3 Hz).

EXAMPLE 48

Trans-N-(2-hydroxy-2-phenylethyl)-1-methanesulfonyl-spiro[indoline-3,1'-cyclohexane]-4'-carboxamide $^1$H-NMR(300 MHz, $CDCl_3$, δppm):1.50–1.63(2H, m), 1.67–1.82(2H, m), 1.92–2.12(4H, m), 2.33–2.42(1H, m), 2.89(3H, s), 3.27–3.47(2H, m), 3.71(2H, s), 3.72–3.82(1H, m), 4.88–4.94(1H, m), 5.91–6.02(1H, m), 7.05(1H, t, J=7.8 Hz), 7.19–7.41(8H, m).

EXAMPLE 49

Trans-N-(benzoylmethyl)-1-methanesulfonylspiro[indoline-3,1'-cyclohexane]-4'-carboxamide $^1$H-NMR(300 MHz, $CDCl_3$, δppm):1.59–1.70(2H, m), 1.80–1.91(2H, m), 2.02–2.21(4H, m), 2.51–2.60(1H, m), 2.90(3H, s), 3.76(2H, s), 4.81 (2H, d, J=4.2 Hz), 6.60–6.70 (1H, m), 7.04(1H, t, J=7.5 Hz), 7.22(1H, t, J=7.5 Hz), 7.38–7.43(2H, m), 7.52(2H, t, J=7.5 Hz), 7.64(1H, t, J=7.5 Hz), 8.00(2H, d, J=6.6 Hz).

EXAMPLE 50

Trans-N-[(S)-1-benzyl-2-(N-benzylmethylamino)ethyl]-1-methylsulfonylspiro[indoline-3,1'-cyclohexane]-4'-carboxamide $^1$H-NMR(300 MHz, $CDCl_3$, δppm):1.50–1.78(4H, m), 1.80–2.10(4H, m), 2.23(3H, s), 2.28–2.46(3H, m), 2.88(3H, s), 2.92(2H, d, J=6.6 Hz), 3.46(1H, d, J=13.2 Hz), 3.53(1H, d, J=13.2 Hz), 3.71(2H, s), 4.25–4.38(1H, m), 5.62(1H, d, J=6.6 Hz), 7.02(1H, t, J=7.5 Hz), 7.12–7.34 (12H, m), 7.38(1H, d, J=7.5 Hz).

EXAMPLE 51

Trans-N-[(S)-1-(N-benzylmethylcarbamoyl)-2-phenylethyl]-1-methylsulfonylspiro[indoline-3,1'-cyclohexane]-4'-carboxamide $^1$H-NMR(300 MHz, $CDCl_3$, δppm):1.45–2.10(8H, m), 2.33–2.46(1H, m), 2.75(3H, s), 2.88(3H, s), 3.00–3.10(2H, m), 3.69(2H, s), 4.46(1H, d, J=14.4 Hz), 4.63(1H, d, J=14.4 Hz), 5.20–5.35(1H, m), 6.75(1H, d, J=7.5 Hz), 7.00–7.36 (13H, m), 7.39(1H, d, J=7.5 Hz).

EXAMPLE 52

Trans-N-[(S)-1-(N-benzylmethylcarbamoyl)-2-(3-pyridyl)ethyl]-1-methanesulfonylspiro[indoline-3,1'-cyclohexane]-4'-carboxamide $^1$H-NMR(300 MHz, $CDCl_3$, δppm):1.45–2.08(8H, m), 2.30–2.45(1H, m), 2.88(3H, s), 2.97(3H, s), 2.95–3.02(1H, m), 3.12(1H, dd, J=13.6, 7.2 Hz), 3.70(2H, s), 4.45–4.62 (2H, m), 5.20–5.30(1H, m), 6.60(1H, br s), 7.00–7.48(11H, m), 8.45(1H, d, J=1.8 Hz), 8.47(1H, dd, J=5.1, 1.8 Hz).

EXAMPLE 53

Trans-N-(4-dimethylaminophenethyl)-1-methanesulfonyl-spiro[indoline-3,1'-cyclohexane]-4'-carboxamide $^1$H-NMR(300 MHz, $CDCl_3$, δppm):1.49–1.80(4H, m), 1.94–2.09(4H, m), 2.22–2.33(1H, m), 2.75(2H, t, J=6.6 Hz), 2.88(3H, s), 2.92(6H, s), 3.52(2H, dt, J=6.6, 6.2 Hz), 3.70 (2H, s), 5.51(1H, t, J=6.2 Hz), 6.70 (2H, d, J=8.8 Hz), 7.04(1H, t, J=8.1 Hz), 7.07(2H, d, J=8.8 Hz), 7.22 (1H, t, J=8.1 Hz), 7.39(2H, d, J=8.1 Hz).

EXAMPLE 54

Trans-1-methanesulfonyl-N-[2-(3-quinolyl)ethyl]spiro[indoline-3,1'-cyclohexane]-4'-carboxamide $^1$H-NMR(300 MHz, $CDCl_3$, δppm):1.49–1.79(4H, m), 1.92–2.09(4H, m), 2.25–2.36(1H, m), 2.88(3H, s), 3.07(2H, t, J=6.6 Hz), 3.65(1H, dt, J=6.7, 6.6 Hz), 3.69(1H, dd, J=6.7, 6.6 Hz), 3.69(2H, s), 5.63(1H, t, J=6.7 Hz), 7.02(1H, t, J=7.3 Hz), 7.22(1H, t, J=7.3 Hz), 7.33(1H, d, J=7.3 Hz), 7.38(1H, d, J=7.3 Hz), 7.54(1H, t, J=7.9 Hz), 7.69(1H, t, J=7.9 Hz), 7.77(1H, d, J-7.9 Hz), 7.99(1H, d, J=2.2 Hz), 8.08(1H, d, J=7.9 Hz), 8.79(1H, d, J=2.2 Hz).

EXAMPLE 55

Trans-N-[2-(4-dimethylaminophenyl)-2-hydroxyethyl]-1-methylsulfonylspiro[indoline-3,1'-cyclohexane]-4'-carboxamide $^1$H-NMR(300 MHz, $CDCl_3$, δppm):1.49–1.82(4H, m), 1.98–2.12(4H, m), 2.32–2.42(1H, m), 2.63–2.70(1H, m), 2.89(3H, s), 2.94(6H, s), 3.35–3.45(1H, m), 3.71(2H, s), 3.60–3.78(1H, m), 4.72–4.80(1H, s), 5.90–5.98(1H, m), 6.65–6.75(2H, m), 7.00–7.09(1H, m), 7.18–7.30(3H, m), 7.35–7.45(2H, m).

EXAMPLE 56

Trans-N-[2-hydroxy-2-(3-quinolyl)ethyl]-1-methane-sulfonylspiro[indoline-3,1'-cyclohexane]-4'-carboxamide $^1$H-NMR(300 MHz, $CDCl_3$, δppm):1.50–1.82(4H, m), 1.92–2.10(4H, m), 2.32–2.45(1H, m), 2.88(3H, s), 3.48–3.60(2H, m), 3.69(2H, s), 3.82–3.95(1H, m), 4.19–4.30(1H, m), 5.12–5.20(1H, m), 7.04(1H, t, J=7.8 Hz), 7.23(1H, t, J=7.8 Hz), 7.33(1H, d, J=7.8 Hz), 7.38(1H, d, J=7.8 Hz), 7.55(1H, t, J=7.8 Hz), 7.71(1H, t, J=7.8 Hz), 7.80(1H, d, J=7.8 Hz), 8.10(1H, d, J=7.8 Hz), 8.21(1H, d, J=2.4 Hz), 8.88(1H, d, J=2.4 Hz).

EXAMPLE 57

Trans-N-[2-(3,5-difluorophenyl)-2-hydroxyethyl]-1-methylsulfonylspiro[indoline-3,1'-cyclohexane]-4'-carboxamide $^1$H-NMR(300 MHz, $CDCl_3$, δppm):1.51–2.32(4H, m), 1.94–2.01(4H, m), 2.35–2.46(1H, s), 2.89(3H, s), 3.31–3.42 (1H, m), 3.71(2H, s), 3.70–3.82(1H, m), 3.98(1H, d, J=4.3 Hz), 4.87–4.94(1H, m), 5.98(1H, t, J=3.0 Hz), 6.68–6.76 (1H, m), 6.87–6.98(2H, m), 7.06(1H, t, J=7.7 Hz), 7.23(1H, t, J=7.7 Hz), 7.32–7.41(2H, m).

EXAMPLE 58

Trans-N-[(S)-1-benzyl-2-[(3-pyridylmethyl)amino]ethyl]-1-methylsulfonylspiro[indoline-3,1'-cyclohexane]-4'-carboxamide $^1$H-NMR(300 MHz, $CDCl_3$, δppm):1.45–1.75(4H, m), 1.80–2.09(4H, m), 2.25–2.38(1H, m), 2.70(2H, d, J=7.5 Hz), 2.86(3H, s), 2.84–2.90(2H, m), 3.69(2H, s), 3.78(2H, s), 4.25–4.40(1H, m), 5.70(1H, d, J=7.5 Hz), 7.03(1H, dd, J=7.5, 2.4 Hz), 7.12–7.40(9H, m), 7.57–7.63(1H, m), 8.50 (1H, dd, J=5.1, 1.5 Hz), 8.55(1H, d, J=1.5 Hz).

EXAMPLE 59

Trans-N-[(S)-1-benzyl-2-[(2-pyridylmethyl)amino]ethyl]-1-methylsulfonylspiro[indoline-3,1'-cyclohexane]-4'-carboxamide $^1$H-NMR(300 MHz, $CDCl_3$, δppm):1.45–2.10(8H, m), 2.30–2.40(1H, m), 2.66–2.76(2H, m), 2.88(3H, s), 2.80–2.99(2H, m), 3.70(2H, s), 3.90 (2H, dd, J=14.4, 5.7 Hz), 4.23–4.37(1H, m), 6.14(1H, d, J=7.5 Hz), 7.02(1H, t, J=7.5 Hz), 7.12–7.30(9H, m), 7.36(1H, t, J=7.5 Hz), 7.62 (1H, dt, J=7.5, 2.1 Hz), 8.54(1H, dd, J=5.1, 2.1 Hz).

EXAMPLE 60

Trans-N-[(S)-2-anilino-1-benzylethyl]-1-methane-sulfonyl-spiro[indoline-3,1'-cyclohexane]-4'-carboxamide $^1$H-NMR(300 MHz, $CDCl_3$, δppm):1.42–2.07(8H, m), 2.24–2.33(1H, m), 2.87(3H, s), 2.84–2.91(1H, m), 3.00(1H, dd, J=14.1, 6.3 Hz), 3.20 (1H, dd, J=12.4, 7.5 Hz), 3.33(1H, dd, J=12.4, 4.5 Hz), 3.67(2H, s), 4.47–4.58(1H, m), 5.49 (1H, d, J=7.5 Hz), 6.60(1H, d, J=7.5 Hz), 6.70 (1H, t, J=7.5 Hz), 7.00(1H, t, J=7.5 Hz), 7.12–7.40(10H, m).

EXAMPLE 61

Trans-N-[(S)-1-benzyl-2-(isobutylamino)ethyl]-1-methane-sulfonylspiro[indoline-3,1'-cyclohexane]-4'-carboxamide $^1$H-NMR(300 MHz, $CDCl_3$, δppm):0.89(6H, d, J=6.3 Hz), 1.45–2.10(9H, m), 2.30–2.40(1H, m), 2.43(2H, d, J=6.3 Hz), 2.65–2.78(2H, m), 2.88 (3H, s), 2.80–2.93(2H, m), 3.70(2H, s), 4.22–4.35(1H, m), 6.02(1H, d, J=7.5 Hz), 7.15–7.40(9H, m).

EXAMPLE 62

Trans-1-methanesulfonyl-N-[2-phenyl-1-(methoxy-carbonyl)ethyl]spiro[indoline-3,1'-cyclohexane]-4'-carboxamide $^1$H-NMR(300 MHz, $CDCl_3$, δppm):1.49–1.60(2H, m), 1.63–1.78(2H, m), 1.87–2.10(4H, m), 2.33–2.41(1H, m), 2.88(3H, s), 3.10(1H, dd, J=14.1, 6.3 Hz), 3.22(1H, dd, J=14.1, 5.7 Hz), 3.71(2H, s), 3.77(3H, s), 4.91–4.97(1H, m), 5.95(1H, br d, J=7.8 Hz), 7.04(1H, t, J=6.9 Hz), 7.11(2H, d, J=6.3 Hz), 7.19–7.40(6H, m).

EXAMPLE 63

Trans-N-(1-hydroxymethyl-2-phenylethyl)-1-methanesulfonyl-spiro[indoline-3,1'-cyclohexane]-4'-carboxamide $^1$H-NMR(200 MHz, $CDCl_3$, δppm):1.43–2.11(7H, m), 2.29–2.40(1H, m), 2.52–2.67(1H, m), 2.79–3.02(2H, m), 2.88(3H, s), 3.59–3.81(2H, m), 3.69(2H, s), 4.18–4.35(1H, m), 5.69–5.81(1H, m), 7.04(1H, dt, J=7.6, 1.2 Hz), 7.18–7.41(8H, m).

EXAMPLE 64

Trans-N-[1-(3-trifluoromethylphenyl)-4-piperidyl]-3-oxospiro[6-azaisobenzofuran-1(3H),1'-cyclohexane]-4'-carboxamide $^1$H-NMR(300 MHz, $CDCl_3$, δppm):1.56–1.65(2H, m), 1.80–1.88(2H, m), 2.04–2.21(6H, m), 2.35–2.44(2H, m), 2.50–2.53(1H, m), 2.91–3.00 (2H, m), 3.62–3.73(2H, m), 4.00–4.16(1H, m), 5.58–5.60(1H, m), 7.06–7.13(3H, m), 7.27–7.37(4H, m), 7.76(1H, d, J=3.7 Hz), 8.87(1H, d, J=4.9 Hz), 9.04(1H, s).

EXAMPLE 65

Trans-N-[trans-2-(3-fluorophenyl)cyclopropyl]-3'-oxospiro[cyclohexane-1,1'(3'H)-isobenzofuran]-4-carboxamide $^1$H-NMR(300 MHz, $CDCl_3$, δppm):1.18–1.31(2H, m), 1.70–1.82(2H, m), 2.00–2.21(5H, m), 2.22–2.38(2H, m), 2.46–2.56(1H, m), 2.89–2.98 (1H, m), 6.89(1H, br s), 6.83–6.91(2H, m), 6.97(1H, d, J=7.2 Hz), 7.19–7.29(1H, m), 7.52(1H, t, J=7.2 Hz), 7.55–7.69(2H, m), 7.87(1H, d, J=7.8 Hz).

EXAMPLE 66

Trans-N-[trans-2-(4-fluorophenyl)cyclopropyl]-3'-oxospiro[cyclohexane-1,1'(3'H)-isobenzofuran]-4-carboxamide $^1$H-NMR(300 MHz, $CDCl_3$, δppm):1.12–1.28(2H, m), 1.71–1.82(2H, m), 1.99–2.20(5H, m), 2.21–2.38(2H, m), 2.46–2.54(1H, m), 2.81–2.90 (1H, m), 5.86(1H, br s), 6.98 (2H, t, J=8.7 Hz), 7.13–7.21(2H, m), 7.52(1H, t, J=7.2 Hz), 7.58–7.70(2H, m), 7.88(1H, d, J=7.8 Hz).

EXAMPLE 67

Trans-N-[1-(2-fluorophenyl)-4-piperidyl]-3-oxospiro[6-azaisobenzofuran]-1(3H),1'-cyclohexane]-4'-carboxamide $^1$H-NMR(300 MHz, $CDCl_3$, δppm):1.56–1.74(2H, m), 1.78–1.90(2H, m), 2.01–2.23(6H, m), 2.32–2.48(2H, m), 2.48–2.57(1H, m), 2.77–2.90 (2H, m), 3.38–3.50(2H, m), 3.90–4.07(1H, m), 5.51(1H, m), 6.90–7.10 (4H, m), 7.74 (1H, d, J=5.0 Hz), 8.87(1H, d, J=5.0 Hz), 9.05(1H, s).

EXAMPLE 68

Trans-3'-oxo-N-[5-oxo-1-(2-fluorophenyl)-3-pyrrolidinyl]spiro[cyclohexane-1,1'(3'H)-isobenzofuran]-4-carboxamide $^1$H-NMR(300 MHz, $CDCl_3$, δppm):1.68–1.81(2H, m), 1.96–2.15(4H, m), 2.15–2.30(2H, m), 2.43–2.54(2H, m), 2.99(1H, dd, J=17.4, 7.6 Hz), 3.73(1H, dd, J=10.6, 2.4 Hz), 4.16(1H, dd, J=10.6, 6.0 Hz), 4.65–4.76 (1H, m), 6.80(1H, br s), 7.09–7.21(2H, m), 7.23–7.32(1H, m), 7.32–7.42(1H, m), 7.47–7.57(2H, m), 7.59–7.68(1H, m), 7.88(1H, d, J=7.5 Hz).

EXAMPLE 69

Trans-3'-oxo-N-[5-oxo-1-(3-fluorophenyl)-3-pyrrolidinyl]spiro[cyclohexane-1,1'(3'H)-isobenzofuran]-4-carboxamide $^1$H-NMR(300 MHz, $CDCl_3$, δppm):1.71–1.94(2H, m), 2.01–2.34(6H, m), 2.52–2.64(2H, m), 2.98–3.11(1H, m), 3.77(1H, dd, J=10.5, 2.9 Hz), 4.23(1H, dd, J=10.5, 6.4 Hz), 4.65–4.77(1H, m), 6.78–7.13(2H, m), 7.17–7.33(2H, m), 7.42–7.69(4H, m), 7.80–7.88(1H, m).

EXAMPLE 70

Trans-3-oxo-N-[5-oxo-1-(3-fluorophenyl)-3-pyrrolidinyl]spiro[6-azaisobenzofuran-1(3H),1'-cyclohexane]-4'-carboxamide $^1$H-NMR(300 MHz, $CDCl_3$, δppm):1.76–1.91(2H, m), 2.06–2.23(4H, m), 2.25–2.40(2H, m), 2.50–2.62(2H, m), 3.07(1H, dd, J=17.6, 8.1 Hz), 3.77(1H, dd, J=10.7, 2.4 Hz), 4.24(1H, dd, J=10.6, 6.2 Hz), 4.67–4.79 (1H, m), 6.79–6.92 (2H, m), 7.16–7.35(2H, m), 7.46–7.54(1H, m), 7.75 (1H, d, J=5.0 Hz), 8.87(1H, d, J=5.0 Hz), 9.04(1H, s).

EXAMPLE 71

Trans-N-[trans-4-(3-trifluoromethylphenyl)cyclohexyl]-3-oxospiro[6-azaisobenzofuran-1(3H),1'-cyclohexane]-4'-carboxamide $^1$H-NMR(300 MHz, $CDCl_3$, δppm):1.26–1.40(2H, m), 1.59–1.72(2H, m), 1.80–1.88(2H, m), 1.97–2.20(7H, m), 2.36–2.63(4H, m), 3.88–3.93 (1H, m), 5.42(1H, d, J=8.4 Hz), 7.40–7.47(4H, m), 7.76(1H, d, J=6.0 Hz), 8.87(1H, d, J=4.9 Hz), 9.04(1H, s).

EXAMPLE 72

Trans-3'-oxo-N-[2-oxo-1-phenyl-4-piperidyl]spiro[cyclo-hexane-1,1'(3'H)-isobenzofuran]-4-carboxamide $^1$H-NMR(300 MHz, $CDCl_3$, δppm):1.65–1.85(1H, m), 1.95–2.20(5H, m), 2.20–2.40(3H, m), 2.43–2.60(2H, m), 2.92–3.00(1H, m), 3.60–3.80 (2H, m), 4.40–4.45(1H, m), 5.68–5.70(1H, m), 7.20–7.23(3H, m), 7.38–7.42(2H, m), 7.45–7.56(2H, m), 7.62–7.66(1H, m), 7.86–7.87(1H, m).

EXAMPLE 73

Trans-3'-oxo-N-[2-oxo-1-(3-fluorophenyl)-4-piperidyl]spiro[cyclohexane-1,1'(3'H)-isobenzofuran]-4-carboxamide $^1$H-NMR(300 MHz, $CDCl_3$, δppm):1.60–1.90(1H, m), 1.95–2.20(5H, m), 2.22–2.60(5H, m), 2.96–3.00(1H, m), 3.62–3.80(2H, m), 4.38–4.50 (1H, m), 5.70–5.80(1H, m), 7.20–7.30(4H, m), 7.40–7.42(2H, m), 7.72–7.80(1H, m), 8.84–8.85(1H, m), 9.01(1H, s).

EXAMPLE 74

Trans-N-[trans-2-(2-fluorophenyl)cyclopropyl]-3'-oxospiro[cyclohexane-1,1'(3'H)-isobenzofuran]-4-carboxamide $^1$H-NMR(300 MHz, $CDCl_3$, δppm):1.20–1.37(2H, m), 1.70–1.82(2H, m), 2.01–2.38(7H, m), 2.48–2.57(1H, m), 3.00–3.09(1H, m), 5.92(1H, br s), 6.99–7.21(4H, m), 7.51 (1H, t, J=7.2 Hz), 7.56–7.69(2H, m), 7.87 (1H, d, J=7.5 Hz).

EXAMPLE 75

Trans-N-[trans-2-(3-fluorophenyl)cyclopropyl]-3-oxospiro[6-azaisobenzofuran-1(3H),1'-cyclohexane]-4'-carboxamide $^1$H-NMR(300 MHz, $CDCl_3$, δppm):1.17–1.32(2H, m), 1.75–1.89(2H, m), 2.00–2.25(5H, m), 2.31–2.58(3H, m), 2.89–2.99(1H, m), 5.84(1H, br s), 6.80–7.03(3H, m), 7.20–7.32(1H, m), 7.76((1H, dd, J=5.1, 0.9 Hz), 8.87(1H, d, J=5.1 Hz), 9.03(1H, d, J=0.9 Hz).

EXAMPLE 76

Trans-N-[trans-2-(4-fluorophenyl)cyclopropyl]-3-oxospiro[6-azaisobenzofuran-1(3H),1'-cyclohexane]-4'-carboxamide $^1$H-NMR(300 MHz, $CDCl_3$, δppm):1.12–1.30(2H, m), 1.78–1.90(2H, m), 2.01–2.22(5H, m), 2.31–2.48(2H, m), 2.48–2.57(1H, m), 2.82–2.91 (1H, m), 5.84(1H, br s), 6.98 (2H, t, J=8.7 Hz), 7.12–7.22(2H, m), 7.76(1H, dd, J=4.8, 1.2 Hz), 8.87(1H, d, J=4.8 Hz), 9.04(1H, s).

EXAMPLE 77

Preparation of 1-methanesulfonyl-N-(1-phenyl-4-piperidyl)spiro[indoline-3,4'-piperidine]-1'-carboxamide (1) Preparation of phenyl N-(1-phenyl-4-piperidyl)carbamate Pyridine (24 μL) and phenyl chlorocarbonate (32 μL) were added to a solution of 1-phenyl-4-piperidylamine (35 mg) in tetrahydrofuran (1 mL), and the mixture was stirred at room temperature for 12 hours. The reaction mixture was poured into saturated aqueous sodium bicarbonate, and extracted with ethyl acetate. The organic layer was dried over anhydrous magnesium sulfate and concentrated. The residue was purified by column chromatography on silica gel (ethyl acetate/chloroform=1/1) to give the title compound (37 mg).

(2) Preparation of 1-methanesulfonyl-N-(1-phenyl-4-piperidyl)spiro[indoline-3,4'-piperidine]-1'-carboxamide 1-Methanesulfonyl-spiro[indoline-3,4'-piperidine] hydrochloride (37 mg) and triethylamine (170 μL) were added to a solution of phenyl N-(1-phenyl-4-piperidyl)carbamate (36 mg) in chloroform (3 mL), and the mixture was heated to reflux for 15 hours. The reaction mixture was poured into saturated aqueous sodium bicarbonate and extracted with ethyl acetate. The organic layer was dried over anhydrous magnesium sulfate and concentrated. The residue was crystallized from diethyl ether to give the title compound (18 mg) as a colorless crystal.

$^1$H-NMR(300 MHz, $CDCl_3$, δppm):1.49–2.13(12H, m), 2.71–2.83(1H, m), 2.84–3.00(2H, m), 2.92(3H, s), 3.10–3.19(1H, m), 3.60–3.70(1H, m), 3.85(2H, s), 3.90–4.01(1H, m), 4.37(1H, d, J=7.8 Hz), 6.84(1H, t, J=7.2 Hz), 6.94(1H, d, J=8.7 Hz), 7.07(1H, t, J=7.2 Hz), 7.11–7.29 (5H, m), 7.40(1H, d, J=8.4 Hz).

Compounds of Examples 78 to 83 were obtained by following the same procedure as in Example 77-(2), except that phenyl N-(1-phenyl-4-piperidyl)carbamate and 1-methanesulfonylspiro[indoline-3,4'-piperidine]hydrochloride used in Example 77-(2) were replaced with the corresponding starting material of each desired compound.

EXAMPLE 78

3-Oxo-N-(1-phenyl-3-piperidyl)spiro[isobenzofuran-1(3H),4'-piperidine]-1'-carboxamide $^1$H-NMR(300 MHz, $CDCl_3$, δppm):1.60–1.90(2H, m), 2.04–2.18(2H, m), 2.53–2.60(1H, m), 3.01–3.49(9H, m), 3.92–4.20(3H, m), 5.03(1H, d, J=7.8 Hz), 6.88(1H, t, J=7.5 Hz), 6.97(2H, d, J=7.5 Hz), 7.21–7.30(2H, m), 7.35(1H, d, J=7.8 Hz), 7.54(1H, t, J=7.5 Hz), 7.68(1H, t, J=7.5 Hz), 7.88(1H, d, J=7.5 Hz).

EXAMPLE 79

3-Oxo-N-[(3S)-1-phenyl-3-pyrrolidinyl]spiro[isobenzofuran-1(3H),4'-piperidine]-1'-carboxamide $^1$H-NMR(300 MHz, $CDCl_3$, δppm):1.98–2.20(3H, m), 2.30–2.41(1H, m), 2.99–3.10(2H, m), 3.22–3.40(4H, m), 3.42–3.53(1H, m), 3.59–3.65 (1H, m), 3.96–4.11(2H, m), 4.53–4.64(1H, m), 4.68–4.77(1H, m), 6.60 (2H, d, J=7.8 Hz), 6.72(1H, t, J=7.5 Hz), 7.25(2H, t, J=7.5 Hz), 7.37 (1H, d, J=7.5 Hz), 7.55(1H, t, J=7.5 Hz), 7.69(1H, t, J=7.5 Hz), 7.89 (1H, d, J=7.8 Hz).

EXAMPLE 80

N-[1-Benzylcarbamoyl-2-cyclohexylethyl]-3,4-dihydro-3-oxo-spiro[isoquinoline-1(2H),4'-piperidine]-1'-carboxamide $^1$H-NMR(300 MHz, $CDCl_3$, δppm):0.88–1.03(2H, m), 1.10–1.25(3H, m), 1.27–1.45(1H, m), 1.50–1.86(8H, m), 2.03–2.19(2H, m), 3.05–3.19 (2H, m), 3.66(2H, s), 3.94–4.05(2H, m), 4.34–4.43(2H, m), 4.52(1H, dd, J=13.5, 6.0 Hz), 5.10(1H, d, J=7.5 Hz), 6.60(2H, br s), 7.15–7.37 (9H, m).

EXAMPLE 81

N-[(S)-1-Benzyloxymethyl-2-cyclohexylethyl]-3,4-dihydro-3-oxospiro[isoquinoline-1(2H),4'-piperidine]-1'-carboxamide $^1$H-NMR(300 MHz, $CDCl_3$, δppm):0.80–1.32(7H, m), 1.40–1.50(2H, m), 1.60–1.85(6H, m), 2.03–2.20(2H, m), 3.02–3.18(2H, m), 3.47(1H, dd, J=9.7, 3.3 Hz), 3.54(1H, dd, J=9.7, 3.3 Hz), 3.66(2H, s), 3.90–4.02 (2H, m), 4.02–4.17 (1H, m), 4.49(1H, d, J=12.2 Hz), 4.54(1H, d, J=12.2 Hz), 4.70(1H, d, J=8.7 Hz), 6.64(1H, s), 7.10–7.40(9H, m).

EXAMPLE 82

N-[(S)-1-Benzylcarbamoyl-2-phenylethyl]-3,4-dihydro-3-oxospiro[isoquinoline-1(2H),4'-piperidine]-1'-carboxamide $^1$H-NMR(300 MHz, $CDCl_3$, δppm):1.70–1.80(2H, m), 1.90–2.12(2H, m), 3.00–3.20(2H, m), 3.64(2H, s), 3.83–4.00(2H, m), 4.30(1H, dd, J=15.0, 5.7 Hz), 4.39(1H, dd, J=15.0, 5.7 Hz), 4.58(1H, dd, J=14.5, 7.5 Hz), 5.37(1H, d, J=7.5 Hz), 6.31(1H, br s), 6.73(1H, br s), 7.08(2H, dd, J=7.5, 2.4 Hz), 7.13–7.37(12H, m).

EXAMPLE 83

N-[(S)-1-Benzyl-2-(benzylamino)ethyl]-3,4-dihydro-3-oxospiro[isoquinoline-1(2H),4'-piperidine]-1'-carboxamide $^1$H-NMR(300 MHz, $CDCl_3$, δppm):1.60–1.85(2H, m), 1.93–2.14(2H, m), 2.68(2H, d, J=5.4 Hz), 2.77(1H, dd, J=13.5, 7.5 Hz), 2.97(1H, dd, J=13.5, 5.4 Hz), 3.02–3.18 (2H, m), 3.65(2H, s), 3.75(2H, s), 3.82–4.04 (2H, m), 4.07–4.20(1H, m), 5.00(1H, d, J=6.9 Hz), 6.79(1H, br s), 7.10–7.36(14H, m).

EXAMPLE 84

Preparation of N-(2-indanyl)-1-methanesulfonyl-spiro[indoline-3,4'-piperidine]-1'-carboxamide 1-Methanesulfonylspiro[indoline-3,4'-piperidine]hydrochloride (60 mg) and 10M aqueous sodium hydroxide (33 μL) were added to a solution of phenyl N-(2-indanyl) carbamate (50 mg) in dimethyl sulfoxide (2 mL), and the mixture was stirred at room temperature for one hour. The reaction mixture was poured into water, and extracted with ethyl acetate. The organic layer was dried over anhydrous magnesium sulfate and concentrated. The residue was washed with ethyl acetate to give the title compound (65 mg) as a colorless crystal.

$^1$H-NMR(300 MHz, $CDCl_3$, δppm):1.72(2H, d, J=13.9 Hz), 1.83–1.95(2H, m), 2.81–2.98(4H, m), 2.91(3H, s), 3.37(2H, dd, J=16.4, 6.4 Hz), 3.84 (2H, s), 3.95(2H, d, J=13.5 Hz), 4.69(2H, br s), 7.06–7.28(7H, m), 7.40(1H, d, J=8.4 Hz).

Compounds of Examples 85 to 88 were obtained by following the same procedure as in Example 84, except that phenyl N-(2-indanyl)carbamate and 1-methanesulfonylspiro [indoline-3,4'-piperidine]hydrochloride used in Example 84 were replaced with the corresponding starting materials of each desired compound.

EXAMPLE 85

1-Methanesulfonyl-N-phenethylspiro[indoline-3,4'-piperidine]-1'-carboxamide $^1$H-NMR(300 MHz, $CDCl_3$, δppm):1.61–1.72(2H, m), 1.79–1.89(2H, m), 2.83–2.96(4H, m), 2.86(3H, s), 3.83(2H, s), 3.85–3.94(2H, m), 4.49 (1H, br s), 7.04–7.41(9H, m).

EXAMPLE 86

1-Methanesulfonyl-N-(3-phenylpropyl)spiro[indoline-3,4'-piperidine]-1'-carboxamide $^1$H-NMR(300 MHz, $CDCl_3$, δppm):1.70–1.77(2H, m), 1.86–2.02(2H, m), 2.71(2H, t, J=7.4 Hz), 2.88–2.99(2H, m), 2.92(3H, s), 3.33(2H, t, J=7.0 Hz), 3.74–3.82(2H, m), 3.84 (2H, s), 7.08(1H, t, J=7.4 Hz), 7.15–7.32(8H, m), 7.40(1H, d, J=7.7 Hz).

EXAMPLE 87

1-Methanesulfonyl-N-(4-phenylbutyl)spiro[indoline-3,4'-piperidine]-1'-carboxamide $^1$H-NMR(300 MHz, $CDCl_3$, δppm):1.54–2.00(8H, m), 2.66(2H, t, J=7.3 Hz), 2.92(3H, s), 2.93–3.04(2H, m), 3.29 (2H, t, J=7.0 Hz), 3.85(2H, s), 3.86–3.94(2H, m), 7.07–7.11 (1H, m), 7.15–7.31(8H, m), 7.38–7.42(1H, m).

EXAMPLE 88

N-(4-Bromophenethyl)-1-methanesulfonylspiro[indoline-3,4'-piperidine]-1'-carboxamide $^1$H-NMR(300 MHz, DMSO-$d_6$, δppm):1.55–1.70(4H, m), 2.73(2H, t, J=7.1 Hz), 2.78–2.88(2H, m), 3.04(3H, s), 3.22–3.32(2H, m), 3.87(2H, s), 3.91(2H, brd, J=13.2 Hz), 7.06(1H, t, J=7.2 Hz), 7.18–7.29(5H, m), 7.48(2H, d, J=8.2 Hz).

EXAMPLE 89

Preparation of N-(3,4-dimethoxyphenethyl)-1-methane-sulfonylspiro[indoline-3,4'-piperidine]-1'-carboxamide 2-(4-Formyl-3-methoxyphenoxy)ethyl polystyrene resin (500 mg), 1% acetic acid-dimethylformamide (10 mL), 2-(3,4-dimethoxyphenyl)ethylamine (236 μL) and sodium triacetoxyborohydride (590 mg) were successively added into a 75 mL-reservoir equipped with a frit. The mixture was stirred at room temperature overnight and then filtered. The remaining resin was washed successively with dimethylformamide, methanol and methylene chloride (10 mL each), and dried under reduced pressure to give 2-[4-[2-(3,4-dimethoxyphenyl)ethyl]amino-methyl-3-methoxyphenoxy] ethyl polystyrene resin. Then, the resin (50 mg) obtained above, methylene chloride (5 mL), triphosgene (22 mg) and triethylamine (38 μL) were added to a 15 mL-reservoir equipped with a frit. The mixture was stirred at room temperature for 6 hours and then filtered. The remaining resin was washed with methylene chloride, and methylene chloride (5 mL), 1-methanesulfonylspiro(indoline-3,4'-piperidine) hydrochloride (22 mg) and triethylamine (77 μL) were added thereto. The mixture was stirred at room temperature overnight and then filtered. The resin thus obtained was washed successively with dimethylformamide, methanol and methylene chloride (10 mL each), and stirred in 50% trifluoroacetic acid-methylene chloride solution for one hour to give a crude product. The product was purified by chromatography on silica gel to give the title compound (7 mg).

$^1$H-NMR(300 MHz, $CDCl_3$, δppm):1.65–1.75(2H, m), 1.78–1.93(2H, m), 2.80(2H, t, J=6.9 Hz), 2.83–2.98(2H, m), 2.92(3H, s), 3.50(1H, t, J=6.5 Hz), 3.52(1H, t, J=6,5 Hz), 3.83(2H, s), 3.86(3H, s), 3.88(3H, s), 3.80–3.95(2H, m), 4.51(1H, t), 6.71–6.78(2H, m), 6.79–6.84(1H, m), 7.03–7.15 (2H, m), 7.20–7.28(1H, m), 7.40(1H, d, J=1.8 Hz).

Compounds of Examples 90 to 95 were obtained by following the same procedure as in Example 89, except that 2-(3,4-dimethoxyphenyl)ethylamine and 1-methanesulfonylspiro[indoline-3,4'-piperidine]hydrochloride used in Example 89 were replaced with the corresponding starting materials of each desired compound.

EXAMPLE 90

1-Methanesulfonyl-N-(3-methoxyphenethyl)spiro [indoline-3,4'-piperidine]-1'-carboxamide $^1$H-NMR(300 MHz, $CDCl_3$, δppm):1.64–1.75(2H, br d, J=13.2 Hz), 1.87 (2H, dt, J=13.2,4.2 Hz), 2.83(2H, t, J=6.5 Hz), 2.85–2.97(2H, m), 2.91(3H, s), 3.51(1H, t, J=6.5 Hz), 3.53(1H, t, J=6.5 Hz), 3.79(3H, s), 3.83(2H, s), 3.84–3.95 (2H, br d, J=13.5 Hz), 4.48(1H, t), 6.75–6.81(3H, m), 7.07(1H, t, J=7.4 Hz), 7.14(1H, dd, J=7.4, 1.7 Hz), 7.18–7.30(2H, m).

EXAMPLE 91

N-(4-Dimethylamino-2-methoxyphenethyl)-1-methanesulfonyl-spiro[indoline-3,4'-piperidine]-1'-carboxamide $^1$H-NMR(300 MHz, $CDCl_3$, δppm):1.65–1.78(2H, m), 2.76(2H, t, J=6.4 Hz), 2.91(3H, s), 2.93(6H, s), 2.80–3.00 (2H, m), 3.42(1H, t, J=6.4 Hz), 3.44(1H, t, J=6.4 Hz), 3.83(5H, s), 3.85–3.97(2H, m), 4.86–4.95(1H, m), 6.27(1H, d, J=2.3 Hz), 6.31(1H, dd, J=8.4, 2.3 Hz), 6.95–7.20(4H, m), 7.20–7.30(2H, m), 7.39(1H, d, J=6.0 Hz).

EXAMPLE 92

N-[(S)-1-Benzyloxycarbonyl-2-(3-indolyl)ethyl]-3, 4-dihydro-3-oxospiro[isoquinoline-1(2H), 4'-piperidine]-1'-carboxamide $^1$H-NMR(300 MHz, $CDCl_3$, δppm):1.71(2H, br d, J=14.3 Hz), 1.91–2.12 (2H, m), 2.82–3.08(2H, m), 3.30(1H, dd, J=14.4, 5.0 Hz), 3.38(1H, dd, J=14.4, 5.0 Hz), 3.63(2H, s), 3.85(2H, br d, J=14.3 Hz), 4.91 (1H, dt, J=8.0, 5.0 Hz), 5.01(1H, d, J=8.0 Hz), 5.14(1H, d, J=11.9 Hz), 5.22(1H, d, J=11.9 Hz), 6.34(1H, br s), 6.65(1H, s), 7.09(1H, t, J=6.9 Hz), 7.12–7.40(11H, m), 7.55(1H, d, J=8.9 Hz), 7.98(1H, br s).

EXAMPLE 93

N-[(R)-1-Benzyloxycarbonyl-2-(3-indolyl)ethyl]-3, 4-dihydro-3-oxospiro[isoquinoline-1(2H),4'-piperidine]-1'-carboxamide $^1$H-NMR(300 MHz, $CDCl_3$, δppm):1.71(2H, br d, J=14.3 Hz), 1.91–2.12 (2H, m), 2.82–3.08(2H, m), 3.30(1H, dd, J=14.4, 5.0 Hz), 3.38(1H, dd, J=14.4, 5.0 Hz), 3.63(2H, s), 3.85(2H, brd, J=14.3 Hz), 4.91(1H, dt, J=8.0, 5.0 Hz), 5.01(1H, d, J=8.0 Hz), 5.14(1H, d, J=11.9 Hz), 5.22 (1H, d, J=11.9 Hz), 6.34(1H, br s), 6.65(1H, s), 7.09(1H, t, J=6.9 Hz), 7.12–7.40(11H, m), 7.55(1H, d, J=8.9 Hz), 7.98(1H, br s).

EXAMPLE 94

N-[(S)-1-Benzyloxycarbonyl-2-cyclohexylethyl]-3, 4-dihydro-3-oxospiro[isoquinoline-1(2H),4'-piperidine]-1'-carboxamide $^1$H-NMR(300 MHz, $CDCl_3$, δppm):0.82–1.00(2H, m), 1.05–1.41(5H, m), 1.46–1.81(6H, m), 1.82(2H, br d, J=12.1 Hz), 2.05–2.10(2H, m), 3.05–3.22(2H, m), 3.66(2H, s), 4.03(2H, br t, J=12.1 Hz), 4.60(1H, dt, J=8.3, 5.6 Hz), 4.93(1H, d, J=8.3 Hz), 5.11(1H, d, J=12.4 Hz), 5.24(1H, d, J=12.4 Hz), 6.70(1H, br s), 7.12–7.42(9H, m).

EXAMPLE 95

3,4-Dihydro-N-(3-methoxyphenethyl)-3-oxospiro [isoquinoline-1(2H),4'-piperidine]-1'-carboxamide $^1$H-NMR(300 MHz, $CDCl_3$, δppm):1.75–1.85(2H, m), 2.02–2.16(2H, m), 2.83(2H, t, J=6.8 Hz), 3.02–3.15(2H, m), 3.52(1H, t, J=6.8 Hz), 3.54 (1H, t, J=6.8 Hz), 3.66(2H, s), 3.80(3H, s), 3.85–3.98(2H, m), 4.47–4.56(1H, m), 6.52(1H, s), 6.72–6.82(3H, m), 7.15–7.32(5H, m).

Industrial Applicability

Compounds of the present invention have NPY antagonistic actions, therefore they are useful as agents for the treatment of various diseases related to NPY, for example, cardiovascular disorders such as hypertension, nephropathy, heart disease, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, etc., metabolic diseases such as obesity, diabetes, hormone abnormality, hypercholesterolemia, hyperlipidemia, etc., sexual and reproductive dysfunctions, gastro-intestinal disorders such as gastro-intestinal motility disorder, respiratory disorders, inflammatory diseases or glaucoma.

The invention claimed is:

1. A compound of the formula (I-d):

(I-d)

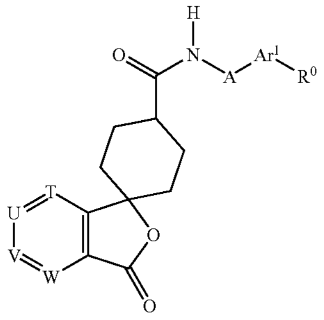

wherein

A is a group selected from formula (A'-1):

(A'-I)

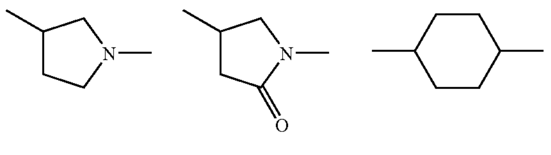

-continued

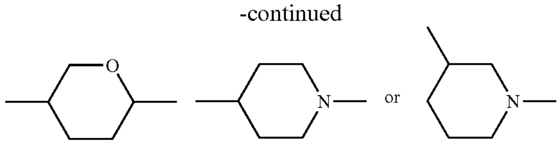

which is optionally substituted by a substituent selected from the group consisting of oxo, amino, lower alkylamino, di-lower alkylamino, hydroxy, lower alkoxy, lower alkoxycarbonyl, lower alkylene, aryl, heteroaryl and —$R^a$;

$Ar^1$ is aryl which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl and lower alkoxycarbonyl;

$R^a$ is lower alkyl which is optionally substituted by a substituent selected from the group consisting of amino, lower alkylamino, di-lower alkylamino and hydroxy, and cyclo-lower alkyl, aryl and heteroaryl, the last three groups being optionally substituted by fluorine;

$R^0$ is hydrogen;

T, U, V and W are independently methine or nitrogen atom, said methine being optionally substituted by a substituent selected from the group consisting of halogen, lower alkyl, hydroxy and lower alkoxy, and at least two of T, U, V and W are said methine group, or a salt or ester of a carboxyl group thereof when the compound has carboxyl group.

2. The compound as claimed in claim 1, wherein all of T, U, V and W are unsubstituted methine.

3. The compound as claimed in claim 1, wherein aryl as $Ar^1$ is phenyl.

4. The compound as claimed in claim 1, wherein $Ar^1$ is aryl which is optionally substituted by a substituent selected from the group consisting of halogen, nitro, oxo, lower alkyl, halo-lower alkyl, hydroxy-lower alkyl, cyclo-lower alkyl, lower alkenyl, lower alkoxy, halo-lower alkoxy, lower alkylamino, di-lower alkylamino, lower alkylthio, carboxyl, lower alkanoyl and lower alkoxycarbonyl.

5. The compound as claimed in claim 1, selected from the group consisting of:

trans-3'-oxo-N-(trans-4-phenylcyclohexyl)spiro[cyclohexane-1,1'(3'H)-isobenzofuran]-4-carboxamide, trans-N-[(3S)-1-(2-fluorophenyl)-3-pyrrolidinyl]-3'-oxo-spiro[cyclohexane-1,1'(3'H)-isobenzofuran]-4-carboxamide, trans-N-[(3S)-1-(3-fluorophenyl)-3-pyrrolidinyl]-3'-oxo-spiro[cyclohexane-1,1'(3'H)-isobenzofuran]-4-carboxamide, trans-N-[(3S)-1-(4-fluorophenyl)-3-pyrrolidinyl]-3'-oxo-spiro[cyclohexane-1,1'(3'H)-isobenzofuran]-4-carboxamide, trans-N-[1-(2-fluorophenyl)-4-piperidyl]-3'-oxospiro[cyclo-hexane-1,1'(3'H)-isobenzofuran]-4-carboxamide, trans-N-[1-(3-fluorophenyl)-4-piperidyl]-3'-oxospiro[cyclo-hexane-1,1'(3'H)-isobenzofuran]-4-carboxamide, trans-N-[1-(4-fluorophenyl)-4-piperidyl]-3'-oxospiro[cyclo-hexane-1,1'(3'H)-isobenzofuran]-4-carboxamide, trans-N-[1-(3-fluorophenyl)-4-piperidyl]-3-oxospiro[4-azaisobenzofuran-1(3H),1'-cyclohexane]-4'-carboxamide trans-N-[1-(3-fluorophenyl)-4-piperidyl]-3-oxospiro[5-aza-isobenzofuran-1(3H),1'-cyclohexane]-4'-carboxamide, trans-N-[1-(3-fluorophenyl)-4-piperidyl]-3-oxospiro[6-aza-isobenzofuran-1(3H),1'-cyclohexane]-4'-carboxamide, trans-N-[1-(3-fluorophenyl)-4-piperidyl]-3-oxospiro[7-aza-isobenzofuran-1(3H),1'-cyclohexane]-4'-carboxamide, trans-3'-oxo-N-[(3S)-5-oxo-1-phenyl-3-pyrrolidinyl]spiro[cyclohexane-1,1'(3'H)-isobenzofuran]-4-carboxamide, trans-N-[(3S)-1-(2-fluorophenyl)-3-pyrrolidinyl]-3-oxo-spiro[6-azaisobenzofuran-1(3H),1'-cyclohexane]-4'-carboxamide, trans-N-[(3S)-1-(3-fluorophenyl)-3-pyrrolidinyl]-3-oxo-spiro[6-azaisobenzofuran-1(3H),1'-cyclohexane]-4'-carboxamide, trans-3-oxo-N-(trans-4-phenylcyclohexyl)spiro[5-aza-isobenzofuran-1(3H),1'-cyclohexane]-4'-carboxamide, trans-3-oxo-N-(trans-4-phenylcyclohexyl)spiro[6-aza-isobenzofuran-1(3H),1'-cyclohexane]-4'-carboxamide, trans-3-oxo-N-(trans-4-phenylcyclohexyl)spiro[7-aza-isobenzofuran-1(3H),1'-cyclohexane]-4'-carboxamide, trans-3-oxo-N-[(3S)-1-phenyl-3-pyrrolidinyl]spiro[6-aza-isobenzofuran-1(3H),1'-cyclohexane]-4'-carboxamide, trans-3-oxo-N-[(3S)-1-(3-trifluoromethylphenyl)-3-pyrrolidinyl]spiro[6-aza-isobenzofuran-1(3H),1'-cyclohexane]-4'-carboxamide, trans-N-[trans-4-(4-fluorophenyl)cyclohexyl]-3-oxo-spiro[6-azaisobenzofuran-1(3H),1'-cyclohexane]-4'-carboxamide, trans-N-[trans-4-(3-fluorophenyl)cyclohexyl]-3-oxo-spiro[6-azaisobenzofuran-1(3H),1'-cyclohexane]-4'-carboxamide, trans-N-[trans-4-(3-fluorophenyl)cyclohexyl]-3-oxo-spiro[4-azaisobenzofuran-1(3H),1'-cyclohexane]-4'-carboxamide, trans-N-[trans-4-(3-fluorophenyl)cyclohexyl]-3-oxo-spiro[7-azaisobenzofuran-1(3H),1'-cyclohexane]-4'-carboxamide, trans-N-[(3S)-1-(3,5-difluorophenyl)-3-pyrrolidinyl-3-oxo-spiro[6-azaisobenzofuran-1(3H),1'-cyclohexane]-4'-carboxamide, trans-N-[1-(3,5-difluorophenyl)-4-piperidyl]-3-oxospiro[6-azaisobenzofuran-1(3H),1'-cyclohexane]-4'-carboxamide, trans-N-[3-(3-fluorophenyl)-tetrahydropyran-6-yl]-3-oxo-spiro[6-azaisobenzofuran-1(3H),1'-cyclohexane]-4'-carboxamide, trans-N-[trans-4-(2-fluorophenyl)cyclohexyl]-3-oxospiro[6-azaisobenzofuran-1(3H),1'-cyclohexane]-4'-carboxamide, trans-N-[1-(3-trifluoromethylphenyl)-4-piperidyl]3-oxo-spiro[6-azaisobenzofuran-1(3H),1'-cyclohexane]-4'-carboxamide, trans-N-[1-(2-fluorophenyl)-4-piperidyl]-3-oxospiro[6-aza-isobenzofuran-1(3H),1'-cyclohexane]-4'-carboxamide, trans-3'-oxo-N-[5-oxo-1-(2-fluorophenyl)-3-pyrrolidinyl]spiro[cyclohexane-1,1'(3'H)-isobenzofuran]-4-carboxamide, trans-3'-oxo-N-[5-oxo-1-(3-fluorophenyl)-3-pyrrolidinyl]spiro[cyclohexane-1,1'(3'H)-isobenzofuran]-4-carboxamide, trans-3-oxo-N-[5-oxo-1-(3-fluorophenyl)-3-pyrrolidinyl] spiro[6-azaisobenzofuran-1(3H),1'-cyclo-hexane]-4'-carboxamide, trans-N-[trans-4-(3-trifluoromethylphenyl)cyclohexyl]3-oxospiro[6-azaisobenzofuran-1(3H),1'-cyclohexane]-4'-carboxamide, trans-3'-oxo-N-[2-oxo-1-phenyl-4-piperidyl]spiro[cyclohexane-1,1'(3'H)-isobenzofuran]-4-carboxamide, trans-3'-oxo-N-[2-oxo-1-(3-fluorophenyl)-4-piperidyl] spiro[cyclohexane-1,1'(3'H)-isobenzofuran]-4-carboxamide.

6. A composition comprising a compound according to claim 1 together with a pharmaceutically acceptable additive.

7. The compound or salt thereof of claim 1, wherein the compound is trans-3'-oxo-N-(trans-4-phenylcyclohexyl)-spiro[cyclohexane-1,1'(3'H)-isobenzofuran]-4-carboxamide.

8. The compound or salt thereof of claim 1, wherein the compound is trans-N-[1-(2-fluorophenyl)-4-piperidyl]-3'-oxo-spiro[cyclohexane-1,1'(3'H)-isobenzofuran]-4-carboxamide.

9. The compound or salt thereof of claim 1, wherein the compound is trans-N-[1-(3,5-difluorophenyl)-4-piperidyl]-3-oxospiro[4-azaisobenzofuran-1(3H),1'-cyclohexane]-4'-carboxamide.

* * * * *